(12) United States Patent
Gudkov et al.

(10) Patent No.: US 10,336,793 B2
(45) Date of Patent: Jul. 2, 2019

(54) FLAGELLIN-BASED AGENTS AND USES INCLUDING EFFECTIVE VACCINATION

(71) Applicant: Genome Protection, Inc., Buffalo, NY (US)

(72) Inventors: Andrei V. Gudkov, Buffalo, NY (US); Vadim Mett, Buffalo, NY (US); Vadim Krivokrysenko, Buffalo, NY (US)

(73) Assignee: GENOME PROTECTION, INC., Buffalo, NY (US)

( * ) Notice: Subject to any disclaimer, the term of this patent is extended or adjusted under 35 U.S.C. 154(b) by 0 days.

(21) Appl. No.: 15/500,133

(22) PCT Filed: Jul. 30, 2015

(86) PCT No.: PCT/US2015/042887
§ 371 (c)(1),
(2) Date: Jan. 30, 2017

(87) PCT Pub. No.: WO2016/019134
PCT Pub. Date: Feb. 4, 2016

(65) Prior Publication Data
US 2017/0266278 A1    Sep. 21, 2017

Related U.S. Application Data

(60) Provisional application No. 62/117,366, filed on Feb. 17, 2015, provisional application No. 62/110,744, filed on Feb. 2, 2015, provisional application No. 62/031,116, filed on Jul. 30, 2014.

(51) Int. Cl.
| | |
|---|---|
| *A61K 39/00* | (2006.01) |
| *A61K 49/00* | (2006.01) |
| *A61K 39/38* | (2006.01) |
| *C07K 14/195* | (2006.01) |
| *A61K 38/16* | (2006.01) |
| *A61K 39/39* | (2006.01) |
| *A61K 39/02* | (2006.01) |
| *A61K 45/06* | (2006.01) |

(52) U.S. Cl.
CPC .......... *C07K 14/195* (2013.01); *A61K 38/164* (2013.01); *A61K 39/0013* (2013.01); *A61K 39/02* (2013.01); *A61K 39/39* (2013.01); *A61K 45/06* (2013.01); *A61K 2039/55505* (2013.01); *A61K 2039/55516* (2013.01); *A61K 2039/55583* (2013.01); *A61K 2039/55594* (2013.01); *A61K 2039/57* (2013.01); *A61K 2039/575* (2013.01); *C07K 2319/00* (2013.01); *C07K 2319/21* (2013.01); *Y02A 50/388* (2018.01); *Y02A 50/39* (2018.01); *Y02A 50/466* (2018.01); *Y02A 50/484* (2018.01)

(58) Field of Classification Search
CPC ......... A61K 39/00; A61K 39/02; A61K 39/04
USPC .................. 424/9.1, 9.2, 184.1, 185.1, 234.1
See application file for complete search history.

(56) References Cited

U.S. PATENT DOCUMENTS

| | | |
|---|---|---|
| 4,554,101 A | 11/1985 | Hopp |
| 5,399,494 A | 3/1995 | Kaper et al. |
| 5,693,476 A | 12/1997 | Scheller |
| 6,130,082 A | 10/2000 | Majarian et al. |
| 7,404,963 B2 | 7/2008 | Sotomayor et al. |
| 7,638,485 B2 | 12/2009 | Gudkov |
| 7,794,731 B2 | 9/2010 | Mizel et al. |
| 8,007,812 B2 | 8/2011 | Gudkov et al. |
| 8,106,005 B2 | 1/2012 | Gudkov |
| 8,287,882 B2 | 10/2012 | Gudkov et al. |
| 8,324,163 B2 | 12/2012 | Gudkov et al. |
| 8,580,321 B2 | 11/2013 | Gudkov et al. |
| 2002/0009747 A1 | 1/2002 | Miller et al. |
| 2003/0044429 A1 | 3/2003 | Aderem et al. |
| 2005/0147627 A1 | 7/2005 | Aderem et al. |
| 2005/0266391 A1 | 12/2005 | Bennett et al. |
| 2006/0275255 A1 | 12/2006 | Gudkov |
| 2007/0202551 A1 | 8/2007 | Gudkov |
| 2007/0269406 A1 | 11/2007 | Ichim |
| 2008/0124361 A1 | 5/2008 | Mizel et al. |
| 2008/0182797 A1 | 7/2008 | Nudler et al. |
| 2009/0011982 A1 | 1/2009 | Gudkov et al. |
| 2009/0081157 A1 | 3/2009 | Kornbluth et al. |
| 2009/0123467 A1 | 5/2009 | Bedi et al. |
| 2009/0175880 A1 | 7/2009 | Keler et al. |
| 2009/0246303 A1 | 10/2009 | Gudkov et al. |
| 2010/0056454 A1 | 3/2010 | Gudkov |
| 2011/0206699 A1* | 8/2011 | Hossain ................. A61K 35/28 424/172.1 |

(Continued)

FOREIGN PATENT DOCUMENTS

| | | |
|---|---|---|
| WO | 1992005816 | 4/1992 |
| WO | 1993018150 | 9/1993 |

(Continued)

OTHER PUBLICATIONS

Pashenkov et al. "Phase II trial of a toll-like receptor 9-activating oligonucleotide in patients with metastic melanoma" J Clin Oncol 24: 5716-5724 2006.

(Continued)

*Primary Examiner* — Rodney P Swartz
(74) *Attorney, Agent, or Firm* — Morgan, Lewis & Bockius LLP

(57) ABSTRACT

The present invention relates to, in part, compositions comprising improved flagellin derived constructs and methods of using for vaccination, including adjuvants comprising flagellin-based agents.

15 Claims, 18 Drawing Sheets
Specification includes a Sequence Listing.

(56) References Cited

U.S. PATENT DOCUMENTS

| | | |
|---|---|---|
| 2011/0319595 A1 | 12/2011 | Gudkov et al. |
| 2012/0208871 A1* | 8/2012 | Gudkov .......... A61K 31/59 514/44 R |
| 2013/0004515 A1 | 1/2013 | Gudkov et al. |
| 2013/0324462 A1 | 12/2013 | Gudkov et al. |

FOREIGN PATENT DOCUMENTS

| | | |
|---|---|---|
| WO | 1999029312 | 6/1999 |
| WO | 2001040280 | 6/2001 |
| WO | 2001055210 | 8/2001 |
| WO | 2002044363 | 6/2002 |
| WO | 2003027251 | 4/2003 |
| WO | 2003028659 | 4/2003 |
| WO | 2004086039 | 10/2004 |
| WO | 2005056041 | 6/2005 |
| WO | 2005056042 | 6/2005 |
| WO | 2005056054 | 6/2005 |
| WO | 2005056055 | 6/2005 |
| WO | 2005057218 | 6/2005 |
| WO | 2006066214 | 6/2006 |
| WO | 2006069198 | 6/2006 |
| WO | 2007030581 | 3/2007 |
| WO | 2008157473 | 12/2008 |
| WO | 2009102818 | 8/2009 |
| WO | 2010040096 A2 | 4/2010 |
| WO | 2010133885 | 11/2010 |
| WO | 2011027222 | 3/2011 |
| WO | 2011044246 | 4/2011 |

OTHER PUBLICATIONS

Patchen M. L. "Amifostine plus granulocyte colony-stimulating factor therapy enhances recovery from supralethal radiation exposures: preclinical experience in animals models" European Journal of Cancer 31A(1):S17-S21 (1995).
Rensing-Ehl et al., Local Fas/APO-1 )(CD95) Ligand-Mediated Tumor Cell Killing in vivo, Eur J Immunol, 1995, vol. 25, pp. 2253-2258.
Rhee et al. "Toll-like receptor 5 engagement modulates tumor development and growth in a mouse xenograft model of human colon cancer" Gastroenterology Aug. 2008; 135(2): 518-528.
Samatey F. A. et al. "Structure of the bacterial flagellar protofilament and implications for a switch for supercoiling" Nature 410:331-337 (2001).
Satyamitra M. et al. "In vivo postirradiation protection by a vitamin E analog a-TMG" Radiation Research 160(6):655-661 (2003).
Schmidt et al. "Intratumoural injection of the toll-like receptor-2/6 agonist 'macrophage-activating lipopeptide-2' in patients with pancreatic carcinoma: a phase I/II trial" Brit J Cancer 97: 598-604 2007.
Sebastiani G. et. al. "Cloning and characterization of the murine Toll-like Receptor 5 (Tlr5) gene: sequence and mRNA expression studies in *Salmonella*-susceptible MOLF/Ei mice" Genomics 64(3):230-240 (2000).
Seed T. et al. "New strategies for the prevention of radiation injury: possible implications for countering radiation hazards of long-term space travel" Journal of Radiation Research 43:S239-S244 (2002).
Selander R. K. et al. "Molecular evolutionary genetics of the cattle-adapted serovar *Salmonella dublin*" Journal of Bacteriology 174(11):3587-3592 (1992).
Service R. F. "Tumor-Killer Made; How Does It Work?" Science 274:2009 (1996).
Sfondrini et al. "Antitumor Activity of the TLR-5 Ligand Flagellin in Mouse Models of Cancer" The Journal of Immunology 2006 176:6624-6630.
Smith K. D. et al. "Toll-like receptor 5 recognizes a conserved site on flagellin required for protofilament formation and bacterial motility" Nature Immunology 4(12):1247-1253 (2003).
Song et al. "Flagellin promotes the proliferation of gastric cancers via the Toll-like receptor 5" Int J Mol Med 28:115-119 2011.

Spadaro J. A. et al. "Radioprotectant combinations spare radiation-induced damage to the physis more than fractionation alone" Int. J. Radiat. Biol. 81(10):759-765 (2005) Abstract.
Sredni B. et al. "The immunomodulator AS101 administered orally as a chemoprotective and radioprotective agent" Int. J. Immunopharmacol. 14(4):613-619 (1992).
Streeter P. R. et al. "Activation of the G-CSF and Flt-3 receptors protects hematopoietic stem cells from lethal irradiation" Experimental Hematology 31(11):1119-1125 (2003).
Symon Z. et al. "Selective radioprotection of hepatocytes by systemic and portal vein infusions of amifostine in a rat liver tumor model" Int. J. Radiation Oncology Biol. Phys. 50(2):473-478 (2001).
Tallant T. et al. "Flagellin acting via TLR5 is the major activator of key signaling pathways leading to NF-KB and proinflammatory gene program activation in intestinal epithelial cells" BMC Microbiology 4(1):33 (2004).
Timmer et al. "Fas receptor-mediated apoptosis: a clinical application?" J Pathol 196: 125-134 2002.
Trauth et al. "Monoclonal antibody-mediated tumor regression by induction of apoptosis" Science 245: 301-305 1989.
Tsujimoto H. et al. "Flagellin enhances NK cell proliferation and activation directly and through dendritic cell- NK cell interactions" Journal of Leukocyte Biology 78(4):888-897 (2005).
Vasquez R. J. et al. "Nanomolar concentrations of nocodazole alter microtubule dynamic instability in vivo and in ultra" Molecular Biology of the Cell 8(6):973-985 (1997).
Vijay-Kumar et al. "Flagellin Treatment Protects against Chemicals Bacteria Viruses and Radiation" The Journal of Immunology 2008 180:8280-8285.
Waddick K. G. et al. "In vitro and in vivo antileukemic activity of B43-pokeweed antiviral protein against radiation-resistant human B-cell precursor leukemia cells" Blood 86(11):4228-4233 (1995).
Watson A. J. et al. "Lessons from genetically engineered animal models. VII. Apoptosis in intestinal epithelium: lessons from transgenic and knockout mice" Am. J. Physiol. Gastrointest. Liver Physiol. 278(1):G1-G5 (2000).
Wheeler C. M. "Preventative vaccines for cervial cancer" Salud Publica de Mexico 39(4) (1997) 9 pages.
Whitnall M. H. et al. "In vivo radioprotection by 5-androstenediol: stimulation of the innate immune system" Radiation Research 156(3):283-293 (2001).
Wolska et al. "Toll-like receptors and their role in carcinogensis and anti-tumor treatment" Cell Mol Biol Letters 14:248-272 2009.
Wong G. H. W. "Protective roles of cytokines against radiation: induction of mitochondrial MnSOD" Biochimica et Bioophysica Acta 1271:205-209 (1995).
Yang et al. "Antigen replacement of domains D2 and D3 in flagellin promotes mucosal IgA production and attenuates flagellin-induced inflammatory response after intranasal immunization" Human Vaccines and Immunotherap 9:5 1084-1092 2013.
Coffman et al., "Vaccine Adjuvants: Putting Innate Immunity to Work," Immunity, 2010, vol. 33, No. 4, pp. 492-503.
International Search Report and Written Opinion, Application No. PCT/US2015/042887, dated: Dec. 3, 2015, 9 pages.
U.S. Appl. No. 13/979,104, U.S. Pat. No. 9,376,473, filed Feb. 3, 2014.
U.S. Appl. No. 15/631,427, filed Jun. 23, 2017.
U.S. Appl. No. 15/329,870, filed Jan. 27, 2017.
U.S. Appl. No. 11/722,682, U.S. Pat. No. 8,007,812, filed May 2, 2008.
U.S. Appl. No. 13/110,704, U.S. Pat. No. 8,932,609, filed May 18, 2011.
U.S. Appl. No. 13/110,720, U.S. Pat. No. 8,287,882, filed May 18, 2011.
U.S. Appl. No. 14/284,354, U.S. Pat. No. 8,871,215, filed May 21, 2014.
U.S. Appl. No. 14/559,669, U.S. Pat. No. 9,139,623, filed Dec. 3, 2014.
U.S. Appl. No. 14/828,111, U.S. Pat. No. 9,228,000, filed Aug. 17, 2015.
U.S. Appl. No. 14/949,492, U.S. Pat. No. 9,457,061, filed Nov. 23, 2015.
U.S. Appl. No. 15/254,695, filed Sep. 1, 2016.

(56) References Cited

OTHER PUBLICATIONS

U.S. Appl. No. 13/530,580, U.S. Pat. No. 8,618,059, filed Jun. 22, 2012.
U.S. Appl. No. 14/088,097, U.S. Pat. No. 9,006,180, filed Nov. 22, 2013.
U.S. Appl. No. 15/519,462, filed Apr. 14, 2017.
U.S. Appl. No. 13/056,973, U.S. Pat. No. 8,324,163, filed Jan. 31, 2011.
Alavanja M. CR. "Biologic damage resulting from exposure to tobacco smoke from radon: implication for preventive interventions" Oncogene 21:7365-7375 (2002).
Andreassen C. N. et al. "Chemical radioprotection: a critical review of amifostine as a cytoprotector in radiotherapy" Seminars in Radiation Oncology 13(1):62-72 (2003).
Androstenediol and Androstenedione Wikipedia (online). URL: < http://en.wikipedia.org/wiki/Androstenediol> [Retrieved from the Internet: Dec. 5, 2006] 4 pages.
Bachmann M. F. et al. "Recall proliferation potential of memory CD8+ T cells and antiviral protection" The Journal of Immunology 175:4677-4685 (2005).
Ben-Yedidia T. et al. "Intranasal administration of peptide vaccine protects human/mouse radiation chimera from influenza infection" International Immunology 11(7):1043-1051 (1998).
Booth D. et. al. "Transforming growth factor-B3 protects murine small intestinal crypt stem cells and animal survival after irradiation possibly by reducing stem-cell cycling" Int. J. Cancer 86(1):53-59 (2000).
Borges H. L. et al. "DNA damage-induced cell death: lessons from the central nervous system" Cell Research 18:17-26 (2008).
Bulinski J. C. et al. "Overexpression of MAP4 inhibits organelle motility and trafficking in vivo" Journal of Cell Sciences 110:3055-3064 (1997).
Burdelya L. G. et al. "An agonist of toll-like receptor 5 has radioprotective activity in mouse and primate models" Science 320:226-230 (2008).
Cai et al. "Activation of toll-like receptor 5 on breast cancer cells by flagellin suppresses cell proliferation and tumor growth" Cancer Res 71 (7): 2466-2475 2011.
Cai et al. "Activation of toll-like receptor 5 on breast cancer cells by flagellin suppresses tumor development and growth" Cancer Res 70: #3819 Apr. 2010.
Carnes B. A. et al. "Mortality of atomic bomb survivors predicted from laboratory animals" Radiation Research 160(2):159-167 (2003) Abstract.
Caron G. et. al. "Direct stimulation of human T cells via TLR5 and TLR7/8: Flagellin and R-848 up-regulate proliferation and IFN-γ production by memory CD4+ T cells" The Journal of Immunology 175(3):1551-1557 (2005).
Dummer et al. "An exploratory study of systemic administration of the toll-like receptor-7 agonist 852A in patients with refractory metastic melanoma" Clin Cancer Res 14(3): 856-864 2008.
Eaves-Pyles T. D. et al. "*Salmonella* flagellin-dependent proinflammatory responses are localized to the conserved amino and carboxyl regions of the protein" The Journal of Immunology 167(12):7009-7016 (2001).
Eaves-Pyles T. et al. "Flagellin a novel mediator of *Salmonella*-induced epithelial activation and systemic inflammation: IKBa degradation induction of nitric oxide synthase induction of proinflammatory mediators and Cardiovascular dysfunction" The Journal of Immunology 166(2):1248-1260 (2001).
Efferson C. L. et al. "Stimulation of human T cells by an influenza A vector expressing a CTL epitope from the HER-2/neu protooncogene results in higher numbers of antigen-specific TCRhi cells than stimulation with peptide. Divergent roles of IL-2 and IL-15" Anti-cancer Research 25:715-724 (2005).
Egan L. J. et al. "IkB-kinase13-dependent NF-k13 activation provides radioprotection to the intestinal epithelium" PNAS 101(8):2452-2457 (2004).

Elewaut D. et al. "NF-KB is a central regulator of the intestinal epithelial cell innate immune response induced by infection with enteroinvasive bacteria" The Journal of Immunology 163:1457-1466 (1999).
Etter et al. "The combination of chemotherapy and intraperitoneal MegaFas ligand improves treatment of ovarian carcinoma" Gynecologic Oncol 107: 14-21 2007.
Foldes G. et al. "Toll-like receptor modulation in cardiovascular disease: a target for intervention?" Expert Opinion on Investigational Drugs 15(8):857-871 (2006).
Fukuzawa N. et al. "A TLR5 agonist inhibits acute renal ischemic failure" The Journal of Immunology 187:3831-3839 (2011).
GenBank databases NCBI Accession No. M84972 Apr. 26, 1993 [online] [retrieved on Sep. 29, 2011] Retrieved from the Internet: <URL: http://www.ncbi.nlm.nih.gov/nuccore/M84972>.
Gewirtz A.T. et. al. "Cutting edge: Bacterial flagellin activates basolaterally expressed TLR5 to induce epithelial proinflammatory gene expression" The Journal of Immunology 167(4):1882-1885 (2001).
Grdina D. J. et al. "Relationships between cytoprotection and mutation prevention by WR-1065" Military Medicine 167(2):51-53 (2002).
Guan K. L. et al. "Eukaryotic proteins expressed in *Escherichia coli*: an improved thrombin cleavage and purification procedure of fusion proteins with glutathione S-transferase" Analytical Biochemistry 192:262-267 (1991).
Gudkov A. V. et al. "The role of p53 in determining sensitivity to radiotherapy" Nat. Rev. Cancer 3:117-129 (2003).
Guicciardi et al., Life and Death by Death Receptors, FASEB J, 2009, vol. 23, No. 6, pp. 1625-1637.
Haimovitz-Friedman A. et al. "Ionizing radiation acts on cellular membranes to generate ceramide and apoptosis" J. Exp. Med. 180:525-535 (1994).
Hall "Physics and Chemisty of Radiation Absorption" Radiobiology for the Radiobiologist pp. 5-15 5th ed. Lippincott Williams and Wilkins Philadelphia PA (2000).
Herbert J. M. et al. "Involvement of u-PA in the anti-apoptotic activity of TGF-beta for vascular smooth muscle cells", FEBS Letters 413(3):401-404 (1997).
Honko A. N. et al. "Effects of flagellin on innate and adaptive immunity" Immunologic Research 33(1):83-101 (2005).
Jung C. W. et al. "Antiproliferative effect of a vitamin D3 analog EB1089 on HL-60 cells by the induction of TGF-beta receptor" Leukemia Research 23(12):1105-1112 (1999).
Kemp G. et al. "Amifostine pretreatment for protection against cyclophosphamide-induced and cisplatininduced toxicities: results of a randomized control in patients with advanced ovarian cancer" Journal of Clinical Oncolouv 14(7):2101-2112 (1996).
Krieg A.M. "Development of TLR9 agonists for cancer therapy" J Clinical Invest 117(5): 1184-1194 2007.
Kyte J. et al. "A simple method for displaying the hydropathic character of a protein" J. Mol. Biol. 157:105-132 (1982).
Lehnert B. E. et al. "A new mechanism for DNA alterations induced by alpha particles such as those emitted by radon and radon progeny" Environmental Health Perspectives 105(5):1095-1101 (1997).
Leigh et al. "A Flagellin-Derived Toll-Like Receptor 5 Agonist Stimulates Cytotoxic Lymphocyte-Mediated Tumor Immunity" Plos One Jan. 2014 vol. 9 Issue 1 pp. 1-10.
Li G. et al. "A special issue on DNA damage responses and genome maintenance" Cell Research 18(1):1-2 (2008).
Li J. et al. "Evolutionary origin and radiation of the avian-adapted non-motile *Salmonellae*" Journal of Medical Microbiology 38(2):129-139 (1993).
McQuiston J. R. et al. "Sequencing and comparative analysis of flagellin genes fliC fljB and flpA from *Salmonella*" Journal of Clinical Microbiology 42(5):1923-1932 (2004).
Melby T. E. et al. "The symmetrical structure of structural maintenance of chromosomes (SMC) and MukB proteins: Long antiparallel coiled coils folded at a flexible hinge" The Journal of Cell Biology 142(6):1595-1604 (1998).
Mercurio F. et al. "NF-kB as a primary regulator of the stress response" Oncogene 18:6163-6171 (1999).

(56) References Cited

OTHER PUBLICATIONS

Murley J. S. et al. "Delayed cytoprotection after enhancement of Sod2 (MnSOD) gene expression in SA-NH mouse sarcoma cells exposed to WR-1065 the active metabolite of amifostine" Radiation Research 158(1):101-109 (2002).

Murley J. S. et al. "Delayed radioprotection by NFKB-mediated induction of Sod2 (MnSOD) in SA—NH tumor cells after exposure to clinically used thiol-containing drugs" Radiation Research 162(5):536-546 (2004).

Mutlu-Turkoglu U. et al. "The effect of selenium and/or vitamin E treatments on radiation-induced intestinal injury in rats" Life Sciences 66(20):1905-1913 (2000).

Neisha A.S. "TLRS in the Gut. II. Flagellin-induced inflammation and antiapoptosis" American Journal of Physiology: Gastrointestinal and Liver Physiology 292(2):G462-G466 (2006).

Newton S. M. C. et al. "Immune response to cholera toxin epitope inserted in *Salmonella flagellin*" Science 244:70-72 (1989).

Offringa "Tumour immunology—Exploitation of the weapon of immune destruction for cancer therapy: taking aim before firing" Current Opinion in Immunology 2005 17:159-162.

Panda D. et al. "Stabilization of microtubule dynamics by estramustine by binding to a novel site in tubulin: A possible mechanistic basis for its antitumor action" Proc. Natl. Acad. Sci. USA 94(20):10560-10564 (1997).

\* cited by examiner

FIG. 1A

```
Q53970   1 MAQVINTNSLSLLTQNNLNKSQSSLSSAIERLSSGLRINSAKDDAAGQAIANRFTSNIKGLTQASRNAND —
P72151   1 MALTVNTNIASLNTQRNLNASSNDLNTSLQRLTTGYRINSAKDDAAGLQISNRLSNQISGLNVATRNAND —
Q5X5M6   1 MAQVINTNVASLTAQRNLGVSGNMMQTSIQRLSSGLRINSAKDDAAGLAISQRMTAQIRGMNQAVRNAND —
Q6VMV6   1 MAQVINTNSLSLLTQNNLNKSQSSLSSAIERLSSGLRINSAKDDAAGQAIANRFTANIKGLTQASRNAND —
P13713   1 MAQVINTNSLSLMAQNNLNKSQSSLGTAIERLSSGLRINSAKDDAAGQAISNRFTANIKGLTQASRNAND —
Q93RK8   1 --MRINHNIAALNTSRQLNAGSNSAAKNMEKLSSGLRINRAGDDAAGLAISEKMRSQIRGLDMASKNAQD —
Q02551   1 --MKVNTNIISLKTQEYLRKNNEGMTQAQRRLASGKRINSSLDDAAGLAVVTRMNVKSTGLDAASKNSSM —
Q09012   1 MAQVINTNSLSLLTQNNLNKSQSSLSSAIERLSSGLRINSAKDDAAGQAIANRFTANIKGLTQASRNAND —
Q8GNT8   1 MAQVINTNSLSLMAQNNLNKSQSALGTAIERLSSGLRINSAKDDAAGQAISNRFTANINGLTQASRNAND —
Q9FAE7   1 MASTINTNVSSLTAQRNLSLSQSSLNTSIQRLSSGLRINSAKDDAAGLAISERFTSQIRGLNQAVRNAND —
Q8ZF76   1 MA-VINTNSLSLLTQNNLNKSQSSLGTAIERLSSGLRINSAKDDAAGQAIANRFTSNIKGLTQASRNAND —
Q7N5J4   1 MAQVINTNSLSLLTQNNLNRSQGTLGSAIERLSSGLRINSAKDDAAGQAIANRFTANVRGLTQAARNAND —
O33578   1 -MTTINTNIGAIAAQANMTKVNDQFNTAMTRLSTGLRINAAKDDAAGMAIGEKMTAQVMGLNQAIRNAQD —
Q56826   1 MASVINTNDSALLAQNNLTKSKGILGSAIERLSSGLRINSQSALGNAIERLSSGMRINSAKDDAAGQAIANRFTANVKGLTQAARNAND —
P42273   1 MAQVINTNYLSLVTQNNLNRSQSALGNAIERLSSGMRINSAKDDAAGQAIANRFTSNINGLTQASRNAND —
O31059   1 --MVVQHNMQAANASRMLGITTGDQSKSTEKLSSGFKINRAADDAAGLSISEKMRKQIRGLDQASTNASD —
Q7VZC2   1 MAAVINTNYLSLVAQNNLNKSQSALGSAIERLSSGLRINSAKDDAAGQAIANRFTANVKGLTQAARNAND —
Q9F4A4   1 --MIINHNMNALNAHRNMMGNIATAGKSMEKLSSGLRINRAGDDAAGLAISEKMRGQIRGLDQASRNAQD —
Q8P9C4   1 MAQVINTNVMSLNAQRNLNTNSSSMALSIQQLSSGKRITSASVDAAGLAISERFTTQIRGLDVASRNAND —
Q82UA3   1 MPQVINTNIASLNAQRNLNVSQNSLSTALQRLSSGLRINSAKDDAAGLAISERMTSQIRGMNQAARNAND —
Q84IC5   1 -GFRINTNGASLNAQVNAGLNSRNLDSSLARLSSGLRINSAADDASGLAIADSLKTQANSLGQAINNAND —
             .: *    ..        .      .::  *.::*   **:**  .   *   **:  ..          
```

C=indicates a conserved amino acid important for TLR5 activity

FIG. 1A (continued)

```
Q53970  71  GISIAQTTEGALNEINNNLQRVRELSVQATNGTNSDSDLKSIQDEIQQRLEEIDRVSNQTQFNGVKVLSQ   —
P72151  71  GISLAQTEGALQOSTNILQRIRDLALQSANGSNSDADRAALQKEVAAQQAELTRISDTTTFGGRKLLDG   —
Q5X5M6  71  GISLAQVAEGAMQETTNILQRMRELSVQAANSTNNSSDRASIQSEISQLKSELERIAQNTEFNGQRILDG
Q6VMV6  71  GISVAQTTEGALNEINNNLQRVRELTVQATNGTNSDSDLSSIQAEITQRLEEIDRVSEQTQFNGVKVLAE
P13713  71  GISLAQTTEGALNEVNDNLQNIRRLTVQAQNGSNSTSDLKSIQDEITQRLSEINRISEQTDFNGVKVLSS
Q93RK8  69  GISLIQTSEGALNETHSILQRMSELATQAANDTNTDSDRSELQKEMDQLASEVTRISTDTEFNTKKLLDG
Q02551  71  GIDLLQTADSALSSMSSILQRMRQLAVQSSNGSFSDEDRKQYTAEFGSLIKELDHVADTTNYNNIKLLDQ
Q09012  69  GISVAQTTEGALSEINNNLQRIRELSVQATNGTNSDSDLNSIQDEITQRLSEIDRVSNQTQFNGVKVLAS
Q8GNT8  71  GISLAQTTEGALNEVNDNLQNIRRLTVQAQNGSNSSSDLQSIQDEITQRLSEIDRISQQTDFNGVKVLSK
Q9FAE7  71  GISLAQTAEGALKSTGDILQRVRELAVQSANATNSSGDRKAIQAEVGQLLSEMDRIAGNTEFNGQKLLDG
Q8ZF76  70  GISIAQTTEGALNEINTNLQRIRELTVQSQNGSNSSDLDSIQDEISLRLAEIDRVSDQTQFNGKKVLAE
Q7N5J4  71  GKNLVDTTEGAHVEVSSMLQRLRELAVQSSNDTNTAADRGSLAAEGKQLIAEINRVAESTTFNGMKVLDG
O33578  70  GISIAQTTEGALNEINNNLQRIRELTVQSENGSNSKSDLDSIQKEVTQRLEEIDRISTQTQFNGIKVLNG
Q56826  71  GISVSQTTEGALNEINNNLQRIRELTVQAKNGTNSNSDINSIQNEVNQRLDEINRVSEQTQFNGVKVLSG
P42273  71  GISAVQTAEGALTEVHSMLQRMNELAVQAANGTNSESDRSSIQDEINQLTTEIDRVAETTKFNETYLLKG
O31059  69  GISIAQTTEGALNEINNNLQRIRELTVQASNGTNSASDIDSIQQEVNQRLEEINRIAEQTDFNGIKVLKS
Q7VZC2  71  GISLIQTAEGALAETHSILQRMRELSVQSANDTNVAVDRTAIQDEINSLTEEINRISGDTEFNTQKLLDG
Q9F4A4  69  GISIAQTAEGAMVEIGNNLQRIRELSVQSANATNSATDREALNSEVKQLTSEIDRVANQTSFNGTKLLNG
Q8P9C4  71  GISLAQTAEGALVEIGNNLQRIRELAVQSANATNSEDDREALQKEVTQLIDEIQRVGEQTSFNGTKLLDG
Q82UA3  71  ANSMLQIADKAMDEQLKILDTIKVKATQAAQDGQTAKTRAMIQGEINKLMEELDNIANTTTYNGKQLLSG
Q84IC5  70                                                                      *

*           *       *         *       *
                                                CCC         C C C                   C

C=indicates a conserved amino acid important for TLR5 activity
```

FIG. 1A (continued)

```
Q53970  141  DNQ-MK---IQVGANDG-------------ETITIDLQ-----------KID-VKSLG----LDGFN
P72151  141  SFGTTS---FQVGSNAY-------------ETIDISLQNASASAIGSYQVG-SNGAGTVASVAGTA
Q5X5M6  141  SFSGAS---FQVGANSN-------------QTINFSIG----------SIK-ASSIGGIATATGTE
Q6VMV6  141  NNE-MK---IQVGANDG-------------ETITINLA-----------KID-AKTLG----LDGFN
P13713  141  DQK-LT---IQVGANDG-------------ETTDIDLK-----------KID-AKQLG----MDTF-
Q93RK8  139  TAQNLT---FQIGANEG-------------QTMSLSIN-----------KMD-SE------SLK
Q02551  139  TATGAATQVSIQASDKAN------------DLINIDLFNAKGLSAGTITLGSGSTVAGYSALSVAD
Q09012  141  DQT-MK---IQVGANDG-------------ETIEIALD-----------KID-AKTLG----LDNFS
Q8GNT8  141  DQK-LT---IQVGANDG-------------ETIDIDLK-----------NIN-AQSLG----LDKFN
Q9FAE7  141  SFGSAT---FQVGANAN-------------QTITATTGNFRTNNY-GAQLT-ASASG--AATSGAS
Q8ZF76  140  NTT-MS---IQVGANDG-------------ETIDINLQ-----------KID-SKSLG----LGSYS
Q7N5J4  141  DSK-MT---IQVGANDN-------------EVIDIDLK-----------KID-KEALN----LGKFT
O33578  140  SFTGKQ---LQIGADSG-------------QTMAINVDSAAATDIGAHKISSASTVVADAALTDTT
Q56826  141  DVTEMK---IQVGANDN-------------ETIGIKLG-----------KIN-SEKLN----LKEFS
P42273  141  EKSKMT---IQVGTNDN-------------EVIEFNLD-----------KID-NDTLG----VASDK
O31059  139  GNGDRT---VRVYAHDAGLVGSLSQNTTKATFQMRKLEIGDSYTIGGTTYKIG-AETVK--EAMTALK
Q7VZC2  141  NATDMTLSIQVGAKDN--------------ETIDIKID-----------RNS-NWNLY---DAVGT
Q9F4A4  139  GFKG-E---FQIGANSN-------------QTVKLDIG-----------NMS-AA------SLG
Q8P9C4  139  DFSGAL---FQVGADAG-------------QTIGINS-----------IVDAN-VDSLG--KANFAAS
Q82UA3  141  SFASQI---FQVGANEG-------------ETIDFTD-----------KANFAAS
Q84IC5  140  SFSNAQ---FQIGDKAN-------------QTVNATIG----------STN-SAKVGQTRFETGAV
```

C=indicates a conserved amino acid important for TLR5 activity

FIG. 1B

```
Q53970  410  PLASIDSALSKVDAVRSSLGAIQNREFDSAITNLGNTVTNLNSARSRIEDADYATEVSNMSKAQILQQAGTSVLAQANQVPQNVLSLLR---
P72151  401  ATAVVDNALAAIDAQRADLGAVQNRFKNTIDNLTNISENATNARSRIKDTDFAAETAALSKNQVLQQAGTAILAQANQLPQAVLSLLR---
Q5X5M6  387  AIKRIDAALNSVNSNRANMGALQNRFESTIANLQNVSDNLSAARSRIQDADYAAEMASLTKNQILQQAGTAMLQANSLPQSVLSLLGR---
Q6VMV6  400  PLETIDKALAKVDNLRSDLGAVQNRFDSAITNLGNTVNNLSSARSRIRDADYATEVSNMSRAQILQQAGTSVLAQANQTTQNVLSLLQG---
P13713  264  PLATLDKALAQVDGLRSSLGAVQNRFDSVINNLNSTVNNLSASQSRIQDADYATEVSNMSRANILQQAGTSVLAQANQSTQNVLSLLR---
Q93RK8  245  ALTTIXTAIDTVSSERAKLGAVQNRLEHTINNLGTSSENLTSABSRIRDVDMASEMMEYTKNNILTQASQAMLAQANQPQQVLQLLKG---
Q02551  481  VIGLADAALTKIMKQRADMGAYYNRLEYTAKGLMGAYENMQASESRIRDADMAREEVVSLTTKQILVQSGTAMLAQANMKPNSVIKLLQQI
Q09012  437  PLSKLDEALAKVDKLRSSLGIGAVQNRFDSAITNLGNTVNDLSSARSRIEDADYATEVSNMSRAQILQQAGTSVLAQANQTTQNVLSLLR---
Q8GNT8  329  PLATLDKALSQVDILRSGLIGAVQNRFDSVINNLNSTVNNLQSTSENMSASRSRIQDADFAAETANLSRSQILQQAGTSVLAQANQLPQGVLSLLK---
Q9FAE7  405  ALKIIDAALSAVNQQRASFGALQSREFTTVNNLQSRFESAVTNLNNTVTNLNNTVNNLSAARSRIEDADYATEVSNMSRAQILQQAGTSVLSQANQVPQTVLSLLN---
Q8ZF76  282  PLETLDDAIKQVDGLRSSLGAIQNRFESAVTNLNNTVTNLNNTVNNLSAARSRIEDADYATEVSNMSRGQILQQAGTAVLAQAMQVPQNVMSLLR---
Q7N5J4  268  PLETLDSALAQVDSLRSSLGAIQNRLESTVNNRLDSTISNLTNISTSVQAAKSQVMDADFAAESTNLARSQILSQASTAMLAQANSSKQNVLSLLRG---
O33578  405  AIGVIDVALSKISQSRSELGAVSNRLDSTINNLNNTVNNLNNTVNNLSAARSRIEDADYAVEVSNMSRGQILQQAGTAVLAQANQVPQTVLSLLR---
Q56826  226  PLDTLDKALAQVDDNRSSLGAIQNRFQSTINNLNNTVNNLSASRSRILDADYATEVSNMSKNQILQQAGTAVLAQANQVPQTVLSLLR---
P42273  280  ALATLDNAISKVDESRSKLGAIQNRLEHSIANLDNVVENTNAAESRIRDTDMADEMVTYSKNNILMQAGQSMLAQANQATQGVLSILQ---
O31059  385  AIDAISADALAKVSAQRSALGSIQNRLESTVANLNNTITNLNTSSENLTAAESRVRDVDMAKEMMAFSKNNILSQAAQAMLGQANQPQGVQLLR---
Q7VZC2  304  ALSKLDDAMKAVDEQRSSLGAIQNRFESTVANLNNTITNLNTSSENLTAAESRVRDVDMAKEMMAFSKNNILSQAAQAMLGQANQPQGVQLLR---
Q9F4A4  326  SIKTINSAIEQVSTQRSKLGAVQNRLEHTINNLNTSSENLTAAESLTASRSRIADTDYAKTTAELTRTQILQQAGTAMLAQAKSVPQNVLSLLQ---
Q8P9C4  312  ALEIVDKALTSVNSSRADMGAVQNRFTSTLANLAATSENLTASRSRIADTDYAKTTAELTRTQILQQAGTAMLAQAKSVPQNVLSLLQ---
Q82UA3  192  ----IDDALKIVNSTRADLGAIQNRFSSAIANLQTSAENLSASRSRIQDADFAAETAALTRAQILQQAGVAMLSQANALPNNVLSLLR---
Q84IC5  403  VMDIADTAIANLDTIRANIGATQNQITSTINNISVTQVNVKAAESQIRDVDFASEKSANYSKANILAQSSYAMAQANAASQNVLRLLQ---
                  *:  :  :    .    :*:            . :       :           :           . .   : ::   :. :*
              CC   C        C                         C                  C
```

C=indicates a conserved amino acid important for TLR5 activity

FIG. 2
A.
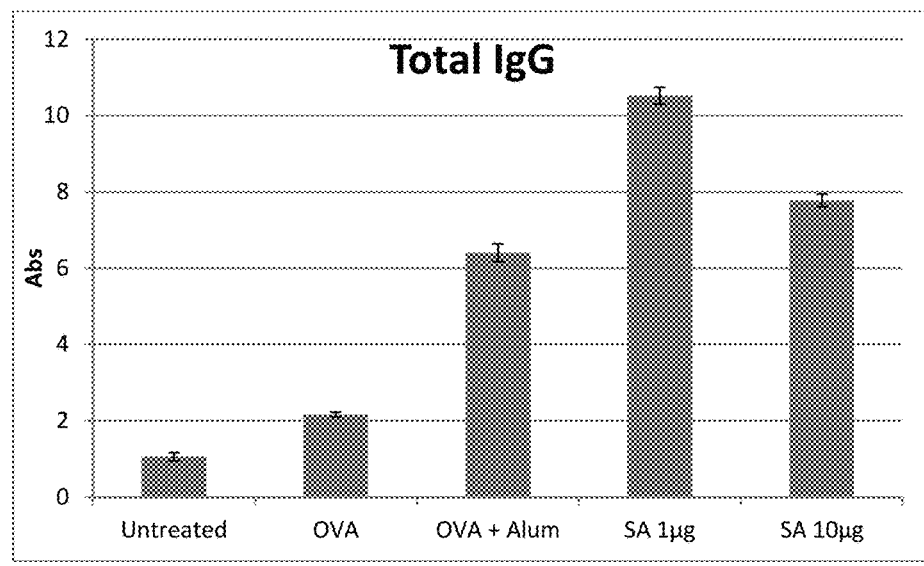
B.
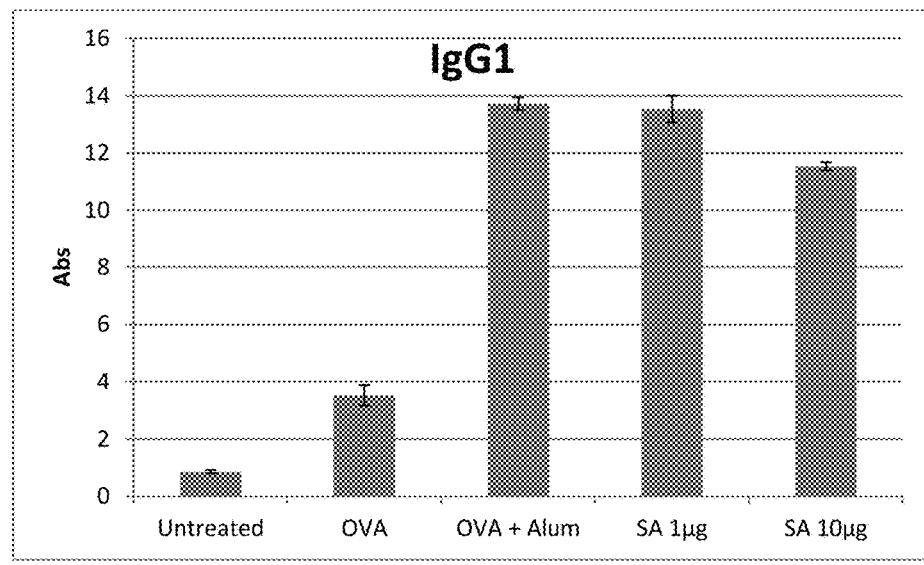

FIG. 2 (CONT.)
C.
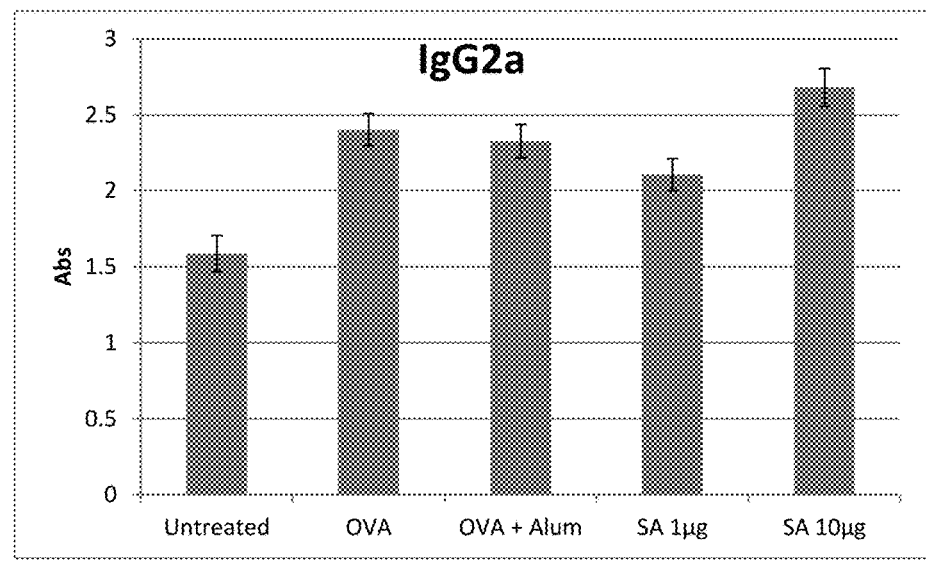
D.
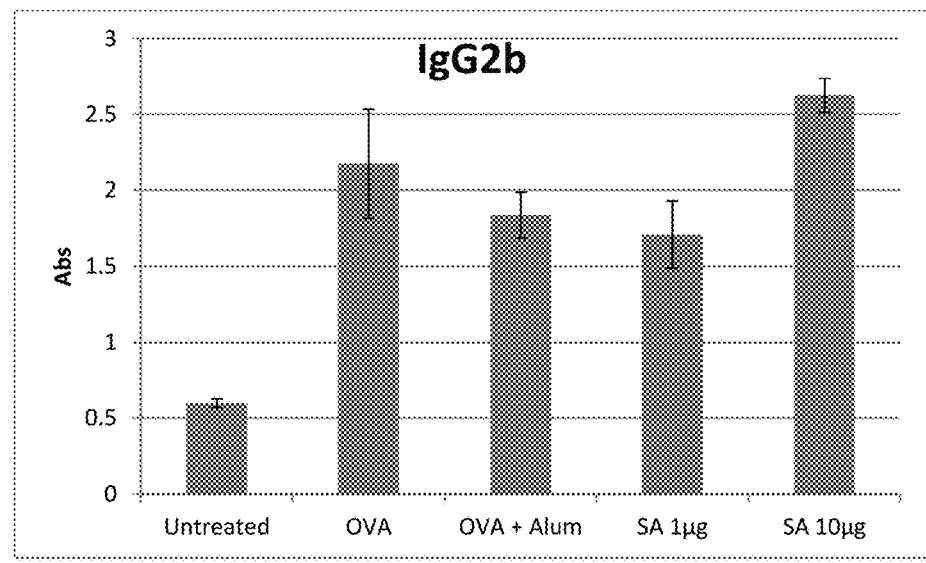

E.

FIG. 3
A.
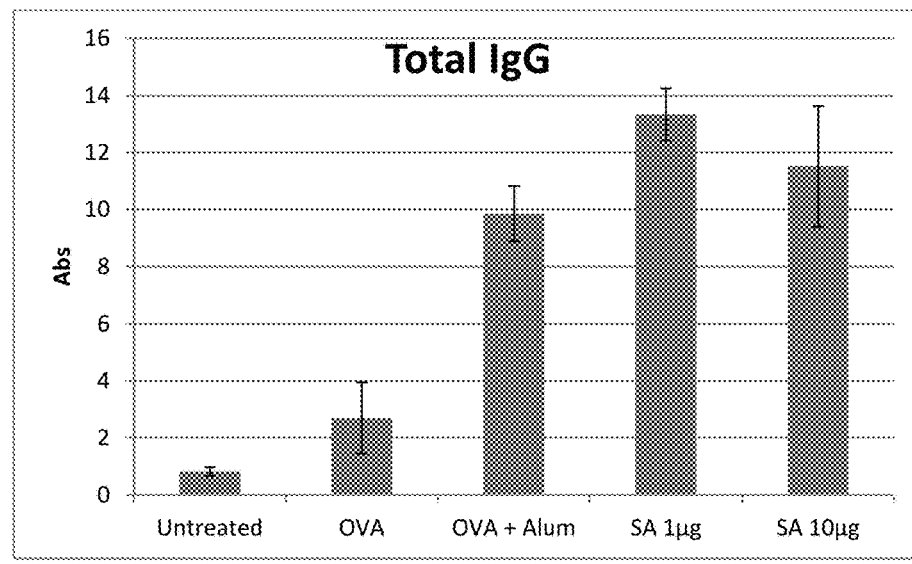
B.
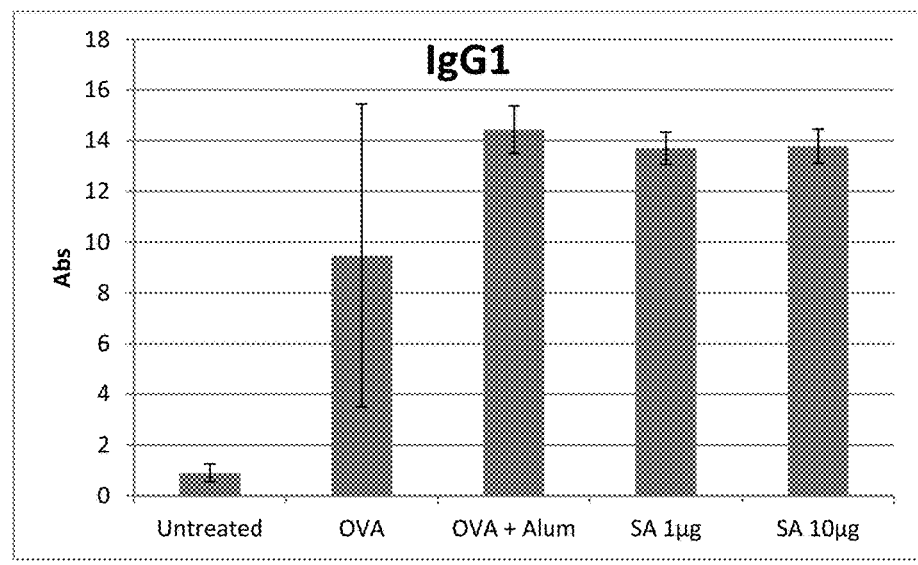

FIG. 3 (CONT.)
C.
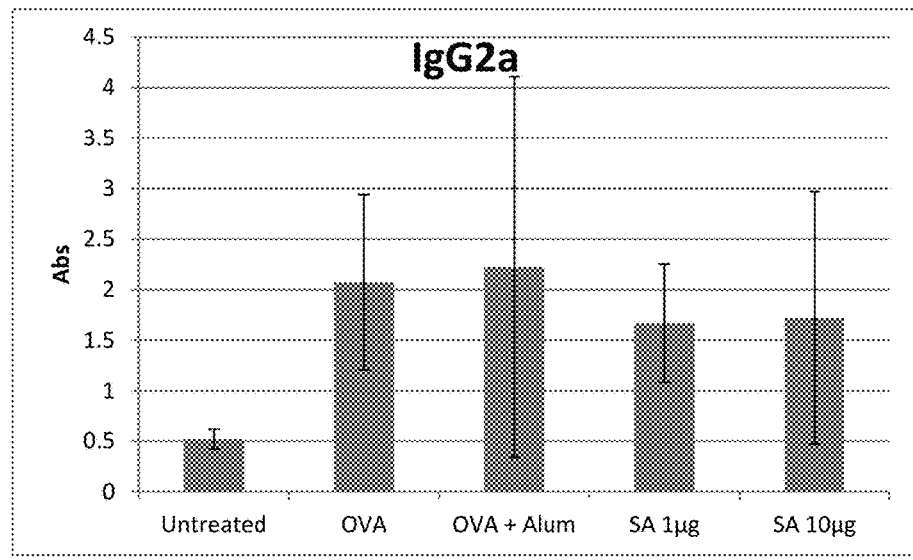
D.
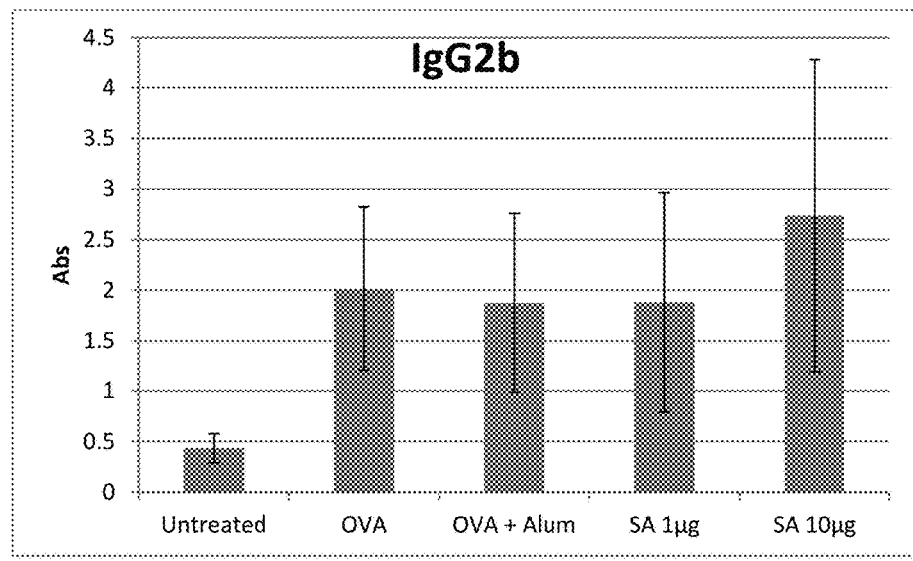

E.

FIG. 4
A.
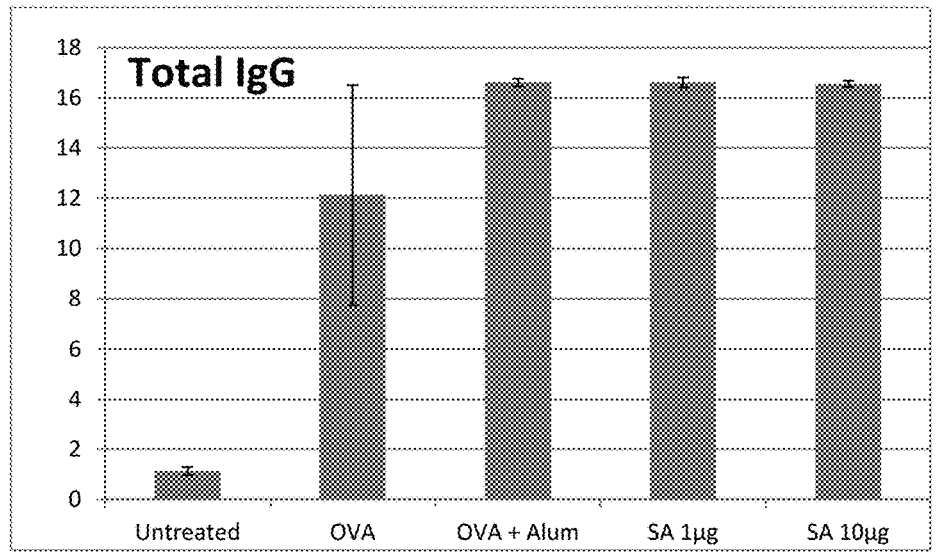
B.
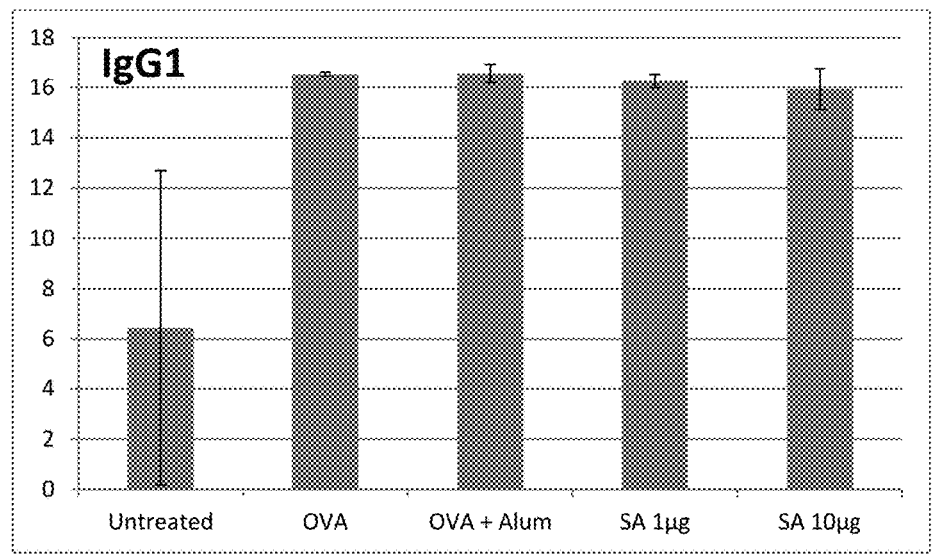

FIG. 4 (CONT.)
C.
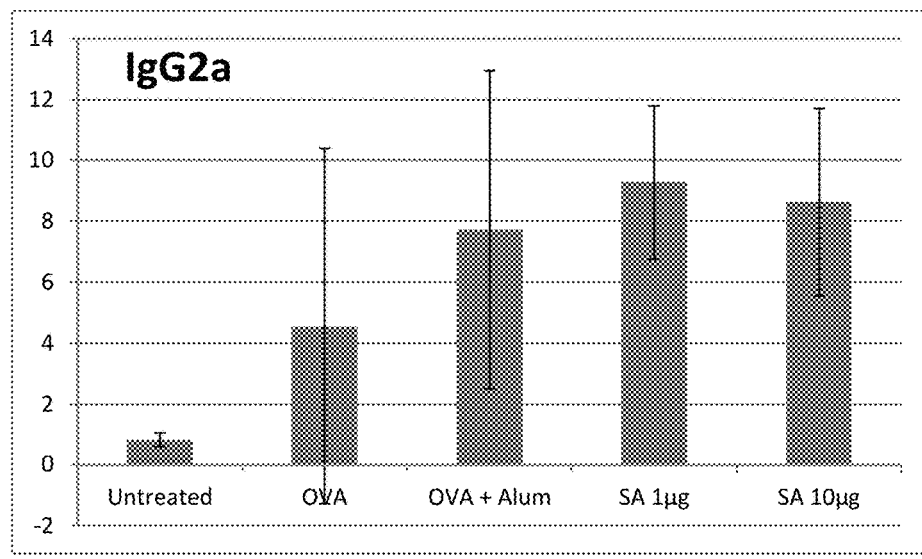
D.
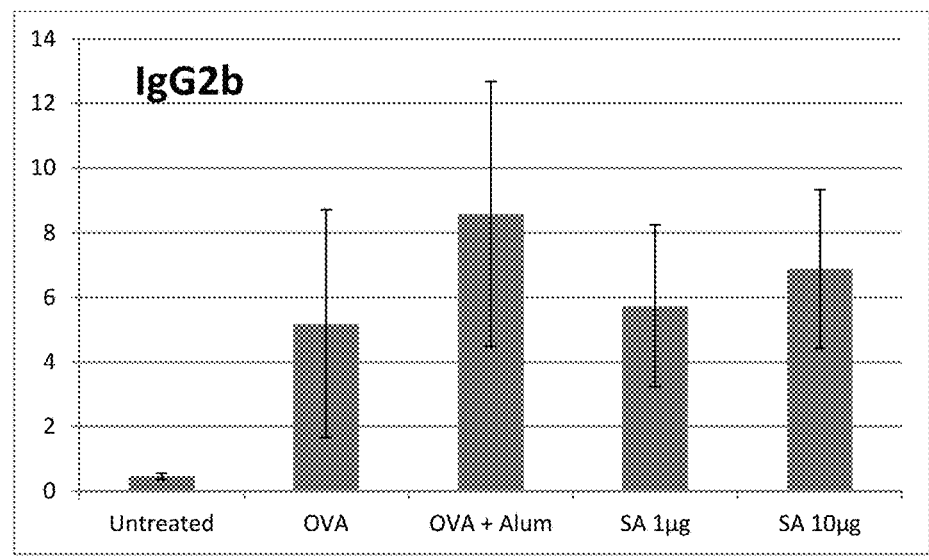

FIG. 11
A.
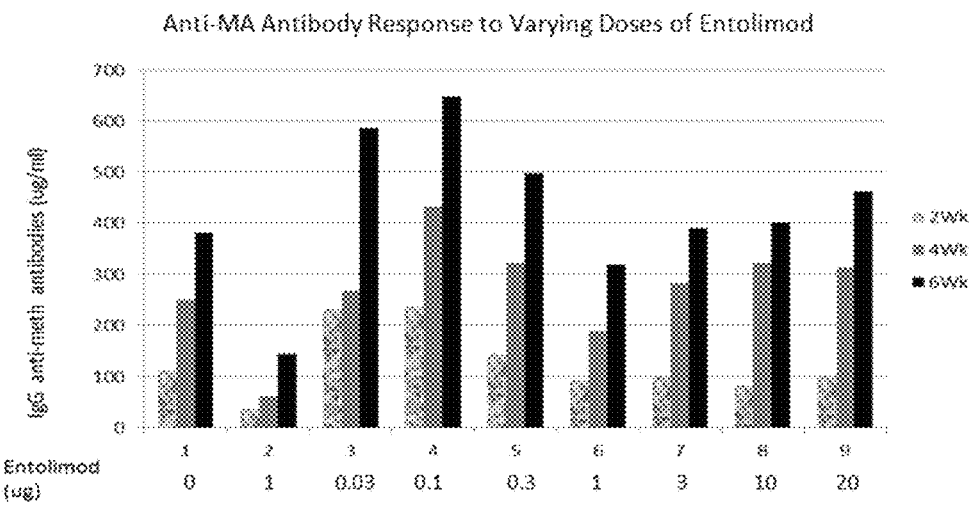
B.
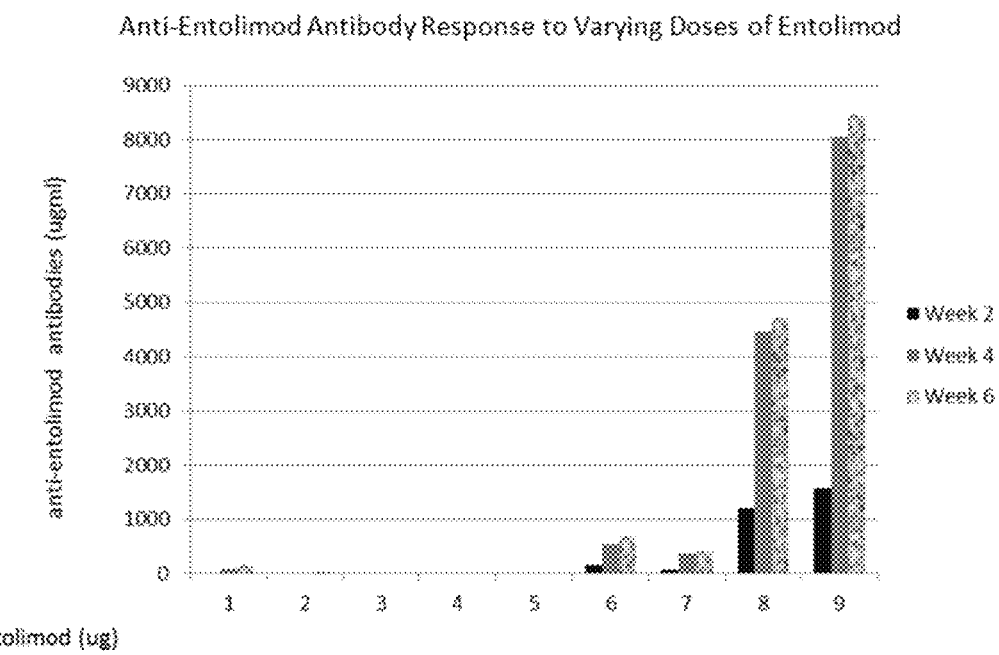

SEQUENCE LISTING

```
<160> NUMBER OF SEQ ID NOS: 294

<210> SEQ ID NO 1
<211> LENGTH: 505
<212> TYPE: PRT
<213> ORGANISM: Salmonella dublin

<400> SEQUENCE: 1

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
```

```
                35                  40                  45
Ala Ile Ala Asn Arg Phe Thr Ser Asn Ile Lys Gly Leu Thr Gln Ala
 50                  55                  60

Ser Arg Asn Ala Asn Asp Gly Ile Ser Ile Ala Gln Thr Thr Glu Gly
 65                  70                  75                  80

Ala Leu Asn Glu Ile Asn Asn Asn Leu Gln Arg Val Arg Glu Leu Ser
                 85                  90                  95

Val Gln Ala Thr Asn Gly Thr Asn Ser Asp Ser Asp Leu Lys Ser Ile
                100                 105                 110

Gln Asp Glu Ile Gln Gln Arg Leu Glu Glu Ile Asp Arg Val Ser Asn
            115                 120                 125

Gln Thr Gln Phe Asn Gly Val Lys Val Leu Ser Gln Asp Asn Gln Met
130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Gly Pro Lys Glu Ala Thr Val Gly Asp Leu Lys Ser Ser Phe Lys Asn
            180                 185                 190

Val Thr Gly Tyr Asp Thr Tyr Ala Ala Gly Ala Asp Lys Tyr Arg Val
            195                 200                 205

Asp Ile Asn Ser Gly Ala Val Val Thr Asp Ala Ala Pro Asp Lys
210                 215                 220

Val Tyr Val Asn Ala Ala Asn Gly Gln Leu Thr Thr Asp Asp Ala Glu
225                 230                 235                 240

Asn Asn Thr Ala Val Asp Leu Phe Lys Thr Thr Lys Ser Thr Ala Gly
                245                 250                 255

Thr Ala Glu Ala Lys Ala Ile Ala Gly Ala Ile Lys Gly Gly Lys Glu
            260                 265                 270

Gly Asp Thr Phe Asp Tyr Lys Gly Val Thr Phe Thr Ile Asp Thr Lys
            275                 280                 285

Thr Gly Asp Asp Gly Asn Gly Lys Val Ser Thr Thr Ile Asn Gly Glu
            290                 295                 300

Lys Val Thr Leu Thr Val Ala Asp Ile Ala Thr Gly Ala Ala Asp Val
305                 310                 315                 320

Asn Ala Ala Thr Leu Gln Ser Ser Lys Asn Val Tyr Thr Ser Val Val
                325                 330                 335

Asn Gly Gln Phe Thr Phe Asp Asp Lys Thr Lys Asn Glu Ser Ala Lys
            340                 345                 350

Leu Ser Asp Leu Glu Ala Asn Asn Ala Val Lys Gly Glu Ser Lys Ile
            355                 360                 365

Thr Val Asn Gly Ala Glu Tyr Thr Ala Asn Ala Thr Gly Asp Lys Ile
            370                 375                 380

Thr Leu Ala Gly Lys Thr Met Phe Ile Asp Lys Thr Ala Ser Gly Val
385                 390                 395                 400

Ser Thr Leu Ile Asn Glu Asp Ala Ala Ala Lys Lys Ser Thr Ala
                405                 410                 415

Asn Pro Leu Ala Ser Ile Asp Ser Ala Leu Ser Lys Val Asp Ala Val
            420                 425                 430

Arg Ser Ser Leu Gly Ala Ile Gln Asn Arg Phe Asp Ser Ala Ile Thr
            435                 440                 445

Asn Leu Gly Asn Thr Val Thr Asn Leu Asn Ser Ala Arg Ser Arg Ile
            450                 455                 460
```

```
Glu Asp Ala Asp Tyr Ala Thr Glu Val Ser Asn Met Ser Lys Ala Gln
465                 470                 475                 480

Ile Leu Gln Gln Ala Gly Thr Ser Val Leu Ala Gln Ala Asn Gln Val
                485                 490                 495

Pro Gln Asn Val Leu Ser Leu Leu Arg
            500                 505

<210> SEQ ID NO 2
<211> LENGTH: 329
<212> TYPE: PRT
<213> ORGANISM: Artificial Sequence
<220> FEATURE:
<223> OTHER INFORMATION: Synthetic sequence

<400> SEQUENCE: 2

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
            35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
            115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Asp Gly Phe Asn Val
            195                 200                 205

Asn Ser Pro Gly Ile Ser Gly Gly Gly Gly Ile Leu Asp Ser Met
    210                 215                 220

Gly Thr Leu Ile Asn Glu Asp Ala Ala Ala Lys Lys Ser Thr Ala
225                 230                 235                 240

Asn Pro Leu Ala Ser Ile Asp Ser Ala Leu Ser Lys Val Asp Ala Val
                245                 250                 255

Arg Ser Ser Leu Gly Ala Ile Gln Asn Arg Phe Asp Ser Ala Ile Thr
            260                 265                 270

Asn Leu Gly Asn Thr Val Thr Asn Leu Asn Ser Ala Arg Ser Arg Ile
            275                 280                 285

Glu Asp Ala Asp Tyr Ala Thr Glu Val Ser Asn Met Ser Lys Ala Gln
    290                 295                 300

Ile Leu Gln Gln Ala Gly Thr Ser Val Leu Ala Gln Ala Asn Gln Val
305                 310                 315                 320
```

Pro Gln Asn Val Leu Ser Leu Leu Arg
                325

<210> SEQ ID NO 3
<211> LENGTH: 21
<212> TYPE: DNA
<213> ORGANISM: Artificial Sequence
<220> FEATURE:
<223> OTHER INFORMATION: Synthetic sequence

<400> SEQUENCE: 3
taatacgact cactataggg g                                              21

<210> SEQ ID NO 4
<211> LENGTH: 20
<212> TYPE: DNA
<213> ORGANISM: Artificial Sequence
<220> FEATURE:
<223> OTHER INFORMATION: Synthetic sequence

<400> SEQUENCE: 4
attgcgcaga ccactgaagg                                                20

<210> SEQ ID NO 5
<211> LENGTH: 6
<212> TYPE: PRT
<213> ORGANISM: Artificial Sequence
<220> FEATURE:
<223> OTHER INFORMATION: Synthetic sequence

<400> SEQUENCE: 5

Leu Val Pro Arg Gly Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic sequence

<400> SEQUENCE: 6

Asp Asp Asp Asp Lys
1               5

<210> SEQ ID NO 7
<211> LENGTH: 13
<212> TYPE: PRT
<213> ORGANISM: Artificial Sequence
<220> FEATURE:
<223> OTHER INFORMATION: Synthetic sequence

<400> SEQUENCE: 7

Ser Ser Gly Leu Arg Ile Asn Ser Ala Lys Asp Asp Ala
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Synthetic sequence

<400> SEQUENCE: 8

Glu Asp Ala Asp Tyr Ala
1               5

```
<210> SEQ ID NO 9
<211> LENGTH: 14
<212> TYPE: PRT
<213> ORGANISM: Artificial Sequence
<220> FEATURE:
<223> OTHER INFORMATION: Synthetic sequence

<400> SEQUENCE: 9

Ala Ala Ser Ala Gly Ala Gly Gln Gly Gly Gly Gly Ser Gly
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic sequence

<400> SEQUENCE: 10

Glu Gly Lys Ser Ser Gly Ser Gly Ser Glu Ser Lys Ser Thr
1               5                   10

<210> SEQ ID NO 11
<211> LENGTH: 22
<212> TYPE: PRT
<213> ORGANISM: Artificial Sequence
<220> FEATURE:
<223> OTHER INFORMATION: Synthetic sequence

<400> SEQUENCE: 11

Gly Gly Gly Arg Thr Ser Ser Ser Ala Ala Ser Ala Gly Ala Gly Gln
1               5                   10                  15

Gly Gly Gly Gly Ser Gly
            20

<210> SEQ ID NO 12
<211> LENGTH: 4
<212> TYPE: PRT
<213> ORGANISM: Artificial Sequence
<220> FEATURE:
<223> OTHER INFORMATION: Synthetic sequence

<400> SEQUENCE: 12

Gly Pro Ser Gly
1

<210> SEQ ID NO 13
<211> LENGTH: 12
<212> TYPE: PRT
<213> ORGANISM: Artificial Sequence
<220> FEATURE:
<223> OTHER INFORMATION: Synthetic sequence

<400> SEQUENCE: 13

Gly Ser Ala Gly Ser Ala Ala Gly Ser Gly Glu Phe
1               5                   10

<210> SEQ ID NO 14
<211> LENGTH: 4
<212> TYPE: PRT
<213> ORGANISM: Artificial Sequence
<220> FEATURE:
<223> OTHER INFORMATION: Synthetic sequence

<400> SEQUENCE: 14
```

```
Gly Ser Pro Gly
1
```

<210> SEQ ID NO 15
<211> LENGTH: 18
<212> TYPE: PRT
<213> ORGANISM: Artificial Sequence
<220> FEATURE:
<223> OTHER INFORMATION: Synthetic sequence

<400> SEQUENCE: 15

```
Lys Glu Ser Gly Ser Val Ser Ser Glu Gln Leu Ala Gln Phe Arg Ser
1               5                  10                  15

Leu Asp
```

<210> SEQ ID NO 16
<211> LENGTH: 16
<212> TYPE: PRT
<213> ORGANISM: Artificial Sequence
<220> FEATURE:
<223> OTHER INFORMATION: Synthetic sequence

<400> SEQUENCE: 16

```
Ser Pro Gly Ile Ser Gly Gly Gly Gly Ile Leu Asp Ser Met Gly
1               5                  10                  15
```

<210> SEQ ID NO 17
<211> LENGTH: 300
<212> TYPE: PRT
<213> ORGANISM: Artificial Sequence
<220> FEATURE:
<223> OTHER INFORMATION: Synthetic sequence

<400> SEQUENCE: 17

```
Met Arg Gly Ser His His His His His His Gly Met Ala Ser Met Thr
1               5                  10                  15

Gly Gly Gln Gln Met Gly Arg Asp Leu Tyr Asp Leu Val Pro Arg Gly
                20                  25                  30

Ser Ala Lys Asp Pro Ser Gly Leu Arg Ile Asn Ser Ala Lys Asp Asp
            35                  40                  45

Ala Ala Gly Gln Ala Ile Ala Asn Arg Phe Thr Ser Asn Ile Lys Gly
        50                  55                  60

Leu Thr Gln Ala Ser Arg Asn Ala Asn Asp Gly Ile Ser Ile Ala Gln
65                  70                  75                  80

Thr Thr Glu Gly Ala Leu Asn Glu Ile Asn Asn Asn Leu Gln Arg Val
                85                  90                  95

Arg Glu Leu Ser Val Gln Ala Thr Asn Gly Thr Asn Ser Asp Ser Asp
                100                 105                 110

Leu Lys Ser Ile Gln Asp Glu Ile Gln Gln Arg Leu Glu Glu Ile Asp
            115                 120                 125

Arg Val Ser Asn Gln Thr Gln Phe Asn Gly Val Lys Val Leu Ser Gln
        130                 135                 140

Asp Asn Gln Met Lys Ile Gln Val Gly Ala Asn Asp Gly Glu Thr Ile
145                 150                 155                 160

Thr Ile Asp Leu Gln Lys Ile Asp Val Lys Ser Leu Gly Leu Asp Gly
                165                 170                 175

Phe Asn Val Asn Ser Pro Gly Ile Ser Gly Gly Gly Gly Ile Leu
                180                 185                 190

Asp Ser Met Gly Thr Leu Ile Asn Glu Asp Ala Ala Ala Ala Lys Lys
            195                 200                 205
```

```
Ser Thr Ala Asn Pro Leu Ala Ser Ile Asp Ser Ala Leu Ser Lys Val
    210                 215                 220

Asp Ala Val Arg Ser Ser Leu Gly Ala Ile Gln Asn Arg Phe Asp Ser
225                 230                 235                 240

Ala Ile Thr Asn Leu Gly Asn Thr Val Thr Asn Leu Asn Ser Ala Arg
                245                 250                 255

Ser Arg Ile Glu Asp Ala Asp Tyr Ala Thr Glu Val Ser Asn Met Ser
            260                 265                 270

Lys Ala Gln Ile Leu Gln Gln Ala Gly Thr Ser Val Leu Ala Gln Ala
        275                 280                 285

Asn Gln Val Pro Gln Asn Val Leu Ser Leu Leu Arg
        290                 295                 300

<210> SEQ ID NO 18
<211> LENGTH: 48
<212> TYPE: DNA
<213> ORGANISM: Artificial Sequence
<220> FEATURE:
<223> OTHER INFORMATION: Synthetic sequence

<400> SEQUENCE: 18
gcagattctg cagcaggctg gttgataatc tggcgcaggc taaccagg            48

<210> SEQ ID NO 19
<211> LENGTH: 60
<212> TYPE: DNA
<213> ORGANISM: Artificial Sequence
<220> FEATURE:
<223> OTHER INFORMATION: Synthetic sequence

<400> SEQUENCE: 19
tctaaagcgc agattctgca gcaggctggt acttccgttc tggcgcaggc taaccaggtt   60

<210> SEQ ID NO 20
<211> LENGTH: 48
<212> TYPE: DNA
<213> ORGANISM: Artificial Sequence
<220> FEATURE:
<223> OTHER INFORMATION: Synthetic sequence

<400> SEQUENCE: 20
cctggttagc ctgcgccaga ttatcaacca gcctgctgca gaatctgc             48

<210> SEQ ID NO 21
<211> LENGTH: 936
<212> TYPE: DNA
<213> ORGANISM: Artificial Sequence
<220> FEATURE:
<223> OTHER INFORMATION: Synthetic sequence

<400> SEQUENCE: 21
taatacgact cactataggg gaattgtgag cggataacaa ttcccctcta gaataatttt   60
gtttaacttt aagaaggaga tatacatatg cggggttctc atcatcatca tcatcatggt  120
atggctagca tgactggtgg acagcaaatg ggtcgggatc tgtacgacct ggttccgcgc  180
ggtagcgcga aggatccgtc tggtctgcgt atcaacagcg cgaaagacga tgcggcaggc  240
caggcgattg ctaaccgctt cacttctaat atcaaaggtc tgactcaggc ttcccgtaac  300
gctaacgacg gcatttctat tgcgcagacc actgaaggtg cgctgaatga aatcaacaac  360
aacctgcagc gtgtgcgtga gttgtctgtt caggccacta cgggactaa ctctgattcc  420
```

```
gatctgaaat ctatccagga tgaaattcag caacgtctgg aagaaatcga tcgcgtttct    480
aatcagactc aatttaacgg tgttaaagtc ctgtctcagg acaaccagat gaaaatccag    540
gttggtgcta acgatggtga aaccattacc atcgatctgc aaaaaattga tgtgaaaagc    600
cttggccttg atgggttcaa tgttaattcc ccgggaattt ccggtggtgg tggtggaatt    660
ctagactcca tgggtacatt aatcaatgaa gacgctgccg cagccaagaa aagtaccgct    720
aacccactgg cttcaattga ttctgcattg tcaaaagtgg acgcagttcg ttcttctctg    780
ggggcaattc aaaaccgttt tgattcagcc attaccaacc ttggcaatac ggtaaccaat    840
ctgaactccg cgcgtagccg tatcgaagat gctgactatg caacggaagt ttctaatatg    900
tctaaagcgc agattctgca gcaggctggt tgataa                              936
```

<210> SEQ ID NO 22
<211> LENGTH: 281
<212> TYPE: PRT
<213> ORGANISM: Artificial Sequence
<220> FEATURE:
<223> OTHER INFORMATION: Synthetic sequence

<400> SEQUENCE: 22

```
Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Ser Gly Leu Arg Ile Asn Ser Ala Lys Asp Asp
        35                  40                  45

Ala Ala Gly Gln Ala Ile Ala Asn Arg Phe Thr Ser Asn Ile Lys Gly
    50                  55                  60

Leu Thr Gln Ala Ser Arg Asn Ala Asn Asp Gly Ile Ser Ile Ala Gln
65                  70                  75                  80

Thr Thr Glu Gly Ala Leu Asn Glu Ile Asn Asn Asn Leu Gln Arg Val
                85                  90                  95

Arg Glu Leu Ser Val Gln Ala Thr Asn Gly Thr Asn Ser Asp Ser Asp
            100                 105                 110

Leu Lys Ser Ile Gln Asp Glu Ile Gln Gln Arg Leu Glu Glu Ile Asp
        115                 120                 125

Arg Val Ser Asn Gln Thr Gln Phe Asn Gly Val Lys Val Leu Ser Gln
    130                 135                 140

Asp Asn Gln Met Lys Ile Gln Val Gly Ala Asn Asp Gly Glu Thr Ile
145                 150                 155                 160

Thr Ile Asp Leu Gln Lys Ile Asp Val Lys Ser Leu Gly Leu Asp Gly
                165                 170                 175

Phe Asn Val Asn Ser Pro Gly Ile Ser Gly Gly Gly Gly Ile Leu
            180                 185                 190

Asp Ser Met Gly Thr Leu Ile Asn Glu Asp Ala Ala Ala Ala Lys Lys
        195                 200                 205

Ser Thr Ala Asn Pro Leu Ala Ser Ile Asp Ser Ala Leu Ser Lys Val
    210                 215                 220

Asp Ala Val Arg Ser Ser Leu Gly Ala Ile Gln Asn Arg Phe Asp Ser
225                 230                 235                 240

Ala Ile Thr Asn Leu Gly Asn Thr Val Thr Asn Leu Asn Ser Ala Arg
                245                 250                 255

Ser Arg Ile Glu Asp Ala Asp Tyr Ala Thr Glu Val Ser Asn Met Ser
            260                 265                 270
```

```
Lys Ala Gln Ile Leu Gln Gln Ala Gly
        275                 280
```

<210> SEQ ID NO 23
<211> LENGTH: 329
<212> TYPE: PRT
<213> ORGANISM: Artificial Sequence
<220> FEATURE:
<223> OTHER INFORMATION: Synthetic sequence

<400> SEQUENCE: 23

```
Met Ala Gln Val Ile Asn Thr Asn Ser Leu Ser Leu Thr Gln Asn
1               5                   10                  15

Asn Leu Asn Lys Ser Gln Ser Ser Leu Ser Ser Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ser Asn Ile Lys Gly Leu Thr Gln Ala
        50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                    85                  90                  95

Val Gln Ala Thr Asn Gly Thr Asn Ser Asp Ser Asp Leu Lys Ser Ile
                100                 105                 110

Gln Asp Glu Ile Gln Gln Arg Leu Glu Glu Ile Asp Arg Val Ser Asn
            115                 120                 125

Gln Thr Gln Phe Asn Gly Val Lys Val Leu Ser Gln Asp Asn Gln Met
        130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                    165                 170                 175

Ser Pro Gly Ile Ser Gly Gly Gly Gly Ile Leu Asp Ser Met Gly
                180                 185                 190

Thr Leu Ile Asn Glu Asp Ala Ala Ala Lys Lys Ser Thr Ala Asn
            195                 200                 205

Pro Leu Ala Ser Ile Asp Ser Ala Leu Ser Lys Val Asp Ala Val Arg
        210                 215                 220

Ser Ser Leu Gly Ala Ile Gln Asn Arg Phe Asp Ser Ala Ile Thr Asn
225                 230                 235                 240

Leu Gly Asn Thr Val Thr Asn Leu Asn Ser Ala Arg Ser Arg Ile Glu
                    245                 250                 255

Asp Ala Asp Tyr Ala Thr Glu Val Ser Asn Met Ser Lys Ala Gln Ile
                260                 265                 270

Leu Gln Gln Ala Gly Thr Ser Val Leu Ala Gln Ala Asn Gln Val Pro
            275                 280                 285

Gln Asn Val Leu Ser Leu Leu Val Pro Arg Gly Ser His His His
        290                 295                 300

His His Gly Met Ala Ser Met Thr Gly Gly Gln Gln Met Gly Arg Asp
305                 310                 315                 320

Leu Tyr Asp Asp Asp Asp Lys Asp Pro
                325
```

<210> SEQ ID NO 24
<211> LENGTH: 1005

<212> TYPE: DNA
<213> ORGANISM: Artificial Sequence
<220> FEATURE:
<223> OTHER INFORMATION: Synthetic sequence

<400> SEQUENCE: 24

```
atggcacaag tcattaatac aaacagcctg tcgctgttga cccagaataa cctgaacaaa        60
tctcagtcct cactgagttc cgctattgag cgtctgtcct ctggtctgcg tatcaacagc       120
gcgaaagacg atgcggcagg ccaggcgatt gctaaccgct tcacttctaa tatcaaaggt       180
ctgactcagg cttcccgtaa cgctaacgac ggcatttcta ttgcgcagac cactgaaggt       240
gcgctgaatg aaatcaacaa caacctgcag cgtgtgcgtg agttgtctgt tcaggccact       300
aacgggacta actctgattc cgatctgaaa tctatccagg atgaaattca gcaacgtctg       360
gaagaaatcg atcgcgtttc taatcagact caatttaacg gtgttaaagt cctgtctcag       420
gacaaccaga tgaaaatcca ggttggtgct aacgatggtg aaaccattac catcgatctg       480
caaaaaattg atgtgaaaag ccttggcctt gatgggttca atgttaattc cccgggaatt       540
tccggtggtg gtggtggaat tctagactcc atgggtacat taatcaatga agacgctgcc       600
gcagccaaga aaagtaccgc taacccactg gcttcaattg attctgcatt gtcaaaagtg       660
gacgcagttc gttcttctct gggggcaatt caaaaccgtt ttgattcagc cattaccaac       720
cttggcaata cggtaaccaa tctgaactcc gcgcgtagcc gtatcgaaga tgctgactat       780
gcaacggaag tttctaatat gtctaaagcg cagattctgc agcaggctgg tacttccgtt       840
ctggcgcagg ctaaccaggt tccgcaaaac gtcctctctt tactggttcc gcggggttct       900
catcatcatc atcatcatgg tatggctagc atgactggtg gacagcaaat gggtcgggat       960
ctgtacgacg atgacgataa ggatccgtaa gtcgacaagc ttgcg                      1005
```

<210> SEQ ID NO 25
<211> LENGTH: 31
<212> TYPE: DNA
<213> ORGANISM: Artificial Sequence
<220> FEATURE:
<223> OTHER INFORMATION: Synthetic sequence

<400> SEQUENCE: 25

```
cgaaagacca tatggcaggc caggcgattg c                                       31
```

<210> SEQ ID NO 26
<211> LENGTH: 33
<212> TYPE: DNA
<213> ORGANISM: Artificial Sequence
<220> FEATURE:
<223> OTHER INFORMATION: Synthetic sequence

<400> SEQUENCE: 26

```
cgcaagcttg tcgacttacg gatccttatc gtc                                     33
```

<210> SEQ ID NO 27
<211> LENGTH: 952
<212> TYPE: DNA
<213> ORGANISM: Artificial Sequence
<220> FEATURE:
<223> OTHER INFORMATION: Synthetic sequence

<400> SEQUENCE: 27

```
taatacgact cactataggg gaattgtgag cggataacaa ttcccctcta gaaataattt        60
tgtttaactt taagaaggag atatacatat ggcaggccag gcgattgcta accgcttcac       120
```

```
ttctaatatc aaaggtctga ctcaggcttc ccgtaacgct aacgacggca tttctattgc    180
gcagaccact gaaggtgcgc tgaatgaaat caacaacaac ctgcagcgtg tgcgtgagtt    240
gtctgttcag gccactaacg ggactaactc tgattccgat ctgaaatcta tccaggatga    300
aattcagcaa cgtctggaag aaatcgatcg cgtttctaat cagactcaat taacggtgt     360 taaagtcctg tctcaggaca accagatgaa aatccaggtt ggtgctaacg atggtgaaac    420
cattaccatc gatctgcaaa aaattgatgt gaaaagcctt ggccttgatg ggttcaatgt    480
taattccccg ggaatttccg gtggtggtgg tggaattcta gactccatgg gtacattaat    540
caatgaagac gctgccgcag ccaagaaaag taccgctaac ccactggctt caattgattc    600
tgcattgtca aaagtggacg cagttcgttc ttctctgggg gcaattcaaa accgctttga    660
ttcagccatt accaaccttg gcaatacggt aaccaatctg aactccgcgc gtagccgtat    720
cgaagatgct gactatgcaa cggaagtttc taatatgtct aaagcgcaga ttctgcagca    780
ggctggtact tccgttctgg cgcaggctaa ccaggttccg caaaacgtcc tctctttact    840
ggttccgcgg ggttctcatc atcatcatca tcatggtatg gctagcatga ctggtggaca    900
gcaaatgggt cgggatctgt acgacgatga cgataaggat ccgtaagtcg ac            952
```

<210> SEQ ID NO 28
<211> LENGTH: 285
<212> TYPE: PRT
<213> ORGANISM: Artificial Sequence
<220> FEATURE:
<223> OTHER INFORMATION: Synthetic sequence

<400> SEQUENCE: 28

```
Met Ala Gly Gln Ala Ile Ala Asn Arg Phe Thr Ser Asn Ile Lys Gly
1               5                   10                  15

Leu Thr Gln Ala Ser Arg Asn Ala Asn Asp Gly Ile Ser Ile Ala Gln
            20                  25                  30

Thr Thr Glu Gly Ala Leu Asn Glu Ile Asn Asn Asn Leu Gln Arg Val
        35                  40                  45

Arg Glu Leu Ser Val Gln Ala Thr Asn Gly Thr Asn Ser Asp Ser Asp
    50                  55                  60

Leu Lys Ser Ile Gln Asp Glu Ile Gln Gln Arg Leu Glu Glu Ile Asp
65                  70                  75                  80

Arg Val Ser Asn Gln Thr Gln Phe Asn Gly Val Lys Val Leu Ser Gln
                85                  90                  95

Asp Asn Gln Met Lys Ile Gln Val Gly Ala Asn Asp Gly Glu Thr Ile
            100                 105                 110

Thr Ile Asp Leu Gln Lys Ile Asp Val Lys Ser Leu Gly Leu Asp Gly
        115                 120                 125

Phe Asn Val Asn Ser Pro Gly Ile Ser Gly Gly Gly Gly Ile Leu
    130                 135                 140

Asp Ser Met Gly Thr Leu Ile Asn Glu Asp Ala Ala Ala Ala Lys Lys
145                 150                 155                 160

Ser Thr Ala Asn Pro Leu Ala Ser Ile Asp Ser Ala Leu Ser Lys Val
                165                 170                 175

Asp Ala Val Arg Ser Ser Leu Gly Ala Ile Gln Asn Arg Phe Asp Ser
            180                 185                 190

Ala Ile Thr Asn Leu Gly Asn Thr Val Thr Asn Leu Asn Ser Ala Arg
        195                 200                 205

Ser Arg Ile Glu Asp Ala Asp Tyr Ala Thr Glu Val Ser Asn Met Ser
    210                 215                 220
```

```
Lys Ala Gln Ile Leu Gln Gln Ala Gly Thr Ser Val Leu Ala Gln Ala
225                 230                 235                 240

Asn Gln Val Pro Gln Asn Val Leu Ser Leu Leu Val Pro Arg Gly Ser
            245                 250                 255

His His His His His His Gly Met Ala Ser Met Thr Gly Gly Gln Gln
        260                 265                 270

Met Gly Arg Asp Leu Tyr Asp Asp Asp Lys Asp Pro
    275                 280                 285
```

<210> SEQ ID NO 29
<211> LENGTH: 765
<212> TYPE: DNA
<213> ORGANISM: Artificial Sequence
<220> FEATURE:
<223> OTHER INFORMATION: Synthetic sequence

<400> SEQUENCE: 29

```
atgagcgggt tacggatcaa cagcgcgaaa gacgatgcgg caggccaggc gattgctaac      60
cgcttcactt ctaatatcaa aggtctgact caggcttccc gtaacgctaa cgacggcatt     120
tctattgcgc agaccactga aggtgcgctg aatgaaatca acaacaacct gcagcgtgtg     180
cgtgagttgt ctgttcaggc cactaacggg actaactctg attccgatct gaaatctatc     240
ggaccatcag gtcaggatga aattcagcaa cgtctggaag aaatcgatcg cgtttctaat     300
cagactcaat ttaacggtgt taaagtcctg tctcaggaca accagatgaa atccaggtt      360
ggtgctaacg atggtgaaac cattaccatc gatctgcaaa aaattgatgt gaaaagcctt     420
ggccttgatg ggttcaatgt taattccccg ggaagtaccg ctaacccact ggcttcaatt     480
gattctgcat tgtcaaaagt ggacgcagtt cgttcttctc tgggggcaat tcaaaaccgc     540
tttgattcag ccattaccaa ccttggcaat acggtaacca atctgaactc cgcgcgtagc     600
cgtatcgaag atgctgacta tgcaacggaa gtttctaata tgtctaaagc gcagattctg     660
cagcaggctg gtacttccgt tctggcgcag gctaaccagg ttccgcaaaa cgtcctctct     720
ttactggttc cgcggggttc tcatcatcat catcatcatg gttaa                     765
```

<210> SEQ ID NO 30
<211> LENGTH: 254
<212> TYPE: PRT
<213> ORGANISM: Artificial Sequence
<220> FEATURE:
<223> OTHER INFORMATION: Synthetic sequence

<400> SEQUENCE: 30

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gly Pro Ser Gly Gln Asp Glu Ile Gln Gln Arg Leu Glu Glu Ile Asp
                85                  90                  95

Arg Val Ser Asn Gln Thr Gln Phe Asn Gly Val Lys Val Leu Ser Gln
            100                 105                 110
```

Asp Asn Gln Met Lys Ile Gln Val Gly Ala Asn Asp Gly Glu Thr Ile
            115                 120                 125

Thr Ile Asp Leu Gln Lys Ile Asp Val Lys Ser Leu Gly Leu Asp Gly
        130                 135                 140

Phe Asn Val Asn Ser Pro Gly Ser Thr Ala Asn Pro Leu Ala Ser Ile
145                 150                 155                 160

Asp Ser Ala Leu Ser Lys Val Asp Ala Val Arg Ser Ser Leu Gly Ala
                165                 170                 175

Ile Gln Asn Arg Phe Asp Ser Ala Ile Thr Asn Leu Gly Asn Thr Val
            180                 185                 190

Thr Asn Leu Asn Ser Ala Arg Ser Arg Ile Glu Asp Ala Asp Tyr Ala
        195                 200                 205

Thr Glu Val Ser Asn Met Ser Lys Ala Gln Ile Leu Gln Gln Ala Gly
            210                 215                 220

Thr Ser Val Leu Ala Gln Ala Asn Gln Val Pro Gln Asn Val Leu Ser
225                 230                 235                 240

Leu Leu Val Pro Arg Gly Ser His His His His His Gly
                245                 250

```
<210> SEQ ID NO 31
<211> LENGTH: 32
<212> TYPE: DNA
<213> ORGANISM: Artificial Sequence
<220> FEATURE:
<223> OTHER INFORMATION: Synthetic sequence

<400> SEQUENCE: 31
gatatacata tgagcgggtt acggatcaac ag                                    32

<210> SEQ ID NO 32
<211> LENGTH: 29
<212> TYPE: DNA
<213> ORGANISM: Artificial Sequence
<220> FEATURE:
<223> OTHER INFORMATION: Synthetic sequence

<400> SEQUENCE: 32
agatctcccg gggaattaac attgaaccc                                        29

<210> SEQ ID NO 33
<211> LENGTH: 816
<212> TYPE: DNA
<213> ORGANISM: Artificial Sequence
<220> FEATURE:
<223> OTHER INFORMATION: Synthetic sequence

<400> SEQUENCE: 33
taatacgact cactataggg gaattgtgag cggataacaa ttcccctcta gaataatttt       60
gtttaacttt aagaaggaga tatacatatg agcgggttac ggatcaacag cgcgaaagac     120
gatgcggcag gccaggcgat tgctaaccgc ttcacttcta atatcaaagg tctgactcag     180
gcttcccgta acgctaacga cggcatttct attgcgcaga ccactgaagg tgcgctgaat     240
gaaatcaaca caaccctgca gcgtgtgcgt gagttgtctg ttcaggccac tggaccatca     300
ggtgaaattc agcaacgtct ggaagaaatc gatcgcgttt ctaatcagac tcaatttaac     360
ggtgttaaag tcctgtctca ggacaaccag atgaaaatcc aggttggtgc aacgatggt      420 gaaccatta ccatcgatct gcaaaaaatt gatgtgaaaa gccttggcct tgatgggttc      480
aatgttaatt ccccgggaag taccgctaac ccactggctt caattgattc tgcattgtca    540
```

```
aaagtggacg cagttcgttc ttctctgggg gcaattcaaa accgctttga ttcagccatt      600
accaaccttg gcaatacggt aaccaatctg aactccgcgc gtagccgtat cgaagatgct      660
gactatgcaa cggaagtttc taatatgtct aaagcgcaga ttctgcagca ggctggtact      720
tccgttctgg cgcaggctaa ccaggttccg caaaacgtcc tctctttact ggttccgcgg      780
ggttctcatc atcatcatca tcatggttaa gtcgac                                 816
```

```
<210> SEQ ID NO 34
<211> LENGTH: 240
<212> TYPE: PRT
<213> ORGANISM: Artificial Sequence
<220> FEATURE:
<223> OTHER INFORMATION: Synthetic sequence

<400> SEQUENCE: 34

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Gly Pro Ser Gly Glu Ile Gln Gln Arg Leu Glu Glu
65                  70                  75                  80

Ile Asp Arg Val Ser Asn Gln Thr Gln Phe Asn Gly Val Lys Val Leu
                85                  90                  95

Ser Gln Asp Asn Gln Met Lys Ile Gln Val Gly Ala Asn Asp Gly Glu
            100                 105                 110

Thr Ile Thr Ile Asp Leu Gln Lys Ile Asp Val Lys Ser Leu Gly Leu
        115                 120                 125

Asp Gly Phe Asn Val Asn Ser Pro Gly Ser Thr Ala Asn Pro Leu Ala
    130                 135                 140

Ser Ile Asp Ser Ala Leu Ser Lys Val Asp Ala Val Arg Ser Ser Leu
145                 150                 155                 160

Gly Ala Ile Gln Asn Arg Phe Asp Ser Ala Ile Thr Asn Leu Gly Asn
                165                 170                 175

Thr Val Thr Asn Leu Asn Ser Ala Arg Ser Arg Ile Glu Asp Ala Asp
            180                 185                 190

Tyr Ala Thr Glu Val Ser Asn Met Ser Lys Ala Gln Ile Leu Gln Gln
        195                 200                 205

Ala Gly Thr Ser Val Leu Ala Gln Ala Asn Gln Val Pro Gln Asn Val
    210                 215                 220

Leu Ser Leu Leu Val Pro Arg Gly Ser His His His His His Gly
225                 230                 235                 240

<210> SEQ ID NO 35
<211> LENGTH: 275
<212> TYPE: PRT
<213> ORGANISM: Artificial Sequence
<220> FEATURE:
<223> OTHER INFORMATION: Synthetic sequence

<400> SEQUENCE: 35

Met Ser Gly Leu Arg Ile Asn Ser Ala Lys Asp Asp Ala Ala Gly Gln
1               5                   10                  15
```

```
Ala Ile Ala Asn Arg Phe Thr Ser Asn Ile Lys Gly Leu Thr Gln Ala
             20                  25                  30

Ser Arg Asn Ala Asn Asp Gly Ile Ser Ile Ala Gln Thr Thr Glu Gly
         35                  40                  45

Ala Leu Asn Glu Ile Asn Asn Leu Gln Arg Val Arg Glu Leu Ser
     50                  55                  60

Val Gln Ala Thr Asn Gly Thr Asn Ser Asp Ser Asp Leu Lys Ser Ile
65                  70                  75                  80

Gln Asp Glu Ile Gln Arg Leu Glu Glu Ile Asp Arg Val Ser Asn
                 85                  90                  95

Gln Thr Gln Phe Asn Gly Val Lys Val Leu Ser Gln Asp Asn Gln Met
                100                 105                 110

Lys Ile Gln Val Gly Ala Asn Asp Gly Glu Thr Ile Thr Ile Asp Leu
             115                 120                 125

Gln Lys Ile Asp Val Lys Ser Leu Gly Leu Asp Gly Phe Asn Val Asn
         130                 135                 140

Ser Pro Gly Ile Ser Gly Gly Gly Gly Ile Leu Asp Ser Met Gly
145                 150                 155                 160

Thr Leu Ile Asn Glu Asp Ala Ala Ala Ala Lys Lys Ser Thr Ala Asn
                 165                 170                 175

Pro Leu Ala Ser Ile Asp Ser Ala Leu Ser Lys Val Asp Ala Val Arg
             180                 185                 190

Ser Ser Leu Gly Ala Ile Gln Asn Arg Phe Asp Ser Ala Ile Thr Asn
         195                 200                 205

Leu Gly Asn Thr Val Thr Asn Leu Asn Ser Ala Arg Ser Arg Ile Glu
     210                 215                 220

Asp Ala Asp Tyr Ala Thr Glu Val Ser Asn Met Ser Lys Ala Gln Ile
225                 230                 235                 240

Leu Gln Gln Ala Gly Thr Ser Val Leu Ala Gln Ala Asn Gln Val Pro
                 245                 250                 255

Gln Asn Val Leu Ser Leu Leu Val Pro Arg Gly Ser His His His His
             260                 265                 270

His His Gly
        275

<210> SEQ ID NO 36
<211> LENGTH: 828
<212> TYPE: DNA
<213> ORGANISM: Artificial Sequence
<220> FEATURE:
<223> OTHER INFORMATION: Synthetic sequence

<400> SEQUENCE: 36
atgagcgggt tacggatcaa cagcgcgaaa gacgatgcgg caggccaggc gattgctaac      60
cgcttcactt ctaatatcaa aggtctgact caggcttccc gtaacgctaa cgacggcatt     120
tctattgcgc agaccactga aggtgcgctg aatgaaatca caacaaccct gcagcgtgtg     180
cgtgagttgt ctgttcaggc cactaacggg actaactctg attccgatct gaaatctatc     240
caggatgaaa ttcagcaacg tctggaagaa atcgatcgcg tttctaatca gactcaattt     300
aacggtgtta aagtcctgtc tcaggacaac cagatgaaaa tccaggttgg tgctaacgat     360
ggtgaaacca ttaccatcga tctgcaaaaa attgatgtga aaagccttgg ccttgatggg     420
ttcaatgtta attccccggg aatttccggt ggtggtggtg aattctaga ctccatgggt      480 acattaatca atgaagacgc tgccgcagcc aagaaaagta ccgctaaccc actggcttca    540
```

| | |
|---|---|
| attgattctg cattgtcaaa agtggacgca gttcgttctt ctctgggggc aattcaaaac | 600 |
| cgctttgatt cagccattac caaccttggc aatacggtaa ccaatctgaa ctccgcgcgt | 660 |
| agccgtatcg aagatgctga ctatgcaacg gaagtttcta atatgtctaa agcgcagatt | 720 |
| ctgcagcagg ctggtacttc cgttctggcg caggctaacc aggttccgca aaacgtcctc | 780 |
| tctttactgg ttccgcgggg ttctcatcat catcatcatc atggttaa | 828 |

```
<210> SEQ ID NO 37
<211> LENGTH: 41
<212> TYPE: DNA
<213> ORGANISM: Artificial Sequence
<220> FEATURE:
<223> OTHER INFORMATION: Synthetic sequence

<400> SEQUENCE: 37
```

| | |
|---|---|
| tctagacccg ggaagtaccg ctaacccact ggcttcaatt g | 41 |

```
<210> SEQ ID NO 38
<211> LENGTH: 40
<212> TYPE: DNA
<213> ORGANISM: Artificial Sequence
<220> FEATURE:
<223> OTHER INFORMATION: Synthetic sequence

<400> SEQUENCE: 38
```

| | |
|---|---|
| ccagtcatgt cgacttaacc atgatgatga tgatgatgag | 40 |

```
<210> SEQ ID NO 39
<211> LENGTH: 55
<212> TYPE: DNA
<213> ORGANISM: Artificial Sequence
<220> FEATURE:
<223> OTHER INFORMATION: Synthetic sequence

<400> SEQUENCE: 39
```

| | |
|---|---|
| ctcatcatca tcatcatcat ggttaagtcg acaagcttgc ggccgcagag ctcgc | 55 |

```
<210> SEQ ID NO 40
<211> LENGTH: 846
<212> TYPE: DNA
<213> ORGANISM: Artificial Sequence
<220> FEATURE:
<223> OTHER INFORMATION: Synthetic sequence

<400> SEQUENCE: 40
```

| | |
|---|---|
| taatacgact cactataggg gaattgtgag cggataacaa ttcccctcta gaataatttt | 60 |
| gtttaacttt aagaaggaga tatacatatg agcgggttac ggatcaacag cgcgaaagac | 120 |
| gatgcggcag gccaggcgat tgctaaccgc ttcacttcta atatcaaagg tctgactcag | 180 |
| gcttcccgta acgctaacga cggcatttct attgcgcaga ccactgaagg tgcgctgaat | 240 |
| gaaatcaaca caaacctgca gcgtgtgcgt gagttgtctg ttcaggccac taacgggact | 300 |
| aactctgatt ccgatctgaa atctatccag gatgaaattc agcaacgtct ggaagaaatc | 360 |
| gatcgcgttt ctaatcagac tcaatttaac ggtgttaaag tcctgtctca ggacaaccag | 420 |
| atgaaaatcc aggttggtgc taacgatggt gaaaccatta ccatcgatct gcaaaaaatt | 480 |
| gatgtgaaaa gccttggcct tgatgggttc aatgttaatt ccccgggaag taccgctaac | 540 |
| ccactggctt caattgattc tgcattgtca aaagtggacg cagttcgttc ttctctgggg | 600 |
| gcaattcaaa accgctttga ttcagccatt accaaccttg gcaatacggt aaccaatctg | 660 |
| aactccgcgc gtagccgtat cgaagatgct gactatgcaa cggaagtttc taatatgtct | 720 |

```
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                              846
```

<210> SEQ ID NO 41
<211> LENGTH: 753
<212> TYPE: DNA
<213> ORGANISM: Artificial Sequence
<220> FEATURE:
<223> OTHER INFORMATION: Synthetic sequence

<400> SEQUENCE: 41

```
atgagcgggt tacggatcaa cagcgcgaaa gacgatgcgg caggccaggc gattgctaac     60
cgcttcactt ctaatatcaa aggtctgact caggcttccc gtaacgctaa cgacggcatt    120
tctattgcgc agaccactga aggtgcgctg aatgaaatca acaacaacct gcagcgtgtg    180
cgtgagttgt ctgttcaggc cactaacggg actaactctg attccgatct gaaatctatc    240
caggatgaaa ttcagcaacg tctggaagaa atcgatcgcg tttctaatca gactcaattt    300
aacggtgtta aagtcctgtc tcaggacaac cagatgaaaa tccaggttgg tgctaacgat    360
ggtgaaacca ttaccatcga tctgcaaaaa attgatgtga aaagccttgg ccttgatggg    420
ttcaatgtta attccccggg aagtaccgct aacccactgg cttcaattga ttctgcattg    480
tcaaaagtgg acgcagttcg ttcttctctg ggggcaattc aaaaccgctt tgattcagcc    540
attaccaacc ttggcaatac ggtaaccaat ctgaactccg cgcgtagccg tatcgaagat    600
gctgactatg caacggaagt ttctaatatg tctaaagcgc agattctgca gcaggctggt    660
acttccgttc tggcgcaggc taaccaggtt ccgcaaaacg tcctctcttt actggttccg    720
cggggttctc atcatcatca tcatcatggt taa                                 753
```

<210> SEQ ID NO 42
<211> LENGTH: 250
<212> TYPE: PRT
<213> ORGANISM: Artificial Sequence
<220> FEATURE:
<223> OTHER INFORMATION: Synthetic sequence

<400> SEQUENCE: 42

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140
```

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
            165                 170                 175

Phe Asp Ser Ala Ile Thr Asn Leu Gly Asn Thr Val Thr Asn Leu Asn
        180                 185                 190

Ser Ala Arg Ser Arg Ile Glu Asp Ala Asp Tyr Ala Thr Glu Val Ser
            195                 200                 205

Asn Met Ser Lys Ala Gln Ile Leu Gln Gln Ala Gly Thr Ser Val Leu
        210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 43
<211> LENGTH: 1005
<212> TYPE: DNA
<213> ORGANISM: Artificial Sequence
<220> FEATURE:
<223> OTHER INFORMATION: Synthetic sequence

<400> SEQUENCE: 43
atggcacaag tcattaatac aaacagcctg tcgctgttga cccagaataa cctgaacaaa      60
tctcagtcct cactgagttc cgctattgag cgtctgtcct ctggtctgcg tatcaacggc     120
gcgaaagacg atgcggcagg ccaggcgatt gctaaccgct tcacttctaa tatcaaaggt     180
ctgactcagg cttcccgtaa cgctaacgac ggcatttcta ttgcgcagac cactgaaggt     240
gcgctgaatg aaatcaacaa caacctgcag cgtgtgcgtg agttgtctgt tcaggccact     300
aacgggacta actctgattc cgatctgaaa tctatccagg atgaaattca gcaacgtctg     360
gaagaaatcg atcgcgtttc taatcagact caatttaacg tgttaaagt cctgtctcag      420 gacaaccaga tgaaaatcca ggttggtgct aacgatggtg aaaccattac catcgatctg     480
caaaaaattg atgtgaaaag ccttggcctt gatgggttca atgttaattc cccgggaatt     540
tccggtggtg gtggtggaat tctagactcc atgggtacat taatcaatga agacgctgcc     600
gcagccaaga aaagtaccgc taacccactg gcttcaattg attctgcatt gtcaaaagtg     660
gacgcagttc gttcttctct gggggcaatt caaaaccgct tgattcagc cattaccaac      720 cttggcaata cggtaaccaa tctgaactcc gcgcgtagcc gtatcgaaga tgctgactat     780
gcaacggaag tttctaatat gtctaaagcg cagattctgc agcaggctgg tacttccgtt     840
ctggcgcagg ctaaccaggt tccgcaaaac gtcctctctt tactggttcc gcggggttct     900
catcatcatc atcatcatgg tatggctagc atgactggtg gacagcaaat gggtcgggat     960
ctgtacgacg atgacgataa ggatccgtaa gtcgacaagc ttgcg                    1005

<210> SEQ ID NO 44
<211> LENGTH: 329
<212> TYPE: PRT
<213> ORGANISM: Artificial Sequence
<220> FEATURE:
<223> OTHER INFORMATION: Synthetic sequence

<400> SEQUENCE: 44

Met Ala Gln Val Ile Asn Thr Asn Ser Leu Ser Leu Leu Thr Gln Asn
1               5                   10                  15

Asn Leu Asn Lys Ser Gln Ser Leu Ser Ser Ala Ile Glu Arg Leu
            20                  25                  30

Ser Ser Gly Leu Arg Ile Asn Gly Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Ser Pro Gly Ile Ser Gly Gly Gly Gly Ile Leu Asp Ser Met Gly
            180                 185                 190

Thr Leu Ile Asn Glu Asp Ala Ala Ala Lys Lys Ser Thr Ala Asn
        195                 200                 205

Pro Leu Ala Ser Ile Asp Ser Ala Leu Ser Lys Val Asp Ala Val Arg
    210                 215                 220

Ser Ser Leu Gly Ala Ile Gln Asn Arg Phe Asp Ser Ala Ile Thr Asn
225                 230                 235                 240

Leu Gly Asn Thr Val Thr Asn Leu Asn Ser Ala Arg Ser Arg Ile Glu
                245                 250                 255

Asp Ala Asp Tyr Ala Thr Glu Val Ser Asn Met Ser Lys Ala Gln Ile
            260                 265                 270

Leu Gln Gln Ala Gly Thr Ser Val Leu Ala Gln Ala Asn Gln Val Pro
        275                 280                 285

Gln Asn Val Leu Ser Leu Leu Val Pro Arg Gly Ser His His His
    290                 295                 300

His His Gly Met Ala Ser Met Thr Gly Gly Gln Gln Met Gly Arg Asp
305                 310                 315                 320

Leu Tyr Asp Asp Asp Asp Lys Asp Pro
                325

<210> SEQ ID NO 45
<211> LENGTH: 36
<212> TYPE: DNA
<213> ORGANISM: Artificial Sequence
<220> FEATURE:
<223> OTHER INFORMATION: Synthetic sequence

<400> SEQUENCE: 45
ctctggtcat atgatcaaca gcgcgaaaga cgatgc                            36

<210> SEQ ID NO 46
<211> LENGTH: 46
<212> TYPE: DNA
<213> ORGANISM: Artificial Sequence
<220> FEATURE:
<223> OTHER INFORMATION: Synthetic sequence

<400> SEQUENCE: 46
tctagagtcg actattaagc cataccatga tgatgatgat gatgag                46

<210> SEQ ID NO 47
<211> LENGTH: 918
<212> TYPE: DNA
<213> ORGANISM: Artificial Sequence
<220> FEATURE:
<223> OTHER INFORMATION: Synthetic sequence

<400> SEQUENCE: 47
taatacgact cactataggg gaattgtgag cggataacaa ttcccctcta gaaataattt    60
tgtttaactt taagaaggag atatacatat gatcaacagc gcgaaagacg atgcggcagg   120
ccaggcgatt gctaaccgct tcacttctaa tatcaaaggt ctgactcagg cttcccgtaa   180
cgctaacgac ggcatttcta ttgcgcagac cactgaaggt gcgctgaatg aaatcaacaa   240
caacctgcag cgtgtgcgtg agttgtctgt tcaggccact aacgggacta actctgattc   300
cgatctgaaa tctatccagg atgaaattca gcaacgtctg aagaaatcg atcgcgtttc   360
taatcagact caatttaacg gtgttaaagt cctgtctcag acaaccaga tgaaaatcca   420
ggttggtgct aacgatggtg aaaccattac catcgatctg caaaaaattg atgtgaaaag   480
ccttggcctt gatgggttca atgttaattc cccgggaatt tccggtgtgt gtggtggaat   540
tctagactcc atgggtacat taatcaatga agacgctgcc gcagccaaga aaagtaccgc   600
taacccactg gcttcaattg attctgcatt gtcaaaagtg gacgcagttc gttcttctct   660
gggggcaatt caaaaccgct tgattcagc cattaccaac cttggcaata cggtaaccaa   720
tctgaactcc gcgcgtagcc gtatcgaaga tgctgactat gcaacggaag tttctaatat   780
gtctaaagcg cagattctgc agcaggctgg tacttccgtt ctggcgcagg ctaaccaggt   840
tccgcaaaac gtcctctctt tactggttcc gcggggttct catcatcatc atcatcatgg   900
tatggcttaa tagtcgac                                                918

<210> SEQ ID NO 48
<211> LENGTH: 273
<212> TYPE: PRT
<213> ORGANISM: Artificial Sequence
<220> FEATURE:
<223> OTHER INFORMATION: Synthetic sequence

<400> SEQUENCE: 48

Met Ile Asn Ser Ala Lys Asp Asp Ala Ala Gly Gln Ala Ile Ala Asn
1               5                   10                  15

Arg Phe Thr Ser Asn Ile Lys Gly Leu Thr Gln Ala Ser Arg Asn Ala
            20                  25                  30

Asn Asp Gly Ile Ser Ile Ala Gln Thr Thr Glu Gly Ala Leu Asn Glu
        35                  40                  45

Ile Asn Asn Asn Leu Gln Arg Val Arg Glu Leu Ser Val Gln Ala Thr
    50                  55                  60

Asn Gly Thr Asn Ser Asp Ser Asp Leu Lys Ser Ile Gln Asp Glu Ile
65                  70                  75                  80

Gln Gln Arg Leu Glu Glu Ile Asp Arg Val Ser Asn Gln Thr Gln Phe
                85                  90                  95

Asn Gly Val Lys Val Leu Ser Gln Asp Asn Gln Met Lys Ile Gln Val
            100                 105                 110

Gly Ala Asn Asp Gly Glu Thr Ile Thr Ile Asp Leu Gln Lys Ile Asp

```
            115                 120                 125
Val Lys Ser Leu Gly Leu Asp Gly Phe Asn Val Asn Ser Pro Gly Ile
    130                 135                 140

Ser Gly Gly Gly Gly Ile Leu Asp Ser Met Gly Thr Leu Ile Asn
145                 150                 155                 160

Glu Asp Ala Ala Ala Lys Lys Ser Thr Ala Asn Pro Leu Ala Ser
                165                 170                 175

Ile Asp Ser Ala Leu Ser Lys Val Asp Ala Val Arg Ser Ser Leu Gly
            180                 185                 190

Ala Ile Gln Asn Arg Phe Asp Ser Ala Ile Thr Asn Leu Gly Asn Thr
        195                 200                 205

Val Thr Asn Leu Asn Ser Ala Arg Ser Arg Ile Glu Asp Ala Asp Tyr
    210                 215                 220

Ala Thr Glu Val Ser Asn Met Ser Lys Ala Gln Ile Leu Gln Gln Ala
225                 230                 235                 240

Gly Thr Ser Val Leu Ala Gln Ala Asn Gln Val Pro Gln Asn Val Leu
                245                 250                 255

Ser Leu Leu Val Pro Arg Gly Ser His His His His His His Gly Met
            260                 265                 270

Ala
```

<210> SEQ ID NO 49
<211> LENGTH: 333
<212> TYPE: PRT
<213> ORGANISM: Artificial Sequence
<220> FEATURE:
<223> OTHER INFORMATION: Synthetic sequence

<400> SEQUENCE: 49

```
Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
                20                  25                  30

Ser Ala Lys Asp Pro Met Ala Gln Val Ile Asn Thr Asn Ser Leu Ser
            35                  40                  45

Leu Leu Thr Gln Asn Asn Leu Asn Lys Ser Gln Ser Ser Leu Ser Ser
    50                  55                  60

Ala Ile Glu Arg Leu Ser Ser Gly Leu Arg Ile Asn Ser Ala Lys Asp
65                  70                  75                  80

Asp Ala Ala Gly Gln Ala Ile Ala Asn Arg Phe Thr Ser Asn Ile Lys
                85                  90                  95

Gly Leu Thr Gln Ala Ser Arg Asn Ala Asn Asp Gly Ile Ser Ile Ala
            100                 105                 110

Gln Thr Thr Glu Gly Ala Leu Asn Glu Ile Asn Asn Leu Gln Arg
        115                 120                 125

Val Arg Glu Leu Ser Val Gln Ala Thr Asn Gly Thr Asn Ser Asp Ser
    130                 135                 140

Asp Leu Lys Ser Ile Gln Asp Glu Ile Gln Gln Arg Leu Glu Glu Ile
145                 150                 155                 160

Asp Arg Val Ser Asn Gln Thr Gln Phe Asn Gly Val Lys Val Leu Ser
                165                 170                 175

Gln Asp Asn Gln Met Lys Ile Gln Val Gly Ala Asn Asp Gly Glu Thr
            180                 185                 190

Ile Thr Ile Asp Leu Gln Lys Ile Asp Val Lys Ser Leu Gly Leu Asp
        195                 200                 205
```

```
Gly Phe Asn Val Asn Ser Pro Gly Ile Ser Gly Gly Gly Gly Ile
    210                 215                 220
Leu Asp Ser Met Gly Thr Leu Ile Asn Glu Asp Ala Ala Ala Lys
225                 230                 235                 240
Lys Ser Thr Ala Asn Pro Leu Ala Ser Ile Asp Ser Ala Leu Ser Lys
                245                 250                 255
Val Asp Ala Val Arg Ser Ser Leu Gly Ala Ile Gln Asn Arg Phe Asp
                260                 265                 270
Ser Ala Ile Thr Asn Leu Gly Asn Thr Val Thr Asn Leu Asn Ser Ala
                275                 280                 285
Arg Ser Arg Ile Glu Asp Ala Asp Tyr Ala Thr Glu Val Ser Asn Met
    290                 295                 300
Ser Lys Ala Gln Ile Leu Gln Gln Ala Gly Thr Ser Val Leu Ala Gln
305                 310                 315                 320
Ala Asn Gln Val Pro Gln Asn Val Leu Ser Leu Leu Arg
                325                 330
```

```
<210> SEQ ID NO 50
<211> LENGTH: 1002
<212> TYPE: DNA
<213> ORGANISM: Artificial Sequence
<220> FEATURE:
<223> OTHER INFORMATION: Synthetic sequence

<400> SEQUENCE: 50
atgcggggtt ctcatcatca tcatcatcat ggtatggcta gcatgactgg tggacagcaa      60
atgggtcggg atctgtacga cctggttccg cgcggtagcg cgaaggatcc gatggcacaa     120
gtcattaata caaacagcct gtcgctgttg acccagaata acctgaacaa atctcagtcc     180
tcactgagtt ccgctattga gcgtctgtcc tctggtctgc gtatcaacag cgcgaaagac     240
gatgcggcag ccaggcgat tgctaaccgc ttcacttcta atatcaaagg tctgactcag     300
gcttcccgta acgctaacga cggcatttct attgcgcaga ccactgaagg tgcgctgaat     360
gaaatcaaca caacctgca gcgtgtgcgt gagttgtctg ttcaggccac taacgggact     420
aactctgatt ccgatctgaa atctatccag gatgaaattc agcaacgtct ggaagaaatc     480
gatcgcgttt ctaatcagac tcaatttaac ggtgttaaag tcctgtctca ggacaaccag     540
atgaaaatcc aggttggtgc taacgatggt gaaaccatta ccatcgatct gcaaaaaatt     600
gatgtgaaaa gccttggcct tgatgggttc aatgttaatt ccccgggaat ttccggtggt     660
ggtggtggaa ttctagactc catgggtaca ttaatcaatg aagacgctgc cgcagccaag     720
aaaagtaccg ctaacccact ggcttcaatt gattctgcat tgtcaaaagt ggacgcagtt     780
cgttcttctc tggggcaat tcaaaaccgt tttgattcag ccattaccaa ccttggcaat     840
acggtaacca atctgaactc cgcgcgtagc cgtatcgaag atgctgacta tgcaacggaa     900
gtttctaata tgtctaaagc gcagattctg cagcaggctg gtacttccgt tctggcgcag     960
gctaaccagg ttccgcaaaa cgtcctctct ttactgcgtt aa                        1002
```

```
<210> SEQ ID NO 51
<211> LENGTH: 42
<212> TYPE: DNA
<213> ORGANISM: Artificial Sequence
<220> FEATURE:
<223> OTHER INFORMATION: Synthetic sequence

<400> SEQUENCE: 51
```
ggcaattcaa aaccgttttg attaagccat taccaacctt gg    42

<210> SEQ ID NO 52
<211> LENGTH: 42
<212> TYPE: DNA
<213> ORGANISM: Artificial Sequence
<220> FEATURE:
<223> OTHER INFORMATION: Synthetic sequence

<400> SEQUENCE: 52
ccaaggttgg taatggctta atcaaaacgg ttttgaattg cc    42

<210> SEQ ID NO 53
<211> LENGTH: 906
<212> TYPE: DNA
<213> ORGANISM: Artificial Sequence
<220> FEATURE:
<223> OTHER INFORMATION: Synthetic sequence

<400> SEQUENCE: 53
taatacgact cactataggg gaattgtgag cggataacaa ttcccctcta gaataatttt    60
gtttaacttt aagaaggaga tatacatatg cggggttctc atcatcatca tcatcatggt   120
atggctagca tgactggtgg acagcaaatg ggtcggatc tgtacgacct ggttccgcgc   180
ggtagcgcga aggatccgat ggcacaagtc attaatacaa acagcctgtc gctgttgacc   240
cagaataacc tgaacaaatc tcagtcctca ctgagttccg ctattgagcg tctgtcctct   300
ggtctgcgta tcaacagcgc gaaagacgat gcggcaggcc aggcgattgc taaccgcttc   360
acttctaata tcaaaggtct gactcaggct tcccgtaacg ctaacgacgg catttctatt   420
gcgcagacca ctgaaggtgc gctgaatgaa atcaacaaca acctgcagcg tgtgcgtgag   480
ttgtctgttc aggccactaa cgggactaac tctgattccg atctgaaatc tatccaggat   540
gaaattcagc aacgtctgga agaaatcgat cgcgtttcta atcagactca atttaacggt   600
gttaaagtcc tgtctcagga caaccagatg aaaatccagg ttggtgctaa cgatggtgaa   660
accattacca tcgatctgca aaaaattgat gtgaaaagcc ttggccttga tgggttcaat   720
gttaattccc cgggaatttc cggtggtggt ggtggaattc tagactccat gggtacatta   780
atcaatgaag acgctgccgc agccaagaaa agtaccgcta acccactggc ttcaattgat   840
tctgcattgt caaaagtgga cgcagttcgt tcttctctgg ggcaattca aaaccgtttt   900
gattaa                                                              906

<210> SEQ ID NO 54
<211> LENGTH: 272
<212> TYPE: PRT
<213> ORGANISM: Artificial Sequence
<220> FEATURE:
<223> OTHER INFORMATION: Synthetic sequence

<400> SEQUENCE: 54

Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Met Ala Gln Val Ile Asn Thr Asn Ser Leu Ser
        35                  40                  45

Leu Leu Thr Gln Asn Asn Leu Asn Lys Ser Gln Ser Ser Leu Ser Ser
    50                  55                  60

Ala Ile Glu Arg Leu Ser Ser Gly Leu Arg Ile Asn Ser Ala Lys Asp

```
            65                  70                  75                  80
Asp Ala Ala Gly Gln Ala Ile Ala Asn Arg Phe Thr Ser Asn Ile Lys
                85                  90                  95

Gly Leu Thr Gln Ala Ser Arg Asn Ala Asn Asp Gly Ile Ser Ile Ala
            100                 105                 110

Gln Thr Thr Glu Gly Ala Leu Asn Glu Ile Asn Asn Asn Leu Gln Arg
        115                 120                 125

Val Arg Glu Leu Ser Val Gln Ala Thr Asn Gly Thr Asn Ser Asp Ser
130                 135                 140

Asp Leu Lys Ser Ile Gln Asp Glu Ile Gln Gln Arg Leu Glu Glu Ile
145                 150                 155                 160

Asp Arg Val Ser Asn Gln Thr Gln Phe Asn Gly Val Lys Val Leu Ser
                165                 170                 175

Gln Asp Asn Gln Met Lys Ile Gln Val Gly Ala Asn Asp Gly Glu Thr
            180                 185                 190

Ile Thr Ile Asp Leu Gln Lys Ile Asp Val Lys Ser Leu Gly Leu Asp
        195                 200                 205

Gly Phe Asn Val Asn Ser Pro Gly Ile Ser Gly Gly Gly Gly Ile
    210                 215                 220

Leu Asp Ser Met Gly Thr Leu Ile Asn Glu Asp Ala Ala Ala Ala Lys
225                 230                 235                 240

Lys Ser Thr Ala Asn Pro Leu Ala Ser Ile Asp Ser Ala Leu Ser Lys
                245                 250                 255

Val Asp Ala Val Arg Ser Ser Leu Gly Ala Ile Gln Asn Arg Phe Asp
            260                 265                 270

<210> SEQ ID NO 55
<211> LENGTH: 45
<212> TYPE: DNA
<213> ORGANISM: Artificial Sequence
<220> FEATURE:
<223> OTHER INFORMATION: Synthetic sequence

<400> SEQUENCE: 55
caatctgaac tccgcgcgtt gacgtatcta agatgctgac tatgc                45

<210> SEQ ID NO 56
<211> LENGTH: 45
<212> TYPE: DNA
<213> ORGANISM: Artificial Sequence
<220> FEATURE:
<223> OTHER INFORMATION: Synthetic sequence

<400> SEQUENCE: 56
gcatagtcag catcttagat acgtcaacgc gcggagttca gattg                45

<210> SEQ ID NO 57
<211> LENGTH: 966
<212> TYPE: DNA
<213> ORGANISM: Artificial Sequence
<220> FEATURE:
<223> OTHER INFORMATION: Synthetic sequence

<400> SEQUENCE: 57
taatacgact cactataggg gaattgtgag cggataacaa ttcccctcta gaataatttt    60
gtttaacttt aagaaggaga tatacatatg cggggttctc atcatcatca tcatcatggt   120
atggctagca tgactggtgg acagcaaatg ggtcggatc tgtacgacct ggttccgcgc   180
ggtagcgcga aggatccgat ggcacaagtc attaatacaa acagcctgtc gctgttgacc   240
```

-continued

```
cagaataacc tgaacaaatc tcagtcctca ctgagttccg ctattgagcg tctgtcctct    300
ggtctgcgta tcaacagcgc gaaagacgat gcggcaggcc aggcgattgc taaccgcttc    360
acttctaata tcaaaggtct gactcaggct tcccgtaacg ctaacgacgg catttctatt    420
gcgcagacca ctgaaggtgc gctgaatgaa atcaacaaca acctgcagcg tgtgcgtgag    480
ttgtctgttc aggccactaa cgggactaac tctgattccg atctgaaatc tatccaggat    540
gaaattcagc aacgtctgga agaaatcgat cgcgtttcta atcagactca atttaacggt    600
gttaaagtcc tgtctcagga caaccagatg aaaatccagg ttggtgctaa cgatggtgaa    660
accattacca tcgatctgca aaaaattgat gtgaaaagcc ttggccttga tgggttcaat    720
gttaattccc cgggaatttc cggtggtggt ggtggaattc tagactccat gggtacatta    780
atcaatgaag acgctgccgc agccaagaaa agtaccgcta acccactggc ttcaattgat    840
tctgcattgt caaaagtgga cgcagttcgt tcttctctgg gggcaattca aaaccgtttt    900
gattcagcca ttaccaacct tggcaatacg gtaaccaatc tgaactccgc gcgttgacgt    960
atctaa                                                               966
```

<210> SEQ ID NO 58
<211> LENGTH: 289
<212> TYPE: PRT
<213> ORGANISM: Artificial Sequence
<220> FEATURE:
<223> OTHER INFORMATION: Synthetic sequence
<400> SEQUENCE: 58

```
Met Arg Gly Ser His His His His His Gly Met Ala Ser Met Thr
1               5                   10                  15

Gly Gly Gln Gln Met Gly Arg Asp Leu Tyr Asp Leu Val Pro Arg Gly
                20                  25                  30

Ser Ala Lys Asp Pro Met Ala Gln Val Ile Asn Thr Asn Ser Leu Ser
            35                  40                  45

Leu Leu Thr Gln Asn Asn Leu Asn Lys Ser Gln Ser Ser Leu Ser Ser
        50                  55                  60

Ala Ile Glu Arg Leu Ser Ser Gly Leu Arg Ile Asn Ser Ala Lys Asp
65                  70                  75                  80

Asp Ala Ala Gly Gln Ala Ile Ala Asn Arg Phe Thr Ser Asn Ile Lys
                85                  90                  95

Gly Leu Thr Gln Ala Ser Arg Asn Ala Asn Asp Gly Ile Ser Ile Ala
            100                 105                 110

Gln Thr Thr Glu Gly Ala Leu Asn Glu Ile Asn Asn Asn Leu Gln Arg
        115                 120                 125

Val Arg Glu Leu Ser Val Gln Ala Thr Asn Gly Thr Asn Ser Asp Ser
    130                 135                 140

Asp Leu Lys Ser Ile Gln Asp Glu Ile Gln Gln Arg Leu Glu Glu Ile
145                 150                 155                 160

Asp Arg Val Ser Asn Gln Thr Gln Phe Asn Gly Val Lys Val Leu Ser
                165                 170                 175

Gln Asp Asn Gln Met Lys Ile Gln Val Gly Ala Asn Asp Gly Glu Thr
            180                 185                 190

Ile Thr Ile Asp Leu Gln Lys Ile Asp Val Lys Ser Leu Gly Leu Asp
        195                 200                 205

Gly Phe Asn Val Asn Ser Pro Gly Ile Ser Gly Gly Gly Gly Ile
    210                 215                 220
```

```
Leu Asp Ser Met Gly Thr Leu Ile Asn Glu Asp Ala Ala Ala Ala Lys
225                 230                 235                 240

Lys Ser Thr Ala Asn Pro Leu Ala Ser Ile Asp Ser Ala Leu Ser Lys
                245                 250                 255

Val Asp Ala Val Arg Ser Ser Leu Gly Ala Ile Gln Asn Arg Phe Asp
            260                 265                 270

Ser Ala Ile Thr Asn Leu Gly Asn Thr Val Thr Asn Leu Asn Ser Ala
        275                 280                 285

Arg

<210> SEQ ID NO 59
<211> LENGTH: 48
<212> TYPE: DNA
<213> ORGANISM: Artificial Sequence
<220> FEATURE:
<223> OTHER INFORMATION: Synthetic sequence

<400> SEQUENCE: 59
cgtagccgta tcgaagatgc ttaataggca acggaagttt ctaatatg              48

<210> SEQ ID NO 60
<211> LENGTH: 48
<212> TYPE: DNA
<213> ORGANISM: Artificial Sequence
<220> FEATURE:
<223> OTHER INFORMATION: Synthetic sequence

<400> SEQUENCE: 60
catattagaa acttccgttg cctattaagc atcttcgata cggctacg               48

<210> SEQ ID NO 61
<211> LENGTH: 978
<212> TYPE: DNA
<213> ORGANISM: Artificial Sequence
<220> FEATURE:
<223> OTHER INFORMATION: Synthetic sequence

<400> SEQUENCE: 61
taatacgact cactataggg gaattgtgag cggataacaa ttcccctcta gaataatttt    60
gtttaacttt aagaaggaga tatacatatg cggggttctc atcatcatca tcatcatggt   120
atggctagca tgactggtgg acagcaaatg ggtcgggatc tgtacgacct ggttccgcgc   180
ggtagcgcga aggatccgat ggcacaagtc attaatacaa acagcctgtc gctgttgacc   240
cagaataacc tgaacaaatc tcagtcctca ctgagttccg ctattgagcg tctgtcctct   300
ggtctgcgta tcaacagcgc gaaagacgat gcggcaggcc aggcgattgc taaccgcttc   360
acttctaata tcaaaggtct gactcaggct tcccgtaacg ctaacgacgg catttctatt   420
gcgcagacca ctgaaggtgc gctgaatgaa atcaacaaca cctgcagcg tgtgcgtgag   480 ttgtctgttc aggccactaa cgggactaac tctgattccg atctgaaatc tatccaggat   540
gaaattcagc aacgtctgga agaaatcgat cgcgtttcta atcagactca atttaacggt   600
gttaaagtcc tgtctcagga caaccagatg aaaatccagg ttggtgctaa cgatggtgaa   660
accattacca tcgatctgca aaaaattgat gtgaaaagcc ttggccttga tgggttcaat   720
gttaattccc cgggaatttc cggtggtggt ggtggaattc tagactccat gggtacatta   780
atcaatgaag acgctgccgc agccaagaaa gtaccgcta acccactggc ttcaattgat   840
tctgcattgt caaagtggag cgcagttcgt tcttctctgg gggcaattca aaaccgtttt   900
gattcagcca ttaccaacct tggcaatacg gtaaccaatc tgaactccgc gcgtagccgt   960
```
atcgaagatg cttaatag                                                        978

<210> SEQ ID NO 62
<211> LENGTH: 295
<212> TYPE: PRT
<213> ORGANISM: Artificial Sequence
<220> FEATURE:
<223> OTHER INFORMATION: Synthetic sequence

<400> SEQUENCE: 62

Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Met Ala Gln Val Ile Asn Thr Asn Ser Leu Ser
        35                  40                  45

Leu Leu Thr Gln Asn Asn Leu Asn Lys Ser Gln Ser Ser Leu Ser Ser
    50                  55                  60

Ala Ile Glu Arg Leu Ser Ser Gly Leu Arg Ile Asn Ser Ala Lys Asp
65                  70                  75                  80

Asp Ala Ala Gly Gln Ala Ile Ala Asn Arg Phe Thr Ser Asn Ile Lys
                85                  90                  95

Gly Leu Thr Gln Ala Ser Arg Asn Ala Asn Asp Gly Ile Ser Ile Ala
            100                 105                 110

Gln Thr Thr Glu Gly Ala Leu Asn Glu Ile Asn Asn Asn Leu Gln Arg
        115                 120                 125

Val Arg Glu Leu Ser Val Gln Ala Thr Asn Gly Thr Asn Ser Asp Ser
    130                 135                 140

Asp Leu Lys Ser Ile Gln Asp Glu Ile Gln Gln Arg Leu Glu Glu Ile
145                 150                 155                 160

Asp Arg Val Ser Asn Gln Thr Gln Phe Asn Gly Val Lys Val Leu Ser
                165                 170                 175

Gln Asp Asn Gln Met Lys Ile Gln Val Gly Ala Asn Asp Gly Glu Thr
            180                 185                 190

Ile Thr Ile Asp Leu Gln Lys Ile Asp Val Lys Ser Leu Gly Leu Asp
        195                 200                 205

Gly Phe Asn Val Asn Ser Pro Gly Ile Ser Gly Gly Gly Gly Ile
    210                 215                 220

Leu Asp Ser Met Gly Thr Leu Ile Asn Glu Asp Ala Ala Ala Ala Lys
225                 230                 235                 240

Lys Ser Thr Ala Asn Pro Leu Ala Ser Ile Asp Ser Ala Leu Ser Lys
                245                 250                 255

Val Asp Ala Val Arg Ser Ser Leu Gly Ala Ile Gln Asn Arg Phe Asp
            260                 265                 270

Ser Ala Ile Thr Asn Leu Gly Asn Thr Val Thr Asn Leu Asn Ser Ala
        275                 280                 285

Arg Ser Arg Ile Glu Asp Ala
    290                 295

<210> SEQ ID NO 63
<211> LENGTH: 990
<212> TYPE: DNA
<213> ORGANISM: Artificial Sequence
<220> FEATURE:
<223> OTHER INFORMATION: Synthetic sequence

<400> SEQUENCE: 63

```
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggtc tgactcaggc ttcccgtaac     300
gctaacgacg gcatttctat tgcgcagacc actgaaggtg cgctgaatga atcaacaac     360 aacctgcagc gtgtgcgtga gttgtctgtt caggccacta acgggactaa ctctgattcc     420
gatctgaaat ctatccagga tgaaattcag caacgtctgg aagaaatcga tcgcgtttct     480
aatcagactc aatttaacgg tgttaaagtc ctgtctcagg acaaccagat gaaaatccag     540
gttggtgcta acgatggtga aaccattacc atcgatctgc aaaaaattga tgtgaaaagc     600
cttggccttg atgggttcaa tgttaattcc ccgggaattt ccggtggtgg tggtggaatt     660
ctagactcca tgggtacatt aatcaatgaa gacgctgccg cagccaagaa aagtaccgct     720
aacccactgg cttcaattga ttctgcattg tcaaaagtgg acgcagttcg ttcttctctg     780
ggggcaattc aaaaccgttt tgattcagcc attaccaacc ttggcaatac ggtaaccaat     840
ctgaactccg cgcgtagccg tatcgaagat gctgactatg caacggaagt ttctaatatg     900
tctaaagcgc agattctgca gcaggctggt acttccgttc tggcgcaggc taaccaggtt     960
ccgcaaaacg tcctctcttt actgcgttaa                                     990

<210> SEQ ID NO 64
<211> LENGTH: 33
<212> TYPE: DNA
<213> ORGANISM: Artificial Sequence
<220> FEATURE:
<223> OTHER INFORMATION: Synthetic sequence

<400> SEQUENCE: 64
cgataaggat catatggcac aagtcattaa tac                                  33

<210> SEQ ID NO 65
<211> LENGTH: 78
<212> TYPE: DNA
<213> ORGANISM: Artificial Sequence
<220> FEATURE:
<223> OTHER INFORMATION: Synthetic sequence

<400> SEQUENCE: 65
agatctgtcg acttaaccat gatgatgatg atgatgagaa ccccgcggaa ccagtgcata     60
gtcagcatct tcgatacg                                                   78

<210> SEQ ID NO 66
<211> LENGTH: 918
<212> TYPE: DNA
<213> ORGANISM: Artificial Sequence
<220> FEATURE:
<223> OTHER INFORMATION: Synthetic sequence

<400> SEQUENCE: 66
taatacgact cactataggg gaattgtgag cggataacaa ttcccctcta gaataatttt     60
gtttaacttt aagaaggaga tatacatatg gcacaagtca ttaatacaaa cagcctgtcg    120
ctgttgaccc agaataacct gaacaaatct cagtcctcac tgagttccgc tattgagcgt    180
ctgtcctctg gtctgcgtat caacagcgcg aaagacgatg cggcaggcca ggcgattgct    240
```

```
aaccgcttca cttctaatat caaaggtctg actcaggctt cccgtaacgc taacgacggc    300
atttctattg cgcagaccac tgaaggtgcg ctgaatgaaa tcaacaacaa cctgcagcgt    360
gtgcgtgagt tgtctgttca ggccactaac gggactaact ctgattccga tctgaaatct    420
atccaggata aaattcagca acgtctggaa gaaatcgatc gcgtttctaa tcagactcaa    480
tttaacggtg ttaaagtcct gtctcaggac aaccagatga aatccaggt tggtgctaac     540 gatggtgaaa ccattaccat cgatctgcaa aaaattgatg tgaaaagcct tggccttgat    600
gggttcaatg ttaattcccc gggaatttcc ggtggtggtg gtggaattct agactccatg    660
ggtacattaa tcaatgaaga cgctgccgca gccaagaaaa gtaccgctaa cccactggct    720
tcaattgatt ctgcattgtc aaaagtggac gcagttcgtt cttctctggg ggcaattcaa    780
aaccgttttg attcagccat taccaacctt ggcaatacgg taaccaatct gaactccgcg    840
cgtagccgta tcgaagatgc tgactatgca ctggttccgc ggggttctca tcatcatcat    900
catcatggtt aagtcgac                                                 918
```

<210> SEQ ID NO 67
<211> LENGTH: 274
<212> TYPE: PRT
<213> ORGANISM: Artificial Sequence
<220> FEATURE:
<223> OTHER INFORMATION: Synthetic sequence

<400> SEQUENCE: 67

```
Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn Val Asn
                165                 170                 175

Ser Pro Gly Ile Ser Gly Gly Gly Gly Ile Leu Asp Ser Met Gly
            180                 185                 190

Thr Leu Ile Asn Glu Asp Ala Ala Ala Ala Lys Lys Ser Thr Ala Asn
        195                 200                 205

Pro Leu Ala Ser Ile Asp Ser Ala Leu Ser Lys Val Asp Ala Val Arg
    210                 215                 220

Ser Ser Leu Gly Ala Ile Gln Asn Arg Phe Asp Ser Ala Ile Thr Asn
225                 230                 235                 240
```

-continued

```
Leu Gly Asn Thr Val Thr Asn Leu Asn Ser Ala Arg Ser Arg Ile Glu
            245                 250                 255

Asp Ala Asp Tyr Ala Leu Val Pro Arg Gly Ser His His His His
            260                 265                 270

His Gly

<210> SEQ ID NO 68
<211> LENGTH: 40
<212> TYPE: DNA
<213> ORGANISM: Artificial Sequence
<220> FEATURE:
<223> OTHER INFORMATION: Synthetic sequence

<400> SEQUENCE: 68
agatctccgc ggaaccagac cagcctgctg cagaatctgc                     40

<210> SEQ ID NO 69
<211> LENGTH: 795
<212> TYPE: DNA
<213> ORGANISM: Artificial Sequence
<220> FEATURE:
<223> OTHER INFORMATION: Synthetic sequence

<400> SEQUENCE: 69
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca caacctgca gcgtgtgcgt gagttgtctg ttcaggccac taacgggact    300
aactctgatt ccgatctgaa atctatccag gatgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaaccttg caatacggt aaccaatctg    660 aactccgcgc gtagccgtat cgaagatgct gactatgcaa cggaagtttc taatatgtct   720
aaagcgcaga ttctgcagca ggctggtctg gttccgcggg gttctcatca tcatcatcat   780
catggttaag tcgac                                                    795

<210> SEQ ID NO 70
<211> LENGTH: 702
<212> TYPE: DNA
<213> ORGANISM: Artificial Sequence
<220> FEATURE:
<223> OTHER INFORMATION: Synthetic sequence

<400> SEQUENCE: 70
atgagcgggt tacggatcaa cagcgcgaaa gacgatgcgg caggccaggc gattgctaac    60
cgcttcactt ctaatatcaa aggtctgact caggcttccc gtaacgctaa cgacggcatt   120
tctattgcgc agaccactga aggtgcgctg aatgaaatca caacaacct gcagcgtgtg    180 cgtgagttgt ctgttcaggc cactaacggg actaactctg attccgatct gaaatctatc   240
caggatgaaa ttcagcaacg tctggaagaa atcgatcgcg tttctaatca gactcaattt   300
aacggtgtta aagtcctgtc tcaggacaac cagatgaaaa tccaggttgg tgctaacgat   360
```

```
ggtgaaacca ttaccatcga tctgcaaaaa attgatgtga aaagccttgg ccttgatggg      420
ttcaatgtta attccccggg aagtaccgct aacccactgg cttcaattga ttctgcattg      480
tcaaaagtgg acgcagttcg ttcttctctg ggggcaattc aaaaccgctt tgattcagcc      540
attaccaacc ttggcaatac ggtaaccaat ctgaactccg cgcgtagccg tatcgaagat      600
gctgactatg caacggaagt ttctaatatg tctaaagcgc agattctgca gcaggctggt      660
ctggttccgc ggggttctca tcatcatcat catcatggtt aa                         702

<210> SEQ ID NO 71
<211> LENGTH: 233
<212> TYPE: PRT
<213> ORGANISM: Artificial Sequence
<220> FEATURE:
<223> OTHER INFORMATION: Synthetic sequence

<400> SEQUENCE: 71

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Leu Val Pro Arg
    210                 215                 220

Gly Ser His His His His His His Gly
225                 230

<210> SEQ ID NO 72
<211> LENGTH: 120
<212> TYPE: DNA
<213> ORGANISM: Artificial Sequence
<220> FEATURE:
<223> OTHER INFORMATION: Synthetic sequence

<400> SEQUENCE: 72
aacccactgg cttcaattga ttctgcattg tcaaaagtgg acgcagttcg ttcttctctg      60
```

```
ggggcaattc aaaaccgttt tgattcagcc attaccgccc ttggcaatac ggtaaccaat    120
```

<210> SEQ ID NO 73
<211> LENGTH: 40
<212> TYPE: PRT
<213> ORGANISM: Artificial Sequence
<220> FEATURE:
<223> OTHER INFORMATION: Synthetic sequence

<400> SEQUENCE: 73

```
Asn Pro Leu Ala Ser Ile Asp Ser Ala Leu Ser Lys Val Asp Ala Val
1               5                   10                  15

Arg Ser Ser Leu Gly Ala Ile Gln Asn Arg Phe Asp Ser Ala Ile Thr
            20                  25                  30

Ala Leu Gly Asn Thr Val Thr Asn
        35                  40
```

<210> SEQ ID NO 74
<211> LENGTH: 46
<212> TYPE: DNA
<213> ORGANISM: Artificial Sequence
<220> FEATURE:
<223> OTHER INFORMATION: Synthetic sequence

<400> SEQUENCE: 74

```
gttcgttctt ctctgggggc aattgattca gccattaccg cccttg            46
```

<210> SEQ ID NO 75
<211> LENGTH: 46
<212> TYPE: DNA
<213> ORGANISM: Artificial Sequence
<220> FEATURE:
<223> OTHER INFORMATION: Synthetic sequence

<400> SEQUENCE: 75

```
caagggcggt aatggctgaa tcaattgccc ccagagaaga acgaac            46
```

<210> SEQ ID NO 76
<211> LENGTH: 783
<212> TYPE: DNA
<213> ORGANISM: Artificial Sequence
<220> FEATURE:
<223> OTHER INFORMATION: Synthetic sequence

<400> SEQUENCE: 76

```
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca caacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattgatt cagccattac cgcccttggc aatacggtaa ccaatctgaa ctccgcgcgt   660
agccgtatcg aagatgctga ctatgcaacg gaagtttcta atatgtctaa agcgcagatt   720
```

```
ctgcagcagg ctggtctggt tccgcggggt tctcatcatc atcatcatca tggttaagtc    780
gac                                                                  783
```

<210> SEQ ID NO 77
<211> LENGTH: 229
<212> TYPE: PRT
<213> ORGANISM: Artificial Sequence
<220> FEATURE:
<223> OTHER INFORMATION: Synthetic sequence

<400> SEQUENCE: 77

```
Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Asp Ser Ala
                165                 170                 175

Ile Thr Ala Leu Gly Asn Thr Val Thr Asn Leu Asn Ser Ala Arg Ser
            180                 185                 190

Arg Ile Glu Asp Ala Asp Tyr Ala Thr Glu Val Ser Asn Met Ser Lys
        195                 200                 205

Ala Gln Ile Leu Gln Gln Ala Gly Leu Val Pro Arg Gly Ser His His
    210                 215                 220

His His His His Gly
225
```

<210> SEQ ID NO 78
<211> LENGTH: 654
<212> TYPE: DNA
<213> ORGANISM: Artificial Sequence
<220> FEATURE:
<223> OTHER INFORMATION: Synthetic sequence

<400> SEQUENCE: 78

```
atgagcgggt tacgcgatcaa cagcgcgaaa gacgatgcgg caggccaggc gattgctaac     60
cgcttcactt ctaatatcaa aggtctgact caggcttccc gtaacgctaa cgacggcatt    120
tctattgcgc agaccactga aggtgcgctg aatgaaatca acaacaacct gcagcgtgtg    180
cgtgagttgt ctgttcaggc cactaacggg actaactctg attccgatct gaatctatc    240 caggatgaaa ttcagcaacg tctggaagaa atcgatcgcg tttctaatca gactcaattt    300
```

```
aacggtgtta aagtcctgtc tcaggacaac cagatgaaaa tccaggttgg tgctaacgat      360
ggtgaaacca ttaccatcga tctgcaaaaa attgatgtga aaagccttgg ccttgatggg      420
ttcaatgtta attccccggg aagtaccgct aacccactgg cttcaattga ttctgcattg      480
tcaaaagtgg acgcagttcg ttcttctctg ggggcaattc aaaaccgctt tgattcagcc      540
attaccaacc ttggcaatac ggtaaccaat ctgaactccg cgcgtagccg tatcgaagat      600
gctgactatg cactggttcc gcggggttct catcatcatc atcatcatgg ttaa            654
```

<210> SEQ ID NO 79
<211> LENGTH: 217
<212> TYPE: PRT
<213> ORGANISM: Artificial Sequence
<220> FEATURE:
<223> OTHER INFORMATION: Synthetic sequence

<400> SEQUENCE: 79

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Leu Val Pro Arg
        195                 200                 205

Gly Ser His His His His His His Gly
    210                 215
```

<210> SEQ ID NO 80
<211> LENGTH: 714
<212> TYPE: DNA
<213> ORGANISM: Artificial Sequence
<220> FEATURE:
<223> OTHER INFORMATION: Synthetic sequence

<400> SEQUENCE: 80

```
atgagtaaag gagaagaact tttcactgga gttgtcccaa ttcttgttga attagatggt       60
gatgttaatg ggcacaaatt ttctgtcagt ggagagggtg aaggtgatgc aacatacgga      120
```

| | |
|---|---|
| aaacttaccc ttaaatttat ttgcactact ggaaaactac ctgttccatg ccaacactt | 180 |
| gtcactactc tgacgtatgg tgttcaatgc ttttcccgtt atccggatca tatgaaacgg | 240 |
| catgactttt tcaagagtgc catgcccgaa ggttatgtac aggaacgcac tatatctttc | 300 |
| aaagatgacg ggaactacaa gacgcgtgct gaagtcaagt ttgaaggtga tacccttgtt | 360 |
| aatcgtatcg agttaaaagg tattgatttt aaagaagatg aaacattct cggacacaaa | 420 |
| ctcgagtaca actataactc acacaatgta tacatcacgg cagacaaaca aaagaatgga | 480 |
| atcaaagcta acttcaaaat tcgccacaac attgaagatg gatccgttca actagcagac | 540 |
| cattatcaac aaaatactcc aattggcgat ggccctgtcc ttttaccaga caaccattac | 600 |
| ctgtcgacac aatctgccct tttgaaagat cccaacgaaa agcgtgacca catggtcctt | 660 |
| cttgagtttg taactgctgc tgggattaca catggcatgg atgaactata caaa | 714 |

<210> SEQ ID NO 81
<211> LENGTH: 238
<212> TYPE: PRT
<213> ORGANISM: Artificial Sequence
<220> FEATURE:
<223> OTHER INFORMATION: Synthetic sequence

<400> SEQUENCE: 81

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Leu
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 82
<211> LENGTH: 717
<212> TYPE: DNA

<213> ORGANISM: Artificial Sequence
<220> FEATURE:
<223> OTHER INFORMATION: Synthetic sequence

<400> SEQUENCE: 82

```
atgagtaaag gagaagaact tttcactgga gttgtcccaa ttcttgttga attagatggt    60
gatgttaatg ggcacaaatt ttctgtcagt ggagagggtg aaggtgatgc aacatacgga   120
aaacttaccc ttaaatttat ttgcactact ggaaaactac ctgttccatg gccaacactt   180
gtcactactc tgacgtatgg tgttcaatgc ttttcccgtt atccggatca catgaaacgg   240
catgactttt tcaagagtgc catgcccgaa ggttatgtac aggaacgcac tatatctttc   300
aaagatgacg ggaactacaa gacgcgtgct gaagtcaagt ttgaaggtga tacccttgtt   360
aatcgtatcg agttaaaagg tattgatttt aaagaagatg gaaacattct cggacacaaa   420
ctcgagtaca actataactc acacaatgta tacatcacgg cagacaaaca aaagaatgga   480
atcaaagcta acttcaaaat tcgccacaac attgaagatg gatccgttca actagcagac   540
cattatcaac aaaatactcc aattggcgat ggccctgtcc ttttaccaga caaccattac   600
ctgtcgacac aatctgccct tttgaaagat cccaacgaaa agcgtgacca catggtcctt   660
cttgagtttg taactgctgc tgggattaca catggcatgg atgaactata caaataa     717
```

<210> SEQ ID NO 83
<211> LENGTH: 54
<212> TYPE: DNA
<213> ORGANISM: Artificial Sequence
<220> FEATURE:
<223> OTHER INFORMATION: Synthetic sequence

<400> SEQUENCE: 83

```
tctagacggc cgatctcagg taagaatgga atcaaagcta acttcaaaat tcgc          54
```

<210> SEQ ID NO 84
<211> LENGTH: 20
<212> TYPE: PRT
<213> ORGANISM: Artificial Sequence
<220> FEATURE:
<223> OTHER INFORMATION: Synthetic sequence

<400> SEQUENCE: 84

```
Asn Val Tyr Ile Pro Ile Ser Gly Lys Asn Gly Ile Lys Ala Asn Phe
1               5                   10                  15
Lys Ile Arg His
            20
```

<210> SEQ ID NO 85
<211> LENGTH: 45
<212> TYPE: DNA
<213> ORGANISM: Artificial Sequence
<220> FEATURE:
<223> OTHER INFORMATION: Synthetic sequence

<400> SEQUENCE: 85

```
agatctccgc ggtttgtata gttcatccat gccatgtgta atccc                     45
```

<210> SEQ ID NO 86
<211> LENGTH: 1005
<212> TYPE: DNA
<213> ORGANISM: Artificial Sequence
<220> FEATURE:
<223> OTHER INFORMATION: Synthetic sequence

<400> SEQUENCE: 86

```
taatacgact cactataggg gaattgtgag cggataacaa ttcccctcta gaataatttt      60
gtttaacttt aagaaggaga tatacatatg agcgggttac ggatcaacag cgcgaaagac     120
gatgcggcag gccaggcgat tgctaaccgc ttcacttcta atatcaaagg tctgactcag     180
gcttcccgta acgctaacga cggcatttct attgcgcaga ccactgaagg tgcgctgaat     240
gaaatcaaca acaacctgca gcgtgtgcgt gagttgtctg ttcaggccac taacgggact     300
aactctgatt ccgatctgaa atctatccag gatgaaattc agcaacgtct ggaagaaatc     360
gatcgcgttt ctaatcagac tcaatttaac ggtgttaaag tcctgtctca ggacaaccag     420
atgaaaatcc aggttggtgc taacgatggt gaaaccatta ccatcgatct gcaaaaaatt     480
gatgtgaaaa gccttggcct tgatgggttc aatgttaatt ccccgggaag taccgctaac     540
ccactggctt caattgattc tgcattgtca aagtggacg cagttcgttc ttctctgggg      600
gcaattcaaa accgctttga ttcagccatt accaaccttg caatacggt aaccaatctg      660
aactccgcgc gtagccgtat cgaagatgct gactatgcac tggttccgcc gatctcaggt     720
aagaatggaa tcaaagctaa cttcaaaatt cgccacaaca ttgaagatgg atccgttcaa     780
ctagcagacc attatcaaca aaatactcca attggcgatg ccctgtcct tttaccagac     840
aaccattacc tgtcgacaca atctgccctt tgaaagatc ccaacgaaaa gcgtgaccac     900
atggtccttc ttgagtttgt aactgctgct gggattacac atggcatgga tgaactatac     960
aaaccgcggg gttctcatca tcatcatcat catggttaag tcgac                   1005

<210> SEQ ID NO 87
<211> LENGTH: 912
<212> TYPE: DNA
<213> ORGANISM: Artificial Sequence
<220> FEATURE:
<223> OTHER INFORMATION: Synthetic sequence

<400> SEQUENCE: 87
atgagcgggt tacggatcaa cagcgcgaaa gacgatgcgg caggccaggc gattgctaac      60
cgcttcactt ctaatatcaa aggtctgact caggcttccc gtaacgctaa cgacggcatt     120
tctattgcgc agaccactga aggtgcgctg aatgaaatca acaacaacct gcagcgtgtg     180
cgtgagttgt ctgttcaggc cactaacggg actaactctg attccgatct gaaatctatc     240
caggatgaaa ttcagcaacg tctggaagaa atcgatcgcg tttctaatca gactcaattt     300
aacggtgtta aagtcctgtc tcaggacaac cagatgaaaa tccaggttgg tgctaacgat     360
ggtgaaacca ttaccatcga tctgcaaaaa attgatgtga aaagccttgg ccttgatggg     420
ttcaatgtta attccccggg aagtaccgct aacccactgg cttcaattga ttctgcattg     480
tcaaaagtgg acgcagttcg ttcttctctg gggcaattc aaaaccgctt tgattcagcc      540
attaccaacc ttgcaatac ggtaaccaat ctgaactccg cgcgtagccg tatcgaagat      600
gctgactatg cactggttcc gccgatctca ggtaagaatg gaatcaaagc taacttcaaa     660
attcgccaca acattgaaga tggatccgtt caactagcag accattatca acaaaatact     720
ccaattggcg atggccctgt ccttttacca gacaaccatt acctgtcgac acaatctgcc     780
cttttgaaag atcccaacga aaagcgtgac cacatggtcc ttcttgagtt tgtaactgct     840
gctgggatta cacatggcat ggatgaacta tacaaaccgc ggggttctca tcatcatcat     900
catcatggtt aa                                                        912

<210> SEQ ID NO 88
```

<211> LENGTH: 303
<212> TYPE: PRT
<213> ORGANISM: Artificial Sequence
<220> FEATURE:
<223> OTHER INFORMATION: Synthetic sequence

<400> SEQUENCE: 88

```
Met Ser Gly Leu Arg Ile Asn Ser Ala Lys Asp Asp Ala Ala Gly Gln
1               5                   10                  15
Ala Ile Ala Asn Arg Phe Thr Ser Asn Ile Lys Gly Leu Thr Gln Ala
            20                  25                  30
Ser Arg Asn Ala Asn Asp Gly Ile Ser Ile Ala Gln Thr Thr Glu Gly
        35                  40                  45
Ala Leu Asn Glu Ile Asn Asn Asn Leu Gln Arg Val Arg Glu Leu Ser
    50                  55                  60
Val Gln Ala Thr Asn Gly Thr Asn Ser Asp Ser Asp Leu Lys Ser Ile
65                  70                  75                  80
Gln Asp Glu Ile Gln Gln Arg Leu Glu Glu Ile Asp Arg Val Ser Asn
                85                  90                  95
Gln Thr Gln Phe Asn Gly Val Lys Val Leu Ser Gln Asp Asn Gln Met
            100                 105                 110
Lys Ile Gln Val Gly Ala Asn Asp Gly Glu Thr Ile Thr Ile Asp Leu
        115                 120                 125
Gln Lys Ile Asp Val Lys Ser Leu Gly Leu Asp Gly Phe Asn Val Asn
    130                 135                 140
Ser Pro Gly Ser Thr Ala Asn Pro Leu Ala Ser Ile Asp Ser Ala Leu
145                 150                 155                 160
Ser Lys Val Asp Ala Val Arg Ser Ser Leu Gly Ala Ile Gln Asn Arg
                165                 170                 175
Phe Asp Ser Ala Ile Thr Asn Leu Gly Asn Thr Val Thr Asn Leu Asn
            180                 185                 190
Ser Ala Arg Ser Arg Ile Glu Asp Ala Asp Tyr Ala Leu Val Pro Pro
        195                 200                 205
Ile Ser Gly Lys Asn Gly Ile Lys Ala Asn Phe Lys Ile Arg His Asn
    210                 215                 220
Ile Glu Asp Gly Ser Val Gln Leu Ala Asp His Tyr Gln Gln Asn Thr
225                 230                 235                 240
Pro Ile Gly Asp Gly Pro Val Leu Leu Pro Asp Asn His Tyr Leu Ser
                245                 250                 255
Thr Gln Ser Ala Leu Leu Lys Asp Pro Asn Glu Lys Arg Asp His Met
            260                 265                 270
Val Leu Leu Glu Phe Val Thr Ala Ala Gly Ile Thr His Gly Met Asp
        275                 280                 285
Glu Leu Tyr Lys Pro Arg Gly Ser His His His His His Gly
    290                 295                 300
```

<210> SEQ ID NO 89
<211> LENGTH: 585
<212> TYPE: DNA
<213> ORGANISM: Artificial Sequence
<220> FEATURE:
<223> OTHER INFORMATION: Synthetic sequence

<400> SEQUENCE: 89
atgagtaccg ctaacccact ggcttcaatt gattctgcat tgtcaaaagt ggacgcagtt      60
cgttcttctc tgggggcaat tcaaaaccgc tttgattcag ccattaccaa ccttggcaat     120

| | | |
|---|---|---|
| acggtaacca atctgaactc cgcgcgtagc cgtatcgaag atgctgacta tgcatccccg | 180 | |
| ggaagcgggt tacggatcaa cagcgcgaaa gacgatgcgg caggccaggc gattgctaac | 240 | |
| cgcttcactt ctaatatcaa aggtctgact caggcttccc gtaacgctaa cgacggcatt | 300 | |
| tctattgcgc agaccactga aggtgcgctg aatgaaatca acaacaacct gcagcgtgtg | 360 | |
| cgtgagttgt ctgttcaggc cactaacggg actaactctg attccgatct gaaatctatc | 420 | |
| caggatgaaa ttcagcaacg tctggaagaa atcgatcgcg tttctaatca gactcaattt | 480 | |
| aacggtgtta aagtcctgtc tcaggacaac cagatgaaaa tccaggttgg tgctaacgat | 540 | |
| ggtctggttc cgcggggttc tcatcatcat catcatcatg gttaa | 585 | |

<210> SEQ ID NO 90
<211> LENGTH: 194
<212> TYPE: PRT
<213> ORGANISM: Artificial Sequence
<220> FEATURE:
<223> OTHER INFORMATION: Synthetic sequence

<400> SEQUENCE: 90

Met Ser Thr Ala Asn Pro Leu Ala Ser Ile Asp Ser Ala Leu Ser Lys
1               5                   10                  15

Val Asp Ala Val Arg Ser Ser Leu Gly Ala Ile Gln Asn Arg Phe Asp
            20                  25                  30

Ser Ala Ile Thr Asn Leu Gly Asn Thr Val Thr Asn Leu Asn Ser Ala
        35                  40                  45

Arg Ser Arg Ile Glu Asp Ala Asp Tyr Ala Ser Pro Gly Ser Gly Leu
    50                  55                  60

Arg Ile Asn Ser Ala Lys Asp Asp Ala Ala Gly Gln Ala Ile Ala Asn
65                  70                  75                  80

Arg Phe Thr Ser Asn Ile Lys Gly Leu Thr Gln Ala Ser Arg Asn Ala
                85                  90                  95

Asn Asp Gly Ile Ser Ile Ala Gln Thr Thr Glu Gly Ala Leu Asn Glu
            100                 105                 110

Ile Asn Asn Asn Leu Gln Arg Val Arg Glu Leu Ser Val Gln Ala Thr
        115                 120                 125

Asn Gly Thr Asn Ser Asp Ser Asp Leu Lys Ser Ile Gln Asp Glu Ile
    130                 135                 140

Gln Gln Arg Leu Glu Glu Ile Asp Arg Val Ser Asn Gln Thr Gln Phe
145                 150                 155                 160

Asn Gly Val Lys Val Leu Ser Gln Asp Asn Gln Met Lys Ile Gln Val
                165                 170                 175

Gly Ala Asn Asp Gly Leu Val Pro Arg Gly Ser His His His His
            180                 185                 190

His Gly

<210> SEQ ID NO 91
<211> LENGTH: 678
<212> TYPE: DNA
<213> ORGANISM: Artificial Sequence
<220> FEATURE:
<223> OTHER INFORMATION: Synthetic sequence

<400> SEQUENCE: 91

| | | |
|---|---|---|
| taatacgact cactataggg gaattgtgag cggataacaa ttcccctcta gaataatttt | 60 | |
| gtttaacttt aagaaggaga tatacatatg agtaccgcta acccactggc ttcaattgat | 120 | |
| tctgcattgt caaaagtgga cgcagttcgt tcttctctgg gggcaattca aaaccgcttt | 180 | |

```
gattcagcca ttaccaacct tggcaatacg gtaaccaatc tgaactccgc gcgtagccgt    240
atcgaagatg ctgactatgc atccccggga agcgggttac ggatcaacag cgcgaaagac    300
gatgcggcag gccaggcgat tgctaaccgc ttcacttcta atatcaaagg tctgactcag    360
gcttcccgta acgctaacga cggcatttct attgcgcaga ccactgaagg tgcgctgaat    420
gaaatcaaca caacctgca gcgtgtgcgt gagttgtctg ttcaggccac taacgggact    480
aactctgatt ccgatctgaa atctatccag atgaaattc agcaacgtct ggaagaaatc    540
gatcgcgttt ctaatcagac tcaatttaac ggtgttaaag tcctgtctca ggacaaccag    600
atgaaaatcc aggttggtgc taacgatggt ctggttccgc ggggttctca tcatcatcat    660
catcatggtt aagtcgac                                                  678

<210> SEQ ID NO 92
<211> LENGTH: 40
<212> TYPE: DNA
<213> ORGANISM: Artificial Sequence
<220> FEATURE:
<223> OTHER INFORMATION: Synthetic sequence

<400> SEQUENCE: 92
tctagacata tgagtaccgc taacccactg gcttcaattg                          40

<210> SEQ ID NO 93
<211> LENGTH: 38
<212> TYPE: DNA
<213> ORGANISM: Artificial Sequence
<220> FEATURE:
<223> OTHER INFORMATION: Synthetic sequence

<400> SEQUENCE: 93
gcttcccggg gatgcatagt cagcatcttc gatacggc                            38

<210> SEQ ID NO 94
<211> LENGTH: 34
<212> TYPE: DNA
<213> ORGANISM: Artificial Sequence
<220> FEATURE:
<223> OTHER INFORMATION: Synthetic sequence

<400> SEQUENCE: 94
gcatccccgg gaagcgggtt acggatcaac agcg                                34

<210> SEQ ID NO 95
<211> LENGTH: 50
<212> TYPE: DNA
<213> ORGANISM: Artificial Sequence
<220> FEATURE:
<223> OTHER INFORMATION: Synthetic sequence

<400> SEQUENCE: 95
agatctccgc ggaaccagac catcgttagc accaacctgg attttcatct                50

<210> SEQ ID NO 96
<211> LENGTH: 654
<212> TYPE: DNA
<213> ORGANISM: Artificial Sequence
<220> FEATURE:
<223> OTHER INFORMATION: Synthetic sequence

<400> SEQUENCE: 96
atgagtaccg ctaacccact ggcttcaatt gattctgcat tgtcaaaagt ggacgcagtt    60
```

```
cgttcttctc tgggggcaat tcaaaaccgc tttgattcag ccattaccaa ccttggcaat      120
acggtaacca atctgaactc cgcgcgtagc cgtatcgaag atgctgacta tgcatccccg      180
ggaagcgggt tacggatcaa cagcgcgaaa gacgatgcgg caggccaggc gattgctaac      240
cgcttcactt ctaatatcaa aggtctgact caggcttccc gtaacgctaa cgacggcatt      300
tctattgcgc agaccactga aggtgcgctg aatgaaatca caacaacct gcagcgtgtg       360 cgtgagttgt ctgttcaggc cactaacggg actaactctg attccgatct gaaatctatc     420
caggatgaaa ttcagcaacg tctggaagaa atcgatcgcg tttctaatca gactcaattt     480
aacggtgtta aagtcctgtc tcaggacaac cagatgaaaa tccaggttgg tgctaacgat     540
ggtgaaacca ttaccatcga tctgcaaaaa attgatgtga aaagccttgg ccttgatggg     600
ttcaatgtta atctggttcc gcggggttct catcatcatc atcatcatgg ttaa           654
```

<210> SEQ ID NO 97
<211> LENGTH: 217
<212> TYPE: PRT
<213> ORGANISM: Artificial Sequence
<220> FEATURE:
<223> OTHER INFORMATION: Synthetic sequence

<400> SEQUENCE: 97

```
Met Ser Thr Ala Asn Pro Leu Ala Ser Ile Asp Ser Ala Leu Ser Lys
1               5                   10                  15

Val Asp Ala Val Arg Ser Ser Leu Gly Ala Ile Gln Asn Arg Phe Asp
            20                  25                  30

Ser Ala Ile Thr Asn Leu Gly Asn Thr Val Thr Asn Leu Asn Ser Ala
        35                  40                  45

Arg Ser Arg Ile Glu Asp Ala Asp Tyr Ala Ser Pro Gly Ser Gly Leu
    50                  55                  60

Arg Ile Asn Ser Ala Lys Asp Asp Ala Ala Gly Gln Ala Ile Ala Asn
65                  70                  75                  80

Arg Phe Thr Ser Asn Ile Lys Gly Leu Thr Gln Ala Ser Arg Asn Ala
                85                  90                  95

Asn Asp Gly Ile Ser Ile Ala Gln Thr Thr Glu Gly Ala Leu Asn Glu
            100                 105                 110

Ile Asn Asn Asn Leu Gln Arg Val Arg Glu Leu Ser Val Gln Ala Thr
        115                 120                 125

Asn Gly Thr Asn Ser Asp Ser Asp Leu Lys Ser Ile Gln Asp Glu Ile
    130                 135                 140

Gln Gln Arg Leu Glu Glu Ile Asp Arg Val Ser Asn Gln Thr Gln Phe
145                 150                 155                 160

Asn Gly Val Lys Val Leu Ser Gln Asp Asn Gln Met Lys Ile Gln Val
                165                 170                 175

Gly Ala Asn Asp Gly Glu Thr Ile Thr Ile Asp Leu Gln Lys Ile Asp
            180                 185                 190

Val Lys Ser Leu Gly Leu Asp Gly Phe Asn Val Asn Leu Val Pro Arg
        195                 200                 205

Gly Ser His His His His His His Gly
    210                 215
```

<210> SEQ ID NO 98
<211> LENGTH: 747
<212> TYPE: DNA
<213> ORGANISM: Artificial Sequence
<220> FEATURE:
<223> OTHER INFORMATION: Synthetic sequence

<400> SEQUENCE: 98

```
taatacgact cactataggg gaattgtgag cggataacaa ttcccctcta gaataatttt    60
gtttaacttt aagaaggaga tatacatatg agtaccgcta acccactggc ttcaattgat   120
tctgcattgt caaaagtgga cgcagttcgt tcttctctgg gggcaattca aaaccgcttt   180
gattcagcca ttaccaacct tggcaatacg gtaaccaatc tgaactccgc gcgtagccgt   240
atcgaagatg ctgactatgc atccccggga agcgggttac ggatcaacag cgcgaaagac   300
gatgcggcag gccaggcgat tgctaaccgc ttcacttcta atatcaaagg tctgactcag   360
gcttcccgta acgctaacga cggcatttct attgcgcaga ccactgaagg tgcgctgaat   420
gaaatcaaca acaacctgca gcgtgtgcgt gagttgtctg ttcaggccac taacgggact   480
aactctgatt ccgatctgaa atctatccag gatgaaattc agcaacgtct ggaagaaatc   540
gatcgcgttt ctaatcagac tcaatttaac ggtgttaaag tcctgtctca ggacaaccag   600
atgaaaatcc aggttggtgc taacgatggt gaaaccatta ccatcgatct gcaaaaaatt   660
gatgtgaaaa gccttggcct tgatgggttc aatgttaatc tggttccgcg gggttctcat   720
catcatcatc atcatggtta agtcgac                                       747
```

<210> SEQ ID NO 99
<211> LENGTH: 45
<212> TYPE: DNA
<213> ORGANISM: Artificial Sequence
<220> FEATURE:
<223> OTHER INFORMATION: Synthetic sequence

<400> SEQUENCE: 99

```
agatctccgc ggaaccagat taacattgaa cccatcaagg ccaag                    45
```

<210> SEQ ID NO 100
<211> LENGTH: 38
<212> TYPE: DNA
<213> ORGANISM: Artificial Sequence
<220> FEATURE:
<223> OTHER INFORMATION: Synthetic sequence

<400> SEQUENCE: 100

```
cccgttatcc ggatcacatg aaacggcatg acttttc                             38
```

<210> SEQ ID NO 101
<211> LENGTH: 38
<212> TYPE: DNA
<213> ORGANISM: Artificial Sequence
<220> FEATURE:
<223> OTHER INFORMATION: Synthetic sequence

<400> SEQUENCE: 101

```
gaaaaagtca tgccgtttca tgtgatccgg ataacggg                            38
```

<210> SEQ ID NO 102
<211> LENGTH: 21
<212> TYPE: DNA
<213> ORGANISM: Artificial Sequence
<220> FEATURE:
<223> OTHER INFORMATION: Synthetic sequence

<400> SEQUENCE: 102

```
ctgttccatg gccaacactt g                                              21
```

<210> SEQ ID NO 103

<211> LENGTH: 46
<212> TYPE: DNA
<213> ORGANISM: Artificial Sequence
<220> FEATURE:
<223> OTHER INFORMATION: Synthetic sequence

<400> SEQUENCE: 103
tctagacata tgagtaaagg agaagaactt ttcactggag ttgtcc           46

<210> SEQ ID NO 104
<211> LENGTH: 63
<212> TYPE: DNA
<213> ORGANISM: Artificial Sequence
<220> FEATURE:
<223> OTHER INFORMATION: Synthetic sequence

<400> SEQUENCE: 104
ggcctatgcg gccgcagtaa aggagaagaa cttttcactg gagttgtccc aattcttgtt     60
gaa                                                                   63

<210> SEQ ID NO 105
<211> LENGTH: 57
<212> TYPE: DNA
<213> ORGANISM: Artificial Sequence
<220> FEATURE:
<223> OTHER INFORMATION: Synthetic sequence

<400> SEQUENCE: 105
agatctatta atgcggcctg ataggccttg tttgtctgcc gtgatgtata cattgtg       57

<210> SEQ ID NO 106
<211> LENGTH: 18
<212> TYPE: PRT
<213> ORGANISM: Artificial Sequence
<220> FEATURE:
<223> OTHER INFORMATION: Synthetic sequence

<400> SEQUENCE: 106

Ser His Asn Val Tyr Ile Thr Ala Asp Lys Gln Gly Leu Ser Gly Arg
1               5                   10                  15

Asn Met

<210> SEQ ID NO 107
<211> LENGTH: 1494
<212> TYPE: DNA
<213> ORGANISM: Artificial Sequence
<220> FEATURE:
<223> OTHER INFORMATION: Synthetic sequence

<400> SEQUENCE: 107
taatacgact cactataggg gaattgtgag cggataacaa ttcccctcta gaataatttt     60
gtttaacttt aagaaggaga tatacatatg agtaaaggag aagaactttt cactggagtt    120
gtcccaattc ttgttgaatt agatggtgat gttaatgggc acaaattttc tgtcagtgga    180
gagggtgaag gtgatgcaac atacggaaaa cttaccctta aatttatttg cactactgga    240
aaactacctg ttccatggcc aacacttgtc actactctga cgtatggtgt tcaatgcttt    300
tcccgttatc cggatcacat gaaacggcat gactttttca agagtgccat gcccgaaggt    360
tatgtacagg aacgcactat atctttcaaa gatgacggga actacaagac gcgtgctgaa    420
gtcaagtttg aaggtgatac ccttgttaat cgtatcgagt taaaaggtat tgattttaaa    480
gaagatggaa acattctcgg acacaaactc gagtacaact ataactcaca caatgtatac    540

```
atcacggcag acaaacaagg cctatcaggc cgcattatga gcgggttacg gatcaacagc      600
gcgaaagacg atgcggcagg ccaggcgatt gctaaccgct tcacttctaa tatcaaaggt      660
ctgactcagg cttcccgtaa cgctaacgac ggcatttcta ttgcgcagac cactgaaggt      720
gcgctgaatg aaatcaacaa caacctgcag cgtgtgcgtg agttgtctgt tcaggccact      780
aacgggacta actctgattc cgatctgaaa tctatccagg atgaaattca gcaacgtctg      840
gaagaaatcg atcgcgtttc taatcagact caatttaacg gtgttaaagt cctgtctcag      900
gacaaccaga tgaaaatcca ggttggtgct aacgatggtg aaaccattac catcgatctg      960
caaaaaattg atgtgaaaag ccttggcctt gatgggttca atgttaattc cccgggaagt     1020
accgctaacc cactggcttc aattgattct gcattgtcaa agtggacgc agttcgttct      1080 tctctggggg caattcaaaa ccgctttgat tcagccatta ccaaccttgg caatacggta     1140
accaatctga actccgcgcg tagccgtatc gaagatgctg actatgcact ggttccgccg     1200
atctcaggta agaatggaat caaagctaac ttcaaaattc gccacaacat gaagatggaa     1260
tccgttcaac tagcagacca ttatcaacaa atactccaa ttggcgatgg ccctgtcctt      1320
ttaccagaca accattacct gtcgacacaa tctgcccttt tgaaagatcc caacgaaaag     1380
cgtgaccaca tggtccttct tgagtttgta actgctgctg ggattacaca tggcatggat     1440
gaactataca aaccgcgggg ttctcatcat catcatcatc atggttaagt cgac           1494
```

<210> SEQ ID NO 108
<211> LENGTH: 1401
<212> TYPE: DNA
<213> ORGANISM: Artificial Sequence
<220> FEATURE:
<223> OTHER INFORMATION: Synthetic sequence

<400> SEQUENCE: 108

```
atgagtaaag gagaagaact tttcactgga gttgtcccaa ttcttgttga attagatggt       60
gatgttaatg ggcacaaatt ttctgtcagt ggagagggtg aaggtgatgc aacatacgga      120
aaacttaccc ttaaatttat ttgcactact ggaaaactac ctgttccatg gccaacactt      180
gtcactactc tgacgtatgg tgttcaatgc ttttcccgtt atccggatca catgaaacgg      240
catgactttt tcaagagtgc catgcccgaa ggttatgtac aggaacgcac tatatctttc      300
aaagatgacg ggaactacaa gacgcgtgct gaagtcaagt ttgaaggtga tacccttgtt      360
aatcgtatcg agttaaaagg tattgatttt aaagaagatg gaaacattct cggacacaaa      420
ctcgagtaca actataactc acacaatgta tacatcacgg cagacaaaca aggcctatca      480
ggccgcatta tgagcgggtt acggatcaac agcgcgaaag acgatgcggc aggccaggcg      540
attgctaacc gcttcacttc taatatcaaa ggtctgactc aggcttcccg taacgctaac      600
gacggcattt ctattgcgca gaccactgaa ggtgcgctga atgaaatcaa caacaacctg      660
cagcgtgtgc gtgagttgtc tgttcaggcc actaacggga ctaactctga ttccgatctg      720
aaatctatcc aggatgaaat tcagcaacgt ctggaagaaa tcgatcgcgt ttctaatcag      780
actcaattta cggtgttaa agtcctgtct caggacaacc agatgaaaat ccaggttggt      840
gctaacgatg gtgaaaccat taccatcgat ctgcaaaaaa ttgatgtgaa aagccttggc      900
cttgatgggt tcaatgttaa ttccccggga agtaccgcta acccactggc ttcaattgat      960
tctgcattgt caaagtgga cgcagttcgt tcttctctgg gggcaattca aaaccgcttt     1020
gattcagcca ttaccaacct tggcaatacg gtaaccaatc tgaactccgc gcgtagccgt     1080
atcgaagatg ctgactatgc actggttccg ccgatctcag gtaagaatgg aatcaaagct     1140
```

```
aacttcaaaa ttcgccacaa cattgaagat ggatccgttc aactagcaga ccattatcaa   1200
caaaatactc caattggcga tggccctgtc cttttaccag acaaccatta cctgtcgaca   1260
caatctgccc ttttgaaaga tcccaacgaa aagcgtgacc acatggtcct tcttgagttt   1320
gtaactgctg ctgggattac acatggcatg gatgaactat acaaaccgcg gggttctcat   1380
catcatcatc atcatggtta a                                            1401
```

<210> SEQ ID NO 109
<211> LENGTH: 466
<212> TYPE: PRT
<213> ORGANISM: Artificial Sequence
<220> FEATURE:
<223> OTHER INFORMATION: Synthetic sequence

<400> SEQUENCE: 109

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Gly Leu Ser
145                 150                 155                 160

Gly Arg Ile Met Ser Gly Leu Arg Ile Asn Ser Ala Lys Asp Asp Ala
                165                 170                 175

Ala Gly Gln Ala Ile Ala Asn Arg Phe Thr Ser Asn Ile Lys Gly Leu
            180                 185                 190

Thr Gln Ala Ser Arg Asn Ala Asn Asp Gly Ile Ser Ile Ala Gln Thr
        195                 200                 205

Thr Glu Gly Ala Leu Asn Glu Ile Asn Asn Asn Leu Gln Arg Val Arg
    210                 215                 220

Glu Leu Ser Val Gln Ala Thr Asn Gly Thr Asn Ser Asp Ser Asp Leu
225                 230                 235                 240

Lys Ser Ile Gln Asp Glu Ile Gln Gln Arg Leu Glu Glu Ile Asp Arg
                245                 250                 255

Val Ser Asn Gln Thr Gln Phe Asn Gly Val Lys Val Leu Ser Gln Asp
            260                 265                 270

Asn Gln Met Lys Ile Gln Val Gly Ala Asn Asp Gly Glu Thr Ile Thr
        275                 280                 285

Ile Asp Leu Gln Lys Ile Asp Val Lys Ser Leu Gly Leu Asp Gly Phe
    290                 295                 300

Asn Val Asn Ser Pro Gly Ser Thr Ala Asn Pro Leu Ala Ser Ile Asp
```

```
            305                 310                 315                 320
Ser Ala Leu Ser Lys Val Asp Ala Val Arg Ser Ser Leu Gly Ala Ile
                325                 330                 335

Gln Asn Arg Phe Asp Ser Ala Ile Thr Asn Leu Gly Asn Thr Val Thr
            340                 345                 350

Asn Leu Asn Ser Ala Arg Ser Arg Ile Glu Asp Ala Asp Tyr Ala Leu
        355                 360                 365

Val Pro Pro Ile Ser Gly Lys Asn Gly Ile Lys Ala Asn Phe Lys Ile
    370                 375                 380

Arg His Asn Ile Glu Asp Gly Ser Val Gln Leu Ala Asp His Tyr Gln
385                 390                 395                 400

Gln Asn Thr Pro Ile Gly Asp Gly Pro Val Leu Leu Pro Asp Asn His
            405                 410                 415

Tyr Leu Ser Thr Gln Ser Ala Leu Leu Lys Asp Pro Asn Glu Lys Arg
        420                 425                 430

Asp His Met Val Leu Leu Glu Phe Val Thr Ala Ala Gly Ile Thr His
    435                 440                 445

Gly Met Asp Glu Leu Tyr Lys Pro Arg Gly Ser His His His His
    450                 455                 460

His Gly
465

<210> SEQ ID NO 110
<211> LENGTH: 124
<212> TYPE: DNA
<213> ORGANISM: Artificial Sequence
<220> FEATURE:
<223> OTHER INFORMATION: Synthetic sequence

<400> SEQUENCE: 110
cttggccttg atgggttcaa tgttaattcc ccgggaattt ccggtggtgg tggtggaatt     60
acattaatca tgaagacgc tgccgcagcc aagaaaagta ccgctaaccc actggcttca    120
attg                                                                124

<210> SEQ ID NO 111
<211> LENGTH: 41
<212> TYPE: PRT
<213> ORGANISM: Artificial Sequence
<220> FEATURE:
<223> OTHER INFORMATION: Synthetic sequence

<400> SEQUENCE: 111

Leu Gly Leu Asp Gly Phe Asn Val Asn Ser Pro Gly Ile Ser Gly Gly
1               5                   10                  15

Gly Gly Gly Ile Thr Leu Ile Asn Glu Asp Ala Ala Ala Lys Lys
            20                  25                  30

Ser Thr Ala Asn Pro Leu Ala Ser Ile
        35                  40

<210> SEQ ID NO 112
<211> LENGTH: 72
<212> TYPE: DNA
<213> ORGANISM: Artificial Sequence
<220> FEATURE:
<223> OTHER INFORMATION: Synthetic sequence

<400> SEQUENCE: 112
agatctccgc ggaaccagta aagagaggac gttttgcgga acctggtttg catagtcagc     60
```
atcttcgata cg                                                           72

<210> SEQ ID NO 113
<211> LENGTH: 777
<212> TYPE: DNA
<213> ORGANISM: Artificial Sequence
<220> FEATURE:
<223> OTHER INFORMATION: Synthetic sequence

<400> SEQUENCE: 113
taatacgact cactataggg gaattgtgag cggataacaa ttcccctcta gaataatttt     60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
gaaatcaaca acaacctgca gcgtgtgcgt gagttgtctg ttcaggccac taacgggact    300
aactctgatt ccgatctgaa atctatccag gatgaaattc agcaacgtct ggaagaaatc    360
gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgttttga ttcagccatt accaacttg gcaatacggt aaccaatctg     660
aactccgcgc gtagccgtat cgaagatgct gactatgcaa accaggttcc gcaaaacgtc    720
ctctctttac tggttccgcg gggttctcat catcatcatc atcatggtta agtcgac        777

<210> SEQ ID NO 114
<211> LENGTH: 684
<212> TYPE: DNA
<213> ORGANISM: Artificial Sequence
<220> FEATURE:
<223> OTHER INFORMATION: Synthetic sequence

<400> SEQUENCE: 114
atgagcgggt tacggatcaa cagcgcgaaa gacgatgcgg caggccaggc gattgctaac     60
cgcttcactt ctaatatcaa aggtctgact caggcttccc gtaacgctaa cgacggcatt    120
tctattgcgc agaccactga aggtgcgctg aatgaaatca acaacaacct gcagcgtgtg    180
cgtgagttgt ctgttcaggc cactaacggg actaactctg attccgatct gaaatctatc    240
caggatgaaa ttcagcaacg tctggaagaa atcgatcgcg tttctaatca gactcaattt    300
aacggtgtta aagtcctgtc tcaggacaac cagatgaaaa tccaggttgg tgctaacgat    360
ggtgaaacca ttaccatcga tctgcaaaaa attgatgtga aaagccttgg ccttgatggg    420
ttcaatgtta attccccggg aagtaccgct aacccactgg cttcaattga ttctgcattg    480
tcaaaagtgg acgcagttcg ttcttctctg ggggcaattc aaaaccgttt tgattcagcc    540
attaccaacc ttggcaatac ggtaaccaat ctgaactccg cgcgtagccg tatcgaagat    600
gctgactatg caaaccaggt tccgcaaaac gtcctctctt tactggttcc gcggggttct    660
catcatcatc atcatcatgg ttaa                                           684

<210> SEQ ID NO 115
<211> LENGTH: 227
<212> TYPE: PRT
<213> ORGANISM: Artificial Sequence
<220> FEATURE:
<223> OTHER INFORMATION: Synthetic sequence

<400> SEQUENCE: 115

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Asn Gln Val Pro
        195                 200                 205

Gln Asn Val Leu Ser Leu Leu Val Pro Arg Gly Ser His His His
    210                 215                 220

His His Gly
225

<210> SEQ ID NO 116
<211> LENGTH: 42
<212> TYPE: DNA
<213> ORGANISM: Artificial Sequence
<220> FEATURE:
<223> OTHER INFORMATION: Synthetic sequence

<400> SEQUENCE: 116
agatctcccg gggaaccatc gttagcacca acctggattt tc                          42

<210> SEQ ID NO 117
<211> LENGTH: 777
<212> TYPE: DNA
<213> ORGANISM: Artificial Sequence
<220> FEATURE:
<223> OTHER INFORMATION: Synthetic sequence

<400> SEQUENCE: 117
taatacgact cactataggg gaattgtgag cggataacaa ttcccctcta gaataatttt      60
gtttaacttt aagaaggaga tatacatatg agcgggttac ggatcaacag cgcgaaagac     120
gatgcggcag gccaggcgat tgctaaccgc ttcacttcta atatcaaagg tctgactcag     180
gcttcccgta acgctaacga cggcatttct attgcgcaga ccactgaagg tgcgctgaat     240
gaaatcaaca acaacctgca gcgtgtgcgt gagttgtctg ttcaggccac taacgggact     300

```
aactctgatt ccgatctgaa atctatccag gatgaaattc agcaacgtct ggaagaaatc    360
gatcgcgttt ctaatcagac tcaatttaac ggtgttaaag tcctgtctca ggacaaccag    420
atgaaaatcc aggttggtgc taacgatggt tccccgggaa gtaccgctaa cccactggct    480
tcaattgatt ctgcattgtc aaaagtggac gcagttcgtt cttctctggg ggcaattcaa    540
aaccgctttg attcagccat taccaacctt ggcaatacgg taaccaatct gaactccgcg    600
cgtagccgta tcgaagatgc tgactatgca acggaagttt ctaatatgtc taaagcgcag    660
attctgcagc aggctggtac ttccgttctg gcgcaggcta accaggttcc gcaaaacgtc    720
ctctctttac tggttccgcg gggttctcat catcatcatc atcatggtta agtcgac      777
```

<210> SEQ ID NO 118
<211> LENGTH: 684
<212> TYPE: DNA
<213> ORGANISM: Artificial Sequence
<220> FEATURE:
<223> OTHER INFORMATION: Synthetic sequence

<400> SEQUENCE: 118

```
atgagcgggt tacggatcaa cagcgcgaaa gacgatgcgg caggccaggc gattgctaac     60
cgcttcactt ctaatatcaa aggtctgact caggcttccc gtaacgctaa cgacggcatt    120
tctattgcgc agaccactga aggtgcgctg aatgaaatca caacaaccct gcagcgtgtg    180
cgtgagttgt ctgttcaggc cactaacggg actaactctg attccgatct gaaatctatc    240
caggatgaaa ttcagcaacg tctggaagaa atcgatcgcg tttctaatca gactcaattt    300
aacggtgtta aagtcctgtc tcaggacaac cagatgaaaa tccaggttgg tgctaacgat    360
ggttccccgg gaagtaccgc taacccactg gcttcaattg attctgcatt gtcaaaagtg    420
gacgcagttc gttcttctct gggggcaatt caaaaccgct tgattcagc cattaccaac    480 cttggcaata cggtaaccaa tctgaactcc gcgcgtagcc gtatcgaaga tgctgactat    540
gcaacggaag tttctaatat gtctaaagcg cagattctgc agcaggctgg tacttccgtt    600
ctggcgcagg ctaaccaggt tccgcaaaac gtcctctctt tactggttcc gcggggttct    660
catcatcatc atcatcatgg ttaa                                            684
```

<210> SEQ ID NO 119
<211> LENGTH: 227
<212> TYPE: PRT
<213> ORGANISM: Artificial Sequence
<220> FEATURE:
<223> OTHER INFORMATION: Synthetic sequence

<400> SEQUENCE: 119

```
Met Ser Gly Leu Arg Ile Asn Ser Ala Lys Asp Asp Ala Ala Gly Gln
1               5                  10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95
```

```
Gln Thr Gln Phe Asn Gly Val Lys Val Leu Ser Gln Asp Asn Gln Met
            100                 105                 110
Lys Ile Gln Val Gly Ala Asn Asp Gly Ser Pro Gly Ser Thr Ala Asn
        115                 120                 125
Pro Leu Ala Ser Ile Asp Ser Ala Leu Ser Lys Val Asp Ala Val Arg
    130                 135                 140
Ser Ser Leu Gly Ala Ile Gln Asn Arg Phe Asp Ser Ala Ile Thr Asn
145                 150                 155                 160
Leu Gly Asn Thr Val Thr Asn Leu Asn Ser Ala Arg Ser Arg Ile Glu
                165                 170                 175
Asp Ala Asp Tyr Ala Thr Glu Val Ser Asn Met Ser Lys Ala Gln Ile
            180                 185                 190
Leu Gln Gln Ala Gly Thr Ser Val Leu Ala Gln Ala Asn Gln Val Pro
        195                 200                 205
Gln Asn Val Leu Ser Leu Leu Val Pro Arg Gly Ser His His His
    210                 215                 220
His His Gly
225

<210> SEQ ID NO 120
<211> LENGTH: 90
<212> TYPE: DNA
<213> ORGANISM: Artificial Sequence
<220> FEATURE:
<223> OTHER INFORMATION: Synthetic sequence

<400> SEQUENCE: 120
agatctccgc ggaaccagca ggttattctg ggtcaacagc gacaggctgt ttgtattaat    60
gacttgtgca tagtcagcat cttcgatacg                                    90

<210> SEQ ID NO 121
<211> LENGTH: 795
<212> TYPE: DNA
<213> ORGANISM: Artificial Sequence
<220> FEATURE:
<223> OTHER INFORMATION: Synthetic sequence

<400> SEQUENCE: 121
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag ccaggcgat tgctaaccgc ttcacttcta atatcaaagg tctgactcag   180
gcttcccgta acgctaacga cggcatttct attgcgcaga ccactgaagg tgcgctgaat   240
gaaatcaaca caacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaacttg gcaatacggt aaccaatctg   660
aactccgcgc gtagccgtat cgaagatgct gactatgcac aagtcattaa tacaaacagc   720
ctgtcgctgt tgacccagaa taacctgctg gttccgcggg gttctcatca tcatcatcat   780
catggttaag tcgac                                                   795
```

<210> SEQ ID NO 122
<211> LENGTH: 702
<212> TYPE: DNA
<213> ORGANISM: Artificial Sequence
<220> FEATURE:
<223> OTHER INFORMATION: Synthetic sequence

<400> SEQUENCE: 122

```
atgagcgggt tacggatcaa cagcgcgaaa gacgatgcgg caggccaggc gattgctaac      60
cgcttcactt ctaatatcaa aggtctgact caggcttccc gtaacgctaa cgacggcatt     120
tctattgcgc agaccactga aggtgcgctg aatgaaatca caacaacct gcagcgtgtg      180
cgtgagttgt ctgttcaggc cactaacggg actaactctg attccgatct gaaatctatc     240
caggatgaaa ttcagcaacg tctggaagaa atcgatcgcg tttctaatca gactcaattt     300
aacggtgtta aagtcctgtc tcaggacaac cagatgaaaa tccaggttgg tgctaacgat     360
ggtgaaacca ttaccatcga tctgcaaaaa attgatgtga aaagccttgg ccttgatggg     420
ttcaatgtta attccccggg aagtaccgct aacccactgg cttcaattga ttctgcattg     480
tcaaaagtgg acgcagttcg ttcttctctg ggggcaattc aaaaccgctt tgattcagcc     540
attaccaacc ttggcaatac ggtaaccaat ctgaactccg cgcgtagccg tatcgaagat     600
gctgactatg cacaagtcat taatacaaac agcctgtcgc tgttgaccca gaataacctg     660
ctggttccgc ggggttctca tcatcatcat catcatggtt aa                        702
```

<210> SEQ ID NO 123
<211> LENGTH: 233
<212> TYPE: PRT
<213> ORGANISM: Artificial Sequence
<220> FEATURE:
<223> OTHER INFORMATION: Synthetic sequence

<400> SEQUENCE: 123

```
Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190
```

Ser Ala Arg Ser Arg Ile Glu Asp Ala Asp Tyr Ala Gln Val Ile Asn
        195                 200                 205

Thr Asn Ser Leu Ser Leu Leu Thr Gln Asn Asn Leu Leu Val Pro Arg
    210                 215                 220

Gly Ser His His His His His His Gly
225                 230

<210> SEQ ID NO 124
<211> LENGTH: 49
<212> TYPE: DNA
<213> ORGANISM: Artificial Sequence
<220> FEATURE:
<223> OTHER INFORMATION: Synthetic sequence

<400> SEQUENCE: 124
gctgactatg caacggcagt ttctgctatg tctgcagcgc agattctgc          49

<210> SEQ ID NO 125
<211> LENGTH: 49
<212> TYPE: DNA
<213> ORGANISM: Artificial Sequence
<220> FEATURE:
<223> OTHER INFORMATION: Synthetic sequence

<400> SEQUENCE: 125
gcagaatctg cgctgcagac atagcagaaa ctgccgttgc atagtcagc          49

<210> SEQ ID NO 126
<211> LENGTH: 795
<212> TYPE: DNA
<213> ORGANISM: Artificial Sequence
<220> FEATURE:
<223> OTHER INFORMATION: Synthetic sequence

<400> SEQUENCE: 126
taatacgact cactataggg gaattgtgag cggataacaa ttcccctcta gaataatttt     60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
gaaatcaaca caaacctgca gcgtgtgcgt gagttgtctg ttcaggccac taacgggact    300
aactctgatt ccgatctgaa atctatccag gatgaaattc agcaacgtct ggaagaaatc    360
gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaacttg gcaatacggt aaccaatctg    660
aactccgcgc gtagccgtat cgaagatgct gactatgcaa cggcagtttc tgctatgtct    720
gcagcgcaga ttctgcagca ggctggtctg gttccgcggg gttctcatca tcatcatcat    780
catggttaag tcgac                                                   795

<210> SEQ ID NO 127
<211> LENGTH: 702
<212> TYPE: DNA
<213> ORGANISM: Artificial Sequence
<220> FEATURE:
<223> OTHER INFORMATION: Synthetic sequence

<400> SEQUENCE: 127

```
atgagcgggt tacggatcaa cagcgcgaaa gacgatgcgg caggccaggc gattgctaac      60
cgcttcactt ctaatatcaa aggtctgact caggcttccc gtaacgctaa cgacggcatt     120
tctattgcgc agaccactga aggtgcgctg aatgaaatca acaacaacct gcagcgtgtg     180
cgtgagttgt ctgttcaggc cactaacggg actaactctg attccgatct gaaatctatc     240
caggatgaaa ttcagcaacg tctggaagaa atcgatcgcg tttctaatca gactcaattt     300
aacggtgtta aagtcctgtc tcaggacaac cagatgaaaa tccaggttgg tgctaacgat     360
ggtgaaacca ttaccatcga tctgcaaaaa attgatgtga aaagccttgg ccttgatggg     420
ttcaatgtta attccccggg aagtaccgct aacccactgg cttcaattga ttctgcattg     480
tcaaaagtgg acgcagttcg ttcttctctg ggggcaattc aaaaccgctt tgattcagcc     540
attaccaacc ttggcaatac ggtaaccaat ctgaactccg cgcgtagccg tatcgaagat     600
gctgactatg caacgcagt ttctgctatg tctgcagcgc agattctgca gcaggctggt     660
ctggttccgc ggggttctca tcatcatcat catcatggtt aa                        702
```

<210> SEQ ID NO 128
<211> LENGTH: 233
<212> TYPE: PRT
<213> ORGANISM: Artificial Sequence
<220> FEATURE:
<223> OTHER INFORMATION: Synthetic sequence

<400> SEQUENCE: 128

```
Met Ser Gly Leu Arg Ile Asn Ser Ala Lys Asp Asp Ala Ala Gly Gln
 1               5                  10                  15
Ala Ile Ala Asn Arg Phe Thr Ser Asn Ile Lys Gly Leu Thr Gln Ala
            20                  25                  30
Ser Arg Asn Ala Asn Asp Gly Ile Ser Ile Ala Gln Thr Thr Glu Gly
        35                  40                  45
Ala Leu Asn Glu Ile Asn Asn Asn Leu Gln Arg Val Arg Glu Leu Ser
    50                  55                  60
Val Gln Ala Thr Asn Gly Thr Asn Ser Asp Ser Asp Leu Lys Ser Ile
65                  70                  75                  80
Gln Asp Glu Ile Gln Gln Arg Leu Glu Glu Ile Asp Arg Val Ser Asn
                85                  90                  95
Gln Thr Gln Phe Asn Gly Val Lys Val Leu Ser Gln Asp Asn Gln Met
            100                 105                 110
Lys Ile Gln Val Gly Ala Asn Asp Gly Glu Thr Ile Thr Ile Asp Leu
        115                 120                 125
Gln Lys Ile Asp Val Lys Ser Leu Gly Leu Asp Gly Phe Asn Val Asn
    130                 135                 140
Ser Pro Gly Ser Thr Ala Asn Pro Leu Ala Ser Ile Asp Ser Ala Leu
145                 150                 155                 160
Ser Lys Val Asp Ala Val Arg Ser Ser Leu Gly Ala Ile Gln Asn Arg
                165                 170                 175
Phe Asp Ser Ala Ile Thr Asn Leu Gly Asn Thr Val Thr Asn Leu Asn
            180                 185                 190
Ser Ala Arg Ser Arg Ile Glu Asp Ala Asp Tyr Ala Thr Ala Val Ser
        195                 200                 205
Ala Met Ser Ala Ala Gln Ile Leu Gln Gln Ala Gly Leu Val Pro Arg
    210                 215                 220
```

Gly Ser His His His His His Gly
225                 230

<210> SEQ ID NO 129
<211> LENGTH: 54
<212> TYPE: DNA
<213> ORGANISM: Artificial Sequence
<220> FEATURE:
<223> OTHER INFORMATION: Synthetic sequence

<400> SEQUENCE: 129
gtttctaata tgtctaaagc ggcgattctg ggagcggctg gtctggttcc gcgg          54

<210> SEQ ID NO 130
<211> LENGTH: 54
<212> TYPE: DNA
<213> ORGANISM: Artificial Sequence
<220> FEATURE:
<223> OTHER INFORMATION: Synthetic sequence

<400> SEQUENCE: 130
ccgcggaacc agaccagccg ctcccagaat cgccgcttta gacatattag aaac          54

<210> SEQ ID NO 131
<211> LENGTH: 795
<212> TYPE: DNA
<213> ORGANISM: Artificial Sequence
<220> FEATURE:
<223> OTHER INFORMATION: Synthetic sequence

<400> SEQUENCE: 131
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca acaacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaaccttg caatacggtt aaccaatctg   660
aactccgcgc gtagccgtat cgaagatgct gactatgcaa cggaagtttc taatatgtct   720
aaagcggcga ttctgggagc ggctggtctg gttccgcggg ttctcatca tcatcatcat   780
catggttaag tcgac                                                   795

<210> SEQ ID NO 132
<211> LENGTH: 702
<212> TYPE: DNA
<213> ORGANISM: Artificial Sequence
<220> FEATURE:
<223> OTHER INFORMATION: Synthetic sequence

<400> SEQUENCE: 132
atgagcgggt tacggatcaa cagcgcgaaa gacgatgcgg caggccaggc gattgctaac    60
cgcttcactt ctaatatcaa aggtctgact caggcttccc gtaacgctaa cgacggcatt   120

```
tctattgcgc agaccactga aggtgcgctg aatgaaatca acaacaacct gcagcgtgtg    180
cgtgagttgt ctgttcaggc cactaacggg actaactctg attccgatct gaaatctatc    240
caggatgaaa ttcagcaacg tctggaagaa atcgatcgcg tttctaatca gactcaattt    300
aacggtgtta agtcctgtc tcaggacaac cagatgaaaa tccaggttgg tgctaacgat    360
ggtgaaacca ttaccatcga tctgcaaaaa attgatgtga aaagccttgg ccttgatggg    420
ttcaatgtta attccccggg aagtaccgct aacccactgg cttcaattga ttctgcattg    480
tcaaaagtgg acgcagttcg ttcttctctg ggggcaattc aaaaccgctt tgattcagcc    540
attaccaacc ttggcaatac ggtaaccaat ctgaactccg cgcgtagccg tatcgaagat    600
gctgactatg caacggaagt ttctaatatg tctaaagcgg cgattctggg agcggctggt    660
ctggttccgc ggggttctca tcatcatcat catcatggtt aa                       702
```

<210> SEQ ID NO 133
<211> LENGTH: 233
<212> TYPE: PRT
<213> ORGANISM: Artificial Sequence
<220> FEATURE:
<223> OTHER INFORMATION: Synthetic sequence

<400> SEQUENCE: 133

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Ala Ile Leu Gly Ala Ala Gly Leu Val Pro Arg
    210                 215                 220

Gly Ser His His His His His His Gly
225                 230
```

<210> SEQ ID NO 134
<211> LENGTH: 25
<212> TYPE: DNA

```
<213> ORGANISM: Artificial Sequence
<220> FEATURE:
<223> OTHER INFORMATION: Synthetic sequence

<400> SEQUENCE: 134
tctagaggat ccggcaggcc aggcg                                           25

<210> SEQ ID NO 135
<211> LENGTH: 22
<212> TYPE: DNA
<213> ORGANISM: Artificial Sequence
<220> FEATURE:
<223> OTHER INFORMATION: Synthetic sequence

<400> SEQUENCE: 135
cgcaagcttg tcgacttaac gc                                              22

<210> SEQ ID NO 136
<211> LENGTH: 970
<212> TYPE: DNA
<213> ORGANISM: Artificial Sequence
<220> FEATURE:
<223> OTHER INFORMATION: Synthetic sequence

<400> SEQUENCE: 136
taatacgact cactataggg gaattgtgag cggataacaa ttcccctcta gaataatttt     60
gtttaacttt aagaaggaga tatacatatg cggggttctc atcatcatca tcatcatggt    120
atggctagca tgactggtgg acagcaaatg ggtcgggatc tgtacgacct ggttccgcgc    180
ggtagcgcga aggatccggc aggccaggcg attgctaacc gcttcacttc taatatcaaa    240
ggtctgactc aggcttcccg taacgctaac gacggcattt ctattgcgca gaccactgaa    300
ggtgcgctga tgaaatcaa caacaacctg cagcgtgtgc gtgagttgtc tgttcaggcc    360
actaacggga ctaactctga ttccgatctg aaatctatcc aggatgaaat tcagcaacgt    420
ctggaagaaa tcgatcgcgt ttctaatcag actcaattta acggtgttaa agtcctgtct    480
caggacaacc agatgaaaat ccaggttggt gctaacgatg gtgaaaccat taccatcgat    540
ctgcaaaaaa ttgatgtgaa aagccttggc cttgatgggt tcaatgttaa ttcccccggga    600
atttccggtg gtggtggtgg aattctagac tccatgggta cattaatcaa tgaagacgct    660
gccgcagcca gaaaagtac cgctaaccca ctggcttcaa ttgattctgc attgtcaaaa    720
gtggacgcag ttcgttcttc tctgggggca attcaaaacc gttttgattc agccattacc    780
aaccttggca atacggtaac caatctgaac tccgcgcgta gccgtatcga agatgctgac    840
tatgcaacgg aagtttctaa tatgtctaaa gcgcagattc tgcagcaggc tggtacttcc    900
gttctggcgc aggctaacca ggttccgcaa aacgtcctct ctttactgcg ttaagtcgac    960
aagcttgcgg                                                          970

<210> SEQ ID NO 137
<211> LENGTH: 288
<212> TYPE: PRT
<213> ORGANISM: Artificial Sequence
<220> FEATURE:
<223> OTHER INFORMATION: Synthetic sequence

<400> SEQUENCE: 137

Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30
```

Ser Ala Lys Asp Pro Ala Gly Gln Ala Ile Ala Asn Arg Phe Thr Ser
    35                  40                  45

Asn Ile Lys Gly Leu Thr Gln Ala Ser Arg Asn Ala Asn Asp Gly Ile
 50                  55                  60

Ser Ile Ala Gln Thr Thr Glu Gly Ala Leu Asn Glu Ile Asn Asn Asn
 65                  70                  75                  80

Leu Gln Arg Val Arg Glu Leu Ser Val Gln Ala Thr Asn Gly Thr Asn
                 85                  90                  95

Ser Asp Ser Asp Leu Lys Ser Ile Gln Asp Glu Ile Gln Gln Arg Leu
            100                 105                 110

Glu Glu Ile Asp Arg Val Ser Asn Gln Thr Gln Phe Asn Gly Val Lys
        115                 120                 125

Val Leu Ser Gln Asp Asn Gln Met Lys Ile Gln Val Gly Ala Asn Asp
130                 135                 140

Gly Glu Thr Ile Thr Ile Asp Leu Gln Lys Ile Asp Val Lys Ser Leu
145                 150                 155                 160

Gly Leu Asp Gly Phe Asn Val Asn Ser Pro Gly Ile Ser Gly Gly Gly
                165                 170                 175

Gly Gly Ile Leu Asp Ser Met Gly Thr Leu Ile Asn Glu Asp Ala Ala
            180                 185                 190

Ala Ala Lys Lys Ser Thr Ala Asn Pro Leu Ala Ser Ile Asp Ser Ala
        195                 200                 205

Leu Ser Lys Val Asp Ala Val Arg Ser Ser Leu Gly Ala Ile Gln Asn
210                 215                 220

Arg Phe Asp Ser Ala Ile Thr Asn Leu Gly Asn Thr Val Thr Asn Leu
225                 230                 235                 240

Asn Ser Ala Arg Ser Arg Ile Glu Asp Ala Asp Tyr Ala Thr Glu Val
                245                 250                 255

Ser Asn Met Ser Lys Ala Gln Ile Leu Gln Gln Ala Gly Thr Ser Val
            260                 265                 270

Leu Ala Gln Ala Asn Gln Val Pro Gln Asn Val Leu Ser Leu Leu Arg
        275                 280                 285

<210> SEQ ID NO 138
<211> LENGTH: 1236
<212> TYPE: DNA
<213> ORGANISM: Artificial Sequence
<220> FEATURE:
<223> OTHER INFORMATION: Synthetic sequence

<400> SEQUENCE: 138
taatacgact cactataggg gaattgtgag cggataacaa ttcccctcta gaataatttt      60
gtttaacttt aagaaggaga tatacatatg agtaaaggag aagaactttt cactggagtt    120
gtcccaattc ttgttgaatt agatggtgat gttaatgggc acaaattttc tgtcagtgga    180
gagggtgaag gtgatgcaac atacggaaaa cttaccctta aatttatttg cactactgga    240
aaactacctg ttccatggcc aacacttgtc actactctga cgtatggtgt tcaatgcttt    300
tcccgttatc cggatcacat gaaacggcat gactttttca agagtgccat gcccgaaggt    360
tatgtacagg aacgcactat atctttcaaa gatgacggga actacaagac gcgtgctgaa    420
gtcaagtttg aaggtgatac ccttgttaat cgtatcgagt taaaggtat tgatttaaa     480 gaagatggaa acattctcgg acacaaactc gagtacaact ataactcaca caatgtatac    540
atcacggcag acaaacaagg cctatcaggc cgcattatga gcgggttacg gatcaacagc    600

```
gcgaaagacg atgcggcagg ccaggcgatt gctaaccgct tcacttctaa tatcaaaggt    660
ctgactcagg cttcccgtaa cgctaacgac ggcatttcta ttgcgcagac cactgaaggt    720
gcgctgaatg aaatcaacaa caacctgcag cgtgtgcgtg agttgtctgt tcaggccact    780
aacgggacta actctgattc cgatctgaaa tctatccagg atgaaattca gcaacgtctg    840
gaagaaatcg atcgcgtttc taatcagact caatttaacg gtgttaaagt cctgtctcag    900
gacaaccaga tgaaaatcca ggttggtgct aacgatggtg aaaccattac catcgatctg    960
caaaaaattg atgtgaaaag ccttggcctt gatgggttca atgttaattc cccgggaagt   1020
accgctaacc cactggcttc aattgattct gcattgtcaa agtggacgc agttcgttct    1080 tctctggggg caattcaaaa ccgctttgat tcagccatta ccaaccttgg caatacggta   1140
accaatctga actccgcgcg tagccgtatc gaagatgctg actatgcact ggttccgcgg   1200
ggttctcatc atcatcatca tcatggttaa gtcgac                             1236
```

<210> SEQ ID NO 139
<211> LENGTH: 1143
<212> TYPE: DNA
<213> ORGANISM: Artificial Sequence
<220> FEATURE:
<223> OTHER INFORMATION: Synthetic sequence

<400> SEQUENCE: 139

```
atgagtaaag gagaagaact tttcactgga gttgtcccaa ttcttgttga attagatggt     60
gatgttaatg ggcacaaatt ttctgtcagt ggagagggtg aaggtgatgc aacatacgga    120
aaacttaccc ttaaatttat ttgcactact ggaaaactac ctgttccatg gccaacactt    180
gtcactactc tgacgtatgg tgttcaatgc ttttcccgtt atccggatca catgaaacgg    240
catgactttt tcaagagtgc catgcccgaa ggttatgtac aggaacgcac tatatctttc    300
aaagatgacg ggaactacaa gacgcgtgct gaagtcaagt ttgaaggtga taccttgtt    360 aatcgtatcg agttaaaagg tattgatttt aagaagatg gaaacattct cggacacaaa    420
ctcgagtaca actataactc acacaatgta tacatcacgg cagacaaaca aggcctatca    480
ggccgcatta tgagcgggtt acggatcaac agcgcgaaag acgatgcggc aggccaggcg    540
attgctaacc gcttcacttc taatatcaaa ggtctgactc aggcttcccg taacgctaac    600
gacggcattt ctattgcgca gaccactgaa ggtgcgctga tgaaatcaa caacaacctg    660 cagcgtgtgc gtgagttgtc tgttcaggcc actaacggga ctaactctga ttccgatctg    720
aaatctatcc aggatgaaat tcagcaacgt ctggaagaaa tcgatcgcgt ttctaatcag    780 actcaatttta acggtgttaa agtcctgtct caggacaacc agatgaaaat ccaggttggt    840
gctaacgatg gtgaaaccat taccatcgat ctgcaaaaaa ttgatgtgaa agccttggc    900 cttgatgggt tcaatgttaa ttccccggga agtaccgcta acccactggc ttcaattgat    960
tctgcattgt caaaagtgga cgcagttcgt tcttctctgg gggcaattca aaaccgcttt   1020
gattcagcca ttaccaacct tggcaatacg gtaaccaatc tgaactccgc gcgtagccgt   1080
atcgaagatg ctgactatgc actggttccg cggggttctc atcatcatca tcatcatggt   1140
taa                                                                 1143
```

<210> SEQ ID NO 140
<211> LENGTH: 380
<212> TYPE: PRT
<213> ORGANISM: Artificial Sequence
<220> FEATURE:
<223> OTHER INFORMATION: Synthetic sequence

<400> SEQUENCE: 140

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Thr Ala Asp Lys Gln Gly Leu Ser
145                 150                 155                 160

Gly Arg Ile Met Ser Gly Leu Arg Ile Asn Ser Ala Lys Asp Asp Ala
                165                 170                 175

Ala Gly Gln Ala Ile Ala Asn Arg Phe Thr Ser Asn Ile Lys Gly Leu
            180                 185                 190

Thr Gln Ala Ser Arg Asn Ala Asn Asp Gly Ile Ser Ile Ala Gln Thr
        195                 200                 205

Thr Glu Gly Ala Leu Asn Glu Ile Asn Asn Asn Leu Gln Arg Val Arg
    210                 215                 220

Glu Leu Ser Val Gln Ala Thr Asn Gly Thr Asn Ser Asp Ser Asp Leu
225                 230                 235                 240

Lys Ser Ile Gln Asp Glu Ile Gln Gln Arg Leu Glu Glu Ile Asp Arg
                245                 250                 255

Val Ser Asn Gln Thr Gln Phe Asn Gly Val Lys Val Leu Ser Gln Asp
            260                 265                 270

Asn Gln Met Lys Ile Gln Val Gly Ala Asn Asp Gly Glu Thr Ile Thr
        275                 280                 285

Ile Asp Leu Gln Lys Ile Asp Val Lys Ser Leu Gly Leu Asp Gly Phe
    290                 295                 300

Asn Val Asn Ser Pro Gly Ser Thr Ala Asn Pro Leu Ala Ser Ile Asp
305                 310                 315                 320

Ser Ala Leu Ser Lys Val Asp Ala Val Arg Ser Ser Leu Gly Ala Ile
                325                 330                 335

Gln Asn Arg Phe Asp Ser Ala Ile Thr Asn Leu Gly Asn Thr Val Thr
            340                 345                 350

Asn Leu Asn Ser Ala Arg Ser Arg Ile Glu Asp Ala Asp Tyr Ala Leu
        355                 360                 365

Val Pro Arg Gly Ser His His His His His Gly
    370                 375                 380

<210> SEQ ID NO 141
<211> LENGTH: 36
<212> TYPE: DNA

```
<213> ORGANISM: Artificial Sequence
<220> FEATURE:
<223> OTHER INFORMATION: Synthetic sequence

<400> SEQUENCE: 141
tctagaggat ccgtctggtc tgcgtatcaa cagcgc                                36

<210> SEQ ID NO 142
<211> LENGTH: 996
<212> TYPE: DNA
<213> ORGANISM: Artificial Sequence
<220> FEATURE:
<223> OTHER INFORMATION: Synthetic sequence

<400> SEQUENCE: 142
taatacgact cactatuggg gaattgtgag cggataacaa ttcccctcta gaataatttt      60
gtttaacttt aagaaggaga tatacatatg cggggttctc atcatcatca tcatcatggt    120
atggctagca tgactggtgg acagcaaatg ggtcgggatc tgtacgacct ggttccgcgc    180
ggtagcgcga aggatccgtc tggtctgcgt atcaacagcg cgaaagacga tgcggcaggc    240
caggcgattg ctaaccgctt cacttctaat atcaaaggtc tgactcaggc ttcccgtaac    300
gctaacgacg gcatttctat tgcgcagacc actgaaggtg cgctgaatga aatcaacaac    360
aacctgcagc gtgtgcgtga gttgtctgtt caggccacta acgggactaa ctctgattcc    420
gatctgaaat ctatccagga tgaaattcag caacgtctgg aagaaatcga tcgcgtttct    480
aatcagactc aatttaacgg tgttaaagtc ctgtctcagg acaaccagat gaaaatccag    540
gttggtgcta acgatggtga aaccattacc atcgatctgc aaaaaattga tgtgaaaagc    600
cttggccttg atgggttcaa tgttaattcc ccgggaattt ccggtggtgg tggtggaatt    660
ctagactcca tgggtacatt aatcaatgaa gacgctgccg cagccaagaa aagtaccgct    720
aacccactgg cttcaattga ttctgcattg tcaaaagtgg acgcagttcg ttcttctctg    780
ggggcaattc aaaaccgttt tgattcagcc attaccaacc ttggcaatac ggtaaccaat    840
ctgaactccg cgcgtagccg tatcgaagat gctgactatg caacggaagt ttctaatatg    900
tctaaagcgc agattctgca gcaggctggt acttccgttc tggcgcaggc taaccaggtt    960
ccgcaaaacg tcctctcttt actgcgttaa gtcgac                              996

<210> SEQ ID NO 143
<211> LENGTH: 903
<212> TYPE: DNA
<213> ORGANISM: Artificial Sequence
<220> FEATURE:
<223> OTHER INFORMATION: Synthetic sequence

<400> SEQUENCE: 143
atgcggggtt ctcatcatca tcatcatcat ggtatggcta gcatgactgg tggacagcaa     60
atgggtcggg atctgtacga cctggttccg cgcggtagcg cgaaggatcc gtctggtctg    120
cgtatcaaca gcgcgaaaga cgatgcggca ggccaggcga ttgctaaccg cttcacttct    180
aatatcaaag gtctgactca ggcttcccgt aacgctaacg acggcatttc tattgcgcag    240
accactgaag gtgcgctgaa tgaaatcaac aacaacctgc agcgtgtgcg tgagttgtct    300
gttcaggcca ctaacgggac taactctgat tccgatctga aatctatcca ggatgaaatt    360
cagcaacgtc tggaagaaat cgatcgcgtt tctaatcaga ctcaatttaa cggtgttaaa    420
gtcctgtctc aggacaacca gatgaaaatc caggttggtg ctaacgatgg tgaaaccatt    480
accatcgatc tgcaaaaaat tgatgtgaaa agccttggcc ttgatgggtt caatgttaat    540
```

```
tccccgggaa tttccggtgg tggtggtgga attctagact ccatgggtac attaatcaat    600
gaagacgctg ccgcagccaa gaaaagtacc gctaacccac tggcttcaat tgattctgca    660
ttgtcaaaag tggacgcagt tcgttcttct ctggggggcaa ttcaaaaccg tttttgattca   720 gccattacca accttggcaa tacggtaacc aatctgaact ccgcgcgtag ccgtatcgaa    780
gatgctgact atgcaacgga agtttctaat atgtctaaag cgcagattct gcagcaggct    840
ggtacttccg ttctggcgca ggctaaccag gttccgcaaa acgtcctctc tttactgcgt    900
taa                                                                 903
```

<210> SEQ ID NO 144
<211> LENGTH: 300
<212> TYPE: PRT
<213> ORGANISM: Artificial Sequence
<220> FEATURE:
<223> OTHER INFORMATION: Synthetic sequence

<400> SEQUENCE: 144

```
Met Arg Gly Ser His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Ser Gly Leu Arg Ile Asn Ser Ala Lys Asp Asp
        35                  40                  45

Ala Gly Gln Ala Ile Ala Asn Arg Phe Thr Ser Asn Ile Lys Gly
    50                  55                  60

Leu Thr Gln Ala Ser Arg Asn Ala Asn Asp Gly Ile Ser Ile Ala Gln
65                  70                  75                  80

Thr Thr Glu Gly Ala Leu Asn Glu Ile Asn Asn Asn Leu Gln Arg Val
                85                  90                  95

Arg Glu Leu Ser Val Gln Ala Thr Asn Gly Thr Asn Ser Asp Ser Asp
            100                 105                 110

Leu Lys Ser Ile Gln Asp Glu Ile Gln Gln Arg Leu Glu Glu Ile Asp
        115                 120                 125

Arg Val Ser Asn Gln Thr Gln Phe Asn Gly Val Lys Val Leu Ser Gln
    130                 135                 140

Asp Asn Gln Met Lys Ile Gln Val Gly Ala Asn Asp Gly Glu Thr Ile
145                 150                 155                 160

Thr Ile Asp Leu Gln Lys Ile Asp Val Lys Ser Leu Gly Leu Asp Gly
                165                 170                 175

Phe Asn Val Asn Ser Pro Gly Ile Ser Gly Gly Gly Gly Ile Leu
            180                 185                 190

Asp Ser Met Gly Thr Leu Ile Asn Glu Asp Ala Ala Ala Lys Lys
        195                 200                 205

Ser Thr Ala Asn Pro Leu Ala Ser Ile Asp Ser Ala Leu Ser Lys Val
    210                 215                 220

Asp Ala Val Arg Ser Ser Leu Gly Ala Ile Gln Asn Arg Phe Asp Ser
225                 230                 235                 240

Ala Ile Thr Asn Leu Gly Asn Thr Val Thr Asn Leu Asn Ser Ala Arg
                245                 250                 255

Ser Arg Ile Glu Asp Ala Asp Tyr Ala Thr Glu Val Ser Asn Met Ser
            260                 265                 270

Lys Ala Gln Ile Leu Gln Gln Ala Gly Thr Ser Val Leu Ala Gln Ala
        275                 280                 285
```

Asn Gln Val Pro Gln Asn Val Leu Ser Leu Leu Arg
    290                 295                 300

<210> SEQ ID NO 145
<211> LENGTH: 44
<212> TYPE: DNA
<213> ORGANISM: Artificial Sequence
<220> FEATURE:
<223> OTHER INFORMATION: Synthetic sequence

<400> SEQUENCE: 145
agatctccgc ggaaccagtg catagtcagc atcttcgata cggc            44

<210> SEQ ID NO 146
<211> LENGTH: 747
<212> TYPE: DNA
<213> ORGANISM: Artificial Sequence
<220> FEATURE:
<223> OTHER INFORMATION: Synthetic sequence

<400> SEQUENCE: 146

```
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca acaacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaaccttg caatacggt aaccaatctg   660
aactccgcgc gtagccgtat cgaagatgct gactatgcac tggttccgcg gggttctcat   720
catcatcatc atcatggtta agtcgac                                       747
```

<210> SEQ ID NO 147
<211> LENGTH: 654
<212> TYPE: DNA
<213> ORGANISM: Artificial Sequence
<220> FEATURE:
<223> OTHER INFORMATION: Synthetic sequence

<400> SEQUENCE: 147

```
atgagcgggt tacggatcaa cagcgcgaaa gacgatgcgg caggccaggc gattgctaac    60
cgcttcactt ctaatatcaa aggtctgact caggcttccc gtaacgctaa cgacggcatt   120
tctattgcgc agaccactga aggtgcgctg aatgaaatca acaacaacct gcagcgtgtg   180
cgtgagttgt ctgttcaggc cactaacggg actaactctg attccgatct gaaatctatc   240
caggatgaaa ttcagcaacg tctggaagaa atcgatcgcg tttctaatca gactcaattt   300
aacggtgtta aagtcctgtc tcaggacaac cagatgaaaa tccaggttgg tgctaacgat   360
ggtgaaacca ttaccatcga tctgcaaaaa attgatgtga aaagccttgg ccttgatggg   420
ttcaatgtta attccccggg aagtaccgct aacccactgg cttcaattga ttctgcattg   480
tcaaaagtgg acgcagttcg ttcttctctg ggggcaattc aaaaccgctt tgattcagcc   540
```
attaccaacc ttggcaatac ggtaaccaat ctgaactccg cgcgtagccg tatcgaagat     600
gctgactatg cactggttcc gcggggttct catcatcatc atcatcatgg ttaa           654

<210> SEQ ID NO 148
<211> LENGTH: 217
<212> TYPE: PRT
<213> ORGANISM: Artificial Sequence
<220> FEATURE:
<223> OTHER INFORMATION: Synthetic sequence

<400> SEQUENCE: 148

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Leu Val Pro Arg
        195                 200                 205

Gly Ser His His His His His His Gly
    210                 215

<210> SEQ ID NO 149
<211> LENGTH: 753
<212> TYPE: DNA
<213> ORGANISM: Artificial Sequence
<220> FEATURE:
<223> OTHER INFORMATION: Synthetic sequence

<400> SEQUENCE: 149
atgagcgggt tacggatcaa cagcgcgaaa gacgatgcgg caggccaggc gattgctaac     60
cgcttcactt ctaatatcaa aggtctgact caggcttccc gtaacgctgc agacggcatt     120
tctattgcgc agaccactga aggtgcgctg aatgaaatca acaacaacct gcagcgtgtg     180
cgtgagttgt ctgttcaggc cactgccggg gctaacgctg atgccgctct gaaagctatc     240
caggctgaaa ttcagcaacg tctggaagaa atcgatcgcg tttctcagca gactcaagct     300
gccgctgtta aagtcctgtc tcaggacaac gcaatggcaa tccaggttgg tgctaacgat     360
ggtgccgcta ttaccatcga tctgcaaaaa attgatgtga aaagccttgg ccttgatggg     420

```
ttcaatgtta attccccggg aagtaccgct aacccactgg cttcaattga ttctgcattg    480
tcaaaagtgg acgcagttcg ttcttctctg ggggcaattc aaaaccgctt tgattcagcc    540
attaccaacc ttggcaatac ggtaaccaat ctgaactccg cgcgtagccg tatcgaagat    600
gctgactatg caacggaagt ttctcaaatg tctaaagcgc agattctgca gcaggctggt    660
acttccgttc tggcgcaggc taaccaggtt ccgcaaaacg tcctctcttt actggttccg    720
cggggttctc atcatcatca tcatcatggt taa                                753
```

<210> SEQ ID NO 150
<211> LENGTH: 250
<212> TYPE: PRT
<213> ORGANISM: Artificial Sequence
<220> FEATURE:
<223> OTHER INFORMATION: Synthetic sequence

<400> SEQUENCE: 150

```
Met Ser Gly Leu Arg Ile Asn Ser Ala Lys Asp Asp Ala Ala Gly Gln
 1               5                  10                  15

Ala Ile Ala Asn Arg Phe Thr Ser Asn Ile Lys Gly Leu Thr Gln Ala
            20                  25                  30

Ser Arg Asn Ala Ala Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Ala Gly Ala Asn Ala Asp Ala Leu Lys Ala Ile
65                  70                  75                  80

Gln Ala Glu Ile Gln Gln Arg Leu Glu Glu Ile Asp Arg Val Ser Gln
                85                  90                  95

Gln Thr Gln Ala Ala Ala Val Lys Val Leu Ser Gln Asp Asn Ala Met
            100                 105                 110

Ala Ile Gln Val Gly Ala Asn Asp Gly Ala Ala Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Gln Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 151
<211> LENGTH: 846
<212> TYPE: DNA
<213> ORGANISM: Artificial Sequence
<220> FEATURE:
<223> OTHER INFORMATION: Synthetic sequence

<400> SEQUENCE: 151

```
taatacgact cactataggg gaattgtgag cggataacaa ttcccctcta gaataatttt     60
gtttaacttt aagaaggaga tatacatatg agcgggttac ggatcaacag cgcgaaagac    120
gatgcggcag ccaggcgat tgctaaccgc ttcacttcta atatcaaagg tctgactcag     180
gcttcccgta acgctgcaga cggcatttct attgcgcaga ccactgaagg tgcgctgaat    240
gaaatcaaca acaacctgca gcgtgtgcgt gagttgtctg ttcaggccac tgccggggct    300
aacgctgatg ccgctctgaa agctatccag gctgaaattc agcaacgtct ggaagaaatc    360
gatcgcgttt ctcagcagac tcaagctgcc gctgttaaag tcctgtctca ggacaacgca    420
atggcaatcc aggttggtgc taacgatggt gccgctatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaaccttg caatacggt aaccaatctg     660
aactccgcgc gtagccgtat cgaagatgct gactatgcaa cggaagtttc tcaaatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                              846
```

<210> SEQ ID NO 152
<211> LENGTH: 795
<212> TYPE: DNA
<213> ORGANISM: Artificial Sequence
<220> FEATURE:
<223> OTHER INFORMATION: Synthetic sequence

<400> SEQUENCE: 152

```
taatacgact cactataggg gaattgtgag cggataacaa ttcccctcta gaataatttt     60
gtttaacttt aagaaggaga tatacatatg agcgggttac ggatcaacag cgcgaaagac    120
gatgcggcag ccaggcgat tgctaaccgc ttcacttcta atatcaaagg tctgactcag     180
gcttcccgta acgctgcaga cggcatttct attgcgcaga ccactgaagg tgcgctgaat    240
gaaatcaaca acaacctgca gcgtgtgcgt gagttgtctg ttcaggccac tgccggggct    300
aacgctgatg ccgctctgaa agctatccag gctgaaattc agcaacgtct ggaagaaatc    360
gatcgcgttt ctcagcagac tcaagctgcc gctgttaaag tcctgtctca ggacaacgca    420
atggcaatcc aggttggtgc taacgatggt gccgctatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaaccttg caatacggt aaccaatctg     660
aactccgcgc gtagccgtat cgaagatgct gactatgcaa cggaagtttc tcaaatgtct    720
aaagcgcaga ttctgcagca ggctggtctg gttccgcggg gttctcatca tcatcatcat    780
catggttaag tcgac                                                    795
```

<210> SEQ ID NO 153
<211> LENGTH: 702
<212> TYPE: DNA
<213> ORGANISM: Artificial Sequence
<220> FEATURE:
<223> OTHER INFORMATION: Synthetic sequence

<400> SEQUENCE: 153

```
atgagcgggt tacggatcaa cagcgcgaaa gacgatgcgg caggccaggc gattgctaac    60
cgcttcactt ctaatatcaa aggtctgact caggcttccc gtaacgctgc agacggcatt   120
tctattgcgc agaccactga aggtgcgctg aatgaaatca acaacaacct gcagcgtgtg   180
cgtgagttgt ctgttcaggc cactgccggg gctaacgctg atgccgctct gaaagctatc   240
caggctgaaa ttcagcaacg tctggaagaa atcgatcgcg tttctcagca gactcaagct   300
gccgctgtta aagtcctgtc tcaggacaac gcaatggcaa tccaggttgg tgctaacgat   360
ggtgccgcta ttaccatcga tctgcaaaaa attgatgtga aaagccttgg ccttgatggg   420
ttcaatgtta attccccggg aagtaccgct aacccactgg cttcaattga ttctgcattg   480
tcaaaagtgg acgcagttcg ttcttctctg ggggcaattc aaaaccgctt tgattcagcc   540
attaccaacc ttggcaatac ggtaaccaat ctgaactccg cgcgtagccg tatcgaagat   600
gctgactatg caacggaagt ttctcaaatg tctaaagcgc agattctgca gcaggctggt   660
ctggttccgc ggggttctca tcatcatcat catcatggtt aa                     702
```

<210> SEQ ID NO 154  
<211> LENGTH: 233  
<212> TYPE: PRT  
<213> ORGANISM: Artificial Sequence  
<220> FEATURE:  
<223> OTHER INFORMATION: Synthetic sequence

<400> SEQUENCE: 154

```
Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Ala Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Ala Gly Ala Asn Ala Asp Ala Ala Leu Lys Ala Ile
65                  70                  75                  80

Gln Ala Glu Ile Gln Gln Arg Leu Glu Glu Ile Asp Arg Val Ser Gln
                85                  90                  95

Gln Thr Gln Ala Ala Val Lys Val Leu Ser Gln Asp Asn Ala Met
            100                 105                 110

Ala Ile Gln Val Gly Ala Asn Asp Gly Ala Ala Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Gln Met Ser Lys Ala Gln Ile Leu Gln Gln Ala Gly Leu Val Pro Arg
    210                 215                 220

Gly Ser His His His His His His Gly
225                 230
```

<210> SEQ ID NO 155
<211> LENGTH: 990
<212> TYPE: DNA
<213> ORGANISM: Artificial Sequence
<220> FEATURE:
<223> OTHER INFORMATION: Synthetic sequence

<400> SEQUENCE: 155

```
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgcagaaat ctcagtcctc actgagttcc   180
gctattgagc gtctgtcctc tggtctgcgt atcaacagcg cgaaagacga tgcggcaggc   240
caggcgattg ctaaccgctt cacttctaat atcaaaggtc tgactcaggc ttcccgtaac   300
gctaacgacg gcatttctat tgcgcagacc actgaaggtg cgctgaatga aatcaacaac   360
aacctgcagc gtgtgcgtga gttgtctgtt caggccactc aagggactaa ctctgattcc   420
gatctgaaat ctatccagga tgaaattcag caacgtctgg aagaaatcga tcgcgtttct   480
cagcagactc aatttaacgg tgttaaagtc ctgtctcagg acaaccagat gaaaatccag   540
gttggtgcta cgatggtga aaccattacc atcgatctgc aaaaaattga tgtgaaaagc   600
cttggccttg atgggttcaa tgttaattcc cgggaatttc cggtggtgg tggtggaatt   660
ctagactcca tgggtacatt aatcaatgaa gacgctgccg cagccaagaa aagtaccgct   720
aacccactgg cttcaattga ttctgcattg tcaaaagtgg acgcagttcg ttcttctctg   780
ggggcaattc aaaaccgttt tgattcagcc attaccaacc ttggcaatac ggtaaccaat   840
ctgaactccg cgcgtagccg tatcgaagat gctgactatg caacggaagt ttctcaaatg   900
tctaaagcgc agattctgca gcaggctggt acttccgttc tggcgcaggc taaccaggtt   960
ccgcaaaacg tcctctcttt actgcgttaa                                    990
```

<210> SEQ ID NO 156
<211> LENGTH: 180
<212> TYPE: DNA
<213> ORGANISM: Artificial Sequence
<220> FEATURE:
<223> OTHER INFORMATION: Synthetic sequence

<400> SEQUENCE: 156

```
aacccactgg cttcaattga ttctgcattg tcaaaagtgg acgcagttcg ttcttctctg    60
ggggcaattc aaaaccgttt tgattcagcc attaccgccc ttggcgctac ggtaaccgct   120
ctggcctccg cgcgtagcgc tatcgaagat gctgactatg caacggaagt ttctcaaatg   180
```

<210> SEQ ID NO 157
<211> LENGTH: 60
<212> TYPE: PRT
<213> ORGANISM: Artificial Sequence
<220> FEATURE:
<223> OTHER INFORMATION: Synthetic sequence

<400> SEQUENCE: 157

```
Asn Pro Leu Ala Ser Ile Asp Ser Ala Leu Ser Lys Val Asp Ala Val
1               5                   10                  15

Arg Ser Ser Leu Gly Ala Ile Gln Asn Arg Phe Asp Ser Ala Ile Thr
            20                  25                  30

Ala Leu Gly Ala Thr Val Thr Ala Leu Ala Ser Ala Arg Ser Ala Ile
        35                  40                  45
```

Glu Asp Ala Asp Tyr Ala Thr Glu Val Ser Asn Met
    50                  55                  60

<210> SEQ ID NO 158
<211> LENGTH: 50
<212> TYPE: DNA
<213> ORGANISM: Artificial Sequence
<220> FEATURE:
<223> OTHER INFORMATION: Synthetic sequence

<400> SEQUENCE: 158
gcagttcgtt cttctctggg ggcaattgat tcagccatta ccgcccttgg          50

<210> SEQ ID NO 159
<211> LENGTH: 50
<212> TYPE: DNA
<213> ORGANISM: Artificial Sequence
<220> FEATURE:
<223> OTHER INFORMATION: Synthetic sequence

<400> SEQUENCE: 159
ccaagggcgg taatggctga atcaattgcc cccagagaag aacgaactgc          50

<210> SEQ ID NO 160
<211> LENGTH: 1066
<212> TYPE: DNA
<213> ORGANISM: Artificial Sequence
<220> FEATURE:
<223> OTHER INFORMATION: Synthetic sequence

<400> SEQUENCE: 160
taatacgact cactataggg gaattgtgag cggataacaa ttcccctcta gaaataattt       60
tgtttaactt taagaaggag atatacatat gcggggttct catcatcatc atcatcatgg     120
tatggctagc atgactggtg gacagcaaat gggtcgggat ctgtacgacg atgacgataa     180
ggatccgatg gcacaagtca ttaatacaaa cagcctgtcg ctgttgaccc agaataacct     240
gaacaaatct cagtcctcac tgagttccgc tattgagcgt ctgtcctctg gtctgcgtat     300
caacagcgcg aaagacgatg cggcaggcca ggcgattgct aaccgcttca cttctaatat     360
caaaggtctg actcaggctt cccgtaacgc taacgacggc atttctattg cgcagaccac     420
tgaaggtgcg ctgaatgaaa tcaacaacaa cctgcagcgt gtgcgtgagt tgtctgttca     480
ggccactaac gggactaact ctgattccga tctgaaatct atccaggatg aaattcagca     540
acgtctggaa gaaatcgatc gcgtttctaa tcagactcaa tttaacggtg ttaaagtcct     600
gtctcaggac aaccagatga aaatccaggt tggtgctaac gatggtgaaa ccattaccat     660
cgatctgcaa aaaattgatg tgaaaagcct tggccttgat gggttcaatg ttaattcccc     720
gggaatttcc ggtggtggtg gtggaattct agactccatg ggtacattaa tcaatgaaga     780
cgctgccgca gccaagaaaa gtaccgctaa cccactggct tcaattgatt ctgcattgtc     840
aaaagtggac gcagttcgtt cttctctggg ggcaattgat tcagccatta ccgcccttgg     900
cgctacggta accgctctgg cctccgcggc tagccgtatc gaagatgctg actatgcaac     960
ggaagtttct aatatgtcta agcgcagat tctgcagcag ctggtactt ccgttctggc    1020
gcaggctaac caggttccgc aaaacgtcct ctctttactg cgttaa                 1066

<210> SEQ ID NO 161
<211> LENGTH: 325
<212> TYPE: PRT
<213> ORGANISM: Artificial Sequence
<220> FEATURE:
<223> OTHER INFORMATION: Synthetic sequence

<400> SEQUENCE: 161

```
Met Arg Gly Ser His His His His His His Gly Met Ala Ser Met Thr
1               5                   10                  15
Gly Gly Gln Gln Met Gly Arg Asp Leu Tyr Asp Asp Asp Lys Asp
            20                  25                  30
Pro Met Ala Gln Val Ile Asn Thr Asn Ser Leu Ser Leu Leu Thr Gln
        35                  40                  45
Asn Asn Leu Asn Lys Ser Gln Ser Ser Leu Ser Ser Ala Ile Glu Arg
    50                  55                  60
Leu Ser Ser Gly Leu Arg Ile Asn Ser Ala Lys Asp Asp Ala Ala Gly
65                  70                  75                  80
Gln Ala Ile Ala Asn Arg Phe Thr Ser Asn Ile Lys Gly Leu Thr Gln
                85                  90                  95
Ala Ser Arg Asn Ala Asn Asp Gly Ile Ser Ile Ala Gln Thr Thr Glu
            100                 105                 110
Gly Ala Leu Asn Glu Ile Asn Asn Leu Gln Arg Val Arg Glu Leu
        115                 120                 125
Ser Val Gln Ala Thr Asn Gly Thr Asn Ser Asp Ser Asp Leu Lys Ser
    130                 135                 140
Ile Gln Asp Glu Ile Gln Gln Arg Leu Glu Glu Ile Asp Arg Val Ser
145                 150                 155                 160
Asn Gln Thr Gln Phe Asn Gly Val Lys Val Leu Ser Gln Asp Asn Gln
                165                 170                 175
Met Lys Ile Gln Val Gly Ala Asn Asp Gly Glu Thr Ile Thr Ile Asp
            180                 185                 190
Leu Gln Lys Ile Asp Val Lys Ser Leu Gly Leu Asp Gly Phe Asn Val
        195                 200                 205
Asn Ser Pro Gly Ile Ser Gly Gly Gly Gly Ile Leu Asp Ser Met
    210                 215                 220
Gly Thr Leu Ile Asn Glu Asp Ala Ala Ala Lys Lys Ser Thr Ala
225                 230                 235                 240
Asn Pro Leu Ala Ser Ile Asp Ser Ala Leu Ser Lys Val Asp Ala Val
                245                 250                 255
Arg Ser Ser Leu Gly Ala Ile Asp Ser Ala Ile Thr Ala Leu Gly Ala
            260                 265                 270
Thr Val Thr Ala Leu Ala Ser Ala Ser Arg Ile Glu Asp Ala Asp
        275                 280                 285
Tyr Ala Thr Glu Val Ser Asn Met Ser Lys Ala Gln Ile Leu Gln Gln
    290                 295                 300
Ala Gly Thr Ser Val Leu Ala Gln Ala Asn Gln Val Pro Gln Asn Val
305                 310                 315                 320
Leu Ser Leu Leu Arg
                325
```

<210> SEQ ID NO 162
<211> LENGTH: 180
<212> TYPE: DNA
<213> ORGANISM: Artificial Sequence
<220> FEATURE:
<223> OTHER INFORMATION: Synthetic sequence

<400> SEQUENCE: 162
aacccactgg cttcaattga ttctgcattg tcaaaagtgg acgcagttcg ttcttctctg      60

```
gggcaattg caaaggcttt tgattcagcc attaccgccc ttggcgctac ggtaaccgct    120
ctggcctccg cgcgtagcgc tatcgaagat gctgactatg caacggaagt ttctcaaatg    180
```

<210> SEQ ID NO 163
<211> LENGTH: 60
<212> TYPE: PRT
<213> ORGANISM: Artificial Sequence
<220> FEATURE:
<223> OTHER INFORMATION: Synthetic sequence

<400> SEQUENCE: 163

```
Asn Pro Leu Ala Ser Ile Asp Ser Ala Leu Ser Lys Val Asp Ala Val
1               5                   10                  15

Arg Ser Ser Leu Gly Ala Ile Ala Lys Ala Phe Asp Ser Ala Ile Thr
            20                  25                  30

Ala Leu Gly Ala Thr Val Thr Ala Leu Ala Ser Ala Arg Ser Ala Ile
        35                  40                  45

Glu Asp Ala Asp Tyr Ala Thr Glu Val Ser Asn Met
    50                  55                  60
```

<210> SEQ ID NO 164
<211> LENGTH: 50
<212> TYPE: DNA
<213> ORGANISM: Artificial Sequence
<220> FEATURE:
<223> OTHER INFORMATION: Synthetic sequence

<400> SEQUENCE: 164

```
cgttcttctc tgggggcaat tgcaaaggct tttgattcag ccattaccgc                50
```

<210> SEQ ID NO 165
<211> LENGTH: 50
<212> TYPE: DNA
<213> ORGANISM: Artificial Sequence
<220> FEATURE:
<223> OTHER INFORMATION: Synthetic sequence

<400> SEQUENCE: 165

```
gcggtaatgg ctgaatcaaa agcctttgca attgccccca gagaagaacg                50
```

<210> SEQ ID NO 166
<211> LENGTH: 1078
<212> TYPE: DNA
<213> ORGANISM: Artificial Sequence
<220> FEATURE:
<223> OTHER INFORMATION: Synthetic sequence

<400> SEQUENCE: 166

```
taatacgact cactataggg gaattgtgag cggataacaa ttcccctcta gaaataattt     60
tgtttaactt taagaaggag atatacatat gcggggttct catcatcatc atcatcatgg    120
tatggctagc atgactggtg gacagcaaat gggtcgggat ctgtacgacg atgacgataa    180
ggatccgatg gcacaagtca ttaatacaaa cagcctgtcg ctgttgaccc agaataacct    240
gaacaaatct cagtcctcac tgagttccgc tattgagcgt ctgtcctctg gtctgcgtat    300
caacagcgcg aaagacgatg cggcaggcca ggcgattgct aaccgcttca cttctaatat    360
caaaggtctg actcaggctt cccgtaacgc taacgacggc atttctattg cgcagaccac    420
tgaaggtgcg ctgaatgaaa tcaacaacaa cctgcagcgt gtgcgtgagt tgtctgttca    480
ggccactaac gggactaact ctgattccga tctgaaatct atccaggatg aaattcagca    540
```

```
acgtctggaa gaaatcgatc gcgtttctaa tcagactcaa tttaacggtg ttaaagtcct    600
gtctcaggac aaccagatga aaatccaggt tggtgctaac gatggtgaaa ccattaccat    660
cgatctgcaa aaaattgatg tgaaaagcct tggccttgat gggttcaatg ttaattcccc    720
gggaatttcc ggtggtggtg gtggaattct agactccatg ggtacattaa tcaatgaaga    780
cgctgccgca gccaagaaaa gtaccgctaa cccactggct tcaattgatt ctgcattgtc    840
aaaagtggac gcagttcgtt cttctctggg ggcaattgca aaggcttttg attcagccat    900
taccgccctt ggcgctacgg taaccgctct ggcctccgcg gctagccgta tcgaagatgc    960
tgactatgca acggaagttt ctaatatgtc taaagcgcag attctgcagc aggctggtac    1020
ttccgttctg gcgcaggcta accaggttcc gcaaaacgtc ctctctttac tgcgttaa    1078
```

<210> SEQ ID NO 167
<211> LENGTH: 329
<212> TYPE: PRT
<213> ORGANISM: Artificial Sequence
<220> FEATURE:
<223> OTHER INFORMATION: Synthetic sequence

<400> SEQUENCE: 167

```
Met Arg Gly Ser His His His His His Gly Met Ala Ser Met Thr
1               5                  10                  15

Gly Gly Gln Gln Met Gly Arg Asp Leu Tyr Asp Asp Asp Lys Asp
                20                  25                  30

Pro Met Ala Gln Val Ile Asn Thr Asn Ser Leu Ser Leu Leu Thr Gln
            35                  40                  45

Asn Asn Leu Asn Lys Ser Gln Ser Ser Leu Ser Ser Ala Ile Glu Arg
50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Asp Gly Phe Asn Val
        195                 200                 205

Asn Ser Pro Gly Ile Ser Gly Gly Gly Gly Ile Leu Asp Ser Met
    210                 215                 220

Gly Thr Leu Ile Asn Glu Asp Ala Ala Ala Lys Lys Ser Thr Ala
225                 230                 235                 240

Asn Pro Leu Ala Ser Ile Asp Ser Ala Leu Ser Lys Val Asp Ala Val
                245                 250                 255

Arg Ser Ser Leu Gly Ala Ile Ala Lys Ala Phe Asp Ser Ala Ile Thr
            260                 265                 270
```

```
Ala Leu Gly Ala Thr Val Thr Ala Leu Ala Ser Ala Ala Ser Arg Ile
            275                 280                 285

Glu Asp Ala Asp Tyr Ala Thr Glu Val Ser Asn Met Ser Lys Ala Gln
        290                 295                 300

Ile Leu Gln Gln Ala Gly Thr Ser Val Leu Ala Gln Ala Asn Gln Val
305                 310                 315                 320

Pro Gln Asn Val Leu Ser Leu Leu Arg
                325

<210> SEQ ID NO 168
<211> LENGTH: 903
<212> TYPE: DNA
<213> ORGANISM: Artificial Sequence
<220> FEATURE:
<223> OTHER INFORMATION: Synthetic sequence

<400> SEQUENCE: 168
atgcggggtt ctcatcatca tcatcatcat ggtatggcta gcatgactgg tggacagcaa      60
atgggtcggg atctgtacga cctggttccg cgcggtagcg cgaaggatcc gtctggtctg     120
cgtatcaaca gcgcgaaaga cgatgcggca ggccaggcga ttgctaaccg cttcacttct     180
aatatcaaag gtctgactca ggcttcccgt aacgctgcag acggcatttc tattgcgcag     240
accactgaag gtgcgctgaa tgaaatcaac aacaacctgc agcgtgtgcg tgagttgtct     300
gttcaggcca ctaacgggac taactctgat tccgatctga atctatcca ggatgaaatt      360
cagcaacgtc tggaagaaat cgatcgcgtt tctaatcaga ctcaagctaa cggtgttaaa     420
gtcctgtctc aggacaacgc aatgaaaatc caggttggtg ctaacgatgg tgccgctatt     480
accatcgatc tgcaaaaaat tgatgtgaaa agccttggcc ttgatgggtt caatgttaat     540
tccccgggaa tttccggtgg tggtggtgga attctagact ccatgggtac attaatcaat     600
gaagacgctg ccgcagccaa gaaaagtacc gctaacccac tggcttcaat tgattctgca     660
ttgtcaaaag tggacgcagt tcgttcttct ctggggggcaa ttcaagctcg ttttgccgcg     720
gccattgcta accttggcaa tacggtaacc aatctgaact ccgcgcgtag ccgtatcgaa     780
gatgctgact atgcaacgga agtttctaat atgtctaaag cgcagattct gcagcaggct     840
ggtacttccg ttctggcgca ggctaaccag gttccgcaaa acgtcctctc tttactgcgt     900
taa                                                                   903

<210> SEQ ID NO 169
<211> LENGTH: 300
<212> TYPE: PRT
<213> ORGANISM: Artificial Sequence
<220> FEATURE:
<223> OTHER INFORMATION: Synthetic sequence

<400> SEQUENCE: 169

Met Arg Gly Ser His His His His His His Gly Met Ala Ser Met Thr
1               5                   10                  15

Gly Gly Gln Gln Met Gly Arg Asp Leu Tyr Asp Leu Val Pro Arg Gly
            20                  25                  30

Ser Ala Lys Asp Pro Ser Gly Leu Arg Ile Asn Ser Ala Lys Asp Asp
        35                  40                  45

Ala Ala Gly Gln Ala Ile Ala Asn Arg Phe Thr Ser Asn Ile Lys Gly
    50                  55                  60

Leu Thr Gln Ala Ser Arg Asn Ala Ala Asp Gly Ile Ser Ile Ala Gln
65                  70                  75                  80
```

Thr Thr Glu Gly Ala Leu Asn Glu Ile Asn Asn Leu Gln Arg Val
            85                  90                  95

Arg Glu Leu Ser Val Gln Ala Thr Asn Gly Thr Asn Ser Asp Ser Asp
        100                 105                 110

Leu Lys Ser Ile Gln Asp Glu Ile Gln Gln Arg Leu Glu Glu Ile Asp
        115                 120                 125

Arg Val Ser Asn Gln Thr Gln Ala Asn Gly Val Lys Val Leu Ser Gln
    130                 135                 140

Asp Asn Ala Met Lys Ile Gln Val Gly Ala Asn Asp Gly Ala Ala Ile
145                 150                 155                 160

Thr Ile Asp Leu Gln Lys Ile Asp Val Lys Ser Leu Gly Leu Asp Gly
                165                 170                 175

Phe Asn Val Asn Ser Pro Gly Ile Ser Gly Gly Gly Gly Ile Leu
                180                 185                 190

Asp Ser Met Gly Thr Leu Ile Asn Glu Asp Ala Ala Ala Lys Lys
        195                 200                 205

Ser Thr Ala Asn Pro Leu Ala Ser Ile Asp Ser Ala Leu Ser Lys Val
    210                 215                 220

Asp Ala Val Arg Ser Ser Leu Gly Ala Ile Gln Ala Arg Phe Ala Ala
225                 230                 235                 240

Ala Ile Ala Asn Leu Gly Asn Thr Val Thr Asn Leu Asn Ser Ala Arg
                245                 250                 255

Ser Arg Ile Glu Asp Ala Asp Tyr Ala Thr Glu Val Ser Asn Met Ser
            260                 265                 270

Lys Ala Gln Ile Leu Gln Gln Ala Gly Thr Ser Val Leu Ala Gln Ala
        275                 280                 285

Asn Gln Val Pro Gln Asn Val Leu Ser Leu Leu Arg
    290                 295                 300

<210> SEQ ID NO 170
<211> LENGTH: 996
<212> TYPE: DNA
<213> ORGANISM: Artificial Sequence
<220> FEATURE:
<223> OTHER INFORMATION: Synthetic sequence

<400> SEQUENCE: 170
taatacgact cactataggg gaattgtgag cggataacaa ttcccctcta gaataatttt      60
gtttaacttt aagaaggaga tatacatatg cggggttctc atcatcatca tcatcatggt    120
atggctagca tgactggtgg acagcaaatg ggtcgggatc tgtacgacct ggttccgcgc    180
ggtagcgcga aggatccgtc tggtctgcgt atcaacagcg cgaaagacga tgcggcaggc    240
caggcgattg ctaaccgctt cacttctaat atcaaaggtc tgactcaggc ttcccgtaac    300
gctgcagacg gcatttctat tgcgcagacc actgaaggtg cgctgaatga atcaacaac    360 aacctgcagc gtgtgcgtga gttgtctgtt caggccacta cgggactaa ctctgattcc    420 gatctgaaat ctatccagga tgaaattcag caacgtctgg aagaaatcga tcgcgtttct    480
aatcagactc aagctaacgg tgttaaagtc ctgtctcagg acaacgcaat gaaaatccag    540
gttggtgcta acgatggtgc cgctattacc atcgatctgc aaaaaattga tgtgaaaagc    600
cttggccttg atgggttcaa tgttaattcc ccgggaattt ccggtggtgg tggtggaatt    660
ctagactcca tgggtacatt aatcaatgaa gacgctgccg cagccaagaa agtaccgct    720 aacccactgg cttcaattga ttctgcattg tcaaagtgg acgcagttcg ttcttctctg    780
ggggcaattc aagctcgttt tgccgcggcc attgctaacc ttggcaatac ggtaaccaat    840

```
ctgaactccg cgcgtagccg tatcgaagat gctgactatg caacggaagt ttctaatatg      900
tctaaagcgc agattctgca gcaggctggt acttccgttc tggcgcaggc taaccaggtt      960
ccgcaaaacg tcctctcttt actgcgttaa gtcgac                                996
```

<210> SEQ ID NO 171
<211> LENGTH: 79
<212> TYPE: DNA
<213> ORGANISM: Artificial Sequence
<220> FEATURE:
<223> OTHER INFORMATION: Synthetic sequence

<400> SEQUENCE: 171

```
agatctgtcg acttaaccat gatgatgatg atgatgagaa ccccgcggaa ccagtaaaga       60
gaggacgttt tgcggaacc                                                    79
```

<210> SEQ ID NO 172
<211> LENGTH: 846
<212> TYPE: DNA
<213> ORGANISM: Artificial Sequence
<220> FEATURE:
<223> OTHER INFORMATION: Synthetic sequence

<400> SEQUENCE: 172

```
taatacgact cactataggg gaattgtgag cggataacaa ttcccctcta gaataatttt       60
gtttaacttt aagaaggaga tatacatatg agcgggttac ggatcaacag cgcgaaagac      120
gatgcggcag gccaggcgat tgctaaccgc ttcacttcta atatcaaagg tctgactcag      180
gcttcccgta acgctaacga cggcatttct attgcgcaga ccactgaagg tgcgctgaat      240
gaaatcaaca acaacctgca gcgtgtgcgt gagttgtctg ttcaggccac taacgggact      300
aactctgatt ccgatctgaa atctatccag gatgaaattc agcaacgtct ggaagaaatc      360
gatcgcgttt ctaatcagac tcaatttaac ggtgttaaag tcctgtctca ggacaaccag      420
atgaaaatcc aggttggtgc taacgatggt gaaaccatta ccatcgatct gcaaaaaatt      480
gatgtgaaaa gccttggcct tgatgggttc aatgttaatt ccccgggaag taccgctaac      540
ccactggctt caattgattc tgcattgtca aaagtggacg cagttcgttc ttctctgggg      600
gcaattcaag ctcgttttgc cgcggccatt gctaaccttg caatacggt aaccaatctg       660 aactccgcgc gtagccgtat cgaagatgct gactatgcaa cggaagtttc taatatgtct      720
aaagcgcaga ttctgcagca ggctggtact tccgttctgg cgcaggctaa ccaggttccg      780
caaaacgtcc tctctttact ggttccgcgg ggttctcatc atcatcatca tcatggttaa      840
gtcgac                                                                  846
```

<210> SEQ ID NO 173
<211> LENGTH: 250
<212> TYPE: PRT
<213> ORGANISM: Artificial Sequence
<220> FEATURE:
<223> OTHER INFORMATION: Synthetic sequence

<400> SEQUENCE: 173

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45
```

```
Ala Leu Asn Glu Ile Asn Asn Leu Gln Arg Val Arg Glu Leu Ser
 50                  55                  60
Val Gln Ala Thr Asn Gly Thr Asn Ser Asp Ser Asp Leu Lys Ser Ile
 65                  70                  75                  80
Gln Asp Glu Ile Gln Gln Arg Leu Glu Glu Ile Asp Arg Val Ser Asn
                 85                  90                  95
Gln Thr Gln Phe Asn Gly Val Lys Val Leu Ser Gln Asp Asn Gln Met
                100                 105                 110
Lys Ile Gln Val Gly Ala Asn Asp Gly Glu Thr Ile Thr Ile Asp Leu
            115                 120                 125
Gln Lys Ile Asp Val Lys Ser Leu Gly Leu Asp Gly Phe Asn Val Asn
130                 135                 140
Ser Pro Gly Ser Thr Ala Asn Pro Leu Ala Ser Ile Asp Ser Ala Leu
145                 150                 155                 160
Ser Lys Val Asp Ala Val Arg Ser Ser Leu Gly Ala Ile Gln Ala Arg
                165                 170                 175
Phe Ala Ala Ala Ile Ala Asn Leu Gly Asn Thr Val Thr Asn Leu Asn
                180                 185                 190
Ser Ala Arg Ser Arg Ile Glu Asp Ala Asp Tyr Ala Thr Glu Val Ser
            195                 200                 205
Asn Met Ser Lys Ala Gln Ile Leu Gln Gln Ala Gly Thr Ser Val Leu
210                 215                 220
Ala Gln Ala Asn Gln Val Pro Gln Asn Val Leu Ser Leu Leu Val Pro
225                 230                 235                 240
Arg Gly Ser His His His His His His Gly
                245                 250

<210> SEQ ID NO 174
<211> LENGTH: 47
<212> TYPE: DNA
<213> ORGANISM: Artificial Sequence
<220> FEATURE:
<223> OTHER INFORMATION: Synthetic sequence

<400> SEQUENCE: 174
agatctcata tgagcgggtt acggatcaac agcgcgaaag acgatgc          47

<210> SEQ ID NO 175
<211> LENGTH: 846
<212> TYPE: DNA
<213> ORGANISM: Artificial Sequence
<220> FEATURE:
<223> OTHER INFORMATION: Synthetic sequence

<400> SEQUENCE: 175
taatacgact cactataggg gaattgtgag cggataacaa ttcccctcta gaataatttt      60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctgcaga cggcatttct attgcgcaga ccactgaagg tgcgctgaat    240
gaaatcaaca caaacctgca gcgtgtgcgt gagttgtctg ttcaggccac taacgggact    300
aactctgatt ccgatctgaa atctatccag gatgaaattc agcaacgtct ggaagaaatc    360
gatcgcgttt ctaatcagac tcaagctaac ggtgttaaag tcctgtctca ggacaacgca    420
atgaaaatcc aggttggtgc taacgatggt gccgctatta ccatcgatct gcaaaaaatt    480
gatgtgaaaa gccttggcct tgatgggttc aatgttaatt ccccgggaag taccgctaac    540
```

```
ccactggctt caattgattc tgcattgtca aaagtggacg cagttcgttc ttctctgggg    600
gcaattcaaa accgctttga ttcagccatt accaacttg gcaatacggt aaccaatctg    660
aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                                846
```

<210> SEQ ID NO 176
<211> LENGTH: 250
<212> TYPE: PRT
<213> ORGANISM: Artificial Sequence
<220> FEATURE:
<223> OTHER INFORMATION: Synthetic sequence

<400> SEQUENCE: 176

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Ala Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Ala Asn Gly Val Lys Val Leu Ser Gln Asp Asn Ala Met
            100                 105                 110

Lys Ile Gln Val Gly Ala Asn Asp Gly Ala Ala Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 177
<211> LENGTH: 270
<212> TYPE: DNA
<213> ORGANISM: Artificial Sequence
<220> FEATURE:
<223> OTHER INFORMATION: Synthetic sequence

<400> SEQUENCE: 177

```
aacccactgg cttcaattga ttctgcattg tcaaaagtgg acgcagttcg ttcttctctg    60
ggggcaattc aaaaccgttt tgattcagcc attaccaacc ttggcaatac ggtaaccaat   120
ctgaactccg cgcgtagccg tatcgaagat gctgactatg caacggaagt ttctcaaatg   180
tctaaagcgc agattctgca gcaggctggt acttccgttc tggcgcaggc taaccaggtt   240
ccgcaaaacg tcctctcttt actgcgttaa                                    270
```

<210> SEQ ID NO 178
<211> LENGTH: 60
<212> TYPE: DNA
<213> ORGANISM: Artificial Sequence
<220> FEATURE:
<223> OTHER INFORMATION: Synthetic sequence

<400> SEQUENCE: 178

```
attaccaacc ttggcaatac ggtaaccaat ctgaactccg cgcgtagccg tatcgaagat    60
```

<210> SEQ ID NO 179
<211> LENGTH: 20
<212> TYPE: PRT
<213> ORGANISM: Artificial Sequence
<220> FEATURE:
<223> OTHER INFORMATION: Synthetic sequence

<400> SEQUENCE: 179

Ile Thr Asn Leu Gly Asn Thr Val Thr Asn Leu Asn Ser Ala Arg Ser
1               5                   10                  15
Arg Ile Glu Asp
            20

<210> SEQ ID NO 180
<211> LENGTH: 46
<212> TYPE: DNA
<213> ORGANISM: Artificial Sequence
<220> FEATURE:
<223> OTHER INFORMATION: Synthetic sequence

<400> SEQUENCE: 180

```
ccttggcaat acggtaaccg ctctggcctc cgcgcgtagc cgtatc              46
```

<210> SEQ ID NO 181
<211> LENGTH: 46
<212> TYPE: DNA
<213> ORGANISM: Artificial Sequence
<220> FEATURE:
<223> OTHER INFORMATION: Synthetic sequence

<400> SEQUENCE: 181

```
gatacggcta cgcgcggagg ccagagcggt taccgtattg ccaagg              46
```

<210> SEQ ID NO 182
<211> LENGTH: 60
<212> TYPE: DNA
<213> ORGANISM: Artificial Sequence
<220> FEATURE:
<223> OTHER INFORMATION: Synthetic sequence

<400> SEQUENCE: 182

```
acggtaaccg ctctggcctc cgcgcgtagc cgtatcgaag atgctgacta tgcaacggaa    60
```

<210> SEQ ID NO 183
<211> LENGTH: 20

<212> TYPE: PRT
<213> ORGANISM: Artificial Sequence
<220> FEATURE:
<223> OTHER INFORMATION: Synthetic sequence

<400> SEQUENCE: 183

Thr Val Thr Ala Leu Ala Ser Ala Arg Ser Arg Ile Glu Asp Ala Asp
1               5                   10                  15

Tyr Ala Thr Glu
            20

<210> SEQ ID NO 184
<211> LENGTH: 34
<212> TYPE: DNA
<213> ORGANISM: Artificial Sequence
<220> FEATURE:
<223> OTHER INFORMATION: Synthetic sequence

<400> SEQUENCE: 184
gctctggcct ccgcggctag ccgtatcgaa gatg                           34

<210> SEQ ID NO 185
<211> LENGTH: 34
<212> TYPE: DNA
<213> ORGANISM: Artificial Sequence
<220> FEATURE:
<223> OTHER INFORMATION: Synthetic sequence

<400> SEQUENCE: 185
catcttcgat acggctagcc gcggaggcca gagc                           34

<210> SEQ ID NO 186
<211> LENGTH: 60
<212> TYPE: DNA
<213> ORGANISM: Artificial Sequence
<220> FEATURE:
<223> OTHER INFORMATION: Synthetic sequence

<400> SEQUENCE: 186
caaaaccgtt ttgattcagc cattaccaac cttggcaata cggtaaccgc tctggcctcc    60

<210> SEQ ID NO 187
<211> LENGTH: 20
<212> TYPE: PRT
<213> ORGANISM: Artificial Sequence
<220> FEATURE:
<223> OTHER INFORMATION: Synthetic sequence

<400> SEQUENCE: 187

Gln Asn Arg Phe Asp Ser Ala Ile Thr Asn Leu Gly Asn Thr Val Thr
1               5                   10                  15

Ala Leu Ala Ser
            20

<210> SEQ ID NO 188
<211> LENGTH: 48
<212> TYPE: DNA
<213> ORGANISM: Artificial Sequence
<220> FEATURE:
<223> OTHER INFORMATION: Synthetic sequence

<400> SEQUENCE: 188
gttttgattc agccattacc gcccttggcg ctacggtaac cgctctgg              48

<210> SEQ ID NO 189

```
<211> LENGTH: 48
<212> TYPE: DNA
<213> ORGANISM: Artificial Sequence
<220> FEATURE:
<223> OTHER INFORMATION: Synthetic sequence

<400> SEQUENCE: 189
ccagagcggt taccgtagcg ccaagggcgg taatggctga atcaaaac          48

<210> SEQ ID NO 190
<211> LENGTH: 39
<212> TYPE: DNA
<213> ORGANISM: Artificial Sequence
<220> FEATURE:
<223> OTHER INFORMATION: Synthetic sequence

<400> SEQUENCE: 190
caacagcgcg aaagccgatg cgggaggcca ggcgattgc                    39

<210> SEQ ID NO 191
<211> LENGTH: 39
<212> TYPE: DNA
<213> ORGANISM: Artificial Sequence
<220> FEATURE:
<223> OTHER INFORMATION: Synthetic sequence

<400> SEQUENCE: 191
gcaatcgcct ggcctcccgc atcggctttc gcgctgttg                    39

<210> SEQ ID NO 192
<211> LENGTH: 846
<212> TYPE: DNA
<213> ORGANISM: Artificial Sequence
<220> FEATURE:
<223> OTHER INFORMATION: Synthetic sequence

<400> SEQUENCE: 192
taatacgact cactataggg gaattgtgag cggataacaa ttcccctcta gaataatttt    60
gtttaacttt aagaaggaga tatacatatg agcgggttac ggatcaacag cgcgaaagcc   120
gatgcgggag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca caaacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaacttg gcaatacggt aaccaatctg   660
aactccgcgc gtagccgtat cgaagatgct gactatgcaa cggaagtttc taatatgtct   720
aaagcgcaga ttctgcagca ggctggtact tccgttctgg cgcaggctaa ccaggttccg   780
caaaacgtcc tctctttact ggttccgcgg ggttctcatc atcatcatca tcatggttaa   840
gtcgac                                                             846

<210> SEQ ID NO 193
<211> LENGTH: 250
<212> TYPE: PRT
<213> ORGANISM: Artificial Sequence
```

<220> FEATURE:
<223> OTHER INFORMATION: Synthetic sequence

<400> SEQUENCE: 193

Met Ser Gly Leu Arg Ile Asn Ser Ala Lys Ala Asp Ala Gly Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His Gly
                245                 250

<210> SEQ ID NO 194
<211> LENGTH: 43
<212> TYPE: DNA
<213> ORGANISM: Artificial Sequence
<220> FEATURE:
<223> OTHER INFORMATION: Synthetic sequence

<400> SEQUENCE: 194
gtctgttcag gccactgccg gggctaactc tgattccgat ctg                            43

<210> SEQ ID NO 195
<211> LENGTH: 43
<212> TYPE: DNA
<213> ORGANISM: Artificial Sequence
<220> FEATURE:
<223> OTHER INFORMATION: Synthetic sequence

<400> SEQUENCE: 195
cagatcggaa tcagagttag ccccggcagt ggcctgaaca gac                            43

<210> SEQ ID NO 196

```
<211> LENGTH: 846
<212> TYPE: DNA
<213> ORGANISM: Artificial Sequence
<220> FEATURE:
<223> OTHER INFORMATION: Synthetic sequence

<400> SEQUENCE: 196
taatacgact cactataggg gaattgtgag cggataacaa ttcccctcta gaataatttt      60
gtttaacttt aagaaggaga tatacatatg agcgggttac ggatcaacag cgcgaaagac     120
gatgcggcag gccaggcgat tgctaaccgc ttcacttcta atatcaaagg tctgactcag     180
gcttcccgta acgctaacga cggcatttct attgcgcaga ccactgaagg tgcgctgaat     240
gaaatcaaca acaacctgca gcgtgtgcgt gagttgtctg ttcaggccac tgccggggct     300
aactctgatt ccgatctgaa atctatccag gatgaaattc agcaacgtct ggaagaaatc     360
gatcgcgttt ctaatcagac tcaatttaac ggtgttaaag tcctgtctca ggacaaccag     420
atgaaaatcc aggttggtgc taacgatggt gaaaccatta ccatcgatct gcaaaaaatt     480
gatgtgaaaa gccttggcct tgatgggttc aatgttaatt ccccgggaag taccgctaac     540
ccactggctt caattgattc tgcattgtca aaagtggacg cagttcgttc ttctctgggg     600
gcaattcaaa accgctttga ttcagccatt accaacttg gcaatacggt aaccaatctg     660
aactccgcgc gtagccgtat cgaagatgct gactatgcaa cggaagtttc taatatgtct     720
aaagcgcaga ttctgcagca ggctggtact tccgttctgg cgcaggctaa ccaggttccg     780
caaaacgtcc tctctttact ggttccgcgg ggttctcatc atcatcatca tcatggttaa     840
gtcgac                                                                 846

<210> SEQ ID NO 197
<211> LENGTH: 250
<212> TYPE: PRT
<213> ORGANISM: Artificial Sequence
<220> FEATURE:
<223> OTHER INFORMATION: Synthetic sequence

<400> SEQUENCE: 197

Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Ala Gly Ala Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
```

```
              165                 170                 175
Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 198
<211> LENGTH: 45
<212> TYPE: DNA
<213> ORGANISM: Artificial Sequence
<220> FEATURE:
<223> OTHER INFORMATION: Synthetic sequence

<400> SEQUENCE: 198
ctgattccga tctgaaagct atccaggctg aaattcagca acgtc              45

<210> SEQ ID NO 199
<211> LENGTH: 45
<212> TYPE: DNA
<213> ORGANISM: Artificial Sequence
<220> FEATURE:
<223> OTHER INFORMATION: Synthetic sequence

<400> SEQUENCE: 199
gacgttgctg aatttcagcc tggatagctt tcagatcgga atcag              45

<210> SEQ ID NO 200
<211> LENGTH: 846
<212> TYPE: DNA
<213> ORGANISM: Artificial Sequence
<220> FEATURE:
<223> OTHER INFORMATION: Synthetic sequence

<400> SEQUENCE: 200
taatacgact cactataggg gaattgtgag cggataacaa ttcccctcta gaataatttt     60
gtttaacttt aagaaggaga tatacatatg agcgggttac ggatcaacag cgcgaaagac    120
gatgcggcag ccaggcgat tgctaaccgc ttcacttcta atatcaaagg tctgactcag    180
gcttcccgta acgctaacga cggcatttct attgcgcaga ccactgaagg tgcgctgaat    240
gaaatcaaca caacctgca gcgtgtgcgt gagttgtctg ttcaggccac tgccggggct    300
aactctgatt ccgatctgaa agctatccag gctgaaattc agcaacgtct ggaagaaatc    360
gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaacttg gcaatacggt aaccaatctg    660
aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
```

```
gtcgac                                                                846
```

<210> SEQ ID NO 201
<211> LENGTH: 753
<212> TYPE: DNA
<213> ORGANISM: Artificial Sequence
<220> FEATURE:
<223> OTHER INFORMATION: Synthetic sequence

<400> SEQUENCE: 201

```
atgagcgggt tacggatcaa cagcgcgaaa gacgatgcgg caggccaggc gattgctaac    60
cgcttcactt ctaatatcaa aggtctgact caggcttccc gtaacgctaa cgacggcatt   120
tctattgcgc agaccactga aggtgcgctg aatgaaatca caacaacct gcagcgtgtg    180
cgtgagttgt ctgttcaggc cactgccggg gctaactctg attccgatct gaaagctatc   240
caggctgaaa ttcagcaacg tctggaagaa atcgatcgcg tttctaatca gactcaattt   300
aacggtgtta agtcctgtc tcaggacaac cagatgaaaa tccaggttgg tgctaacgat    360
ggtgaaacca ttaccatcga tctgcaaaaa attgatgtga aaagccttgg ccttgatggg   420
ttcaatgtta attccccggg aagtaccgct aacccactgg cttcaattga ttctgcattg   480
tcaaaagtgg acgcagttcg ttcttctctg ggggcaattc aaaaccgctt tgattcagcc   540
attaccaacc ttggcaatac ggtaaccaat ctgaactccg cgcgtagccg tatcgaagat   600
gctgactatg caacggaagt ttctaatatg tctaaagcgc agattctgca gcaggctggt   660
acttccgttc tggcgcaggc taaccaggtt ccgcaaaacg tcctctcttt actggttccg   720
cggggttctc atcatcatca tcatcatggt taa                                753
```

<210> SEQ ID NO 202
<211> LENGTH: 250
<212> TYPE: PRT
<213> ORGANISM: Artificial Sequence
<220> FEATURE:
<223> OTHER INFORMATION: Synthetic sequence

<400> SEQUENCE: 202

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Ala Gly Ala Asn Ser Asp Ser Asp Leu Lys Ala Ile
65                  70                  75                  80

Gln Ala Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
```

```
                      165                 170                 175
Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 203
<211> LENGTH: 45
<212> TYPE: DNA
<213> ORGANISM: Artificial Sequence
<220> FEATURE:
<223> OTHER INFORMATION: Synthetic sequence

<400> SEQUENCE: 203
gccactaacg ggactaacgc tgatgccgct ctgaaatcta tccag    45

<210> SEQ ID NO 204
<211> LENGTH: 45
<212> TYPE: DNA
<213> ORGANISM: Artificial Sequence
<220> FEATURE:
<223> OTHER INFORMATION: Synthetic sequence

<400> SEQUENCE: 204
ctggatagat ttcagagcgg catcagcgtt agtcccgtta gtggc    45

<210> SEQ ID NO 205
<211> LENGTH: 846
<212> TYPE: DNA
<213> ORGANISM: Artificial Sequence
<220> FEATURE:
<223> OTHER INFORMATION: Synthetic sequence

<400> SEQUENCE: 205
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag ccaggcgat tgctaaccgc ttcacttcta atatcaaagg tctgactcag   180
gcttcccgta acgctaacga cggcatttct attgcgcaga ccactgaagg tgcgctgaat   240
gaaatcaaca caacctgca gcgtgtgcgt gagttgtctg ttcaggccac taacgggact   300
aacgctgatg ccgctctgaa atctatccag gatgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaaccttg caatacggt aaccaatctg   660
aactccgcgc gtagccgtat cgaagatgct gactatgcaa cggaagtttc taatatgtct   720
aaagcgcaga ttctgcagca ggctggtact ccgttctggg cgcaggctaa ccaggttccg   780
caaaacgtcc tctctttact ggttccgcgg ggttctcatc atcatcatca tcatggttaa   840
``` gtcgac 846

<210> SEQ ID NO 206
<211> LENGTH: 250
<212> TYPE: PRT
<213> ORGANISM: Artificial Sequence
<220> FEATURE:
<223> OTHER INFORMATION: Synthetic sequence

<400> SEQUENCE: 206

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ala Asp Ala Ala Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His Gly
                245                 250
```

<210> SEQ ID NO 207
<211> LENGTH: 45
<212> TYPE: DNA
<213> ORGANISM: Artificial Sequence
<220> FEATURE:
<223> OTHER INFORMATION: Synthetic sequence

<400> SEQUENCE: 207
gccactgccg gggctaacgc tgatgccgct ctgaaagcta tccag          45

<210> SEQ ID NO 208
<211> LENGTH: 45
<212> TYPE: DNA
<213> ORGANISM: Artificial Sequence
<220> FEATURE:
<223> OTHER INFORMATION: Synthetic sequence

<400> SEQUENCE: 208
ctggatagct tcagagcgg catcagcgtt agccccggca gtggc    45

<210> SEQ ID NO 209
<211> LENGTH: 846
<212> TYPE: DNA
<213> ORGANISM: Artificial Sequence
<220> FEATURE:
<223> OTHER INFORMATION: Synthetic sequence

<400> SEQUENCE: 209
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca acaacctgca gcgtgtgcgt gagttgtctg ttcaggccac tgccggggct   300
aacgctgatg ccgctctgaa agctatccag gctgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaacttg gcaatacggt aaccaatctg   660
aactccgcgc gtagccgtat cgaagatgct gactatgcaa cggaagtttc taatatgtct   720
aaagcgcaga ttctgcagca ggctggtact tccgttctgg cgcaggctaa ccaggttccg   780
caaaacgtcc tctctttact ggttccgcgg ggttctcatc atcatcatca tcatggttaa   840
gtcgac                                                              846

<210> SEQ ID NO 210
<211> LENGTH: 250
<212> TYPE: PRT
<213> ORGANISM: Artificial Sequence
<220> FEATURE:
<223> OTHER INFORMATION: Synthetic sequence

<400> SEQUENCE: 210

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Ala Gly Ala Asn Ala Asp Ala Leu Lys Ala Ile
65                  70                  75                  80

Gln Ala Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

```
Gln Lys Ile Asp Val Lys Ser Leu Gly Leu Asp Gly Phe Asn Val Asn
    130                 135                 140
Ser Pro Gly Ser Thr Ala Asn Pro Leu Ala Ser Ile Asp Ser Ala Leu
145                 150                 155                 160
Ser Lys Val Asp Ala Val Arg Ser Ser Leu Gly Ala Ile Gln Asn Arg
                165                 170                 175
Phe Asp Ser Ala Ile Thr Asn Leu Gly Asn Thr Val Thr Asn Leu Asn
            180                 185                 190
Ser Ala Arg Ser Arg Ile Glu Asp Ala Asp Tyr Ala Thr Glu Val Ser
        195                 200                 205
Asn Met Ser Lys Ala Gln Ile Leu Gln Gln Ala Gly Thr Ser Val Leu
210                 215                 220
Ala Gln Ala Asn Gln Val Pro Gln Asn Val Leu Ser Leu Leu Val Pro
225                 230                 235                 240
Arg Gly Ser His His His His His His Gly
                245                 250
```

<210> SEQ ID NO 211
<211> LENGTH: 846
<212> TYPE: DNA
<213> ORGANISM: Artificial Sequence
<220> FEATURE:
<223> OTHER INFORMATION: Synthetic sequence

<400> SEQUENCE: 211

```
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag gccaggcgat tgctaaccgc ttcacttcta atatcaaagg tctgactcag   180
gcttcccgta acgctaacga cggcatttct attgcgcaga ccactgaagg tgcgctgaat   240
gaaatcaaca caacctgca gcgtgtgcgt gagttgtctg ttcaggccac taacgggact   300
aactctgatt ccgatctgaa agctatccag gctgaaattc agcaacgtct ggaagaaatc   360
gatcgcgttt ctaatcagac tcaatttaac ggtgttaaag tcctgtctca ggacaaccag   420
atgaaaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaacttg gcaatacggt aaccaatctg   660
aactccgcgc gtagccgtat cgaagatgct gactatgcaa cggaagtttc taatatgtct   720
aaagcgcaga ttctgcagca ggctggtact tccgttctgg cgcaggctaa ccaggttccg   780
caaaacgtcc tctctttact ggttccgcgg ggttctcatc atcatcatca tcatggttaa   840
gtcgac                                                              846
```

<210> SEQ ID NO 212
<211> LENGTH: 250
<212> TYPE: PRT
<213> ORGANISM: Artificial Sequence
<220> FEATURE:
<223> OTHER INFORMATION: Synthetic sequence

<400> SEQUENCE: 212

```
Met Ser Gly Leu Arg Ile Asn Ser Ala Lys Asp Asp Ala Ala Gly Gln
1               5                   10                  15
Ala Ile Ala Asn Arg Phe Thr Ser Asn Ile Lys Gly Leu Thr Gln Ala
            20                  25                  30
```

```
Ser Arg Asn Ala Asn Asp Gly Ile Ser Ile Ala Gln Thr Thr Glu Gly
        35                  40                  45

Ala Leu Asn Glu Ile Asn Asn Leu Gln Arg Val Arg Glu Leu Ser
 50                  55                  60

Val Gln Ala Thr Asn Gly Thr Asn Ser Asp Ser Asp Leu Lys Ala Ile
 65                  70                  75                  80

Gln Ala Glu Ile Gln Gln Arg Leu Glu Glu Ile Asp Arg Val Ser Asn
                 85                  90                  95

Gln Thr Gln Phe Asn Gly Val Lys Val Leu Ser Gln Asp Asn Gln Met
                100                 105                 110

Lys Ile Gln Val Gly Ala Asn Asp Gly Glu Thr Ile Thr Ile Asp Leu
                115                 120                 125

Gln Lys Ile Asp Val Lys Ser Leu Gly Leu Asp Gly Phe Asn Val Asn
130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
                180                 185                 190

Ser Ala Arg Ser Arg Ile Glu Asp Ala Asp Tyr Ala Thr Glu Val Ser
                195                 200                 205

Asn Met Ser Lys Ala Gln Ile Leu Gln Gln Ala Gly Thr Ser Val Leu
                210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 213
<211> LENGTH: 45
<212> TYPE: DNA
<213> ORGANISM: Artificial Sequence
<220> FEATURE:
<223> OTHER INFORMATION: Synthetic sequence

<400> SEQUENCE: 213
ctatccagga tgaaattcag gcacgtctgg cagaaatcga tcgcg              45

<210> SEQ ID NO 214
<211> LENGTH: 45
<212> TYPE: DNA
<213> ORGANISM: Artificial Sequence
<220> FEATURE:
<223> OTHER INFORMATION: Synthetic sequence

<400> SEQUENCE: 214
cgcgatcgat ttctgccaga cgtgcctgaa tttcatcctg gatag              45

<210> SEQ ID NO 215
<211> LENGTH: 846
<212> TYPE: DNA
<213> ORGANISM: Artificial Sequence
<220> FEATURE:
<223> OTHER INFORMATION: Synthetic sequence

<400> SEQUENCE: 215
taatacgact cactataggg gaattgtgag cggataacaa ttcccctcta gaataatttt   60
```

```
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
gaaatcaaca acaacctgca gcgtgtgcgt gagttgtctg ttcaggccac taacgggact    300
aactctgatt ccgatctgaa atctatccag gatgaaattc aggcacgtct ggcagaaatc    360
gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaacctg gcaatacggt aaccaatctg    660
aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                               846
```

<210> SEQ ID NO 216
<211> LENGTH: 250
<212> TYPE: PRT
<213> ORGANISM: Artificial Sequence
<220> FEATURE:
<223> OTHER INFORMATION: Synthetic sequence

<400> SEQUENCE: 216

```
Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Ala Arg Leu Ala Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220
```

Ala Gln Ala Asn Gln Val Pro Gln Asn Val Leu Ser Leu Leu Val Pro
225                 230                 235                 240

Arg Gly Ser His His His His His His Gly
            245                 250

<210> SEQ ID NO 217
<211> LENGTH: 59
<212> TYPE: DNA
<213> ORGANISM: Artificial Sequence
<220> FEATURE:
<223> OTHER INFORMATION: Synthetic sequence

<400> SEQUENCE: 217
ggaagaaatc gatgccgttt ctgctgcgac tcaatttaac ggtgttaaag tcctgtctc      59

<210> SEQ ID NO 218
<211> LENGTH: 59
<212> TYPE: DNA
<213> ORGANISM: Artificial Sequence
<220> FEATURE:
<223> OTHER INFORMATION: Synthetic sequence

<400> SEQUENCE: 218
gagacaggac tttaacaccg ttaaattgag tcgcagcaga acggcatcg atttcttcc       59

<210> SEQ ID NO 219
<211> LENGTH: 846
<212> TYPE: DNA
<213> ORGANISM: Artificial Sequence
<220> FEATURE:
<223> OTHER INFORMATION: Synthetic sequence

<400> SEQUENCE: 219
taatacgact cactataggg gaattgtgag cggataacaa ttcccctcta gaataatttt     60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
gaaatcaaca acaacctgca gcgtgtgcgt gagttgtctg ttcaggccac taacgggact    300
aactctgatt ccgatctgaa atctatccag gatgaaattc agcaacgtct ggaagaaatc    360
gatgccgttt ctgctgcgac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaacttg gcaatacggt aaccaatctg    660
aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                              846

<210> SEQ ID NO 220
<211> LENGTH: 250
<212> TYPE: PRT
<213> ORGANISM: Artificial Sequence
<220> FEATURE:
<223> OTHER INFORMATION: Synthetic sequence

<400> SEQUENCE: 220

Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Ala Val Ser Ala
                85                  90                  95

Ala Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 221
<211> LENGTH: 53
<212> TYPE: DNA
<213> ORGANISM: Artificial Sequence
<220> FEATURE:
<223> OTHER INFORMATION: Synthetic sequence

<400> SEQUENCE: 221
cagcaacgtc tggaagaaat cgatgccgtt tctaatcaga ctcaatttaa cgg    53

<210> SEQ ID NO 222
<211> LENGTH: 53
<212> TYPE: DNA
<213> ORGANISM: Artificial Sequence
<220> FEATURE:
<223> OTHER INFORMATION: Synthetic sequence

<400> SEQUENCE: 222
ccgttaaatt gagtctgatt agaaacggca tcgatttctt ccagacgttg ctg    53

<210> SEQ ID NO 223
<211> LENGTH: 753
<212> TYPE: DNA
<213> ORGANISM: Artificial Sequence
<220> FEATURE:
<223> OTHER INFORMATION: Synthetic sequence

<400> SEQUENCE: 223

```
atgagcgggt tacggatcaa cagcgcgaaa gacgatgcgg caggccaggc gattgctaac      60
cgcttcactt ctaatatcaa aggtctgact caggcttccc gtaacgctaa cgacggcatt    120
tctattgcgc agaccactga aggtgcgctg aatgaaatca acaacaacct gcagcgtgtg    180
cgtgagttgt ctgttcaggc cactaacggg actaactctg attccgatct gaaatctatc    240
caggatgaaa ttcagcaacg tctggaagaa atcgatgccg tttctaatca gactcaattt    300
aacggtgtta aagtcctgtc tcaggacaac cagatgaaaa tccaggttgg tgctaacgat    360
ggtgaaacca ttaccatcga tctgcaaaaa attgatgtga aaagccttgg ccttgatggg    420
ttcaatgtta attccccggg aagtaccgct aacccactgg cttcaattga ttctgcattg    480
tcaaaagtgg acgcagttcg ttcttctctg ggggcaattc aaaaccgctt tgattcagcc    540
attaccaacc ttggcaatac ggtaaccaat ctgaactccg cgcgtagccg tatcgaagat    600
gctgactatg caacggaagt ttctaatatg tctaaagcgc agattctgca gcaggctggt    660
acttccgttc tggcgcaggc taaccaggtt ccgcaaaacg tcctctcttt actggttccg    720
cggggttctc atcatcatca tcatcatggt taa                                 753
```

<210> SEQ ID NO 224
<211> LENGTH: 846
<212> TYPE: DNA
<213> ORGANISM: Artificial Sequence
<220> FEATURE:
<223> OTHER INFORMATION: Synthetic sequence

<400> SEQUENCE: 224

```
taatacgact cactataggg gaattgtgag cggataacaa ttcccctcta gaataatttt      60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
gaaatcaaca acaacctgca gcgtgtgcgt gagttgtctg ttcaggccac taacgggact    300
aactctgatt ccgatctgaa atctatccag gatgaaattc agcaacgtct ggaagaaatc    360
gatgccgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaaccttg gcaatacggt aaccaatctg    660
aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                               846
```

<210> SEQ ID NO 225
<211> LENGTH: 250
<212> TYPE: PRT
<213> ORGANISM: Artificial Sequence
<220> FEATURE:
<223> OTHER INFORMATION: Synthetic sequence

<400> SEQUENCE: 225

Met Ser Gly Leu Arg Ile Asn Ser Ala Lys Asp Asp Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Ala Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 226
<211> LENGTH: 53
<212> TYPE: DNA
<213> ORGANISM: Artificial Sequence
<220> FEATURE:
<223> OTHER INFORMATION: Synthetic sequence

<400> SEQUENCE: 226
cgtttctaat cagactcaat tgccgctgt taaagtcctg tctcaggaca acc        53

<210> SEQ ID NO 227
<211> LENGTH: 53
<212> TYPE: DNA
<213> ORGANISM: Artificial Sequence
<220> FEATURE:
<223> OTHER INFORMATION: Synthetic sequence

<400> SEQUENCE: 227
ggttgtcctg agacaggact ttaacagcgg caaattgagt ctgattagaa acg        53

<210> SEQ ID NO 228
<211> LENGTH: 846
<212> TYPE: DNA
<213> ORGANISM: Artificial Sequence
<220> FEATURE:
<223> OTHER INFORMATION: Synthetic sequence

<400> SEQUENCE: 228

```
taatacgact cactataggg gaattgtgag cggataacaa ttcccctcta gaataatttt     60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
gaaatcaaca caacctgca gcgtgtgcgt gagttgtctg ttcaggccac taacgggact    300
aactctgatt ccgatctgaa atctatccag gatgaaattc agcaacgtct ggaagaaatc    360
gatcgcgttt ctaatcagac tcaatttgcc gctgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aagtggacg cagttcgttc ttctctgggg    600
gcaattcaaa accgctttga ttcagccatt accaaccttg gcaatacggt aaccaatctg    660
aactccgcgc gtagccgtat cgaagatgct gactatgcaa cggaagtttc taatatgtct    720
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                               846
```

<210> SEQ ID NO 229
<211> LENGTH: 250
<212> TYPE: PRT
<213> ORGANISM: Artificial Sequence
<220> FEATURE:
<223> OTHER INFORMATION: Synthetic sequence

<400> SEQUENCE: 229

```
Met Ser Gly Leu Arg Ile Asn Ser Ala Lys Asp Asp Ala Ala Gly Gln
 1               5                  10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Ala Ala Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
```

```
            180                 185                 190
Ser Ala Arg Ser Arg Ile Glu Asp Ala Asp Tyr Ala Thr Glu Val Ser
                195                 200                 205
Asn Met Ser Lys Ala Gln Ile Leu Gln Gln Ala Gly Thr Ser Val Leu
        210                 215                 220
Ala Gln Ala Asn Gln Val Pro Gln Asn Val Leu Ser Leu Leu Val Pro
225                 230                 235                 240
Arg Gly Ser His His His His His His Gly
                245                 250
```

<210> SEQ ID NO 230
<211> LENGTH: 52
<212> TYPE: DNA
<213> ORGANISM: Artificial Sequence
<220> FEATURE:
<223> OTHER INFORMATION: Synthetic sequence

<400> SEQUENCE: 230

```
gttaaagtcc tgtctcagga caacgcgatg gcaatccagg ttggtgctaa cg        52
```

<210> SEQ ID NO 231
<211> LENGTH: 52
<212> TYPE: DNA
<213> ORGANISM: Artificial Sequence
<220> FEATURE:
<223> OTHER INFORMATION: Synthetic sequence

<400> SEQUENCE: 231

```
cgttagcacc aacctggatt gccatcgcgt tgtcctgaga caggacttta ac        52
```

<210> SEQ ID NO 232
<211> LENGTH: 846
<212> TYPE: DNA
<213> ORGANISM: Artificial Sequence
<220> FEATURE:
<223> OTHER INFORMATION: Synthetic sequence

<400> SEQUENCE: 232

```
taatacgact cactataggg gaattgtgag cggataacaa ttcccctcta gaataatttt    60
gtttaacttt aagaaggaga tatacatatg agcgggttac ggatcaacag cgcgaaagac   120
gatgcggcag ccaggcgat tgctaaccgc ttcacttcta atatcaaagg tctgactcag   180
gcttcccgta acgctaacga cggcatttct attgcgcaga ccactgaagg tgcgctgaat   240
gaaatcaaca caaacctgca gcgtgtgcgt gagttgtctg ttcaggccac taacgggact   300
aactctgatt ccgatctgaa atctatccag gatgaaattc agcaacgtct ggaagaaatc   360
gatcgcgttt ctaatcagac tcaatttaac ggtgttaaag tcctgtctca ggacaacgcg   420
atggcaatcc aggttggtgc taacgatggt gaaaccatta ccatcgatct gcaaaaaatt   480
gatgtgaaaa gccttggcct tgatgggttc aatgttaatt ccccgggaag taccgctaac   540
ccactggctt caattgattc tgcattgtca aaagtggacg cagttcgttc ttctctgggg   600
gcaattcaaa accgctttga ttcagccatt accaaccttg gcaatacggt aaccaatctg   660
aactccgcgc gtagccgtat cgaagatgct gactatgcaa cggaagtttc taatatgtct   720
aaagcgcaga ttctgcagca ggctggtact tccgttctgg cgcaggctaa ccaggttccg   780
caaaacgtcc tctctttact ggttccgcgg ggttctcatc atcatcatca tcatggttaa   840
gtcgac                                                             846
```

<210> SEQ ID NO 233
<211> LENGTH: 250
<212> TYPE: PRT
<213> ORGANISM: Artificial Sequence
<220> FEATURE:
<223> OTHER INFORMATION: Synthetic sequence

<400> SEQUENCE: 233

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Ala Met
            100                 105                 110

Ala Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250
```

<210> SEQ ID NO 234
<211> LENGTH: 53
<212> TYPE: DNA
<213> ORGANISM: Artificial Sequence
<220> FEATURE:
<223> OTHER INFORMATION: Synthetic sequence

<400> SEQUENCE: 234
gatgaaaatc caggttggtg ctagcgctgc tgaaaccatt accatcgatc tgc    53

<210> SEQ ID NO 235
<211> LENGTH: 53
<212> TYPE: DNA
<213> ORGANISM: Artificial Sequence
<220> FEATURE:
<223> OTHER INFORMATION: Synthetic sequence

<400> SEQUENCE: 235
gcagatcgat ggtaatggtt tcagcagcgc tagcaccaac ctggattttc atc        53

<210> SEQ ID NO 236
<211> LENGTH: 846
<212> TYPE: DNA
<213> ORGANISM: Artificial Sequence
<220> FEATURE:
<223> OTHER INFORMATION: Synthetic sequence

<400> SEQUENCE: 236
taatacgact cactataggg gaattgtgag cggataacaa ttcccctcta gaataatttt        60
gtttaacttt aagaaggaga tatacatatg agcgggttac ggatcaacag cgcgaaagac       120
gatgcggcag gccaggcgat tgctaaccgc ttcacttcta atatcaaagg tctgactcag       180
gcttcccgta acgctaacga cggcatttct attgcgcaga ccactgaagg tgcgctgaat       240
gaaatcaaca acaacctgca gcgtgtgcgt gagttgtctg ttcaggccac taacgggact       300
aactctgatt ccgatctgaa atctatccag gatgaaattc agcaacgtct ggaagaaatc       360
gatcgcgttt ctaatcagac tcaatttaac ggtgttaaag tcctgtctca ggacaaccag       420
atgaaaatcc aggttggtgc tagcgctgct gaaaccatta ccatcgatct gcaaaaaatt       480
gatgtgaaaa gccttggcct tgatgggttc aatgttaatt ccccgggaag taccgctaac       540
ccactggctt caattgattc tgcattgtca aaagtggacg cagttcgttc ttctctgggg       600
gcaattcaaa accgctttga ttcagccatt accaacttg gcaatacggt aaccaatctg       660
aactccgcgc gtagccgtat cgaagatgct gactatgcaa cggaagtttc taatatgtct       720
aaagcgcaga ttctgcagca ggctggtact tccgttctgg cgcaggctaa ccaggttccg       780
caaaacgtcc tctctttact ggttccgcgg ggttctcatc atcatcatca tcatggttaa       840
gtcgac                                                                  846

<210> SEQ ID NO 237
<211> LENGTH: 250
<212> TYPE: PRT
<213> ORGANISM: Artificial Sequence
<220> FEATURE:
<223> OTHER INFORMATION: Synthetic sequence

<400> SEQUENCE: 237

Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Ser Ala Ala Glu Thr Ile Thr Ile Asp Leu
        115                 120                 125

Gln Lys Ile Asp Val Lys Ser Leu Gly Leu Asp Gly Phe Asn Val Asn
    130                 135                 140

```
Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Tyr Ala Thr Glu Val Ser
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His His Gly
                245                 250

<210> SEQ ID NO 238
<211> LENGTH: 56
<212> TYPE: DNA
<213> ORGANISM: Artificial Sequence
<220> FEATURE:
<223> OTHER INFORMATION: Synthetic sequence

<400> SEQUENCE: 238
gccgtatcga agatgctgac gctggagcgg aagttgctaa tatgtctaaa gcgcag      56

<210> SEQ ID NO 239
<211> LENGTH: 56
<212> TYPE: DNA
<213> ORGANISM: Artificial Sequence
<220> FEATURE:
<223> OTHER INFORMATION: Synthetic sequence

<400> SEQUENCE: 239
ctgcgcttta gacatattag caacttccgc tccagcgtca gcatcttcga tacggc      56

<210> SEQ ID NO 240
<211> LENGTH: 846
<212> TYPE: DNA
<213> ORGANISM: Artificial Sequence
<220> FEATURE:
<223> OTHER INFORMATION: Synthetic sequence

<400> SEQUENCE: 240
taatacgact cactataggg gaattgtgag cggataacaa ttcccctcta gaataatttt     60
gtttaacttt aagaaggaga tatacatatg agcgggttac ggatcaacag cgcgaaagac    120
gatgcggcag gccaggcgat tgctaaccgc ttcacttcta atatcaaagg tctgactcag    180
gcttcccgta acgctaacga cggcatttct attgcgcaga ccactgaagg tgcgctgaat    240
gaaatcaaca caacctgca gcgtgtgcgt gagttgtctg ttcaggccac taacgggact    300
aactctgatt ccgatctgaa atctatccag atgaaattc agcaacgtct ggaagaaatc    360
gatcgcgttt ctaatcagac tcaatttaac ggtgttaaag tcctgtctca ggacaaccag    420
atgaaaatcc aggttggtgc taacgatggt gaaaccatta ccatcgatct gcaaaaaatt    480
gatgtgaaaa gccttggcct tgatgggttc aatgttaatt ccccgggaag taccgctaac    540
ccactggctt caattgattc tgcattgtca aaagtggacg cagttcgttc ttctctgggg    600
gcaattcaaa accgctttga ttcagccatt accaacttg gcaatacggt aaccaatctg    660
aactccgcgc gtagccgtat cgaagatgct gacgctggag cggaagttgc taatatgtct    720
```

```
aaagcgcaga ttctgcagca ggctggtact tccgttctgg cgcaggctaa ccaggttccg    780
caaaacgtcc tctctttact ggttccgcgg ggttctcatc atcatcatca tcatggttaa    840
gtcgac                                                                846
```

<210> SEQ ID NO 241
<211> LENGTH: 250
<212> TYPE: PRT
<213> ORGANISM: Artificial Sequence
<220> FEATURE:
<223> OTHER INFORMATION: Synthetic sequence

<400> SEQUENCE: 241

```
Met Ser Gly Leu Arg Ile Asn Ser Ala Lys Asp Asp Ala Ala Gly Gln
1               5                   10                  15

Ala Ile Ala Asn Arg Phe Thr Ser Asn Ile Lys Gly Leu Thr Gln Ala
            20                  25                  30

Ser Arg Asn Ala Asn Asp Gly Ile Ser Ile Ala Gln Thr Thr Glu Gly
        35                  40                  45

Ala Leu Asn Glu Ile Asn Asn Asn Leu Gln Arg Val Arg Glu Leu Ser
    50                  55                  60

Val Gln Ala Thr Asn Gly Thr Asn Ser Asp Ser Asp Leu Lys Ser Ile
65                  70                  75                  80

Gln Asp Glu Ile Gln Gln Arg Leu Glu Glu Ile Asp Arg Val Ser Asn
                85                  90                  95

Gln Thr Gln Phe Asn Gly Val Lys Val Leu Ser Gln Asp Asn Gln Met
            100                 105                 110

Lys Ile Gln Val Gly Ala Asn Asp Gly Glu Thr Ile Thr Ile Asp Leu
        115                 120                 125

Gln Lys Ile Asp Val Lys Ser Leu Gly Leu Asp Gly Phe Asn Val Asn
    130                 135                 140

Ser Pro Gly Ser Thr Ala Asn Pro Leu Ala Ser Ile Asp Ser Ala Leu
145                 150                 155                 160

Ser Lys Val Asp Ala Val Arg Ser Ser Leu Gly Ala Ile Gln Asn Arg
                165                 170                 175

Phe Asp Ser Ala Ile Thr Asn Leu Gly Asn Thr Val Thr Asn Leu Asn
            180                 185                 190

Ser Ala Arg Ser Arg Ile Glu Asp Ala Asp Ala Gly Ala Glu Val Ala
        195                 200                 205

Asn Met Ser Lys Ala Gln Ile Leu Gln Gln Ala Gly Thr Ser Val Leu
    210                 215                 220

Ala Gln Ala Asn Gln Val Pro Gln Asn Val Leu Ser Leu Leu Val Pro
225                 230                 235                 240

Arg Gly Ser His His His His His Gly
                245                 250
```

<210> SEQ ID NO 242
<211> LENGTH: 3
<212> TYPE: PRT
<213> ORGANISM: Artificial Sequence
<220> FEATURE:
<223> OTHER INFORMATION: Synthetic sequence

<400> SEQUENCE: 242

```
Ser Pro Gly
1
```

<210> SEQ ID NO 243

```
<211> LENGTH: 293
<212> TYPE: PRT
<213> ORGANISM: Artificial Sequence
<220> FEATURE:
<223> OTHER INFORMATION: Synthetic sequence

<400> SEQUENCE: 243

Met Gly His His His His His Ser Gly Met Glu Glu Phe Asn Met
1               5                   10                  15

Arg Ile Asn Thr Asn Val Ala Ala Met Asn Thr Tyr Ser Arg Leu Thr
            20                  25                  30

Ala Ala Asn Thr Ala Lys Ser Asn Ser Leu Ala Lys Leu Ser Ser Gly
            35                  40                  45

Leu Arg Ile Asn Lys Ala Gly Asp Ala Ala Gly Leu Ala Ile Ser
    50                  55                  60

Glu Lys Met Lys Ser Gln Ile Gly Gly Leu Thr Gln Ala Lys Arg Asn
65                  70                  75                  80

Ala Gln Asp Gly Ile Ser Leu Val Gln Thr Ala Glu Gly Ala Leu Asn
            85                  90                  95

Glu Thr His Ser Ile Leu Glu Arg Met Arg Asp Leu Ala Val Gln Gly
            100                 105                 110

Ser Asn Gly Thr Leu Thr Ser Ser Asp Arg Gly Ser Ile Asn Lys Glu
            115                 120                 125

Leu Lys Ala Leu His Gln Glu Leu Thr Arg Ile Ser Asn Thr Thr Glu
    130                 135                 140

Phe Asn Thr Gln Lys Leu Phe Ser Gln Thr Lys Gln Lys Ser Val Thr
145                 150                 155                 160

Phe Thr Phe Gln Ile Gly Ala Asn Ala Gly Gln Thr Leu Ser Val Ala
            165                 170                 175

Ile Thr Ala Met Ser Gly Glu Ala Leu Leu Val Ser Thr Asp Ala Lys
            180                 185                 190

Phe Ser Leu Asn Ala Ala Gly Thr Asn Ala Gly Ala Met Ile Lys Ser
            195                 200                 205

Ile Asp Ala Ala Ile Ala Lys Val Ser Asp Gln Arg Ala Asp Leu Gly
    210                 215                 220

Ala Val Gln Asn Arg Leu Glu His Thr Ile Asn Asn Leu Thr Ala Thr
225                 230                 235                 240

Asn Glu Asn Leu Ser Asp Ala Asn Ser Arg Ile Arg Asp Val Asp Met
                245                 250                 255

Ala Glu Glu Met Met Thr Phe Thr Lys Ser Asn Ile Leu Ser Gln Ala
            260                 265                 270

Ala Thr Ser Met Leu Ala Gln Ala Asn Ala Met Pro Asn Ser Val Leu
        275                 280                 285

Asn Leu Leu Gln Gly
        290

<210> SEQ ID NO 244
<211> LENGTH: 280
<212> TYPE: PRT
<213> ORGANISM: Artificial Sequence
<220> FEATURE:
<223> OTHER INFORMATION: Synthetic sequence

<400> SEQUENCE: 244

Met Gly His His His His His Ser Gly Met Arg Ile Asn His Asn
1               5                   10                  15

Ile Ser Ala Leu Asn Ala Trp Arg Asn Ile Asp Gln Thr Gln Tyr Ser
```

```
            20                  25                  30
Met Ser Lys Thr Leu Glu Arg Leu Ser Ser Gly Leu Arg Ile Asn Arg
            35                  40                  45

Ala Gly Asp Ala Ala Gly Leu Ala Ile Ser Glu Lys Met Arg Gly
    50                  55                  60

Gln Ile Lys Gly Leu Asn Met Ala Ile Lys Asn Ala Gln Asp Ala Ile
 65                  70                  75                  80

Ser Leu Ile Gln Thr Ala Glu Gly Ala Leu Thr Glu Val His Ser Ile
                 85                  90                  95

Leu Gln Arg Met Arg Glu Leu Ala Val Gln Ala Ala Ser Asp Thr Asn
                100                 105                 110

Thr Asn Val Asp Arg Glu Gln Ile Gln Lys Glu Ile Asp Gln Leu Arg
            115                 120                 125

Glu Glu Ile Asp Arg Ile Ala Arg Thr Thr Glu Phe Asn Thr Lys Lys
        130                 135                 140

Leu Leu Asp Gly Lys Leu Glu Gly Phe Arg Ser Gln Val Asp Ala Lys
145                 150                 155                 160

Val Val Thr Gly Gly Asn Ile Asn Val Gln Leu Gly Thr Val Ser Ser
                165                 170                 175

Lys Ala Val Glu Gly Thr Tyr Val Ile Glu Val Gly Ala Ala Glu Arg
            180                 185                 190

Ala Ile Met Val Val Asp Ala Ala Ile His Arg Val Ser Thr Ala Arg
        195                 200                 205

Ala Ala Leu Gly Ala Ile Gln Asn Arg Leu Glu His Thr Ile Ser Asn
    210                 215                 220

Leu Gly Val Ala Ala Glu Asn Leu Thr Ala Ala Glu Ser Arg Ile Arg
225                 230                 235                 240

Asp Ala Asp Met Ala Lys Glu Met Met Glu Phe Thr Lys Gln Gln Ile
                245                 250                 255

Leu Leu Gln Ser Ser Met Ala Met Leu Ala Gln Ser Asn Thr Leu Pro
            260                 265                 270

Gln Asn Val Leu Gln Leu Met Arg
        275                 280

<210> SEQ ID NO 245
<211> LENGTH: 168
<212> TYPE: PRT
<213> ORGANISM: Artificial Sequence
<220> FEATURE:
<223> OTHER INFORMATION: Synthetic sequence

<400> SEQUENCE: 245

Met Gly His His His His His His Ser Gly Leu Asn Met Ala Ile Lys
 1               5                  10                  15

Asn Ala Gln Asp Ala Ile Ser Leu Ile Gln Thr Ala Glu Gly Ala Leu
            20                  25                  30

Thr Glu Val His Ser Ile Leu Gln Arg Met Arg Glu Leu Ala Val Gln
        35                  40                  45

Ala Ala Ser Asp Thr Asn Thr Asn Val Asp Arg Glu Gln Ile Gln Lys
    50                  55                  60

Glu Ile Asp Gln Leu Arg Glu Glu Ile Asp Arg Ile Ala Arg Thr Thr
 65                  70                  75                  80

Glu Phe Asn Thr Lys Lys Leu Leu Asp Gly Lys Leu Glu Gly Phe Arg
                 85                  90                  95

Ser Gln Val Asp Ala Lys Val Val Thr Gly Gly Asn Ile Asn Val Gln
```

```
                  100                 105                 110
Leu Gly Thr Val Ser Ser Lys Ala Val Glu Gly Thr Tyr Val Ile Glu
            115                 120                 125

Val Gly Ala Ala Glu Arg Ala Ile Met Val Val Asp Ala Ala Ile His
            130                 135                 140

Arg Val Ser Thr Ala Arg Ala Ala Leu Gly Ala Ile Gln Asn Arg Leu
145                 150                 155                 160

Glu His Thr Ile Ser Asn Leu Gly
                165
```

<210> SEQ ID NO 246
<211> LENGTH: 285
<212> TYPE: PRT
<213> ORGANISM: Artificial Sequence
<220> FEATURE:
<223> OTHER INFORMATION: Synthetic sequence

<400> SEQUENCE: 246

```
Met Gly His His His His His His Ser Gly Met Ser Leu Arg Ile Asn
1               5                   10                  15

Asn Asn Ile Glu Ala Leu Asn Ala Trp Arg Ala Leu Asn Ser Thr Ser
            20                  25                  30

Asn Ala Leu Gln Lys Ser Met Glu Lys Leu Ser Ser Gly Leu Arg Ile
        35                  40                  45

Asn Arg Ala Gly Asp Asp Ala Ala Gly Leu Ala Ile Ser Glu Lys Leu
    50                  55                  60

Arg Ala Gln Ile Arg Gly Leu Asn Gln Ala Ile Arg Asn Ala Gln Asp
65                  70                  75                  80

Gly Ile Ser Leu Ile Gln Thr Ala Glu Gly Gly Leu Ser Glu Ile Gln
                85                  90                  95

Asn Ile Leu Gln Arg Met Arg Glu Leu Gly Val Gln Ala Ala Asn Gly
            100                 105                 110

Thr Leu Asn Asn Gln Asp Ile Ser Ala Ile Thr Thr Glu Leu Asn Gln
        115                 120                 125

Leu Phe Asn Glu Ile Asp Arg Ile Ala Gly Ala Thr Glu Phe Asn Thr
    130                 135                 140

Lys Asn Leu Leu Ala Val Ser Thr Gly Leu Val Val Thr Leu Gln Val
145                 150                 155                 160

Gly Ala Asn Ala Gly Gln Val Ile Ala Phe Thr Ile Asp Asn Ala Gly
                165                 170                 175

Thr Ala Ser Leu Gly Leu Ser Ser Ala Asp Leu Ala Ile Asn Asp Asn
            180                 185                 190

Ala Ser Ala Ser Ala Phe Ile Ser Lys Val Asp Ser Ala Leu Gln Lys
        195                 200                 205

Val Ser Thr Tyr Arg Ala Asn Leu Gly Ser Ile Gln Asn Arg Leu Glu
    210                 215                 220

His Thr Ile Ala Asn Leu Gly Ile Ala Ser Glu Asn Leu Ser Ala Ser
225                 230                 235                 240

Glu Ser Arg Ile Arg Asp Val Asp Met Ala Ala Glu Met Met Asn Phe
                245                 250                 255

Thr Lys Asn Gln Ile Leu Gln Gln Ala Gly Val Ala Ile Leu Ala Gln
            260                 265                 270

Ala Asn Gln Ala Pro Gln Ala Val Leu Gln Leu Leu Arg
        275                 280                 285
```

```
<210> SEQ ID NO 247
<211> LENGTH: 171
<212> TYPE: PRT
<213> ORGANISM: Artificial Sequence
<220> FEATURE:
<223> OTHER INFORMATION: Synthetic sequence

<400> SEQUENCE: 247

Met Gly His His His His His Ser Gly Leu Asn Gln Ala Ile Arg
1               5                   10                  15

Asn Ala Gln Asp Gly Ile Ser Leu Ile Gln Thr Ala Glu Gly Gly Leu
            20                  25                  30

Ser Glu Ile Gln Asn Ile Leu Gln Arg Met Arg Glu Leu Gly Val Gln
        35                  40                  45

Ala Ala Asn Gly Thr Leu Asn Asn Gln Asp Ile Ser Ala Ile Thr Thr
    50                  55                  60

Glu Leu Asn Gln Leu Phe Asn Glu Ile Asp Arg Ile Ala Gly Ala Thr
65                  70                  75                  80

Glu Phe Asn Thr Lys Asn Leu Leu Ala Val Ser Thr Gly Leu Val Val
                85                  90                  95

Thr Leu Gln Val Gly Ala Asn Ala Gly Gln Val Ile Ala Phe Thr Ile
            100                 105                 110

Asp Asn Ala Gly Thr Ala Ser Leu Gly Leu Ser Ser Ala Asp Leu Ala
        115                 120                 125

Ile Asn Asp Asn Ala Ser Ala Ser Ala Phe Ile Ser Lys Val Asp Ser
    130                 135                 140

Ala Leu Gln Lys Val Ser Thr Tyr Arg Ala Asn Leu Gly Ser Ile Gln
145                 150                 155                 160

Asn Arg Leu Glu His Thr Ile Ala Asn Leu Gly
                165                 170

<210> SEQ ID NO 248
<211> LENGTH: 146
<212> TYPE: PRT
<213> ORGANISM: Artificial Sequence
<220> FEATURE:
<223> OTHER INFORMATION: Synthetic sequence

<400> SEQUENCE: 248

Met Gly His His His His His Ser Gly Leu Asn Gln Ala Ile Arg
1               5                   10                  15

Asn Ala Gln Asp Gly Ile Ser Leu Ile Gln Thr Ala Glu Gly Gly Leu
            20                  25                  30

Ser Glu Ile Gln Asn Ile Leu Gln Arg Met Arg Glu Leu Gly Val Gln
        35                  40                  45

Ala Ala Asn Gly Thr Leu Asn Asn Gln Asp Ile Ser Ala Ile Thr Thr
    50                  55                  60

Glu Leu Asn Gln Leu Phe Asn Glu Ile Asp Arg Ile Ala Gly Ala Thr
65                  70                  75                  80

Glu Phe Asn Thr Lys Asn Leu Leu Ala Ala Gly Thr Ala Ser Leu Gly
                85                  90                  95

Leu Ser Ser Ala Asp Leu Ala Ile Asn Asp Asn Ala Ser Ala Ser Ala
            100                 105                 110

Phe Ile Ser Lys Val Asp Ser Ala Leu Gln Lys Val Ser Thr Tyr Arg
        115                 120                 125

Ala Asn Leu Gly Ser Ile Gln Asn Arg Leu Glu His Thr Ile Ala Asn
    130                 135                 140
```

Leu Gly
145

<210> SEQ ID NO 249
<211> LENGTH: 116
<212> TYPE: PRT
<213> ORGANISM: Artificial Sequence
<220> FEATURE:
<223> OTHER INFORMATION: Synthetic sequence

<400> SEQUENCE: 249

Met Gly His His His His His Ser Ala Ser Ala Phe Ile Ser Lys
1               5                   10                  15

Val Asp Ser Ala Leu Gln Lys Val Ser Thr Tyr Arg Ala Asn Leu Gly
            20                  25                  30

Ser Ile Gln Asn Arg Leu Glu His Thr Ile Ala Asn Leu Gly Pro Asp
        35                  40                  45

Gly Leu Asn Gln Ala Ile Arg Asn Ala Gln Asp Gly Ile Ser Leu Ile
    50                  55                  60

Gln Thr Ala Glu Gly Gly Leu Ser Glu Ile Gln Asn Ile Leu Gln Arg
65                  70                  75                  80

Met Arg Glu Leu Gly Val Gln Ala Ala Asn Gly Thr Leu Asn Asn Gln
                85                  90                  95

Asp Ile Ser Ala Ile Thr Thr Glu Leu Asn Gln Leu Phe Asn Glu Ile
            100                 105                 110

Asp Arg Ile Ala
        115

<210> SEQ ID NO 250
<211> LENGTH: 103
<212> TYPE: PRT
<213> ORGANISM: Artificial Sequence
<220> FEATURE:
<223> OTHER INFORMATION: Synthetic sequence

<400> SEQUENCE: 250

Met Gly His His His His His Ser Asn Asn Gln Asp Ile Ser Ala
1               5                   10                  15

Ile Thr Thr Glu Leu Asn Gln Leu Phe Asn Glu Ile Asp Arg Ile Ala
            20                  25                  30

Gly Ala Thr Gly Ser Gly Gly Leu Ser Glu Ile Gln Asn Ile Leu Gln
        35                  40                  45

Arg Met Arg Glu Leu Gly Val Gln Ala Ala Asn Gly Thr Leu Asn Gly
    50                  55                  60

Gly Ser Ala Ser Ala Phe Ile Ser Lys Val Asp Ser Ala Leu Gln Lys
65                  70                  75                  80

Val Ser Thr Tyr Arg Ala Asn Leu Gly Ser Ile Gln Asn Arg Leu Glu
                85                  90                  95

His Thr Ile Ala Asn Leu Gly
            100

<210> SEQ ID NO 251
<211> LENGTH: 170
<212> TYPE: PRT
<213> ORGANISM: Artificial Sequence
<220> FEATURE:
<223> OTHER INFORMATION: Synthetic sequence

<400> SEQUENCE: 251

Met Gly His His His His His Ser Gly Leu Ala Gln Ala Ser Arg

```
1               5                  10                 15
Asn Ala Gln Asp Ala Ile Ser Ile Ala Gln Thr Ala Glu Gly Ala Leu
            20                  25                 30

Asp Glu Thr Gln Ser Ile Leu Gln Arg Val Arg Glu Leu Gly Val Gln
            35                  40                 45

Gly Ala Asn Gly Thr Leu Thr Ala Asp Ile Asn Ala Leu Gln Ala
            50                  55              60

Glu Val Asp Gln Leu Ile Ala Glu Ile Asp Arg Ile Ala Gly Ala Thr
 65                  70                  75                 80

Glu Phe Asn Thr Gln Asn Leu Leu Asp Gly Ser Phe Thr Thr Lys Ala
                85                  90                 95

Phe Gln Val Gly Ala Asn Ser Gly Gln Asn Met Thr Leu Thr Ile Gly
                100                 105                110

Lys Met Asp Thr Thr Thr Leu Gly Leu Ser Ser Ala Asp Leu Ala Ile
            115                 120                125

Asn Asp Asn Ala Phe Ala Asn Gly Ala Ile Ser Thr Val Asp Ser Ala
130                 135                 140

Leu Gln Lys Val Ser Ala Glu Arg Ala Lys Leu Gly Ala Ile Gln Asn
145                 150                 155                160

Arg Leu Glu His Thr Ile Ala Asn Leu Gly
                165                 170

<210> SEQ ID NO 252
<211> LENGTH: 170
<212> TYPE: PRT
<213> ORGANISM: Artificial Sequence
<220> FEATURE:
<223> OTHER INFORMATION: Synthetic sequence

<400> SEQUENCE: 252

Met Gly His His His His His Ser Gly Leu Ala Gln Ala Ser Arg
 1               5                  10                 15

Gln Ala Gln Asp Ala Ile Ser Ile Ala Gln Thr Ala Glu Gly Ala Leu
            20                  25                 30

Asp Glu Thr Gln Ser Ile Leu Gln Arg Val Arg Glu Leu Gly Val Gln
            35                  40                 45

Gly Ala Asp Gly Thr Leu Thr Ala Asp Ile Asp Ala Leu Gln Ala
            50                  55              60

Glu Val Asp Gln Leu Ile Ala Glu Ile Asp Arg Ile Ala Gly Ala Thr
 65                  70                  75                 80

Glu Phe Ala Thr Gln Lys Leu Leu Asp Gly Ser Phe Thr Thr Lys Ala
                85                  90                 95

Phe Gln Val Gly Ala Ala Ser Gly Gln Asp Val Thr Leu Thr Ile Gly
                100                 105                110

Lys Val Asp Thr Thr Thr Leu Gly Leu Ser Ser Ala Asp Leu Ala Ile
            115                 120                125

Asp Ser Ala Ala Phe Ala Asp Gly Ala Ile Ser Thr Val Asp Ser Ala
130                 135                 140

Leu Gln Lys Val Ser Ala Glu Arg Ala Lys Leu Gly Ala Ile Gln Asn
145                 150                 155                160

Arg Leu Glu His Thr Ile Ala Gln Leu Gly
                165                 170

<210> SEQ ID NO 253
<211> LENGTH: 174
<212> TYPE: PRT
```

<213> ORGANISM: Artificial Sequence
<220> FEATURE:
<223> OTHER INFORMATION: Synthetic peptide accession number Q53970

<400> SEQUENCE: 253

```
Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
        115                 120                 125

Gln Thr Gln Phe Asn Gly Val Lys Val Leu Ser Gln Asp Asn Gln Met
    130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn
                165                 170
```

<210> SEQ ID NO 254
<211> LENGTH: 189
<212> TYPE: PRT
<213> ORGANISM: Artificial Sequence
<220> FEATURE:
<223> OTHER INFORMATION: Synthetic peptide accession number P72151

<400> SEQUENCE: 254

```
Met Ala Leu Thr Val Asn Thr Asn Ile Ala Ser Leu Asn Thr Gln Arg
1               5                   10                  15

Asn Leu Asn Ala Ser Ser Asn Asp Leu Asn Thr Ser Leu Gln Arg Leu
            20                  25                  30

Thr Thr Gly Tyr Arg Ile Asn Ser Ala Lys Asp Asp Ala Ala Gly Leu
        35                  40                  45

Gln Ile Ser Asn Arg Leu Ser Asn Gln Ile Ser Gly Leu Asn Val Ala
    50                  55                  60

Thr Arg Asn Ala Asn Asp Gly Ile Ser Leu Ala Gln Thr Ala Glu Gly
65                  70                  75                  80

Ala Leu Gln Gln Ser Thr Asn Ile Leu Gln Arg Ile Arg Asp Leu Ala
                85                  90                  95

Leu Gln Ser Ala Asn Gly Ser Asn Ser Asp Ala Asp Arg Ala Ala Leu
            100                 105                 110

Gln Lys Glu Val Ala Ala Gln Gln Ala Glu Leu Thr Arg Ile Ser Asp
        115                 120                 125

Thr Thr Thr Phe Gly Gly Arg Lys Leu Leu Asp Gly Ser Phe Gly Thr
    130                 135                 140

Thr Ser Phe Gln Val Gly Ser Asn Ala Tyr Glu Thr Ile Asp Ile Ser
145                 150                 155                 160
```

```
Leu Gln Asn Ala Ser Ala Ser Ala Ile Gly Ser Tyr Gln Val Gly Ser
            165                 170                 175

Asn Gly Ala Gly Thr Val Ala Ser Val Ala Gly Thr Ala
            180                 185

<210> SEQ ID NO 255
<211> LENGTH: 179
<212> TYPE: PRT
<213> ORGANISM: Artificial Sequence
<220> FEATURE:
<223> OTHER INFORMATION: Synthetic peptide accession number Q5X5M6

<400> SEQUENCE: 255

Met Ala Gln Val Ile Asn Thr Asn Val Ala Ser Leu Thr Ala Gln Arg
1               5                   10                  15

Asn Leu Gly Val Ser Gly Asn Met Met Gln Thr Ser Ile Gln Arg Leu
            20                  25                  30

Ser Ser Gly Leu Arg Ile Asn Ser Ala Lys Asp Asp Ala Ala Gly Leu
        35                  40                  45

Ala Ile Ser Gln Arg Met Thr Ala Gln Ile Arg Gly Met Asn Gln Ala
    50                  55                  60

Val Arg Asn Ala Asn Asp Gly Ile Ser Leu Ala Gln Val Ala Glu Gly
65                  70                  75                  80

Ala Met Gln Glu Thr Thr Asn Ile Leu Gln Arg Met Arg Glu Leu Ser
                85                  90                  95

Val Gln Ala Ala Asn Ser Thr Asn Asn Ser Ser Asp Arg Ala Ser Ile
            100                 105                 110

Gln Ser Glu Ile Ser Gln Leu Lys Ser Glu Leu Glu Arg Ile Ala Gln
        115                 120                 125

Asn Thr Glu Phe Asn Gly Gln Arg Ile Leu Asp Gly Ser Phe Ser Gly
    130                 135                 140

Ala Ser Phe Gln Val Gly Ala Asn Ser Asn Gln Thr Ile Asn Phe Ser
145                 150                 155                 160

Ile Gly Ser Ile Lys Ala Ser Ser Ile Gly Gly Ile Ala Thr Ala Thr
                165                 170                 175

Gly Thr Glu

<210> SEQ ID NO 256
<211> LENGTH: 174
<212> TYPE: PRT
<213> ORGANISM: Artificial Sequence
<220> FEATURE:
<223> OTHER INFORMATION: Synthetic peptide accession number Q6VMV6

<400> SEQUENCE: 256

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Val Ala Gln Thr Thr Glu Gly
65                  70                  75                  80

Ala Leu Asn Glu Ile Asn Asn Asn Leu Gln Arg Val Arg Glu Leu Thr
                85                  90                  95
```

```
Val Gln Ala Thr Asn Gly Thr Asn Ser Asp Ser Asp Leu Ser Ser Ile
            100                 105                 110

Gln Ala Glu Ile Thr Gln Arg Leu Glu Glu Ile Asp Arg Val Ser Glu
        115                 120                 125

Gln Thr Gln Phe Asn Gly Val Lys Val Leu Ala Glu Asn Asn Glu Met
    130                 135                 140

Lys Ile Gln Val Gly Ala Asn Asp Gly Glu Thr Ile Thr Ile Asn Leu
145                 150                 155                 160

Ala Lys Ile Asp Ala Lys Thr Leu Gly Leu Asp Gly Phe Asn
                165                 170
```

<210> SEQ ID NO 257
<211> LENGTH: 173
<212> TYPE: PRT
<213> ORGANISM: Artificial Sequence
<220> FEATURE:
<223> OTHER INFORMATION: Synthetic peptide accession number P13713

<400> SEQUENCE: 257

```
Met Ala Gln Val Ile Asn Thr Asn Ser Leu Ser Leu Met Ala Gln Asn
1               5                   10                  15

Asn Leu Asn Lys Ser Gln Ser Ser Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ser Asn Arg Phe Thr Ala Asn Ile Lys Gly Leu Thr Gln Ala
    50                  55                  60

Ser Arg Asn Ala Asn Asp Gly Ile Ser Leu Ala Gln Thr Thr Glu Gly
65                  70                  75                  80

Ala Leu Asn Glu Val Asn Asp Asn Leu Gln Asn Ile Arg Arg Leu Thr
                85                  90                  95

Val Gln Ala Gln Asn Gly Ser Asn Ser Thr Ser Asp Leu Lys Ser Ile
            100                 105                 110

Gln Asp Glu Ile Thr Gln Arg Leu Ser Glu Ile Asn Arg Ile Ser Glu
        115                 120                 125

Gln Thr Asp Phe Asn Gly Val Lys Val Leu Ser Ser Asp Gln Lys Leu
    130                 135                 140

Thr Ile Gln Val Gly Ala Asn Asp Gly Glu Thr Thr Asp Ile Asp Leu
145                 150                 155                 160

Lys Lys Ile Asp Ala Lys Gln Leu Gly Met Asp Thr Phe
                165                 170
```

<210> SEQ ID NO 258
<211> LENGTH: 168
<212> TYPE: PRT
<213> ORGANISM: Artificial Sequence
<220> FEATURE:
<223> OTHER INFORMATION: Synthetic peptide accession number Q93RK8

<400> SEQUENCE: 258

```
Met Arg Ile Asn His Asn Ile Ala Ala Leu Asn Thr Ser Arg Gln Leu
1               5                   10                  15

Asn Ala Gly Ser Asn Ser Ala Ala Lys Asn Met Glu Lys Leu Ser Ser
            20                  25                  30

Gly Leu Arg Ile Asn Arg Ala Gly Asp Asp Ala Ala Gly Leu Ala Ile
        35                  40                  45

Ser Glu Lys Met Arg Ser Gln Ile Arg Gly Leu Asp Met Ala Ser Lys
    50                  55                  60
```

Asn Ala Gln Asp Gly Ile Ser Leu Ile Gln Thr Ser Glu Gly Ala Leu
65                  70                  75                  80

Asn Glu Thr His Ser Ile Leu Gln Arg Met Ser Glu Leu Ala Thr Gln
                85                  90                  95

Ala Ala Asn Asp Thr Asn Thr Asp Ser Asp Arg Ser Leu Gln Lys
            100                 105                 110

Glu Met Asp Gln Leu Ala Ser Glu Val Thr Arg Ile Ser Thr Asp Thr
            115                 120                 125

Glu Phe Asn Thr Lys Lys Leu Leu Asp Gly Thr Ala Gln Asn Leu Thr
        130                 135                 140

Phe Gln Ile Gly Ala Asn Glu Gly Gln Thr Met Ser Leu Ser Ile Asn
145                 150                 155                 160

Lys Met Asp Ser Glu Ser Leu Lys
                165

<210> SEQ ID NO 259
<211> LENGTH: 192
<212> TYPE: PRT
<213> ORGANISM: Artificial Sequence
<220> FEATURE:
<223> OTHER INFORMATION: Synthetic peptide accession number Q02551

<400> SEQUENCE: 259

Met Lys Val Asn Thr Asn Ile Ile Ser Leu Lys Thr Gln Glu Tyr Leu
1               5                   10                  15

Arg Lys Asn Asn Glu Gly Met Thr Gln Ala Gln Arg Arg Leu Ala Ser
            20                  25                  30

Gly Lys Arg Ile Asn Ser Ser Leu Asp Asp Ala Ala Gly Leu Ala Val
        35                  40                  45

Val Thr Arg Met Asn Val Lys Ser Thr Gly Leu Asp Ala Ala Ser Lys
    50                  55                  60

Asn Ser Ser Met Gly Ile Asp Leu Leu Gln Thr Ala Asp Ser Ala Leu
65                  70                  75                  80

Ser Ser Met Ser Ser Ile Leu Gln Arg Met Arg Gln Leu Ala Val Gln
                85                  90                  95

Ser Ser Asn Gly Ser Phe Ser Asp Glu Asp Arg Lys Gln Tyr Thr Ala
            100                 105                 110

Glu Phe Gly Ser Leu Ile Lys Glu Leu Asp His Val Ala Asp Thr Thr
        115                 120                 125

Asn Tyr Asn Asn Ile Lys Leu Leu Asp Gln Thr Ala Thr Gly Ala Ala
    130                 135                 140

Thr Gln Val Ser Ile Gln Ala Ser Asp Lys Ala Asn Asp Leu Ile Asn
145                 150                 155                 160

Ile Asp Leu Phe Asn Ala Lys Gly Leu Ser Ala Gly Thr Ile Thr Leu
                165                 170                 175

Gly Ser Gly Ser Thr Val Ala Gly Tyr Ser Ala Leu Ser Val Ala Asp
            180                 185                 190

<210> SEQ ID NO 260
<211> LENGTH: 174
<212> TYPE: PRT
<213> ORGANISM: Artificial Sequence
<220> FEATURE:
<223> OTHER INFORMATION: Synthetic peptide accession number Q09012

<400> SEQUENCE: 260

Met Ala Gln Val Ile Asn Thr Asn Ser Leu Ser Leu Leu Thr Gln Asn

```
                1               5                   10                  15
Met Ala Gln Val Ile Asn Thr Asn Ser Leu Ser Leu Met Ala Gln Asn
1               5                   10                  15

Asn Leu Asn Lys Ser Gln Ser Ser Leu Ser Ser Ala Ile Glu Arg Leu
                20                  25                  30

Ser Ser Gly Leu Arg Ile Asn Ser Ala Lys Asp Asp Ala Ala Gly Gln
                35                  40                  45

Ala Ile Ala Asn Arg Phe Thr Ala Asn Ile Lys Gly Leu Thr Gln Ala
                50                  55                  60

Ser Arg Asn Ala Asn Asp Gly Ile Ser Val Ala Gln Thr Thr Glu Gly
65                  70                  75                  80

Ala Leu Ser Glu Ile Asn Asn Asn Leu Gln Arg Ile Arg Glu Leu Ser
                85                  90                  95

Val Gln Ala Thr Asn Gly Thr Asn Ser Asp Ser Asp Leu Asn Ser Ile
                100                 105                 110

Gln Asp Glu Ile Thr Gln Arg Leu Ser Glu Ile Asp Arg Val Ser Asn
                115                 120                 125

Gln Thr Gln Phe Asn Gly Val Lys Val Leu Ala Ser Asp Gln Thr Met
                130                 135                 140

Lys Ile Gln Val Gly Ala Asn Asp Gly Glu Thr Ile Glu Ile Ala Leu
145                 150                 155                 160

Asp Lys Ile Asp Ala Lys Thr Leu Gly Leu Asp Asn Phe Ser
                165                 170

<210> SEQ ID NO 261
<211> LENGTH: 174
<212> TYPE: PRT
<213> ORGANISM: Artificial Sequence
<220> FEATURE:
<223> OTHER INFORMATION: Synthetic peptide accession number Q8GNT8

<400> SEQUENCE: 261

Met Ala Gln Val Ile Asn Thr Asn Ser Leu Ser Leu Met Ala Gln Asn
1               5                   10                  15

Asn Leu Asn Lys Ser Gln Ser Ala Leu Gly Thr Ala Ile Glu Arg Leu
                20                  25                  30

Ser Ser Gly Leu Arg Ile Asn Ser Ala Lys Asp Asp Ala Ala Gly Gln
                35                  40                  45

Ala Ile Ser Asn Arg Phe Thr Ala Asn Ile Asn Gly Leu Thr Gln Ala
                50                  55                  60

Ser Arg Asn Ala Asn Asp Gly Ile Ser Leu Ala Gln Thr Thr Glu Gly
65                  70                  75                  80

Ala Leu Asn Glu Val Asn Asp Asn Leu Gln Asn Ile Arg Arg Leu Thr
                85                  90                  95

Val Gln Ala Gln Asn Gly Ser Asn Ser Ser Ser Asp Leu Gln Ser Ile
                100                 105                 110

Gln Asp Glu Ile Thr Gln Arg Leu Ser Glu Ile Asp Arg Ile Ser Gln
                115                 120                 125

Gln Thr Asp Phe Asn Gly Val Lys Val Leu Ser Lys Asp Gln Lys Leu
                130                 135                 140

Thr Ile Gln Val Gly Ala Asn Asp Gly Glu Thr Ile Asp Ile Asp Leu
145                 150                 155                 160

Lys Asn Ile Asn Ala Gln Ser Leu Gly Leu Asp Lys Phe Asn
                165                 170

<210> SEQ ID NO 262
<211> LENGTH: 186
<212> TYPE: PRT
```

<213> ORGANISM: Artificial Sequence
<220> FEATURE:
<223> OTHER INFORMATION: Synthetic peptide accession number Q9FAE7

<400> SEQUENCE: 262

```
Met Ala Ser Thr Ile Asn Thr Asn Val Ser Ser Leu Thr Ala Gln Arg
1               5                   10                  15

Asn Leu Ser Leu Ser Gln Ser Ser Leu Asn Thr Ser Ile Gln Arg Leu
            20                  25                  30

Ser Ser Gly Leu Arg Ile Asn Ser Ala Lys Asp Asp Ala Ala Gly Leu
        35                  40                  45

Ala Ile Ser Glu Arg Phe Thr Ser Gln Ile Arg Gly Leu Asn Gln Ala
    50                  55                  60

Val Arg Asn Ala Asn Asp Gly Ile Ser Leu Ala Gln Thr Ala Glu Gly
65                  70                  75                  80

Ala Leu Lys Ser Thr Gly Asp Ile Leu Gln Arg Val Arg Glu Leu Ala
                85                  90                  95

Val Gln Ser Ala Asn Ala Thr Asn Ser Ser Gly Asp Arg Lys Ala Ile
            100                 105                 110

Gln Ala Glu Val Gly Gln Leu Leu Ser Glu Met Asp Arg Ile Ala Gly
        115                 120                 125

Asn Thr Glu Phe Asn Gly Gln Lys Leu Leu Asp Gly Ser Phe Gly Ser
    130                 135                 140

Ala Thr Phe Gln Val Gly Ala Asn Ala Asn Gln Thr Ile Thr Ala Thr
145                 150                 155                 160

Thr Gly Asn Phe Arg Thr Asn Asn Tyr Gly Ala Gln Leu Thr Ala Ser
                165                 170                 175

Ala Ser Gly Ala Ala Thr Ser Gly Ala Ser
            180                 185
```

<210> SEQ ID NO 263
<211> LENGTH: 173
<212> TYPE: PRT
<213> ORGANISM: Artificial Sequence
<220> FEATURE:
<223> OTHER INFORMATION: Synthetic peptide accession number Q8ZF76

<400> SEQUENCE: 263

```
Met Ala Val Ile Asn Thr Asn Ser Leu Ser Leu Leu Thr Gln Asn Asn
1               5                   10                  15

Leu Asn Lys Ser Gln Ser Ser Leu Gly Thr Ala Ile Glu Arg Leu Ser
            20                  25                  30

Ser Gly Leu Arg Ile Asn Ser Ala Lys Asp Asp Ala Ala Gly Gln Ala
        35                  40                  45

Ile Ala Asn Arg Phe Thr Ser Asn Ile Lys Gly Leu Thr Gln Ala Ala
    50                  55                  60

Arg Asn Ala Asn Asp Gly Ile Ser Ile Ala Gln Thr Thr Glu Gly Ser
65                  70                  75                  80

Leu Asn Glu Ile Asn Asn Asn Leu Gln Arg Val Arg Glu Leu Thr Val
                85                  90                  95

Gln Ala Gln Asn Gly Ser Asn Ser Ser Ser Asp Leu Asp Ser Ile Gln
            100                 105                 110

Asp Glu Ile Ser Leu Arg Leu Ala Glu Ile Asp Arg Val Ser Asp Gln
        115                 120                 125

Thr Gln Phe Asn Gly Lys Lys Val Leu Ala Glu Asn Thr Thr Met Ser
    130                 135                 140
```

Ile Gln Val Gly Ala Asn Asp Gly Glu Thr Ile Asp Ile Asn Leu Gln
145                 150                 155                 160

Lys Ile Asp Ser Lys Ser Leu Gly Leu Gly Ser Tyr Ser
            165                 170

<210> SEQ ID NO 264
<211> LENGTH: 174
<212> TYPE: PRT
<213> ORGANISM: Artificial Sequence
<220> FEATURE:
<223> OTHER INFORMATION: Synthetic peptide accession number Q7N5J4

<400> SEQUENCE: 264

Met Ala Gln Val Ile Asn Thr Asn Ser Leu Ser Leu Leu Thr Gln Asn
1               5                   10                  15

Asn Leu Asn Arg Ser Gln Gly Thr Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Arg Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Thr Asn Leu Gln Arg Ile Arg Glu Leu Thr
                85                  90                  95

Val Gln Ser Gln Asn Gly Ser Asn Ser Glu Ser Asp Ile Lys Ser Ile
            100                 105                 110

Gln Glu Glu Val Thr Gln Arg Leu Lys Glu Ile Asp Arg Ile Ser Glu
        115                 120                 125

Gln Thr Gln Phe Asn Gly Val Arg Val Leu Arg Glu Asp Ser Lys Met
    130                 135                 140

Thr Ile Gln Val Gly Ala Asn Asp Asn Glu Val Ile Asp Ile Asp Leu
145                 150                 155                 160

Lys Lys Ile Asp Lys Glu Ala Leu Asn Leu Gly Lys Phe Thr
                165                 170

<210> SEQ ID NO 265
<211> LENGTH: 189
<212> TYPE: PRT
<213> ORGANISM: Artificial Sequence
<220> FEATURE:
<223> OTHER INFORMATION: Synthetic peptide accession number O33578

<400> SEQUENCE: 265

Met Thr Thr Ile Asn Thr Asn Ile Gly Ala Ile Ala Ala Gln Ala Asn
1               5                   10                  15

Met Thr Lys Val Asn Asp Gln Phe Asn Thr Ala Met Thr Arg Leu Ser
            20                  25                  30

Thr Gly Leu Arg Ile Asn Ala Ala Lys Asp Asp Ala Ala Gly Met Ala
        35                  40                  45

Ile Gly Glu Lys Met Thr Ala Gln Val Met Gly Leu Asn Gln Ala Ile
    50                  55                  60

Arg Asn Ala Gln Asp Gly Lys Asn Leu Val Asp Thr Thr Glu Gly Ala
65                  70                  75                  80

His Val Glu Val Ser Ser Met Leu Gln Arg Leu Arg Glu Leu Ala Val
                85                  90                  95

Gln Ser Ser Asn Asp Thr Asn Thr Ala Ala Asp Arg Gly Ser Leu Ala
            100                 105                 110

```
Ala Glu Gly Lys Gln Leu Ile Ala Glu Ile Asn Arg Val Ala Glu Ser
            115                 120                 125

Thr Thr Phe Asn Gly Met Lys Val Leu Asp Gly Ser Phe Thr Gly Lys
    130                 135                 140

Gln Leu Gln Ile Gly Ala Asp Ser Gly Gln Thr Met Ala Ile Asn Val
145                 150                 155                 160

Asp Ser Ala Ala Ala Thr Asp Ile Gly Ala His Lys Ile Ser Ser Ala
                165                 170                 175

Ser Thr Val Val Ala Asp Ala Ala Leu Thr Asp Thr Thr
            180                 185

<210> SEQ ID NO 266
<211> LENGTH: 175
<212> TYPE: PRT
<213> ORGANISM: Artificial Sequence
<220> FEATURE:
<223> OTHER INFORMATION: Synthetic peptide accession number Q56826

<400> SEQUENCE: 266

Met Ala Ser Val Ile Asn Thr Asn Asp Ser Ala Leu Leu Ala Gln Asn
1               5                   10                  15

Asn Leu Thr Lys Ser Lys Gly Ile Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Lys Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Leu Gln Arg Ile Arg Glu Leu Thr
                85                  90                  95

Val Gln Ser Glu Asn Gly Ser Asn Ser Lys Ser Asp Leu Asp Ser Ile
            100                 105                 110

Gln Lys Glu Val Thr Gln Arg Leu Glu Glu Ile Asp Arg Ile Ser Thr
        115                 120                 125

Gln Thr Gln Phe Asn Gly Ile Lys Val Leu Asn Gly Asp Val Thr Glu
    130                 135                 140

Met Lys Ile Gln Val Gly Ala Asn Asp Asn Glu Thr Ile Gly Ile Lys
145                 150                 155                 160

Leu Gly Lys Ile Asn Ser Glu Lys Leu Asn Leu Lys Glu Phe Ser
                165                 170                 175

<210> SEQ ID NO 267
<211> LENGTH: 175
<212> TYPE: PRT
<213> ORGANISM: Artificial Sequence
<220> FEATURE:
<223> OTHER INFORMATION: Synthetic peptide accession number P42273

<400> SEQUENCE: 267

Met Ala Gln Val Ile Asn Thr Asn Tyr Leu Ser Leu Val Thr Gln Asn
1               5                   10                  15

Asn Leu Asn Arg Ser Gln Ser Ala Leu Gly Asn Ala Ile Glu Arg Leu
            20                  25                  30

Ser Ser Gly Met Arg Ile Asn Ser Ala Lys Asp Asp Ala Ala Gly Gln
        35                  40                  45

Ala Ile Ala Asn Arg Phe Thr Ser Asn Ile Asn Gly Leu Thr Gln Ala
```

```
                50                  55                  60
Ser Arg Asn Ala Asn Asp Gly Ile Ser Val Ser Gln Thr Thr Glu Gly
 65                  70                  75                  80

Ala Leu Asn Glu Ile Asn Asn Asn Leu Gln Arg Ile Arg Glu Leu Thr
                 85                  90                  95

Val Gln Ala Lys Asn Gly Thr Asn Ser Asn Ser Asp Ile Asn Ser Ile
            100                 105                 110

Gln Asn Glu Val Asn Gln Arg Leu Asp Glu Ile Asn Arg Val Ser Glu
        115                 120                 125

Gln Thr Gln Phe Asn Gly Val Lys Val Leu Ser Gly Glu Lys Ser Lys
    130                 135                 140

Met Thr Ile Gln Val Gly Thr Asn Asp Asn Glu Val Ile Glu Phe Asn
145                 150                 155                 160

Leu Asp Lys Ile Asp Asn Asp Thr Leu Gly Val Ala Ser Asp Lys
                165                 170                 175

<210> SEQ ID NO 268
<211> LENGTH: 200
<212> TYPE: PRT
<213> ORGANISM: Artificial Sequence
<220> FEATURE:
<223> OTHER INFORMATION: Synthetic peptide accession number O31059

<400> SEQUENCE: 268

Met Val Val Gln His Asn Met Gln Ala Ala Asn Ala Ser Arg Met Leu
  1               5                  10                  15

Gly Ile Thr Thr Gly Asp Gln Ser Lys Ser Thr Glu Lys Leu Ser Ser
             20                  25                  30

Gly Phe Lys Ile Asn Arg Ala Ala Asp Asp Ala Ala Gly Leu Ser Ile
         35                  40                  45

Ser Glu Lys Met Arg Lys Gln Ile Arg Gly Leu Asp Gln Ala Ser Thr
     50                  55                  60

Asn Ala Ser Asp Gly Ile Ser Ala Val Gln Thr Ala Glu Gly Ala Leu
 65                  70                  75                  80

Thr Glu Val His Ser Met Leu Gln Arg Met Asn Glu Leu Ala Val Gln
                 85                  90                  95

Ala Ala Asn Gly Thr Asn Ser Glu Ser Asp Arg Ser Ser Ile Gln Asp
            100                 105                 110

Glu Ile Asn Gln Leu Thr Thr Glu Ile Asp Arg Val Ala Glu Thr Thr
        115                 120                 125

Lys Phe Asn Glu Thr Tyr Leu Leu Lys Gly Gly Asn Gly Asp Arg Thr
    130                 135                 140

Val Arg Val Tyr Ala His Asp Ala Gly Leu Val Gly Ser Leu Ser Gln
145                 150                 155                 160

Asn Thr Thr Lys Ala Thr Phe Gln Met Arg Lys Leu Glu Ile Gly Asp
                165                 170                 175

Ser Tyr Thr Ile Gly Gly Thr Thr Tyr Lys Ile Gly Ala Glu Thr Val
                180                 185                 190

Lys Glu Ala Met Thr Ala Leu Lys
        195                 200

<210> SEQ ID NO 269
<211> LENGTH: 177
<212> TYPE: PRT
<213> ORGANISM: Artificial Sequence
<220> FEATURE:
<223> OTHER INFORMATION: Synthetic peptide accession number Q7VZC2
```

<400> SEQUENCE: 269

```
Met Ala Val Ile Asn Thr Asn Tyr Leu Ser Leu Val Ala Gln Asn
1               5                   10                  15

Asn Leu Asn Lys Ser Gln Ser Ala Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Lys Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Leu Gln Arg Ile Arg Glu Leu Thr
                85                  90                  95

Val Gln Ala Ser Asn Gly Thr Asn Ser Ala Ser Asp Ile Asp Ser Ile
                100                 105                 110

Gln Gln Glu Val Asn Gln Arg Leu Glu Glu Ile Asn Arg Ile Ala Glu
                115                 120                 125

Gln Thr Asp Phe Asn Gly Ile Lys Val Leu Lys Ser Asn Ala Thr Asp
            130                 135                 140

Met Thr Leu Ser Ile Gln Val Gly Ala Lys Asp Asn Glu Thr Ile Asp
145                 150                 155                 160

Ile Lys Ile Asp Arg Asn Ser Asn Trp Asn Leu Tyr Asp Ala Val Gly
                165                 170                 175

Thr
```

<210> SEQ ID NO 270
<211> LENGTH: 167
<212> TYPE: PRT
<213> ORGANISM: Artificial Sequence
<220> FEATURE:
<223> OTHER INFORMATION: Synthetic peptide accession number Q9F4A4

<400> SEQUENCE: 270

```
Met Ile Ile Asn His Asn Met Asn Ala Leu Asn Ala His Arg Asn Met
1               5                   10                  15

Met Gly Asn Ile Ala Thr Ala Gly Lys Ser Met Glu Lys Leu Ser Ser
            20                  25                  30

Gly Leu Arg Ile Asn Arg Ala Gly Asp Asp Ala Ala Gly Leu Ala Ile
        35                  40                  45

Ser Glu Lys Met Arg Gly Gln Ile Arg Gly Leu Asp Gln Ala Ser Arg
    50                  55                  60

Asn Ala Gln Asp Gly Ile Ser Leu Ile Gln Thr Ala Glu Gly Ala Leu
65                  70                  75                  80

Ala Glu Thr His Ser Ile Leu Gln Arg Met Arg Glu Leu Ser Val Gln
                85                  90                  95

Ser Ala Asn Asp Thr Asn Val Ala Val Asp Arg Thr Ala Ile Gln Asp
                100                 105                 110

Glu Ile Asn Ser Leu Thr Glu Glu Ile Asn Arg Ile Ser Gly Asp Thr
                115                 120                 125

Glu Phe Asn Thr Gln Lys Leu Leu Asp Gly Gly Phe Lys Gly Glu Phe
            130                 135                 140

Gln Ile Gly Ala Asn Ser Asn Gln Thr Val Lys Leu Asp Ile Gly Asn
145                 150                 155                 160

Met Ser Ala Ala Ser Leu Gly
```

<210> SEQ ID NO 271
<211> LENGTH: 178
<212> TYPE: PRT
<213> ORGANISM: Artificial Sequence
<220> FEATURE:
<223> OTHER INFORMATION: Synthetic peptide accession number Q8P9C4

<400> SEQUENCE: 271

Met Ala Gln Val Ile Asn Thr Asn Val Met Ser Leu Asn Ala Gln Arg
1               5                   10                  15
Asn Leu Asn Thr Asn Ser Ser Met Ala Leu Ser Ile Gln Gln Leu
            20                  25                  30
Ser Ser Gly Lys Arg Ile Thr Ser Ala Ser Val Asp Ala Ala Gly Leu
        35                  40                  45
Ala Ile Ser Glu Arg Phe Thr Thr Gln Ile Arg Gly Leu Asp Val Ala
    50                  55                  60
Ser Arg Asn Ala Asn Asp Gly Ile Ser Leu Ala Gln Thr Ala Glu Gly
65                  70                  75                  80
Ala Met Val Glu Ile Gly Asn Asn Leu Gln Arg Ile Arg Glu Leu Ser
                85                  90                  95
Val Gln Ser Ala Asn Ala Thr Asn Ser Ala Thr Asp Arg Glu Ala Leu
            100                 105                 110
Asn Ser Glu Val Lys Gln Leu Thr Ser Glu Ile Asp Arg Val Ala Asn
        115                 120                 125
Gln Thr Ser Phe Asn Gly Thr Lys Leu Leu Asn Gly Asp Phe Ser Gly
    130                 135                 140
Ala Leu Phe Gln Val Gly Ala Asp Ala Gly Gln Thr Ile Gly Ile Asn
145                 150                 155                 160
Ser Ile Val Asp Ala Asn Val Asp Ser Leu Gly Lys Ala Asn Phe Ala
                165                 170                 175
Ala Ser

<210> SEQ ID NO 272
<211> LENGTH: 161
<212> TYPE: PRT
<213> ORGANISM: Artificial Sequence
<220> FEATURE:
<223> OTHER INFORMATION: Synthetic peptide accession number Q82UA3

<400> SEQUENCE: 272

Met Pro Gln Val Ile Asn Thr Asn Ile Ala Ser Leu Asn Ala Gln Arg
1               5                   10                  15
Asn Leu Asn Val Ser Gln Asn Ser Leu Ser Thr Ala Leu Gln Arg Leu
            20                  25                  30
Ser Ser Gly Leu Arg Ile Asn Ser Ala Lys Asp Asp Ala Ala Gly Leu
        35                  40                  45
Ala Ile Ser Glu Arg Met Thr Ser Gln Ile Arg Gly Met Asn Gln Ala
    50                  55                  60
Ala Arg Asn Ala Asn Asp Gly Ile Ser Leu Ala Gln Thr Ala Glu Gly
65                  70                  75                  80
Ala Leu Val Glu Ile Gly Asn Asn Leu Gln Arg Ile Arg Glu Leu Ala
                85                  90                  95
Val Gln Ser Ala Asn Ala Thr Asn Ser Glu Asp Asp Arg Glu Ala Leu
            100                 105                 110
Gln Lys Glu Val Thr Gln Leu Ile Asp Glu Ile Gln Arg Val Gly Glu

```
            115                 120                 125

Gln Thr Ser Phe Asn Gly Thr Lys Leu Leu Asp Gly Ser Phe Ala Ser
        130                 135                 140

Gln Ile Phe Gln Val Gly Ala Asn Glu Gly Glu Thr Ile Asp Phe Thr
145                 150                 155                 160

Asp

<210> SEQ ID NO 273
<211> LENGTH: 178
<212> TYPE: PRT
<213> ORGANISM: Artificial Sequence
<220> FEATURE:
<223> OTHER INFORMATION: Synthetic peptide accession number Q84IC5

<400> SEQUENCE: 273

Gly Phe Arg Ile Asn Thr Asn Gly Ala Ser Leu Asn Ala Gln Val Asn
1               5                   10                  15

Ala Gly Leu Asn Ser Arg Asn Leu Asp Ser Ser Leu Ala Arg Leu Ser
            20                  25                  30

Ser Gly Leu Arg Ile Asn Ser Ala Ala Asp Asp Ala Ser Gly Leu Ala
        35                  40                  45

Ile Ala Asp Ser Leu Lys Thr Gln Ala Asn Ser Leu Gly Gln Ala Ile
    50                  55                  60

Asn Asn Ala Asn Asp Ala Asn Ser Met Leu Gln Ile Ala Asp Lys Ala
65                  70                  75                  80

Met Asp Glu Gln Leu Lys Ile Leu Asp Thr Ile Lys Val Lys Ala Thr
                85                  90                  95

Gln Ala Ala Gln Asp Gly Gln Thr Ala Lys Thr Arg Ala Met Ile Gln
            100                 105                 110

Gly Glu Ile Asn Lys Leu Met Glu Glu Leu Asp Asn Ile Ala Asn Thr
        115                 120                 125

Thr Thr Tyr Asn Gly Lys Gln Leu Leu Ser Gly Ser Phe Ser Asn Ala
    130                 135                 140

Gln Phe Gln Ile Gly Asp Lys Ala Asn Gln Thr Val Asn Ala Thr Ile
145                 150                 155                 160

Gly Ser Thr Asn Ser Ala Lys Val Gly Gln Thr Arg Phe Glu Thr Gly
                165                 170                 175

Ala Val

<210> SEQ ID NO 274
<211> LENGTH: 88
<212> TYPE: PRT
<213> ORGANISM: Artificial Sequence
<220> FEATURE:
<223> OTHER INFORMATION: Synthetic polypeptide accession number Q53970

<400> SEQUENCE: 274

Pro Leu Ala Ser Ile Asp Ser Ala Leu Ser Lys Val Asp Ala Val Arg
1               5                   10                  15

Ser Ser Leu Gly Ala Ile Gln Asn Arg Phe Asp Ser Ala Ile Thr Asn
            20                  25                  30

Leu Gly Asn Thr Val Thr Asn Leu Asn Ser Ala Arg Ser Arg Ile Glu
        35                  40                  45

Asp Ala Asp Tyr Ala Thr Glu Val Ser Asn Met Ser Lys Ala Gln Ile
    50                  55                  60

Leu Gln Gln Ala Gly Thr Ser Val Leu Ala Gln Ala Asn Gln Val Pro
65                  70                  75                  80
```

```
Gln Asn Val Leu Ser Leu Leu Arg
                85

<210> SEQ ID NO 275
<211> LENGTH: 88
<212> TYPE: PRT
<213> ORGANISM: Artificial Sequence
<220> FEATURE:
<223> OTHER INFORMATION: Synthetic peptide accession number P72151

<400> SEQUENCE: 275

Ala Ile Ala Val Val Asp Asn Ala Leu Ala Ala Ile Asp Ala Gln Arg
1               5                   10                  15

Ala Asp Leu Gly Ala Val Gln Asn Arg Phe Lys Asn Thr Ile Asp Asn
            20                  25                  30

Leu Thr Asn Ile Ser Glu Asn Ala Thr Asn Ala Arg Ser Arg Ile Lys
        35                  40                  45

Asp Thr Asp Phe Ala Ala Glu Thr Ala Ala Leu Ser Lys Asn Gln Val
    50                  55                  60

Leu Gln Gln Ala Gly Thr Ala Ile Leu Ala Gln Ala Asn Gln Leu Pro
65                  70                  75                  80

Gln Ala Val Leu Ser Leu Leu Arg
                85

<210> SEQ ID NO 276
<211> LENGTH: 89
<212> TYPE: PRT
<213> ORGANISM: Artificial Sequence
<220> FEATURE:
<223> OTHER INFORMATION: Synthetic peptide accession number Q5X5M6

<400> SEQUENCE: 276

Ala Ile Lys Arg Ile Asp Ala Ala Leu Asn Ser Val Asn Ser Asn Arg
1               5                   10                  15

Ala Asn Met Gly Ala Leu Gln Asn Arg Phe Glu Ser Thr Ile Ala Asn
            20                  25                  30

Leu Gln Asn Val Ser Asp Asn Leu Ser Ala Ala Arg Ser Arg Ile Gln
        35                  40                  45

Asp Ala Asp Tyr Ala Ala Glu Met Ala Ser Leu Thr Lys Asn Gln Ile
    50                  55                  60

Leu Gln Gln Ala Gly Thr Ala Met Leu Ala Gln Ala Asn Ser Leu Pro
65                  70                  75                  80

Gln Ser Val Leu Ser Leu Leu Gly Arg
                85

<210> SEQ ID NO 277
<211> LENGTH: 89
<212> TYPE: PRT
<213> ORGANISM: Artificial Sequence
<220> FEATURE:
<223> OTHER INFORMATION: Synthetic peptide accession number Q6VMV6

<400> SEQUENCE: 277

Pro Leu Glu Thr Ile Asp Lys Ala Leu Ala Lys Val Asp Asn Leu Arg
1               5                   10                  15

Ser Asp Leu Gly Ala Val Gln Asn Arg Phe Asp Ser Ala Ile Thr Asn
            20                  25                  30

Leu Gly Asn Thr Val Asn Asn Leu Ser Ser Ala Arg Ser Arg Ile Arg
        35                  40                  45
```

```
Asp Ala Asp Tyr Ala Thr Glu Val Ser Asn Met Ser Arg Ala Gln Ile
         50                  55                  60

Leu Gln Gln Ala Gly Thr Ser Val Leu Ala Gln Ala Asn Gln Thr Thr
 65                  70                  75                  80

Gln Asn Val Leu Ser Leu Leu Gln Gly
                 85

<210> SEQ ID NO 278
<211> LENGTH: 88
<212> TYPE: PRT
<213> ORGANISM: Artificial Sequence
<220> FEATURE:
<223> OTHER INFORMATION: Synthetic peptide accession number P13713

<400> SEQUENCE: 278

Pro Leu Ala Thr Leu Asp Lys Ala Leu Ala Gln Val Asp Gly Leu Arg
 1               5                  10                  15

Ser Ser Leu Gly Ala Val Gln Asn Arg Phe Asp Ser Val Ile Asn Asn
                 20                  25                  30

Leu Asn Ser Thr Val Asn Asn Leu Ser Ala Ser Gln Ser Arg Ile Gln
             35                  40                  45

Asp Ala Asp Tyr Ala Thr Glu Val Ser Asn Met Ser Arg Ala Asn Ile
         50                  55                  60

Leu Gln Gln Ala Gly Thr Ser Val Leu Ala Gln Ala Asn Gln Ser Thr
 65                  70                  75                  80

Gln Asn Val Leu Ser Leu Leu Arg
                 85

<210> SEQ ID NO 279
<211> LENGTH: 89
<212> TYPE: PRT
<213> ORGANISM: Artificial Sequence
<220> FEATURE:
<223> OTHER INFORMATION: Synthetic peptide accession number Q93RK8
<220> FEATURE:
<221> NAME/KEY: misc_feature
<222> LOCATION: (6)..(6)
<223> OTHER INFORMATION: Xaa can be any naturally occurring amino acid

<400> SEQUENCE: 279

Ala Leu Thr Thr Ile Xaa Thr Ala Ile Asp Thr Val Ser Ser Glu Arg
 1               5                  10                  15

Ala Lys Leu Gly Ala Val Gln Asn Arg Leu Glu His Thr Ile Asn Asn
                 20                  25                  30

Leu Gly Thr Ser Ser Glu Asn Leu Thr Ser Ala Asx Ser Arg Ile Arg
             35                  40                  45

Asp Val Asp Met Ala Ser Glu Met Met Glu Tyr Thr Lys Asn Asn Ile
         50                  55                  60

Leu Thr Gln Ala Ser Gln Ala Met Leu Ala Gln Ala Asn Gln Gln Pro
 65                  70                  75                  80

Gln Gln Val Leu Gln Leu Leu Lys Gly
                 85

<210> SEQ ID NO 280
<211> LENGTH: 90
<212> TYPE: PRT
<213> ORGANISM: Artificial Sequence
<220> FEATURE:
<223> OTHER INFORMATION: Synthetic peptide accession number Q02551

<400> SEQUENCE: 280
```

Val Ile Gly Leu Ala Asp Ala Ala Leu Thr Lys Ile Met Lys Gln Arg
1               5                   10                  15

Ala Asp Met Gly Ala Tyr Tyr Asn Arg Leu Glu Tyr Thr Ala Lys Gly
            20                  25                  30

Leu Met Gly Ala Tyr Glu Asn Met Gln Ala Ser Glu Ser Arg Ile Arg
        35                  40                  45

Asp Ala Asp Met Ala Glu Glu Val Val Ser Leu Thr Thr Lys Gln Ile
    50                  55                  60

Leu Val Gln Ser Gly Thr Ala Met Leu Ala Gln Ala Asn Met Lys Pro
65                  70                  75                  80

Asn Ser Val Leu Lys Leu Leu Gln Gln Ile
            85                  90

<210> SEQ ID NO 281
<211> LENGTH: 88
<212> TYPE: PRT
<213> ORGANISM: Artificial Sequence
<220> FEATURE:
<223> OTHER INFORMATION: Synthetic peptide accession number Q09012

<400> SEQUENCE: 281

Pro Leu Ser Lys Leu Asp Glu Ala Leu Ala Lys Val Asp Lys Leu Arg
1               5                   10                  15

Ser Ser Leu Gly Ala Val Gln Asn Arg Phe Asp Ser Ala Ile Thr Asn
            20                  25                  30

Leu Gly Asn Thr Val Asn Asp Leu Ser Ser Ala Arg Ser Arg Ile Glu
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ala Gln Ala Asn Gln Thr Thr
65                  70                  75                  80

Gln Asn Val Leu Ser Leu Leu Arg
            85

<210> SEQ ID NO 282
<211> LENGTH: 88
<212> TYPE: PRT
<213> ORGANISM: Artificial Sequence
<220> FEATURE:
<223> OTHER INFORMATION: Synthetic peptide accession number Q8GNT8

<400> SEQUENCE: 282

Pro Leu Ala Thr Leu Asp Lys Ala Leu Ser Gln Val Asp Ile Leu Arg
1               5                   10                  15

Ser Gly Leu Gly Ala Val Gln Asn Arg Phe Asp Ser Val Ile Asn Asn
            20                  25                  30

Leu Asn Ser Thr Val Asn Asn Leu Ser Ala Ser Arg Ser Arg Ile Gln
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ala Gln Ala Asn Gln Ser Thr
65                  70                  75                  80

Gln Asn Val Leu Ser Leu Leu Arg
            85

<210> SEQ ID NO 283
<211> LENGTH: 88
<212> TYPE: PRT
<213> ORGANISM: Artificial Sequence

```
<220> FEATURE:
<223> OTHER INFORMATION: Synthetic peptide accession number Q9FAE7

<400> SEQUENCE: 283

Ala Leu Lys Ile Ile Asp Ala Ala Leu Ser Ala Val Asn Gln Gln Arg
1               5                   10                  15

Ala Ser Phe Gly Ala Leu Gln Ser Arg Phe Glu Thr Thr Val Asn Asn
            20                  25                  30

Leu Gln Ser Thr Ser Glu Asn Met Ser Ala Ser Arg Ser Arg Ile Gln
        35                  40                  45

Asp Ala Asp Phe Ala Ala Glu Thr Ala Asn Leu Ser Arg Ser Gln Ile
    50                  55                  60

Leu Gln Gln Ala Gly Thr Ala Met Val Ala Gln Ala Asn Gln Leu Pro
65                  70                  75                  80

Gln Gly Val Leu Ser Leu Leu Lys
                85

<210> SEQ ID NO 284
<211> LENGTH: 88
<212> TYPE: PRT
<213> ORGANISM: Artificial Sequence
<220> FEATURE:
<223> OTHER INFORMATION: Synthetic peptide accession number Q8ZF76

<400> SEQUENCE: 284

Pro Leu Glu Thr Leu Asp Asp Ala Ile Lys Gln Val Asp Gly Leu Arg
1               5                   10                  15

Ser Ser Leu Gly Ala Val Gln Asn Arg Phe Glu Ser Ala Val Thr Asn
            20                  25                  30

Leu Asn Asn Thr Val Thr Asn Leu Thr Ser Ala Arg Ser Arg Ile Glu
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ser Gln Ala Asn Gln Val Pro
65                  70                  75                  80

Gln Thr Val Leu Ser Leu Leu Asn
                85

<210> SEQ ID NO 285
<211> LENGTH: 88
<212> TYPE: PRT
<213> ORGANISM: Artificial Sequence
<220> FEATURE:
<223> OTHER INFORMATION: Synthetic peptide accession number Q7N5J4

<400> SEQUENCE: 285

Pro Leu Glu Thr Leu Asp Ser Ala Leu Ala Gln Val Asp Ser Leu Arg
1               5                   10                  15

Ser Ser Leu Gly Ala Ile Gln Asn Arg Leu Glu Ser Thr Val Asn Asn
            20                  25                  30

Leu Asn Asn Thr Val Asn Asn Leu Ser Ala Ala Arg Ser Arg Ile Glu
        35                  40                  45

Asp Ala Asp Tyr Ala Thr Glu Val Ser Asn Met Ser Arg Gly Gln Ile
    50                  55                  60

Leu Gln Gln Ala Gly Thr Ala Val Leu Ala Gln Ala Met Gln Val Pro
65                  70                  75                  80

Gln Asn Val Met Ser Leu Leu Arg
                85
```

<210> SEQ ID NO 286
<211> LENGTH: 89
<212> TYPE: PRT
<213> ORGANISM: Artificial Sequence
<220> FEATURE:
<223> OTHER INFORMATION: Synthetic peptide accession number O33578

<400> SEQUENCE: 286

```
Ala Ile Gly Val Ile Asp Val Ala Leu Ser Lys Ile Ser Gln Ser Arg
1               5                   10                  15

Ser Glu Leu Gly Ala Val Ser Asn Arg Leu Asp Ser Thr Ile Ser Asn
            20                  25                  30

Leu Thr Asn Ile Ser Thr Ser Val Gln Ala Ala Lys Ser Gln Val Met
        35                  40                  45

Asp Ala Asp Phe Ala Ala Glu Ser Thr Asn Leu Ala Arg Ser Gln Ile
    50                  55                  60

Leu Ser Gln Ala Ser Thr Ala Met Leu Ala Gln Ala Asn Ser Ser Lys
65                  70                  75                  80

Gln Asn Val Leu Ser Leu Leu Arg Gly
                85
```

<210> SEQ ID NO 287
<211> LENGTH: 88
<212> TYPE: PRT
<213> ORGANISM: Artificial Sequence
<220> FEATURE:
<223> OTHER INFORMATION: Synthetic peptide accession number Q56826

<400> SEQUENCE: 287

```
Pro Leu Asp Thr Leu Asp Lys Ala Leu Ala Gln Val Asp Asn Asn Arg
1               5                   10                  15

Ser Ser Leu Gly Ala Val Gln Asn Arg Leu Glu Ser Thr Val Asn Asn
            20                  25                  30

Leu Asn Asn Thr Val Asn Asn Leu Ser Ala Ala Arg Ser Arg Ile Glu
        35                  40                  45

Asp Ala Asp Tyr Ala Val Glu Val Ser Asn Met Ser Arg Gly Gln Ile
    50                  55                  60

Leu Gln Gln Ala Gly Thr Ser Val Leu Ala Gln Ala Asn Gln Val Pro
65                  70                  75                  80

Gln Thr Val Leu Ser Leu Leu Arg
                85
```

<210> SEQ ID NO 288
<211> LENGTH: 88
<212> TYPE: PRT
<213> ORGANISM: Artificial Sequence
<220> FEATURE:
<223> OTHER INFORMATION: Synthetic peptide accession number P42273

<400> SEQUENCE: 288

```
Ala Leu Ala Thr Leu Asp Asn Ala Ile Ser Lys Val Asp Glu Ser Arg
1               5                   10                  15

Ser Lys Leu Gly Ala Ile Gln Asn Arg Phe Gln Ser Thr Ile Asn Asn
            20                  25                  30

Leu Asn Asn Thr Val Asn Asn Leu Ser Ala Ser Arg Ser Arg Ile Leu
        35                  40                  45

Asp Ala Asp Tyr Ala Thr Glu Val Ser Asn Met Ser Lys Asn Gln Ile
    50                  55                  60

Leu Gln Gln Ala Gly Thr Ala Val Leu Ala Gln Ala Asn Gln Val Pro
```

```
                65                  70                  75                  80
Gln Thr Val Leu Ser Leu Leu Arg
                85

<210> SEQ ID NO 289
<211> LENGTH: 88
<212> TYPE: PRT
<213> ORGANISM: Artificial Sequence
<220> FEATURE:
<223> OTHER INFORMATION: Synthetic peptide accession number O31059

<400> SEQUENCE: 289

Ala Ile Asp Ala Ile Ser Asp Ala Leu Ala Lys Val Ser Ala Gln Arg
1               5                   10                  15

Ser Ala Leu Gly Ser Ile Gln Asn Arg Leu Glu His Ser Ile Ala Asn
                20                  25                  30

Leu Asp Asn Val Val Glu Asn Thr Asn Ala Ala Glu Ser Arg Ile Arg
                35                  40                  45

Asp Thr Asp Met Ala Asp Glu Met Val Thr Tyr Ser Lys Asn Asn Ile
            50                  55                  60

Leu Met Gln Ala Gly Gln Ser Met Leu Ala Gln Ala Asn Gln Ala Thr
65                  70                  75                  80

Gln Gly Val Leu Ser Ile Leu Gln
                85

<210> SEQ ID NO 290
<211> LENGTH: 88
<212> TYPE: PRT
<213> ORGANISM: Artificial Sequence
<220> FEATURE:
<223> OTHER INFORMATION: Synthetic peptide accession number Q7VZC2

<400> SEQUENCE: 290

Ala Leu Ser Lys Leu Asp Asp Ala Met Lys Ala Val Asp Glu Gln Arg
1               5                   10                  15

Ser Ser Leu Gly Ala Ile Gln Asn Arg Phe Glu Ser Thr Val Ala Asn
                20                  25                  30

Leu Asn Asn Thr Ile Thr Asn Leu Ser Ala Ala Arg Ser Arg Ile Glu
                35                  40                  45

Asp Ser Asp Tyr Ala Thr Glu Val Ser Asn Met Thr Lys Asn Gln Ile
            50                  55                  60

Leu Gln Gln Ala Gly Thr Ser Val Leu Ala Gln Ala Asn Gln Val Pro
65                  70                  75                  80

Gln Asn Val Leu Ser Leu Leu Arg
                85

<210> SEQ ID NO 291
<211> LENGTH: 88
<212> TYPE: PRT
<213> ORGANISM: Artificial Sequence
<220> FEATURE:
<223> OTHER INFORMATION: Synthetic peptide accession number Q9F4A4

<400> SEQUENCE: 291

Ser Ile Lys Thr Ile Asn Ser Ala Ile Glu Gln Val Ser Thr Gln Arg
1               5                   10                  15

Ser Lys Leu Gly Ala Val Gln Asn Arg Leu Glu His Thr Ile Asn Asn
                20                  25                  30

Leu Asn Thr Ser Ser Glu Asn Leu Thr Ala Ala Glu Ser Arg Val Arg
                35                  40                  45
```

Asp Val Asp Met Ala Lys Glu Met Met Ala Phe Ser Lys Asn Asn Ile
            50                  55                  60

Leu Ser Gln Ala Ala Gln Ala Met Leu Gly Gln Ala Asn Gln Gln Pro
65                  70                  75                  80

Gln Gly Val Leu Gln Leu Leu Arg
                85

<210> SEQ ID NO 292
<211> LENGTH: 88
<212> TYPE: PRT
<213> ORGANISM: Artificial Sequence
<220> FEATURE:
<223> OTHER INFORMATION: Synthetic peptide accession number Q8P9C4

<400> SEQUENCE: 292

Ala Leu Glu Ile Val Asp Lys Ala Leu Thr Ser Val Asn Ser Ser Arg
1               5                   10                  15

Ala Asp Met Gly Ala Val Gln Asn Arg Phe Thr Ser Thr Leu Ala Asn
            20                  25                  30

Leu Ala Ala Thr Ser Glu Asn Leu Thr Ala Ser Arg Ser Arg Ile Ala
        35                  40                  45

Asp Thr Asp Tyr Ala Lys Thr Thr Ala Glu Leu Thr Arg Thr Gln Ile
    50                  55                  60

Leu Gln Gln Ala Gly Thr Ala Met Leu Ala Gln Ala Lys Ser Val Pro
65                  70                  75                  80

Gln Asn Val Leu Ser Leu Leu Gln
                85

<210> SEQ ID NO 293
<211> LENGTH: 84
<212> TYPE: PRT
<213> ORGANISM: Artificial Sequence
<220> FEATURE:
<223> OTHER INFORMATION: Synthetic peptide accession number Q82UA3

<400> SEQUENCE: 293

Ile Asp Asp Ala Leu Lys Ile Val Asn Ser Thr Arg Ala Asp Leu Gly
1               5                   10                  15

Ala Ile Gln Asn Arg Phe Ser Ser Ala Ile Ala Asn Leu Gln Thr Ser
            20                  25                  30

Ala Glu Asn Leu Ser Ala Ser Arg Ser Arg Ile Gln Asp Ala Asp Phe
        35                  40                  45

Ala Ala Glu Thr Ala Ala Leu Thr Arg Ala Gln Ile Leu Gln Gln Ala
    50                  55                  60

Gly Val Ala Met Leu Ser Gln Ala Asn Ala Leu Pro Asn Asn Val Leu
65                  70                  75                  80

Ser Leu Leu Arg

<210> SEQ ID NO 294
<211> LENGTH: 89
<212> TYPE: PRT
<213> ORGANISM: Artificial Sequence
<220> FEATURE:
<223> OTHER INFORMATION: Synthetic peptide accession number Q84IC5

<400> SEQUENCE: 294

Val Met Asp Ile Ala Asp Thr Ala Ile Ala Asn Leu Asp Thr Ile Arg
1               5                   10                  15

Ala Asn Ile Gly Ala Thr Gln Asn Gln Ile Thr Ser Thr Ile Asn Asn

```
                20                  25                  30
Ile Ser Val Thr Gln Val Asn Val Lys Ala Ala Glu Ser Gln Ile Arg
            35                  40                  45

Asp Val Asp Phe Ala Ser Glu Lys Ser Ala Asn Tyr Ser Lys Ala Asn
        50                  55                  60

Ile Leu Ala Gln Ser Gly Ser Tyr Ala Met Ala Gln Ala Asn Ala Ala
65                  70                  75                  80

Ser Gln Asn Val Leu Arg Leu Leu Gln
                85
```

FLAGELLIN-BASED AGENTS AND USES INCLUDING EFFECTIVE VACCINATION

CROSS-REFERENCE TO RELATED APPLICATIONS

This application is a national stage of International Patent Application No. PCT/US2015/042887, filed Jul. 30, 2015, which claims the benefit of U.S. Provisional Patent Application No. 62/031,116, filed Jul. 30, 2014; 62/110,744, filed Feb. 2, 2015; and 62/117,366, filed Feb. 17, 2015 the entire contents of which are herein incorporated by reference.

FIELD OF THE INVENTION

The present invention relates to, inter alia, new compositions and methods for vaccination, including adjuvants comprising flagellin-based agents.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: CLE019PC Sequencelisting.txt; date recorded: Jul. 24, 2015; file size: 261 KB).

BACKGROUND

Vaccines are one of the most effective preventative health tools available against infectious diseases, cancers, and allergies. Vaccination aims to generate a strong immune response to the administrated antigen and provide long-term protection against a disorder. Often, however, an antigen alone is insufficient to stimulate protective immunity.

Vaccine adjuvants are compounds that enhance the specific immune responses against antigens in vaccines. Currently, several hundred natural and synthetic compounds are known to have adjuvant activity but only alum salts and AS04 are licensed for use in humans in the United States. This limited list of adjuvants is insufficient for meeting the functional needs of effective vaccination. For example, although alum is able to induce a good $T_{H2}$ response, it has little capacity to stimulate cellular ($T_{H1}$) immune responses which are so important for protection against many pathogens.

Accordingly, there remains a need for improved vaccines and/or adjuvants that can effectively stimulate a subject's immune response.

SUMMARY OF THE INVENTION

Accordingly, in some aspects, the present invention provides for improved vaccines and/or adjuvants.

In some aspects, the present invention provides a vaccine composition, comprising an adjuvant comprising a flagellin-based agent, such as, for example, CBLB502 (a/k/a entolimod) as well as any of the flagellin-based agents or derivatives described herein (e.g. Table 1), and an aluminum gel or salt and an antigen and, optionally, an additional adjuvant. In some aspects, the present invention provides an adjuvant composition, comprising an adjuvant comprising a flagellin-based agent, including CBLB502 as well as any of the flagellin-based agents or derivatives described herein (e.g. Table 1), and an aluminum gel or salt. In various embodiments, the vaccine described herein causes an improvement in adjuvant properties relative to a vaccine comprising the antigen and the aluminum gel or salt alone. In various embodiments, the vaccine and/or adjuvant described herein causes a broader, more diverse, more robust and longer lasting immunostimulatory effect than the vaccine comprising the antigen and the aluminum gel or salt alone and/or the adjuvant comprising the aluminum gel or salt alone. In various embodiments, the vaccine and/or adjuvant described herein causes immunostimulation of one or more of $T_{H1}$ and $T_{H2}$-mediated immune response (e.g. both of $T_{H1}$ and $T_{H2}$-mediated immune response) and/or the vaccine and/or adjuvant described herein causes immunostimulation of $T_{H1}$-mediated immune response at levels greater than a vaccine comprising the antigen and the aluminum gel or salt alone and/or the adjuvant comprising the aluminum gel or salt alone.

In some embodiments, the flagellin-based agent may be a flagellin molecule or flagellin-based agent, or variants thereof that has TLR5 agonist activity. The flagellin-based agent may comprise one or more of the sequences of Table 1 (SEQ ID Nos.: 1-252), or variants thereof that have TLR5 agonist activity and can include a variant of *Salmonella dublin* wild type flagellin (SEQ ID No: 1), CBLB502 (SEQ ID NO: 2) or variants thereof (including closely-related variants such as S33ML (SEQ ID NO: 35), CBLB502-485CT (CBLB533, SEQ ID NO: 71), and CBLB502-S33MX (SEQ ID NO: 150)) and more distantly related variants such as flagellin derivatives from a thermophilic microorganism or flagellin derivatives from a microorganism well-tolerated by human (e.g. SEQ ID NOs: 243-252). In some embodiments, the aluminum gel or salt is selected from aluminum hydroxide, aluminum phosphate, and potassium aluminum sulfate, and ALHYDROGEL In various embodiments, the present vaccine composition is part of the following vaccines (e.g. the antigens of these vaccines may be used as the antigen of the present vaccines): DTP (diphtheria-tetanus-*pertussis* vaccine), DTaP (diphtheria-tetanus-acellular *pertussis* vaccine), Hib (*Haemophilus influenzae* type b) conjugate vaccines, Pneumococcal conjugate vaccine, Hepatitis A vaccines, Poliomyelitis vaccines, Yellow fever vaccines, Hepatitis B vaccines, combination DTaP, Tdap, Hib, Human Papillomavirus (HPV) vaccine, Anthrax vaccine, and Rabies vaccine.

In various embodiments, the vaccine described herein is formed, in part, by mixing the flagellin-based agent and aluminum gel or salt to form a stable complex, the ratio (w/w) of flagellin-based agent to aluminum gel or salt being about 1:500 or less (e.g. about 1:500, or about 1:600, or about 1:700, or about 1:800, or about 1:900, or about 1:1000, or about 1:2000, or about 1:5000). In some embodiments, the flagellin-based agent and aluminum gel or salt are mixed in a ratio that is substantially below a loading capacity of the aluminum gel or salt. In some embodiments, the flagellin-based agent and antigen are adsorbed to the aluminum gel or salt.

In another aspect, the present invention provides a method of vaccinating a subject against a disorder, comprising administering an effective amount of a vaccine comprising an adjuvant comprising a flagellin-based agent and an aluminum gel or salt and an antigen associated with the disorder. In another aspect, the present invention provides a method of immunostimulating a subject in advance of or concurrent with vaccination, comprising administering an effective amount of an adjuvant comprising a flagellin-based agent and an aluminum gel or salt, wherein both $T_{H1}$ and $T_{H2}$-mediated immune responses are immunostimulated. In various embodiments the disorder is selected from infectious diseases, cancer, allergy, and autoimmune diseases (by way of example, diphtheria, tetanus, *pertussis*, influenza, pneumonia, hepatitis A, hepatitis B, polio, yellow fever, Human Papillomavirus (HPV) infection, various cancers, anthrax, rabies, Japanese Encephalitis, meningitis, measles, mumps, rubella, gastroenteritis, smallpox, typhoid fever, varicella (chickenpox), rotavirus, and shingles).

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF THE FIGURES

FIGS. 1A and 1B show the 13 conserved amino acids of flagellin that may be important for TLR5 activity. FIGS. 1A and 1B show a comparison of amino acid sequences of the conserved amino (FIG. 1A) and carboxy (FIG. 1B) terminus from 21 species of bacteria. The 13 conserved amino acids important for TLR5 activity are indicated by the letter "C" at the bottom of each column. The amino acid sequences are identified by their accession numbers from TrEMBL (first letter=Q) or Swiss-Prot (first letter=P). With respect to FIG. 1A. SEQ ID Nos: 253-273 correspond to the sequences listed on the figure from top to bottom, respectively. With respect to FIG. 1B. SEQ ID Nos: 274-294 correspond to the sequences listed on the figure from top to bottom, respectively.

FIG. 11 shows immunopotentiating effects of a 502 adjuvant. Anti-MA IgG (µg/ml) response (panel A) and anti-502 antibody response (panel B) by ELISA to TT-SMA vaccine in the presence and absence of alum or entolimod (a varying range from 0 to 20 µg) in pooled sera collected at week 2, 4 and 6 post initial vaccination is shown. Data represent the levels of antibody in the pooled samples from each group (n=5/group).

DETAILED DESCRIPTION OF THE INVENTION

Figure 2:
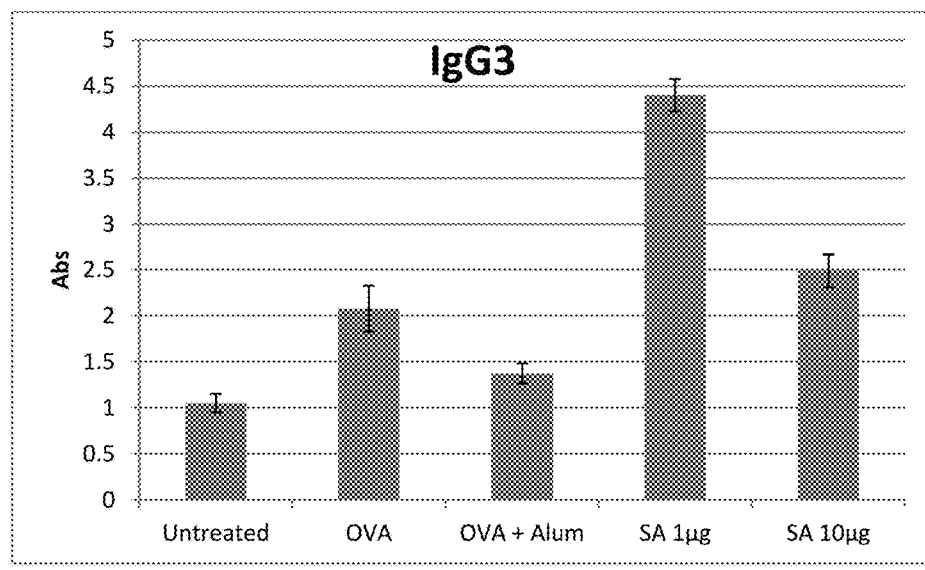
FIG. 2 shows ELISA data for the average response of five mouse treatment groups at the time point of 1 week postboost. Panel A is total IgG, Panel B is IgG1, Panel C is IgG2a, Panel D is IgG2b and Panel E is IgG3. Groups 1-5 are defined in TABLE B (Example 2): Group 1 is also called "Untreated;" Group 2 is also called "OVA," Groups 3 is also called "OVA+Alum," Group 4 is also called "SA 1 µg," and Group 5 is also called "SA 10 µg."

The present invention is also based, in part, on the surprising discovery that flagellin-based agents, including CBLB502 and any of the flagellin-based agents (e.g. agents comprising the sequences of Table 1, including MX-33) described herein, can be mixed with aluminum gels or salts (and, optionally antigens), in ratios well-below the loading/adsorbing capacity of the aluminum gel or salt (e.g. 1:500), and cause a broader, more diverse, more robust and longer lasting immunostimulatory effect than the vaccine comprising the antigen and the aluminum gel or salt alone and/or the adjuvant comprising the aluminum gel or salt alone. The inventors have also surprisingly discovered that the immunostimulatory effect can influence both the $T_{H1}$ and $T_{H2}$-mediated arms of an immune response. The inventors have also surprisingly discovered that low amounts of flagellin-based agents, including CBLB502 and any of the flagellin-based agents (e.g. agents comprising the sequences of Table 1, including MX-33) relative to antigen are effective for immunostimulation.

In one aspect, the invention provides a vaccine composition, comprising an adjuvant comprising a flagellin-based agent and an aluminum gel or salt and an antigen and, optionally, an additional adjuvant. In one aspect, the invention provides an adjuvant comprising a flagellin-based agent and an aluminum gel or salt.

In some embodiments, the described vaccine causes an improvement in adjuvant properties relative to a vaccine comprising the antigen and the aluminum gel or salt alone. In various embodiments, the vaccine and/or adjuvant described herein causes a broader, more diverse, more robust and longer lasting immunostimulatory effect than the vaccine comprising the antigen and the aluminum gel or salt alone (or as compared to the vaccine comprising the antigen and flagellin-based agent alone) and/or the adjuvant comprising the aluminum gel or salt alone (or as compared to the adjuvant comprising the flagellin-based agent alone).

In some embodiments, the described vaccine and/or described adjuvant causes immunostimulation of one or more of $T_{H1}$ and $T_{H2}$-mediated immune response. In some embodiments, the described vaccine and/or described adjuvant causes immunostimulation of both of $T_{H1}$ and $T_{H2}$-mediated immune response. In some embodiments, the described vaccine and/or described adjuvant causes immunostimulation of $T_{H1}$-mediated immune response at levels greater than a vaccine comprising the antigen and the aluminum gel or salt alone or an adjuvant comprising the aluminum gel or salt alone.

$T_{H1}$-mediated immune response (or "Type 1 response") largely involves interaction with macrophages and CD8+ T cells and may be linked to interferon-γ, TNF-β, interleukin-2, and interleukin-10 production. The $T_{H1}$-mediated immune response promotes cellular immune system and maximizes the killing efficacy of the macrophages and the proliferation of cytotoxic $CD8^+$ T cells. The $T_{H1}$-mediated immune response also promotes the production of opsonizing antibodies (e.g. IgG, IgM and IgA). The Type 1 cytokine IFN-γ increases the production of interleukin-12 by dendritic cells and macrophages, and via positive feedback, IL-12 stimulates the production of IFN-γ in helper T cells, thereby promoting the $T_{H1}$ profile. Interferon-γ also inhibits the production of cytokines such as interleukin-4, a cytokine associated with the Type 2 response, and thus it also acts to preserve its own response.

$T_{H2}$-mediated immune response (or "Type 2 response") largely involves interaction with B-cells, eosinophils, and mast cells and may be inked to interleukin-4, interleukin-5, interleukin-6, interleukin-9, interleukin-10, and interleukin-13. $T_{H2}$-mediated immune response promotes humoral immune system and may stimulate B-cells into proliferation, induce B-cell antibody class switching, and increase neutralizing antibody production (e.g. IgG, IgM and IgA as well as IgE antibodies). Other functions of the Type 2 response include promoting its own profile using two different cytokines. Interleukin-4 acts on helper T cells to promote the production of $T_{H2}$ cytokines (including itself it is auto-regulatory), while interleukin-10 (IL-10) inhibits a variety of cytokines including interleukin-2 and IFN-γ in helper T cells and IL-12 in dendritic cells and macrophages. The combined action of these two cytokines suggests that once the T cell has decided to produce these cytokines, that decision is preserved (and also encourages other T cells to do the same).

The division is medically relevant to, inter alia and without wishing to be bound by theory, the fact that alum adjuvants are only effective at inducing a $T_{H2}$-mediated response and not a $T_{H1}$-mediated response (see, e.g., Smith Korsholm, et al. Immunology. January 2010; 129(1): 75-86, the contents of which are hereby incorporated by reference in their entirety).

In various embodiments, the stimulation of $T_{H1}$ and $T_{H2}$-mediated immune responses may be measured by assays known in the art, including a number of antibody surrogate assays (e.g. ELISA and the like). For instance, without wishing to be bound by theory, IgG1 is associated with a $T_{H2}$-like response, while a $T_{H1}$ response is associated with the induction of IgG2a, IgG2b, and IgG3 antibodies.

In some embodiments, the described vaccine and/or described adjuvant causes an increase in titer of one or more of IgG1, IgG2a, IgG2b, and IgG3 antibodies (e.g. relative to the adjuvant comprising the aluminum gel or salt or flagellin-based agent alone, or relative to the vaccine comprising the antigen and the aluminum gel or salt alone (or flagellin-based agent) alone)). In some embodiments, the described vaccine and/or described adjuvant causes a relative increase in the titer of all of IgG1, IgG2a, IgG2b, and IgG3 antibodies. In some embodiments, the described vaccine and/or described adjuvant causes a relative increase in the titer of more IgG3 antibodies than the described vaccine and/or described adjuvant in the absence of a flagellin-based agent (or the described vaccine and/or described adjuvant in the absence of an aluminum gel or salt alone).

Accordingly, in some embodiments, the described vaccine and/or described adjuvant causes a diversified immune response. For example, in some embodiments, the total IgG generated by the described vaccines and/or adjuvants is greater than the described vaccines and/or adjuvants without the flagellin-based agent.

In some embodiments, the flagellin-based agent may be a flagellin molecule or flagellin-related polypeptide, or variants thereof that have TLR5 agonist activity. The flagellin-based agent may be from various sources, including a variety of Gram-positive and Gram-negative bacterial species. In some embodiments, the flagellin-based agents may have an amino acid sequence that is derived from any of the flagellins from bacterial species that are depicted in, for example, FIG. 7 of U.S. Patent Publication No. 2003/0044429, the contents of which are incorporated herein by reference in their entirety. The flagellin-based agent may have nucleotide sequences related to those encoding the flagellin polypeptides listed in, for example, FIG. 7 of U.S. 2003/0044429, which are publicly available at sources including the NCBI Genbank database.

The flagellin-based agent may be the major component of bacterial flagellum. The flagellin-based agents may be composed of one, or two, or three, or four, or five, or six, or seven domains or fragments thereof (see, e.g., FIG. 10 of U.S. Pat. No. 8,324,163, the contents of which are incorporated herein by reference in their entirety). The domains may be selected from ND0, ND1, ND2, D3, CD2, CD1, and CD0. Domains 0 (D0), 1 (D1), and 2 (D2) may be discontinuous and may be formed when residues in the amino terminus and carboxy terminus are juxtaposed by the formation of a hairpin structure. The amino and carboxy terminus comprising the D1 and D2 domains may be most conserved, whereas the middle hypervariable domain (D3) may be highly variable. The non-conserved D3 domain may be on the surface of the flagellar filament and may contain the major antigenic epitopes. The potent proinflammatory activity of flagellin may reside in the highly conserved N and CD1 and D2 regions.

The flagellin-based agents may be from a species of *Salmonella*, representative examples of which are *S. typhimurium* and *S. dublin* (encoded by GenBank Accession Number M84972). The flagellin related-polypeptide may be a fragment, variant, analog, homolog, or derivative of wild type flagellin (SEQ ID NO: 1), or combination thereof. A fragment, variant, analog, homolog, or derivative of flagellin may be obtained by rational-based design based on the domain structure of flagellin and the conserved structure recognized by TLR5.

Figure 7:
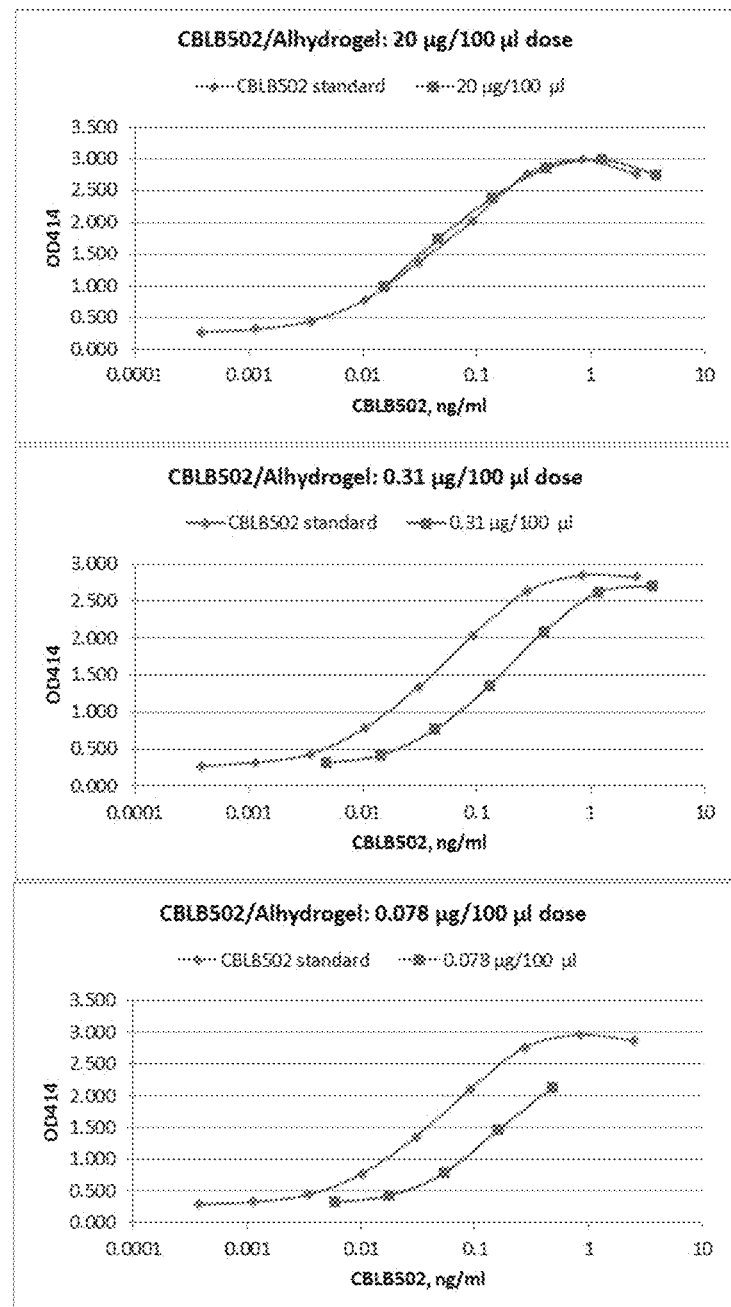
FIG. 7 shows dose-response titration curves CBLB502/ALHYDROGEL generated with 293-hTLR5-LacZ reporter cells. CBLB502 was adsorbed to ALHYDROGEL at indicated doses (20 µg/100 µl: top panel, 0.31 µg/100 µl: middle panel and 0.078 µg/100 µl: bottom panel), serially diluted with media and assayed together with soluble CBLB502 standards.

The flagellin-based agent may be related to a flagellin polypeptide from any Gram-positive or Gram-negative bacterial species including, but not limited to, the flagellin polypeptides disclosed in U.S. Pat Pub. 2003/0044429, the contents of which are incorporated herein, and the flagellin peptides corresponding to the Accession numbers listed in the BLAST results shown in FIG. 7 (panels A-F) of U.S. Patent Pub. 200340044429, or variants thereof.

In some embodiments, the flagellin-based agent comprises or consists of any of the polypeptides or nucleic acids encoding said polypeptides listed in Table 1. In some embodiments, the flagellin-based agent is encoded by the nucleotide sequences listed in Table 1. In a further embodiment, the flagellin-based agent comprises the polypeptides listed in Table 1. In some embodiments, the flagellin-based agent comprises one or more of SEQ ID NOs.: 1-252. In some embodiments, the flagellin-based agent comprises a flexible linker. In a further embodiment, the flexible linker comprises SEQ ID NO: 16. In yet a further embodiment, the flexible linker comprises SEQ ID NO: 242.

In some embodiments, the flagellin-based agent is a variant of SEQ ID NO: 1. In variois embodiments, the flagellin-based agent is not SEQ ID NO: 1.

In some embodiments, the flagellin-based agent comprises or consists of CBLB502 (SEQ ID NO: 2) or is a variant of CBLB502 (SEQ ID NO: 2). In various embodiments, CBLB502 provides the advantage of, inter alia, removal of epitopes that generate neutralizing anti-flagellin antibodies and therefore allow for the surprising adjuvant properties seen here in combination with alum.

In some embodiments, the flagellin-based agent comprises mutations in epitopes recognized by neutralizing anti-CBLB502 antibodies. The flagellin-based agent may comprise one or more mutations in the epitopes recognized by neutralizing anti-CBLB502 antibodies which inhibit or abrogate the ability of the antibodies to neutralize the composition. In yet a further embodiment, the flagellin-based agent comprises a truncation and mutations in one or more epitopes. In a further embodiment, the mutations comprise replacement of the epitope residues with alanine. In a further embodiment, the mutated epitopes comprise one or more of the following residues: E153, S444, T154, N440, Q142, F131, D443, N68, T447, S110, Q117, R124, D113, E120, N127, and 0128.

The flagellin-based agent may comprise insertions, deletions, transposon insertions, and changes to any one of the D0, D1, D2, and the variable D3 domains. The D3 domain may be substituted in part, or in whole, with a hinge or linker polypeptide that allows the D1 and D2 domains to property fold such that the variant stimulates TLR5 activity.

In some embodiments, the flagellin-based agent may be a minimal functional core of a flagellin, for example, deleting residues relative to the already shortened CBLB502 molecule. In some embodiments, the flagellin-based agent has altered amino acid identity relative to wild type, including deletions, additions and substitutions, that provide for improved activity. In some embodiments, the flagellin-based agent is derived from CBLB502 (SEQ ID NO: 2). In some embodiments, the flagellin-based agent comprises a truncation in one or more domains. In a further embodiment, the flagellin-based agent comprises a deletion in an N-terminal domain. In yet a further embodiment, the flagellin-based agent comprises a deletion in the ND0 domain. In yet a further embodiment, the flagellin-based agent comprises a deletion of the entire ND0 domain. In a further embodiment, the flagellin-based agent comprises a deletion in a C-terminal domain. In yet another embodiment, the flagellin-based agent comprises a deletion in the CD0 domain. In yet another embodiment, the flagellin-based agent retains amino acids 470-485 of the CD0 domain. In yet a further embodiment, the flagellin-based agent is CBLB502-S33 (SEQ ID NO: 17).

The flagellin-based agent may comprise at least 10, 11, 12, or 13 of the 13 conserved amino acids shown in FIG. 1A and FIG. 1B (positions 89, 90, 91, 95, 98, 101, 115, 422, 423, 426, 431, 436 and 452). The flagellin may be at least 30-99% identical to amino acids 1-174 and 418-505 of SEQ ID NO: 1.

In some embodiments, the flagellin-based agent comprises a tag. In yet a further embodiment, the tag is attached to the N-terminus of the flagellin-based agent. In yet another embodiment, the tag is attached to the C-terminus of the flagellin-based agent.

In some embodiments, the flagellin-based agent comprises a flexible linker. In a further embodiment, the flexible linker comprises SEQ ID NO: 16. In yet a further embodiment, the flexible linker comprises SEQ ID NO:242.

In various embodiments, the flagellin-based agent is one or more of the flagellin related composition derived from SEQ ID NO: 2. In various embodiments, the flagellin-based agent is one or more of CBLB502-S33ML (SEQ ID NO: 35), CBLB502-485CT (CBLB533, SEQ ID NO: 71), and CBLB502-S33MX (SEQ ID NO: 150).

In various embodiments, the flagellin-based agent is a flagellin derivative from a thermophilic microorganism. In various embodiments, the flagellin-based agent is a flagellin derivative from a microorganism well-tolerated by human. In some embodiments, the flagellin-based agent is one or more of SEQ ID NOs: 243-252.

In some embodiments, a variant includes molecules that have TLR5 agonist activity. In some embodiments, a variant includes molecules comprising an amino acid sequence having at least about 70% (e.g. about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 1 or SEQ ID NO: 2.

In some embodiments, the flagellin-based agent comprises or consists of any of the polypeptides or nucleic acids encoding said polypeptides listed in Table 1. In some embodiments, the flagellin-based agent is encoded by the nucleotide sequences listed in Table 1. In a further embodiment, the flagellin-based agent comprises one or more of the polypeptides listed in Table 1. In some embodiments, the flagellin-based agent comprises or consists of polypeptides encoded by either SEQ ID NOs: 69 or 70. In some embodiments, the flagellin-based agent comprises or consists of the polypeptides of SEQ ID NO: 71, "CBLB543". In some embodiments, the flagellin-based agent comprises or consists of polypeptides encoded by either SEQ ID NOs: 149 or 151. In some embodiments, the flagellin-based agent comprises or consists of the polypeptides of SEQ ID NO: 150, "CBLB533".

TABLE 1

Illustrative Flagellin-Based Agents

| SEQ ID | Construct Name | DNA/PRT | Species | Sequence |
|---|---|---|---|---|
| 0001 | Wild type | PRT | Salmonella dublin | MAQVINTNSLSLLTQNNLNKSQSSLSSAIERLSSGLRINSAKDDAAGQ AIANRFTSNIKGLTQASRNANDGISIAQTTEGALNEINNNLQRVRELS VQATNGTNSDSDLKSIQDEIQQRLEEIDRVSNQTQFNGVKVLSQDNQM KIQVGANDGETITIDLQKIDVKSLGLDGFNVGPKEATVGDLKSS TABLE 1-continued Illustrative Flagellin-Based Agents

| SEQ ID | Construct Name | DNA/PRT | Species | Sequence |
|---|---|---|---|---|
| 0019 | Mutant 33-485 502 template sequence | DNA | Artificial Sequence | TCTAAAGCGCAGATTCTGCAGCAGGCTGGTACTTCCGTTCTGGCGCAG GCTAACCAGGTT |
| 0020 | Mutant 33-485 Reverse Primer CBLB485 | DNA | Artificial Sequence | CCTGGTTAGCCTGCGCCAGATTATCAACCAGCCTGCTGCAGAATCTGC |
| 0021 | Mutant 33-485 DNA sequence of 485 Mutant (T7 Promoter to Stop) | DNA | Artificial Sequence | TAATACGACTCACTATAGGGGAATTGTGAGCGGATAACAATTCCCCTC TAGAATAATTTTGTTTAACTTTAAGAAGGAGATATACATATGCGGGGT TCTCATCATCATCATCATCATGGTATGGCTAGCATGACTGGTGGACAG CAAATGGGTCGGGATCTGTACGACCTGGTTCCGCGCGGTAGCGCGAAG GATCCGTCTGGTCTGCGTATCAACAGCGCGAAAGACGATGCGGCAGGC CAGGCGATTGCTAACCGCTTCACTTCTAATATCAAAGGTCTGACTCAG GCTTCCCGTAACGCTAACGACGGCATTTCTATTGCGCAGACCACTGAA GGTGCGCTGAATGAAATCAACAACAACCTGCAGCGTGTGCGTGAGTTG TCTGTTCAGGCCACTAACGGGACTAACTCTGATTCCGATCTGAAATCT ATCCAGGATGAAATTCAGCAACGTCTGGAAGAAATCGATCGCGTTTCT AATCAGACTCAATTTAACGGTGTTAAAGTCCTGTCTCAGGACAACCAG ATGAAAATCCAGGTTGGTGCTAACGATGGTGAAACCATTACCATCGAT CTGCAAAAAATTGATGTGAAAAGCCTTGGCCTTGATGGGTTCAATGTT AATTCCCCGGGAATTTCCGGTGGTGGTGGTGAATTCTAGACTCCATG GGTACATTAATCAATGAAGACGCTGCCGCAGCCAAGAAAAGTACCGCT AACCCACTGGCTTCAATTGATTCTGCATTGTCAAAAGTGGACGCAGTT CGTTCTTCTCTGGGGGCAATTCAAAACCGTTTTGATTCAGCCATTACC AACCTTGGCAATACGGTAACCAATCTGAACTCCGCGCGTAGCCGTATC GAAGATGCTGACTATGCAACGGAAGTTTCTAATATGTCTAAAGCGCAG ATTCTGCAGCAGGCTGGTTGATAA |
| 0022 | Mutant 33-485 Expressed Mutant 33-485 | PRT | Artificial Sequence | MRGSHHHHHHGMASMTGGQQMGRDLYDLVPRGSAKDPSGLRINSAKDD AAGQAIANRFTSNIKGLTQASRNANDGISIAQTTEGALNEINNNLQRV RELSVQATNGTNSDSDLKSIQDEIQQRLEEIDRVSNQTQFNGVKVLSQ DNQMKIQVGANDGETITIDLQKIDVKSLGLDGFNVNSPGISGGGGGIL DSMGTLINEDAAAAKKSTANPLASIDSALSKVDAVRSSLGAIQNRFDS AITNLGNTVTNLNSARSRIEDADYATEVSNMSKAQILQQAG |
| 0023 | Mutant 45CT Mutant 506T | PRT | Artificial Sequence | MAQVINTNSLSLLTQNNLNKSQSSLSSAIERLSSGLRINSAKDDAAGQ AIANRFTSNIKGLTQASRNANDGISIAQTTEGALNEINNNLQRVRELS VQATNGTNSDSDLKSIQDEIQQRLEEIDRVSNQTQFNGVKVLSQDNQM KIQVGANDGETITIDLQKIDVKSLGLDGFNVNSPGISGGGGGILDSMG TLINEDAAAAKKSTANPLASIDSALSKVDAVRSSLGAIQNRFDSAITN LGNTVTNLNSARSRIEDADYATEVSNMSKAQILQQAGTSVLAQANQVP QNVLSLLVPRGSHHHHHHGMASMTGGQQMGRDLYDDDDKDP |
| 0024 | Mutant 45CT Mutant 506T | DNA | Artificial Sequence | ATGGCACAAGTCATTAATACAAACAGCCTGTCGCTGTTGACCCAGAAT AACCTGAACAAATCTCAGTCCTCACTCTGAGTTCCGCTATTGAGCGTCTG TCCTCTGGTCTGCGTATCAACAGCGCGAAAGACGATGCGGCAGGCCAG GCGATTGCTAACCGCTTCACTTCTAATATCAAAGGTCTGACTCAGGCT TCCCGTAACGCTAACGACGGCATTTCTATTGCGCAGACCACTGAAGGT GCGCTGAATGAAATCAACAACAACCTGCAGCGTGTGCGTGAGTTGTCT GTTCAGGCCACTAACGGGACTAACTCTGATTCCGATCTGAAATCTATC CAGGATGAAATTCAGCAACGTCTGGAAGAAATCGATCGCGTTTCTAAT CAGACTCAATTTAACGGTGTTAAAGTCCTGTCTCAGGACAACCAGATG AAAATCCAGGTTGGTGCTAACGATGGTGAAACCATTACCATCGATCTG CAAAAAATTGATGTGAAAAGCCTTGGCCTTGATGGGTTCAATGTTAAT TCCCCGGGAATTTCCGGTGGTGGTGGTGGAATTCTAGACTCCATGGGT ACATTAATCAATGAAGACGCTGCCGCAGCCAAGAAAAGTACCGCTAAC CCACTGGCTTCAATTGATTCTGCATTGTCAAAAGTGGACGCAGTTCGT TCTTCTCTGGGGGCAATTCAAAACCGTTTTGATTCAGCCATTACCAAC CTTGGCAATACGGTAACCAATCTGAACTCCGCGCGTAGCCGTATCGAA GATGCTGACTATGCAACGGAAGTTTCTAATATGTCTAAAGCGCAGATT CTGCAGCAGGCTGGTACTTCCGTTCTGGCGCAGGCTAACCAGGTTCCG CAAAACGTCCTCTCTTTACTGGTTCCGCGGGGTTCTCATCATCATCAT CATCATGGTATGGCTAGCATGACTGGTGGACAGCAAATGGGTCGGGAT CTGTACGACGATGACGATAAGGATCCGTAAGTCGACAAGCTTGCG |
| 0025 | Mutant 45CT Forward F45CT | DNA | Artificial Sequence | CGAAAGACCATATGGCAGGCCAGGCGATTGC |
| 0026 | Mutant 45CT Reverse R45CT | DNA | Artificial Sequence | CGCAAGCTTGTCGACTTACGGATCCTTATCGTC |
| 0027 | Mutant 45CT Sequence of 45CT construct | DNA | Artificial Sequence | TAATACGACTCACTATAGGGGAATTGTGAGCGGATAACAATTCCCCTC TAGAATAATTTTGTTTAACTTTAAGAAGGAGATATACATATGGCAGG CCAGGCGATTGCTAACCGCTTCACTTCTAATATCAAAGGTCTGACTCA GGCTTCCCGTAACGCTAACGACGGCATTTCTATTGCGCAGACCACTGA |

… TABLE 1-continued

Illustrative Flagellin-Based Agents

| SEQ ID | Construct Name | DNA/PRT | Species | Sequence |
|---|---|---|---|---|
| | | | | AGGTGCGCTGAATGAAATCAACAACAACCTGCAGCGTGTGCGTGAGTT GTCTGTTCAGGCCACTAACGGGACTAACTCTGATTCCGATCTGAAATC TATCCAGGATGAAATTCAGCAACGTCTGGAAGAAATCGATCGCGTTTC TAATCAGACTCAATTTAACGGTGTTAAAGTCCTGTCTCAGGACAACCA GATGAAAATCCAGGTTGGTGCTAACGATGGTGAAACCATTACCATCGA TCTGCAAAAAATTGATGTGAAAAGCCTTGGCCTTGATGGGTTCAATGT TAATTCCCCGGGAATTTCCGGTGGTGGTGGTGGAATTCTAGACTCCAT GGGTACATTAATCAATGAAGACGCTGCCGCAGCCAAGAAAAGTACCGC TAACCCACTGGCTTCAATTGATTCTGCATTGTCAAAAGTGGACGCAGT TCGTTCTTCTCTGGGGGCAATTCAAAACCGCTTTGATTCAGCCATTAC CAACCTTGGCAATACGGTAACCAATCTGAACTCCGCGCGTAGCCGTAT CGAAGATGCTGACTATGCAACGGAAGTTTCTAATATGTCTAAAGCGCA GATTCTGCAGCAGGCTGGTACTTCCGTTCTGGCGCAGGCTAACCAGGT TCCGCAAAACGTCCTCTCTTTACTGGTTCCGCGGGGTTCTCATCATCA TCATCATGGTATGGCTAGCATGACTGGTGGACAGCAAATGGGTCG GGATCTGTACGACGATGACGATAAGGATCCGTAAGTCGAC |
| 0028 | Mutant 45CT Expressed Mutant 45CT | PRT | Artificial Sequence | MAGQAIANRFTSNIKGLTQASRNANDGISIAQTTEGALNEINNNLQRV RELSVQATNGTNSDSDLKSIQDEIQQRLEEIDRVSNQTQFNGVKVLSQ DNQMKIQVGANDGETITIDLQKIDVKSLGLDGFNVNSPGISGGGGGIL DSMGTLINEDAAAKKSTANPLASIDSALSKVDAVRSSLGAIQNRFDS AITNLGNTVTNLNSARSRIEDADYATEVSNMSKAQILQQAGTSVLAQA NQVPQNVLSLLVPRGSHHHHHHGMASMTGGQQMGRDLYDDDDKDP |
| 0029 | Mutant 33GPS Expressed Mutant 33ML | DNA | Artificial Sequence | ATGAGCGGGTTACGGATCAACAGCGCGAAAGACGATGCGGCAGGCCAG GCGATTGCTAACCGCTTCACTTCTAATATCAAAGGTCTGACTCAGGCT TCCCGTAACGCTAACGACGGCATTTCTATTGCGCAGACCACTGAAGGT GCGCTGAATGAAATCAACAACAACCTGCAGCGTGTGCGTGAGTTGTCT GTTCAGGCCACTAACGGGACTAACTCTGATTCCGATCTGAAATCTATC GGACCATCAGGTCAGGATGAAATTCAGCAACGTCTGGAAGAAATCGAT CGCGTTTCTAATCAGACTCAATTTAACGGTGTTAAAGTCCTGTCTCAG GACAACCAGATGAAAATCCAGGTTGGTGCTAACGATGGTGAAACCATT ACCATCGATCTGCAAAAAATTGATGTGAAAAGCCTTGGCCTTGATGGG TTCAATGTTAATTCCCCGGGAAGTACCGCTAACCCACTGGCTTCAATT GATTCTGCATTGTCAAAAGTGGACGCAGTTCGTTCTTCTCTGGGGGCA ATTCAAAACCGCTTTGATTCAGCCATTACCAACCTTGGCAATACGGTA ACCAATCTGAACTCCGCGCGTAGCCGTATCGAAGATGCTGACTATGCA ACGGAAGTTTCTAATATGTCTAAAGCGCAGATTCTGCAGCAGGCTGGT ACTTCCGTTCTGGCGCAGGCTAACCAGGTTCCGCAAAACGTCCTCTCT TTACTGGTTCCGCGGGGTTCTCATCATCATCATCATGGTTAA |
| 0030 | Mutant 33GPS Expressed Mutant 33ML | PRT | Artificial Sequence | MSGLRINSAKDDAAGQAIANRFTSNIKGLTQASRNANDGISIAQTTEG ALNEINNNLQRVRELSVQATNGTNSDSDLKSIGPSGQDEIQQRLEEID RVSNQTQFNGVKVLSQDNQMKIQVGANDGETITIDLQKIDVKSLGLDG FNVNSPGSTANPLASIDSALSKVDAVRSSLGAIQNRFDSAITNLGNTV TNLNSARSRIEDADYATEVSNMSKAQILQQAGTSVLAQANQVPQNVLS LLVPRGSHHHHHH |
| 0031 | Mutant 33GPS Forward primer FSY3CT | DNA | Artificial Sequence | GATATACATATGAGCGGGTTACGGATCAACAG |
| 0032 | Mutant 33GPS Reverse primer RMIMxN | DNA | Artificial Sequence | AGATCTCCCGGGGAATTAACATTGAACCC |
| 0033 | Mutant 33GPS DNA sequence of mutant 33GPS | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTGGACCATCAGGTGAAATTCAGCAACGTCTGGAAGAAATCGATCGC GTTTCTAATCAGACTCAATTTAACGGTGTTAAAGTCCTGTCTCAGGAC AACCAGATGAAAATCCAGGTTGGTGCTAACGATGGTGAAACCATTACC ATCGATCTGCAAAAAATTGATGTGAAAAGCCTTGGCCTTGATGGGTTC AATGTTAATTCCCCGGGAAGTACCGCTAACCCACTGGCTTCAATTGAT TCTGCATTGTCAAAAGTGGACGCAGTCGTTCTTCTCTGGGGGCAATT CAAAACCGCTTTGATTCAGCCATTACCAACCTTGGCAATACGGTAACC AATCTGAACTCCGCGCGTAGCCGTATCGAAGATGCTGACTATGCAACG GAAGTTTCTAATATGTCTAAAGCGCAGATTCTGCAGCAGGCTGGTACT TCCGTTCTGGCGCAGGCTAACCAGGTTCCGCAAAACGTCCTCTCTTTA CTGGTTCCGCGGGGTTCTCATCATCATCATCATGGTTAAGTCGAC |
| 0034 | Mutant 33GP5 Expressed Mutant 33GP5 | PRT | Artificial Sequence | MSGLRINSAKDDAAGQAIANRFTSNIKGLTQASRNANDGISIAQTTEG ALNEINNNLQRVRELSVQATGPSGEIQQRLEEIDRVSNQTQFNGVKVL SQDNQMKIQVGANDGETITIDLQKIDVKSLGLDGFNVNSPGSTANPLA |

TABLE 1-continued

Illustrative Flagellin-Based Agents

| SEQ ID | Construct Name | DNA/ PRT | Species | Sequence |
|---|---|---|---|---|
| | | | | SIDSALSKVDAVRSSLGAIQNRFDSAITNLGNTVTNLNSARSRIEDAD YATEVSNMSKAQILQQAGTSVLAQANQVPQNVLSLLVPRGSHHHHHG |
| 0035 | Mutant 33ML Mutant 33CT (Fixed A) | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDRVSN QTQFNGVKVLSQDNQMKIQVGANDGETITIDLQKIDVKSLGLDGFNVN SPGISGGGGGILDSMGTLINEDAAAAKKSTANPLASIDSALSKVDAVR SSLGAIQNRFDSAITNLGNTVTNLNSARSRIEDADYATEVSNMSKAQI LQQAGTSVLAQANQVPQNVLSLLVPRGSHHHHHG |
| 0036 | Mutant 33ML Mutant 33CT (Fixed A) | DNA | Artificial Sequence | ATGAGCGGGTTACGGATCAACAGCGCGAAAGACGATGCGGCAGGCCAG GCGATTGCTAACCGCTTCACTTCTAATATCAAAGGTCTGACTCAGGCT TCCCGTAACGCTAACGACGGCATTTCTATTGCGCAGACCACTGAAGGT GCGCTGAATGAAATCAACAACAACCTGCAGCGTGTGCGTGAGTTGTCT GTTCAGGCCACTAACGGGACTAACTCTGATTCCGATCTGAAATCTATC CAGGATGAAATTCAGCAACGTCTGGAAGAAATCGATCGCGTTTCTAAT CAGACTCAATTTAACGGTGTTAAAGTCCTGTCTCAGGACAACCAGATG AAAATCCAGGTTGGTGCTAACGATGGTGAAACCATTACCATCGATCTG CAAAAAATTGATGTGAAAAGCCTTGGCCTTGATGGGTTCAATGTTAAT TCCCCGGGAATTTCCGGTGGTGGTGGTGGAATTCTAGACTCCATGGGT ACATTAATCAATGAAGACGCTGCCGCAGCCAAGAAAAGTACCGCTAAC CCACTGGCTTCAATTGATTCTGCATTGTCAAAAGTGGACGCAGTTCGT TCTTCTCTGGGGGCAATTCAAAACCGCTTTGATTCAGCCATTACCAAC CTTGGCAATACGGTAACCAATCTGAACTCCGCGCGTAGCCGTATCGAA GATGCTGACTATGCAACGGAAGTTTCTAATATGTCTAAAGCGCAGATT CTGCAGCAGGCTGGTACTTCCGTTCTGGCGCAGGCTAACCAGGTTCCG CAAAACGTCCTCTCTTTACTGGTTCCGCGGGGTTCTCATCATCATCAT CATCATGGTTAA |
| 0037 | Mutant 33ML Forward primer F502ML | DNA | Artificial Sequence | TCTAGACCCGGGAAGTACCGCTAACCCACTGGCTTCAATTG |
| 0038 | Mutant 33ML Reverse primer R33CT | DNA | Artificial Sequence | CCAGTCATGTCGACTTAACCATGATGATGATGATGAG |
| 0039 | Mutant 33ML 502 template sequence | DNA | Artificial Sequence | CTCATCATCATCATCATCATGGTTAAGTCGACAAGCTTGCGGCCGCAG AGCTCGC |
| 0040 | Mutant 33ML 33ML construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATCATGGTTAAGTCGAC |
| 0041 | Mutant 33ML Expressed Mutant 33ML | DNA | Artificial Sequence | ATGAGCGGGTTACGGATCAACAGCGCGAAAGACGATGCGGCAGGCCAG GCGATTGCTAACCGCTTCACTTCTAATATCAAAGGTCTGACTCAGGCT TCCCGTAACGCTAACGACGGCATTTCTATTGCGCAGACCACTGAAGGT GCGCTGAATGAAATCAACAACAACCTGCAGCGTGTGCGTGAGTTGTCT GTTCAGGCCACTAACGGGACTAACTCTGATTCCGATCTGAAATCTATC CAGGATGAAATTCAGCAACGTCTGGAAGAAATCGATCGCGTTTCTAAT CAGACTCAATTTAACGGTGTTAAAGTCCTGTCTCAGGACAACCAGATG AAAATCCAGGTTGGTGCTAACGATGGTGAAACCATTACCATCGATCTG CAAAAAATTGATGTGAAAAGCCTTGGCCTTGATGGGTTCAATGTTAAT TCCCCGGGAAGTACCGCTAACCCACTGGCTTCAATTGATTCTGCATTG TCAAAAGTGGACGCAGTTCGTTCTTCTCTGGGGGCAATTCAAAACCGC TTTGATTCAGCCATTACCAACCTTGGCAATACGGTAACCAATCTGAAC TCCGCGCGTAGCCGTATCGAAGATGCTGACTATGCAACGGAAGTTTCT AATATGTCTAAAGCGCAGATTCTGCAGCAGGCTGGTACTTCCGTTCTG GCGCAGGCTAACCAGGTTCCGCAAAACGTCCTCTCTTTACTGGTTCCG CGGGGTTCTCATCATCATCATCATCATGGTTAA |

TABLE 1-continued

Illustrative Flagellin-Based Agents

| SEQ ID | Construct Name | DNA/PRT | Species | Sequence |
|---|---|---|---|---|
| 0042 | Mutant 33ML<br>Mutant 33ML | PRT | Artificial Sequence | MSGLRINSAKDDAAGQAIANRFTSNIKGLTQASRNANDGISIAQTTEG<br>ALNEINNNLQRVRELSVQATNGTNSDSDLKSIQDEIQQRLEEIDRVSN<br>QTQFNGVKVLSQDNQMKIQVGANDGETITIDLQKIDVKSLGLDGFNVN<br>SPGSTANPLASIDSALSKVDAVRSSLGAIQNRFDSAITNLGNTVTNLN<br>SARSRIEDADYATEVSNMSKAQILQQAGTSVLAQANQVPQNVLSLLVP<br>RGSHHHHHHG |
| 0043 | Mutant 37CT<br>delta ND0 mutant based on CBLB506T | DNA | Artificial Sequence | ATGGCACAAGTCATTAATACAAACAGCCTGTCGCTGTTGACCCAGAAT<br>AACCTGAACAAATCTCAGTCCTCACTGAGTTCCGCTATTGAGCGTCTG<br>TCCTCTGGTCTGCGTATCAACGGCGCGAAAGACGATGCGGCAGGCCAG<br>GCGATTGCTAACCGCTTCACTTTCTAATATCAAAGGTCTGACTCAGGCT<br>TCCCGTAACGCTAACGACGGCATTTCTATTGCGCAGACCACTGAAGGT<br>GCGCTGAATGAAATCAACAACAACCTGCAGCGTGTGCGTGAGTTGTCT<br>GTTCAGGCCACTAACGGGACTAACTCTGATTCCGATCTGAAATCTATC<br>CAGGATGAAATTCAGCAACGTCTGGAAGAAATCGATCGCGTTTCTAAT<br>CAGACTCAATTTAACGGTGTTAAAGTCCTGTCTCAGGACAACCAGATG<br>AAAATCCAGGTTGGTGCTAACGATGGTGAAACCATTACCATCGATCTG<br>CAAAAAATTGATGTGAAAAGCCTTGGCCTTGATGGGTTCAATGTTAAT<br>TCCCCGGGAATTTCCGGTGGTGGTGGTGGAATTCTAGACTCCATGGGT<br>ACATTAATCAATGAAGACGCTGCCGCAGCCAAGAAAAGTACCGCTAAC<br>CCACTGGCTTCAATTGATTCTGCATTGTCAAAAGTGGACGCAGTTCGT<br>TCTTCTCTGGGGGCAATTCAAAACCGCTTTGATTCAGCCATTACCAAC<br>CTTGGCAATACGGTAACCAATCTGAACTCCGCGCGTAGCCGTATCGAA<br>GATGCTGACTATGCAACGGAAGTTTCTAATATGTCTAAAGCGCAGATT<br>CTGCAGCAGGCTGGTACTTCCGTTCTGGCGCAGGCTAACCAGGTTCCG<br>CAAAACGTCCTCTCTTTACTGGTTCCGCGGGGTTCTCATCATCATCAT<br>CATCATGGTATGGCTAGCATGACTGGTGGACAGCAAATGGGTCGGGAT<br>CTGTACGACGATGACGATAAGGATCCGTAAGTCGACAAGCTTGCG |
| 0044 | Mutant 37CT<br>delta ND0 mutant based on CBLB506T | PRT | Artificial Sequence | MAQVINTNSLSLLTQNNLNKSQSSLSSAIERLSSGLRINGAKDDAAGQ<br>AIANRFTSNIKGLTQASRNANDGISIAQTTEGALNEINNNLQRVRELS<br>VQATNGTNSDSDLKSIQDEIQQRLEEIDRVSNQTQFNGVKVLSQDNQM<br>KIQVGANDGETITIDLQKIDVKSLGLDGFNVNSPGISGGGGGILDSMG<br>TLINEDAAAAKKSTANPLASIDSALSKVDAVRSSLGAIQNRFDSAITN<br>LGNTVTNLNSARSRIEDADYATEVSNMSKAQILQQAGTSVLAQANQVP<br>QNVLSLLVPRGSHHHHHHGMASMTGGQQMGRDLYDDDDKDP |
| 0045 | Mutant 37CT<br>Forward F37CT | DNA | Artificial Sequence | CTCTGGTCATATGATCAACAGCGCGAAAGACGATGC |
| 0046 | Mutant 37CT<br>Reverse R37CT | DNA | Artificial Sequence | TCTAGAGTCGACTATTAAGCCATACCATGATGATGATGATGATGAG |
| 0047 | Mutant 37CT<br>37CT construct | DNA | Artificial Sequence | TAATACGACTCACTATAGGGGAATTGTGAGCGGATAACAATTCCCCTC<br>TAGAAATAATTTTGTTTAACTTTAAGAAGGAGATATACATATGATCAA<br>CAGCGCGAAAGACGATGCGGCAGGCCAGGCGATTGCTAACCGCTTCAC<br>TTTCTAATATCAAAGGTCTGACTCAGGCTTCCCGTAACGCTAACGACGG<br>CATTTCTATTGCGCAGACCACTGAAGGTGCGCTGAATGAAATCAACAA<br>CAACCTGCAGCGTGTGCGTGAGTTGTCTGTTCAGGCCACTAACGGGAC<br>TAACTCTGATTCCGATCTGAAATCTATCCAGGATGAAATTCAGCAACG<br>TCTGGAAGAAATCGATCGCGTTTCTAATCAGACTCAATTTAACGGTGT<br>TAAAGTCCTGTCTCAGGACAACCAGATGAAAATCCAGGTTGGTGCTAA<br>CGATGGTGAAACCATTACCATCGATCTGCAAAAAATTGATGTGAAAAG<br>CCTTGGCCTTGATGGGTTCAATGTTAATTCCCCGGGAATTTCCGGTGG<br>TGGTGGTGGAATTCTAGACTCCATGGGTACATTAATCAATGAAGACGC<br>TGCCGCAGCCAAGAAAAGTACCGCTAACCCACTGGCTTCAATTGATTC<br>TGCATTGTCAAAAGTGGACGCAGTTCGTTCTTCTCTGGGGGCAATTCA<br>AAACCGCTTTGATTCAGCCATTACCAACCTTGGCAATACGGTAACCAA<br>TCTGAACTCCGCGCGTAGCCGTATCGAAGATGCTGACTATGCAACGGA<br>AGTTTCTAATATGTCTAAAGCGCAGATTCTGCAGCAGGCTGGTACTTC<br>CGTTCTGGCGCAGGCTAACCAGGTTCCGCAAAACGTCCTCTCTTTACT<br>GGTTCCGCGGGGTTCTCATCATCATCATCATCATGGTATGGCTTAATA<br>GTCGAC |
| 0048 | Mutant 37CT<br>Mutant 37CT | PRT | Artificial Sequence | MINSAKDDAAGQAIANRFTSNIKGLTQASRNANDGISIAQTTEGALNE<br>INNNLQRVRELSVQATNGTNSDSDLKSIQDEIQQRLEEIDRVSNQTQF<br>NGVKVLSQDNQMKIQVGANDGETITIDLQKIDVKSLGLDGFNVNSPGI<br>SGGGGGILDSMGTLINEDAAAAKKSTANPLASIDSALSKVDAVRSSLG<br>AIQNRFDSAITNLGNTVTNLNSARSRIEDADYATEVSNMSKAQILQQA<br>GTSVLAQANQVPQNVLSLLVPRGSHHHHHHGMA |
| 0049 | Mutant 445<br>502-SY1 | PRT | Artificial Sequence | MRGSHHHHHHGMASMTGGQQMGRDLYDLVPRGSAKDPMAQVINTNSLS<br>LLTQNNLNKSQSSLSSAIERLSSGLRINSAKDDAAGQAIANRFTSNIK<br>GLTQASRNANDGISIAQTTEGALNEINNNLQRVRELSVQATNGTNSDS |

TABLE 1-continued

Illustrative Flagellin-Based Agents

| SEQ ID | Construct Name | DNA/PRT | Species | Sequence |
|---|---|---|---|---|
| | | | | DLKSIQDEIQQRLEEIDRVSNQTQFNGVKVLSQDNQMKIQVGANDGET ITIDLQKIDVKSLGLDGFNVNSPGISGGGGGILDSMGTLINEDAAAAK KSTANPLASIDSALSKVDAVRSSLGAIQNRFDSAITNLGNTVTNLNSA RSRIEDADYATEVSNMSKAQILQQAGTSVLAQANQVPQNVLSLLR |
| 0050 | Mutant 445 502-SY1 | DNA | Artificial Sequence | ATGCGGGGTTCTCATCATCATCATCATCATGGTATGGCTAGCATGACT GGTGGACAGCAAATGGGTCGGGATCTGTACGACCTGGTTCCGCGCGGT AGCGCGAAGGATCCGATGGCACAAGTCATTAATACAAACAGCCTGTCG CTGTTGACCCAGAATAACCTGAACAAATCTCAGTCCTCACTGAGTTCC GCTATTGAGCGTCTGTCCTCTGGTCTGCGTATCAACAGCGCGAAAGAC GATGCGGCAGGCCAGGCGATTGCTAACCGCTTCACTTCTAATATCAAA GGTCTGACTCAGGCTTCCCGTAACGCTAACGACGGCATTTCTATTGCG CAGACCACTGAAGGTGCGCTGAATGAAATCAACAACAACCTGCAGCGT GTGCGTGAGTTGTCTGTTCAGGCCACTAACGGGACTAACTCTGATTCC GATCTGAAATCTATCCAGGATGAAATTCAGCAACGTCTGGAAGAAATC GATCGCGTTTCTAATCAGACTCAATTTAACGGTGTTAAAGTCCTGTCT CAGGACAACCAGATGAAAATCCAGGTTGGTGCTAACGATGGTGAAACC ATTACCATCGATCTGCAAAAAATTGATGTGAAAAGCCTTGGCCTTGAT GGGTTCAATGTTAATTCCCCGGGAATTTCCGGTGGTGGTGGTGGAATT CTAGACTCCATGGGTACATTAATCAATGAAGACGCTGCCGCAGCCAAG AAAAGTACCGCTAACCCACTGGCTTCAATTGATTCTGCATTGTCAAAA GTGGACGCAGTTCGTTCTTCTCTGGGGGCAATTCAAAACCGTTTTGAT TCAGCCATTACCAACCTTGGCAATACGGTAACCAATCTGAACTCCGCG CGTAGCCGTATCGAAGATGCTGACTATGCAACGGAAGTTTCTAATATG TCTAAAGCGCAGATTCTGCAGCAGGCTGGTACTTCCGTTCTGGCGCAG GCTAACCAGGTTCCGCAAAACGTCCTCTCTTTACTGCGTTAA |
| 0051 | Mutant 445 Forward Primer CBLB445 | DNA | Artificial Sequence | GGCAATTCAAAACCGTTTTGATTAAGCCATTACCAACCTTGG |
| 0052 | Mutant 445 Reverse Primer CBLB445 | DNA | Artificial Sequence | CCAAGGTTGGTAATGGCTTAATCAAAACGGTTTTGAATTGCC |
| 0053 | Mutant 445 mutant 445 | DNA | Artificial Sequence | TAATACGACTCACTATAGGGGAATTGTGAGCGGATAACAATTCCCCTC TAGAATAATTTTGTTTAACTTTAAGAAGGAGATATACATATGCGGGGT TCTCATCATCATCATCATCATGGTATGGCTAGCATGACTGGTGGACAG CAAATGGGTCGGGATCTGTACGACCTGGTTCCGCGCGGTAGCGCGAAG GATCCGATGGCACAAGTCATTAATACAAACAGCCTGTCGCTGTTGACC CAGAATAACCTGAACAAATCTCAGTCCTCACTGAGTTCCGCTATTGAG CGTCTGTCCTCTGGTCTGCGTATCAACAGCGCGAAAGACGATGCGGCA GGCCAGGCGATTGCTAACCGCTTCACTTCTAATATCAAAGGTCTGACT CAGGCTTCCCGTAACGCTAACGACGGCATTTCTATTGCGCAGACCACT GAAGGTGCGCTGAATGAAATCAACAACAACCTGCAGCGTGTGCGTGAG TTGTCTGTTCAGGCCACTAACGGGACTAACTCTGATTCCGATCTGAAA TCTATCCAGGATGAAATTCAGCAACGTCTGGAAGAAATCGATCGCGTT TCTAATCAGACTCAATTTAACGGTGTTAAAGTCCTGTCTCAGGACAAC CAGATGAAAATCCAGGTTGGTGCTAACGATGGTGAAACCATTACCATC GATCTGCAAAAAATTGATGTGAAAAGCCTTGGCCTTGATGGGTTCAAT GTTAATTCCCCGGGAATTTCCGGTGGTGGTGGTGGAATTCTAGACTCC ATGGGTACATTAATCAATGAAGACGCTGCCGCAGCCAAGAAAAGTACC GCTAACCCACTGGCTTCAATTGATTCTGCATTGTCAAAGTGGACGCA GTTCGTTCTTCTCTGGGGGCAATTCAAAACCGTTTTGATTAA |
| 0054 | Mutant 445 mutant 445 | PRT | Artificial Sequence | MRGSHHHHHHGMASMTGGQQMGRDLYDLVPRGSAKDPMAQVINTNSLS LLTQNNLNKSQSSLSSAIERLSSGLRINSAKDDAAGQAIANRFTSNIK GLTQASRNANDGISIAQTTEGALNEINNNLQRVRELSVQATNGTNSDS DLKSIQDEIQQRLEEIDRVSNQTQFNGVKVLSQDNQMKIQVGANDGET ITIDLQKIDVKSLGLDGFNVNSPGISGGGGGILDSMGTLINEDAAAAK KSTANPLASIDSALSKVDAVRSSLGAIQNRFD |
| 0055 | Mutant 461 Forward Primer CBLB461 | DNA | Artificial Sequence | CAATCTGAACTCCGCGCGTTGACGTATCTAAGATGCTGACTATGC |
| 0056 | Mutant 461 Reverse Primer CBLB461 | DNA | Artificial Sequence | GCATAGTCAGCATCTTAGATACGTCAACGCGCGGAGTTCAGATTG |
| 0057 | Mutant 461 Mutant 461 | DNA | Artificial Sequence | TAATACGACTCACTATAGGGGAATTGTGAGCGGATAACAATTCCCCTC TAGAATAATTTTGTTTAACTTTAAGAAGGAGATATACATATGCGGGGT TCTCATCATCATCATCATCATGGTATGGCTAGCATGACTGGTGGACAG CAAATGGGTCGGGATCTGTACGACCTGGTTCCGCGCGGTAGCGCGAAG GATCCGATGGCACAAGTCATTAATACAAACAGCCTGTCGCTGTTGACC |

TABLE 1-continued

Illustrative Flagellin-Based Agents

| SEQ ID | Construct Name | DNA/PRT | Species | Sequence |
|---|---|---|---|---|
| | | | | CAGAATAACCTGAACAAATCTCAGTCCTCACTGAGTTCCGCTATTGAG<br>CGTCTGTCCTCTGGTCTGCGTATCAACAGCGCGAAAGACGATGCGGCA<br>GGCCAGGCGATTGCTAACCGCTTCACTTCTAATATCAAAGGTCTGACT<br>CAGGCTTCCCGTAACGCTAACGACGGCATTTCTATTGCGCAGACCACT<br>GAAGGTGCGCTGAATGAAATCAACAACAACCTGCAGCGTGTGCGTGAG<br>TTGTCTGTTCAGGCCACTAACGGGACTAACTCTGATTCCGATCTGAAA<br>TCTATCCAGGATGAAATTCAGCAACGTCTGGAAGAAATCGATCGCGTT<br>TCTAATCAGACTCAATTTAACGGTGTTAAAGTCCTGTCTCAGGACAAC<br>CAGATGAAAATCCAGGTTGGTGCTAACGATGGTGAAACCATTACCATC<br>GATCTGCAAAAAATTGATGTGAAAAGCCTTGGCCTTGATGGGTTCAAT<br>GTTAATTCCCCGGGAATTTCCGGTGGTGGTGGTGGAATTCTAGACTCC<br>ATGGGTACATTAATCAATGAAGACGCTGCCGCAGCCAAGAAAAGTACC<br>GCTAACCCACTGGCTTCAATTGATTCTGCATTGTCAAAAGTGGACGCA<br>GTTCGTTCTTCTCTGGGGGCAATTCAAAACCGTTTTGATTCAGCCATT<br>ACCAACCTTGGCAATACGGTAACCAATCTGAACTCCGCGCGTTGACGT<br>ATCTAA |
| 0058 | Mutant 461<br>Mutant 461 | PRT | Artificial Sequence | MRGSHHHHHGMASMTGGQQMGRDLYDLVPRGSAKDPMAQVINTNSLS<br>LLTQNNLNKSQSSLSSAIERLSSGLRINSAKDDAAGQAIANRFTSNIK<br>GLTQASRNADGISIAQTTEGALNEINNNLQRVRELSVQATNGTNSDS<br>DLKSIQDEIQQRLEEIDRVSNQTQFNGVKVLSQDNQMKIQVGANDGET<br>ITIDLQKIDVKSLGLDGFNVNSPGISGGGGGILDSMGTLINEDAAAAK<br>STANPLASIDSALSKVDAVRSSLGAIQNRFDSAITNLGNTVTNLNSA<br>R |
| 0059 | Mutant 467<br>Forward Primer<br>CBLB467 | DNA | Artificial Sequence | CGTAGCCGTATCGAAGATGCTTAATAGGCAACGGAAGTTTCTAATATG |
| 0060 | Mutant 467<br>Reverse Primer<br>CBLB467 | DNA | Artificial Sequence | CATATTAGAAACTTCCGTTGCCTATTAAGCATCTTCGATACGGCTACG |
| 0061 | Mutant 467<br>Mutant 467 | DNA | Artificial Sequence | TAATACGACTCACTATAGGGGAATTGTGAGCGGATAACAATTCCCCTC<br>TAGAATAATTTTGTTTAACTTTAAGAAGGAGATATACATATGCGGGT<br>TCTCATCATCATCATCATCATGGTATGGCTAGCATGACTGGTGGACAG<br>CAAATGGGTCGGGATCTGTACGACCTGGTTCCGCGCGGTAGCGCGAAG<br>GATCCGATGGCACAAGTCATTAATACAAACAGCCTGTCGCTGTTGACC<br>CAGAATAACCTGAACAAATCTCAGTCCTCACTGAGTTCCGCTATTGAG<br>CGTCTGTCCTCTGGTCTGCGTATCAACAGCGCGAAAGACGATGCGGCA<br>GGCCAGGCGATTGCTAACCGCTTCACTTCTAATATCAAAGGTCTGACT<br>CAGGCTTCCCGTAACGCTAACGACGGCATTTCTATTGCGCAGACCACT<br>GAAGGTGCGCTGAATGAAATCAACAACAACCTGCAGCGTGTGCGTGAG<br>TTGTCTGTTCAGGCCACTAACGGGACTAACTCTGATTCCGATCTGAAA<br>TCTATCCAGGATGAAATTCAGCAACGTCTGGAAGAAATCGATCGCGTT<br>TCTAATCAGACTCAATTTAACGGTGTTAAAGTCCTGTCTCAGGACAAC<br>CAGATGAAAATCCAGGTTGGTGCTAACGATGGTGAAACCATTACCATC<br>GATCTGCAAAAAATTGATGTGAAAAGCCTTGGCCTTGATGGGTTCAAT<br>GTTAATTCCCCGGGAATTTCCGGTGGTGGTGGTGGAATTCTAGACTCC<br>ATGGGTACATTAATCAATGAAGACGCTGCCGCAGCCAAGAAAAGTACC<br>GCTAACCCACTGGCTTCAATTGATTCTGCATTGTCAAAAGTGGACGCA<br>GTTCGTTCTTCTCTGGGGGCAATTCAAAACCGTTTTGATTCAGCCATT<br>ACCAACCTTGGCAATACGGTAACCAATCTGAACTCCGCGCGTAGCCGT<br>ATCGAAGATGCTTAATAG |
| 0062 | Mutant 467<br>Mutant 467 | PRT | Artificial Sequence | MRGSHHHHHGMASMTGGQQMGRDLYDLVPRGSAKDPMAQVINTNSLS<br>LLTQNNLNKSQSSLSSAIERLSSGLRINSAKDDAAGQAIANRFTSNIK<br>GLTQASRNADGISIAQTTEGALNEINNNLQRVRELSVQATNGTNSDS<br>DLKSIQDEIQQRLEEIDRVSNQTQFNGVKVLSQDNQMKIQVGANDGET<br>ITIDLQKIDVKSLGLDGFNVNSPGISGGGGGILDSMGTLINEDAAAAK<br>STANPLASIDSALSKVDAVRSSLGAIQNRFDSAITNLGNTVTNLNSA<br>RSRIEDA |
| 0063 | Mutant 470CT<br>CBLB502 | DNA | Artificial Sequence | ATGCGGGGTTCTCATCATCATCATCATCATGGTATGGCTAGCATGACT<br>GGTGGACAGCAAATGGGTCGGGATCTGTACGACGATGACGATAAGGAT<br>CCGATGGCACAAGTCATTAATACAAACAGCCTGTCGCTGTTGACCCAG<br>AATAACCTGAACAAATCTCAGTCCTCACTGAGTTCCGCTATTGAGCGT<br>CTGTCCTCTGGTCTGCGTATCAACAGCGCGAAAGACGATGCGGCAGGC<br>CAGGCGATTGCTAACCGCTTCACTTCTAATATCAAAGGTCTGACTCAG<br>GCTTCCCGTAACGCTAACGACGGCATTTCTATTGCGCAGACCACTGAA<br>GGTGCGCTGAATGAAATCAACAACAACCTGCAGCGTGTGCGTGAGTTG<br>TCTGTTCAGGCCACTAACGGGACTAACTCTGATTCCGATCTGAAATCT<br>ATCCAGGATGAAATTCAGCAACGTCTGGAAGAAATCGATCGCGTTTCT<br>AATCAGACTCAATTTAACGGTGTTAAAGTCCTGTCTCAGGACAACCAG<br>ATGAAAATCCAGGTTGGTGCTAACGATGGTGAAACCATTACCATCGAT |

TABLE 1-continued

Illustrative Flagellin-Based Agents

| SEQ ID | Construct Name | DNA/PRT | Species | Sequence |
|---|---|---|---|---|
| | | | | CTGCAAAAAATTGATGTGAAAAGCCTTGGCCTTGATGGGTTCAATGTT AATTCCCCGGGAATTTCCGGTGGTGGTGGTGGAATTCTAGACTCCATG GGTACATTAATCAATGAAGACGCTGCCGCAGCCAAGAAAAGTACCGCT AACCCCACTGGCTTCAATTGATTCTGCATTGTCAAAAGTGGACGCAGTT CGTTCTTCTCTGGGGGCAATTCAAAACCGTTTTGATTCAGCCATTACC AACCTTGGCAATACGGTAACCAATCTGAACTCCGCGCGTAGCCGTATC GAAGATGCTGACTATGCAACGGAAGTTTCTAATATGTCTAAAGCGCAG ATTCTGCAGCAGGCTGGTACTTCCGTTCTGGCGCAGGCTAACCAGGTT CCGCAAAACGTCCTCTCTTTACTGCGTTAA |
| 0064 | Mutant 470CT Forward Primer F470CT | DNA | Artificial Sequence | CGATAAGGATCATATGGCACAAGTCATTAATAC |
| 0065 | Mutant 470CT Reverse Primer R470CT | DNA | Artificial Sequence | AGATCTGTCGACTTAACCATGATGATGATGATGAGAACCCCGCGG AACCAGTGCATAGTCAGCATCTTCGATACG |
| 0066 | Mutant 470CT Mutant 470CT | DNA | Artificial Sequence | TAATACGACTCACTATAGGGGAATTGTGAGCGGATAACAATTCCCCTC TAGAATAATTTTGTTTAACTTTAAGAAGGAGATATACATATGGCACAA GTCATTAATACAAACAGCCTGTCGCTGTTGACCCAGAATAACCTGAAC AAATCTCAGTCCTCACTGAGTTCCGCTATTGAGCGTCTGTCCTCTGGT CTGCGTATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATCGCGTTTCTAATCAGACTCAA TTTAACGGTGTTAAAGTCCTGTCTCAGGCAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA ATTTCCGGTGGTGGTGGTGAATTCTAGACTCCATGGGTACATTAATC AATGAAGACGCTGCCGCAGCCAAGAAAAGTACCGCTAACCCACTGGCT TCAATTGATTCTGCATTGTCAAAAGTGGACGCAGTTCGTTCTTCTCTG GGGGCAATTCAAAACCGTTTTGATTCAGCCATTACCAACCTTGGCAAT ACGGTAACCAATCTGAACTCCGCGCGTAGCCGTATCGAAGATGCTGAC TATGCACTGGTTCCGCGGGGTTCTCATCATCATCATCATCATGGTTAA GTCGAC |
| 0067 | Mutant 470CT Mutant 470CT | PRT | Artificial Sequence | MAQVINTNSLSLLTQNNLNKSQSSLSSAIERLSSGLRINSAKDDAAGQ AIANRFTSNIKGLTQASRNANDGISIAQTTEGALNEINNNLQRVRELS VQATNGTNSDSDLKSIQDEIQQRLEEIDRVSNQTQFNGVKVLSQDNQM KIQVGANDGETITIDLQKIDVKSLGLDGFNVNSPGISGGGGGILDSMG TLINEDAAAAKKSTANPLASIDSALSKVDAVRSSLGAIQNRFDSAITN LGNTVTNLNSARSRIEDADYALVPRGSHHHHHHG |
| 0068 | Mutant 485CT Reverse primer R485MC | DNA | Artificial Sequence | AGATCTCCGCGGAACCAGACCAGCCTGCTGCAGAATCTGC |
| 0069 | Mutant 485CT DNA Sequence of 485CT | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATCGCGTTTCTAATCAGACTCAA TTTAACGGTGTTAAAGTCCTGTCTCAGGCAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTCTGGTTCCGCGGGGTTCTCAT CATCATCATCATCATGGTTAAGTCGAC |
| 0070 | Mutant 485CT Mutant 485CT | DNA | Artificial Sequence | ATGAGCGGGTTACGGATCAACAGCGCGAAAGACGATGCGGCAGGCCAG GCGATTGCTAACCGCTTCACTTCTAATATCAAAGGTCTGACTCAGGCT TCCCGTAACGCTAACGACGGCATTTCTATTGCGCAGACCACTGAAGGT GCGCTGAATGAAATCAACAACAACCTGCAGCGTGTGCGTGAGTTGTCT GTTCAGGCCACTAACGGGACTAACTCTGATTCCGATCTGAAATCTATC CAGGATGAAATTCAGCAACGTCTGGAAGAAATCGATCGCGTTTCTAAT CAGACTCAATTTAACGGTGTTAAAGTCCTGTCTCAGGACAACCAGATG AAAATCCAGGTTGGTGCTAACGATGGTGAAACCATTACCATCGATCTG CAAAAAATTGATGTGAAAAGCCTTGGCCTTGATGGGTTCAATGTTAAT TCCCCGGGAAGTACCGCTAACCCACTGGCTTCAATTGATTCTGCATTG |

TABLE 1-continued

Illustrative Flagellin-Based Agents

| SEQ ID | Construct Name | DNA/PRT | Species | Sequence |
|---|---|---|---|---|
| | | | | TCAAAAGTGGACGCAGTTCGTTCTTCTCTGGGGGCAATTCAAAACCGC TTTGATTCAGCCATTACCAACCTTGGCAATACGGTAACCAATCTGAAC TCCGCGCGTAGCCGTATCGAAGATGCTGACTATGCAACGGAAGTTTCT AATATGTCTAAAGCGCAGATTCTGCAGCAGGCTGGTCTGGTTCCGCGG GGTTCTCATCATCATCATCATCATGGTTAA |
| 0071 | Mutant 485CT Mutant 485CT | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDRVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYATEVSNMSKAQILQQAGLVPRGSHHHHHHG |
| 0072 | Mutant 485D DNA template for deletion mutations from Mutant 485CT variant | DNA | Artificial Sequence | AACCCACTGGCTTCAATTGATTCTGCATTGTCAAAAGTGGACGCAGTT CGTTCTTCTCTGGGGGCAATTCAAAACCGTTTTGATTCAGCCATTACC GCCCTTGGCAATACGGTAACCAAT |
| 0073 | Mutant 485D PRT sequence for deletion mutations from Mutant 485CT variant | PRT | Artificial Sequence | NPLASIDSALSKVDAVRSSLGAIQNRFDSAITALGNTVTN |
| 0074 | Mutant 485D Forward Primer F485D | DNA | Artificial Sequence | GTTCGTTCTTCTCTGGGGGCAATTGATTCAGCCATTACCGCCCTTG |
| 0075 | Mutant 485D Reverse Primer R485D | DNA | Artificial Sequence | CAAGGGCGGTAATGGCTGAATCAATTGCCCCCAGAGAAGAACGAAC |
| 0076 | Mutant 485D DNA Sequence of 485CT_Delta construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTGATTCAGCCATTACCGCC CTTGGCAATACGGTAACCAATCTGAACTCCGCGTAGCCGTATCGAA GATGCTGACTATGCAACGGAAGTTTCTAATATGTCTAAAGCGCAGATT CTGCAGCAGGCTGGTCTGGTTCCGCGGGGTTCTCATCATCATCATCAT CATGGTTAAGTCGAC |
| 0077 | Mutant 485D Mutant 485D (CT_Delta 439-442) | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDRVSN QTQFNGVKVLSQDNQMKIQVGANDGETITIDLQKIDVKSLGLDGFNVN SPGSTANPLASIDSALSKVDAVRSSLGAIDSAITALGNTVTNLNSARS RIEDADYATEVSNMSKAQILQQAGLVPRGSHHHHHHG |
| 0078 | Mutant CGD1 Mutant SY3CT | DNA | Artificial Sequence | ATGAGCGGGTTACGGATCAACAGCGCGAAAGACGATGCGGCAGGCCAG GCGATTGCTAACCGCTTCACTTCTAATATCAAAGGTCTGACTCAGGCT TCCCGTAACGCTAACGACGGCATTTCTATTGCGCAGACCACTGAAGGT GCGCTGAATGAAATCAACAACAACCTGCAGCGTGTGCGTGAGTTGTCT GTTCAGGCCACTAACGGGACTAACTCTGATTCCGATCTGAAATCTATC CAGGATGAAATTCAGCAACGTCTGGAAGAAATCGATCGCGTTTCTAAT CAGACTCAATTTAACGGTGTTAAAGTCCTGTCTCAGGACAACCAGATG AAAATCCAGGTTGGTGCTAACGATGGTGAAACCATTACCATCGATCTG CAAAAAATTGATGTGAAAAGCCTTGGCCTTGATGGGTTCAATGTTAAT TCCCCGGGAAGTACCGCTAACCCACTGGCTTCAATTGATTCTGCATTG TCAAAAGTGGACGCAGTTCGTTCTTCTCTGGGGGCAATTCAAAACCGC TTTGATTCAGCCATTACCAACCTTGGCAATACGGTAACCAATCTGAAC TCCGCGCGTAGCCGTATCGAAGATGCTGACTATGCACTGGTTCCGCGG GGTTCTCATCATCATCATCATCATGGTTAA |
| 0079 | Mutant CGD1 Mutant SY3CT | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDRVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYALVPRGSHHHHHHG |

TABLE 1-continued

Illustrative Flagellin-Based Agents

| SEQ ID | Construct Name | DNA/PRT | Species | Sequence |
|---|---|---|---|---|
| 0080 | Mutant CGD1 GFPuv4 | DNA | Artificial Sequence | ATGAGTAAAGGAGAAGAACTTTTCACTGGAGTTGTCCCAATTCTTGTT<br>GAATTAGATGGTGATGTTAATGGGCACAAATTTTCTGTCAGTGGAGAG<br>GGTGAAGGTGATGCAACATACGGAAAACTTACCCTTAAATTTATTTGC<br>ACTACTGGAAAACTACCTGTTCCATGGCCAACACTTGTCACTACTCTG<br>ACGTATGGTGTTCAATGCTTTTCCCGTTATCCGGATCATATGAAACGG<br>CATGACTTTTTCAAGAGTGCCATGCCCGAAGGTTATGTACAGGAACGC<br>ACTATATCTTTCAAAGATGACGGGAACTACAAGACGCGTGCTGAAGTC<br>AAGTTTGAAGGTGATACCCTTGTTAATCGTATCGAGTTAAAAGGTATT<br>GATTTTAAAGAAGATGGAAACATTCTCGGACACAAACTCGAGTACAAC<br>TATAACTCACACAATGTATACATCACGGCAGACAAACAAAGAATGGA<br>ATCAAAGCTAACTTCAAAATTCGCCACAACATTGAAGATGGATCCGTT<br>CAACTAGCAGACCATTATCAACAAAATACTCCAATTGGCGATGGCCCT<br>GTCCTTTTACCAGACAACCATTACCTGTCGACACAATCTGCCCTTTTG<br>AAAGATCCCAACGAAAGCGTGACCACATGGTCCTTCTTGAGTTTGTA<br>ACTGCTGCTGGGATTACACATGGCATGGATGAACTATACAAA |
| 0081 | Mutant CGD1 GFPuv4 | PRT | Artificial Sequence | MSKGEELFTGVVPILVELDGDVNGHKFSVSGEGEGDATYGKLTLKFIC<br>TTGKLPVPWPTLVTTLTYGVQCFSRYPDHMKRHDFFKSAMPEGYVQER<br>TISFKDDGNYKTRAEVKFEGDTLVNRIELKGIDFKEDGNILGHKLEYN<br>YNSHNVYITADKQKNGIKANFKIRHNIEDGSVQLADHYQQNTPIGDGP<br>VLLPDNHYLSTQSALLKDPNEKRDHMVLLEFVTAAGITHGMDELYK |
| 0082 | Mutant CGD1 GFPuv4 mutation of wt NdeI site | DNA | Artificial Sequence | ATGAGTAAAGGAGAAGAACTTTTCACTGGAGTTGTCCCAATTCTTGTT<br>GAATTAGATGGTGATGTTAATGGGCACAAATTTTCTGTCAGTGGAGAG<br>GGTGAAGGTGATGCAACATACGGAAAACTTACCCTTAAATTTATTTGC<br>ACTACTGGAAAACTACCTGTTCCATGGCCAACACTTGTCACTACTCTG<br>ACGTATGGTGTTCAATGCTTTTCCCGTTATCCGGATCACATGAAACGG<br>CATGACTTTTTCAAGAGTGCCATGCCCGAAGGTTATGTACAGGAACGC<br>ACTATATCTTTCAAAGATGACGGGAACTACAAGACGCGTGCTGAAGTC<br>AAGTTTGAAGGTGATACCCTTGTTAATCGTATCGAGTTAAAAGGTATT<br>GATTTTAAAGAAGATGGAAACATTCTCGGACACAAACTCGAGTACAAC<br>TATAACTCACACAATGTATACATCACGGCAGACAAACAAAGAATGGA<br>ATCAAAGCTAACTTCAAAATTCGCCACAACATTGAAGATGGATCCGTT<br>CAACTAGCAGACCATTATCAACAAAATACTCCAATTGGCGATGGCCCT<br>GTCCTTTTACCAGACAACCATTACCTGTCGACACAATCTGCCCTTTTG<br>AAAGATCCCAACGAAAGCGTGACCACATGGTCCTTCTTGAGTTTGTA<br>ACTGCTGCTGGGATTACACATGGCATGGATGAACTATACAAATAA |
| 0083 | Mutant CGD1 Forward primer FCGFP | DNA | Artificial Sequence | TCTAGACGGCCGATCTCAGGTAAGAATGGAATCAAAGCTAACTTCAAA<br>ATTCGC |
| 0084 | Mutant CGD1 PRT altered GFPuv4 sequence | PRT | Artificial Sequence | NVYIPISGKNGIKANFKIRH |
| 0085 | Mutant CGD1 Reverse RCGFP | DNA | Artificial Sequence | AGATCTCCGCGGTTTGTATAGTTCATCCATGCCATGTGTAATCCC |
| 0086 | Mutant CGD1 DNA Sequence of CGD1 construct | DNA | Artificial Sequence | TAATACGACTCACTATAGGGGAATTGTGAGCGGATAACAATTCCCCTC<br>TAGAATAATTTTGTTTAACTTTAAGAAGGAGATATACATATGAGCGGG<br>TTACGGATCAACAGCGCGAAAGACGATGCGGCAGGCCAGGCGATTGCT<br>AACCGCTTCACTTCTAATATCAAAGGTCTGACTCAGGCTTCCCGTAAC<br>GCTAACGACGGCATTTCTATTGCGCAGACCACTGAAGGTGCGCTGAAT<br>GAAATCAACAACAACCTGCAGCGTGTGCGTGAGTTGTCTGTTCAGGCC<br>ACTAACGGGACTAACTCTGATTCCGATCTGAAATCTATCCAGGATGAA<br>ATTCAGCAACGTCTGGAAGAAATCGATCGCGTTTCTAATCAGACTCAA<br>TTTAACGGTGTTAAAGTCCTGTCTCAGGACAACCAGATGAAAATCCAG<br>GTTGGTGCTAACGATGGTGAAACCATTACCATCGATCTGCAAAAAATT<br>GATGTGAAAAGCCTTGGCCTTGATGGGTTCAATGTTAATTCCCCGGGA<br>AGTACCGCTAACCCACTGGCTTCAATTGATTCTGCATTGTCAAAAGTG<br>GACGCAGTTCGTTCTTCTCTGGGGGCAATTCAAAACCGCTTTGATTCA<br>GCCATTACCAACCTTGGCAATACGGTAACCAATCTGAACTCCGCGCGT<br>AGCCGTATCGAAGATGCTGACTATGCACTGGTTCCGCCGATCTCAGGT<br>AAGAATGGAATCAAAGCTAACTTCAAAATTCGCCACAACATTGAAGAT<br>GGATCCGTTCAACTAGCAGACCATTATCAACAAAATACTCCAATTGGC<br>GATGGCCCTGTCCTTTTACCAGACAACCATTACCTGTCGACACAATCT<br>GCCCTTTTGAAAGATCCCAACGAAAGCGTGACCACATGGTCCTTCTT<br>GAGTTTGTAACTGCTGCTGGGATTACACATGGCATGGATGAACTATAC<br>AAACCGCGGGGTTCTCATCATCATCATCATCATGGTTAAGTCGAC |
| 0087 | Mutant CGD1 Expressed Mutant CGD1 | DNA | Artificial Sequence | ATGAGCGGGTTACGGATCAACAGCGCGAAAGACGATGCGGCAGGCCAG<br>GCGATTGCTAACCGCTTCACTTCTAATATCAAAGGTCTGACTCAGGCT<br>TCCCGTAACGCTAACGACGGCATTTCTATTGCGCAGACCACTGAAGGT<br>GCGCTGAATGAAATCAACAACAACCTGCAGCGTGTGCGTGAGTTGTCT |

TABLE 1-continued

Illustrative Flagellin-Based Agents

| SEQ ID | Construct Name | DNA/PRT | Species | Sequence |
|---|---|---|---|---|
| | | | | GTTCAGGCCACTAACGGGACTAACTCTGATTCCGATCTGAAATCTATC<br>CAGGATGAAATTCAGCAACGTCTGGAAGAAATCGATCGCGTTTCTAAT<br>CAGACTCAATTTAACGGTGTTAAAGTCCTGTCTCAGGACAACCAGATG<br>AAAATCCAGGTTGGTGCTAACGATGGTGAAACCATTACCATCGATCTG<br>CAAAAAATTGATGTGAAAAGCCTTGGCCTTGATGGGTTCAATGTTAAT<br>TCCCCGGGAAGTACCGCTAACCCACTGGCTTCAATTGATTCTGCATTG<br>TCAAAAGTGGACGCAGTTCGTTCTTCTCTGGGGGCAATTCAAAACCGC<br>TTTGATTCAGCCATTACCAACCTTGGCAATACGGTAACCAATCTGAAC<br>TCCGCGCGTAGCCGTATCGAAGATGCTGACTATGCACTGGTTCCGCCG<br>ATCTCAGGTAAGAATGGAATCAAAGCTAACTTCAAAATTCGCCACAAC<br>ATTGAAGATGGATCCGTTCAACTAGCAGACCATTATCAACAAAATACT<br>CCAATTGGCGATGGCCCTGTCCTTTTACCAGACAACCATTACCTGTCG<br>ACACAATCTGCCCTTTTGAAAGATCCCAACGAAAAGCGTGACCACATG<br>GTCCTTCTTGAGTTTGTAACTGCTGCTGGGATTACACATGGCATGGAT<br>GAACTATACAAACCGCGGGGTTCTCATCATCATCATCATGGTTAA |
| 0088 | Mutant CGD1<br>Expressed Mutant CGD1 | PRT | Artificial Sequence | MSGLRINSAKDDAAGQAIANRFTSNIKGLTQASRNANDGISIAQTTEG<br>ALNEINNNLQRVRELSVQATNGTNSDSDLKSIQDEIQQRLEEIDRVSN<br>QTQFNGVKVLSQDNQMKIQVGANDGETITIDLQKIDVKSLGLDGFNVN<br>SPGSTANPLASIDSALSKVDAVRSSLGAIQNRFDSAITNLGNTVTNLN<br>SARSRIEDADYALVPPISGKNGIKANFKIRHNIEDGSVQLADHYQQNT<br>PIGDGPVLLPDNHYLSTQSALLKDPNEKRDHMVLLEFVTAAGITHGMD<br>ELYKPRGSHHHHHG |
| 0089 | Mutant CPM194<br>Mutant CPM194 | DNA | Artificial Sequence | ATGAGTACCGCTAACCCACTGGCTTCAATTGATTCTGCATTGTCAAAA<br>GTGGACGCAGTTCGTTCTTCTCTGGGGGCAATTCAAAACCGCTTTGAT<br>TCAGCCATTACCAACCTTGGCAATACGGTAACCAATCTGAACTCCGCG<br>CGTAGCCGTATCGAAGATGCTGACTATGCATCCCCGGGAAGCGGGTTA<br>CGGATCAACAGCGCGAAAGACGATGCGGCAGGCCAGGCGATTGCTAAC<br>CGCTTCACTTCTAATATCAAAGGTCTGACTCAGGCTTCCCGTAACGCT<br>AACGACGGCATTTCTATTGCGCAGACCACTGAAGGTGCGCTGAATGAA<br>ATCAACAACAACCTGCAGCGTGTGCGTGAGTTGTCTGTTCAGGCCACT<br>AACGGGACTAACTCTGATTCCGATCTGAAATCTATCCAGGATGAAATT<br>CAGCAACGTCTGGAAGAAATCGATCGCGTTTCTAATCAGACTCAATTT<br>AACGGTGTTAAAGTCCTGTCTCAGGACAACCAGATGAAAATCCAGGTT<br>GGTGCTAACGATGGTCTGGTTCCGCGGGGTTCTCATCATCATCATCAT<br>CATGGTTAA |
| 0090 | Mutant CPM194<br>Mutant CPM194 | PRT | Artificial Sequence | MSTANPLASIDSALSKVDAVRSSLGAIQNRFDSAITNLGNTVTNLNSA<br>RSRIEDADYASPGSGLRINSAKDDAAGQAIANRFTSNIKGLTQASRNA<br>NDGISIAQTTEGALNEINNNLQRVRELSVQATNGTNSDSDLKSIQDEI<br>QQRLEEIDRVSNQTQFNGVKVLSQDNQMKIQVGANDGLVPRGSHHHHH<br>HG |
| 0091 | Mutant CPM194<br>Mutant CPM194 | DNA | Artificial Sequence | TAATACGACTCACTATAGGGGAATTGTGAGCGGATAACAATTCCCCTC<br>TAGAATAATTTTGTTTAACTTTAAGAAGGAGATATACATATGAGTACC<br>GCTAACCCACTGGCTTCAATTGATTCTGCATTGTCAAAAGTGGACGCA<br>GTTCGTTCTTCTCTGGGGGCAATTCAAAACCGCTTTGATTCAGCCATT<br>ACCAACCTTGGCAATACGGTAACCAATCTGAACTCCGCGCGTAGCCGT<br>ATCGAAGATGCTGACTATGCATCCCCGGGAAGCGGGTTACGGATCAAC<br>AGCGCGAAAGACGATGCGGCAGGCCAGGCGATTGCTAACCGCTTCACT<br>TCTAATATCAAAGGTCTGACTCAGGCTTCCCGTAACGCTAACGACGGC<br>ATTTCTATTGCGCAGACCACTGAAGGTGCGCTGAATGAAATCAACAAC<br>AACCTGCAGCGTGTGCGTGAGTTGTCTGTTCAGGCCACTAACGGGACT<br>AACTCTGATTCCGATCTGAAATCTATCCAGGATGAAATTCAGCAACGT<br>CTGGAAGAAATCGATCGCGTTTCTAATCAGACTCAATTTAACGGTGTT<br>AAAGTCCTGTCTCAGGACAACCAGATGAAAATCCAGGTTGGTGCTAAC<br>GATGGTCTGGTTCCGCGGGGTTCTCATCATCATCATCATGGTTAA<br>GTCGAC |
| 0092 | Mutant CPM194<br>Forward primer FCD1 | DNA | Artificial Sequence | TCTAGACATATGAGTACCGCTAACCCACTGGCTTCAATTG |
| 0093 | Mutant CPM194<br>Reverse primer RCD1J | DNA | Artificial Sequence | GCTTCCCGGGGATGCATAGTCAGCATCTTCGATACGGC |
| 0094 | Mutant CPM194<br>Forward primer FND1J | DNA | Artificial Sequence | GCATCCCCGGGAAGCGGGTTACGGATCAACAGCG |
| 0095 | Mutant CPM194<br>Reverse primer RND1 | DNA | Artificial Sequence | AGATCTCCGCGGAACCAGACCATCGTTAGCACCAACCTGGATTTTCAT<br>CT |
| 0096 | Mutant CPM217<br>Mutant CPM217 | DNA | Artificial Sequence | ATGAGTACCGCTAACCCACTGGCTTCAATTGATTCTGCATTGTCAAAA<br>GTGGACGCAGTTCGTTCTTCTCTGGGGGCAATTCAAAACCGCTTTGAT<br>TCAGCCATTACCAACCTTGGCAATACGGTAACCAATCTGAACTCCGCG |

TABLE 1-continued

Illustrative Flagellin-Based Agents

| SEQ ID | Construct Name | DNA/PRT | Species | Sequence |
|---|---|---|---|---|
| | | | | CGTAGCCGTATCGAAGATGCTGACTATGCATCCCCGGGAAGCGGGTTA<br>CGGATCAACAGCGCGAAAGACGATGCGGCAGGCCAGGCGATTGCTAAC<br>CGCTTCACTTCTAATATCAAAGGTCTGACTCAGGCTTCCCGTAACGCT<br>AACGACGGCATTTCTATTGCGCAGACCACTGAAGGTGCGCTGAATGAA<br>ATCAACAACAACCTGCAGCGTGTGCGTGAGTTGTCTGTTCAGGCCACT<br>AACGGGACTAACTCTGATTCCGATCTGAAATCTATCCAGGATGAAATT<br>CAGCAACGTCTGGAAGAAATCGATCGCGTTTCTAATCAGACTCAATTT<br>AACGGTGTTAAAGTCCTGTCTCAGGACAACCAGATGAAAATCCAGGTT<br>GGTGCTAACGATGGTGAAACCATTACCATCGATCTGCAAAAAATTGAT<br>GTGAAAAGCCTTGGCCTTGATGGGTTCAATGTTAATCTGGTTCCGCGG<br>GGTTCTCATCATCATCATCATGGTTAA |
| 0097 | Mutant CPM217<br>Mutant CPM217 | PRT | Artificial<br>Sequence | MSTANPLASIDSALSKVDAVRSSLGAIQNRFDSAITNLGNTVTNLNSA<br>RSRIEDADYASPGSGLRINSAKDDAAGQAIANRFTSNIKGLTQASRNA<br>NDGISIAQTTEGALNEINNNLQRVRELSVQATNGTNSDSDLKSIQDEI<br>QQRLEEIDRVSNQTQFNGVKVLSQDNQMKIQVGANDGETITIDLQKID<br>VKSLGLDGFNVNLVPRGSHHHHHG |
| 0098 | Mutant CPM217<br>Mutant CPM217 | DNA | Artificial<br>Sequence | TAATACGACTCACTATAGGGGAATTGTGAGCGGATAACAATTCCCCTC<br>TAGAATAATTTTGTTTAACTTTAAGAAGGAGATATACATATGAGTACC<br>GCTAACCCACTGGCTTCAATTGATTCTGCATTGTCAAAAGTGGACGCA<br>GTTCGTTCTTCTCTGGGGGCAATTCAAAACCGCTTTGATTCAGCCATT<br>ACCAACCTTGGCAATACGGTAACCAATCTGAACTCCGCGCGTAGCCGT<br>ATCGAAGATGCTGACTATGCATCCCCGGGAAGCGGGTTACGGATCAAC<br>AGCGCGAAAGACGATGCGGCAGGCCAGGCGATTGCTAACCGCTTCACT<br>TCTAATATCAAAGGTCTGACTCAGGCTTCCCGTAACGCTAACGACGGC<br>ATTTCTATTGCGCAGACCACTGAAGGTGCGCTGAATGAAATCAACAAC<br>AACCTGCAGCGTGTGCGTGAGTTGTCTGTTCAGGCCACTAACGGGACT<br>AACTCTGATTCCGATCTGAAATCTATCCAGGATGAAATTCAGCAACGT<br>CTGGAAGAAATCGATCGCGTTTCTAATCAGACTCAATTTAACGGTGTT<br>AAAGTCCTGTCTCAGGACAACCAGATGAAAATCCAGGTTGGTGCTAAC<br>GATGGTGAAACCATTACCATCGATCTGCAAAAAATTGATGTGAAAAGC<br>CTTGGCCTTGATGGGTTCAATGTTAATCTGGTTCCGCGGGGTTCTCAT<br>CATCATCATCATGGTTAAGTCGAC |
| 0099 | Mutant CPM217<br>Reverse primer<br>RCPM217 | DNA | Artificial<br>Sequence | AGATCTCCGCGGAACCAGATTAACATTGAACCCATCAAGGCCAAG |
| 0100 | Mutant GD1G<br>Forward Primer FGFP77 | DNA | Artificial<br>Sequence | CCCGTTATCCGGATCACATGAAACGGCATGACTTTTTC |
| 0101 | Mutant GD1G<br>Reverse Primer RGFP77 | DNA | Artificial<br>Sequence | GAAAAAGTCATGCCGTTTCATGTGATCCGGATAACGGG |
| 0102 | Mutant GD1G<br>FGFP54 | DNA | Artificial<br>Sequence | CTGTTCCATGGCCAACACTTG |
| 0103 | Mutant GD1G<br>Forward primer FNGFP | DNA | Artificial<br>Sequence | TCTAGACATATGAGTAAAGGAGAAGAACTTTTCACTGGAGTTGTCC |
| 0104 | Mutant GD1G<br>altered GFP DNA<br>sequence | DNA | Artificial<br>Sequence | GGCCTATGCGGCCGCAGTAAAGGAGAAGAACTTTTCACTGGAGTTGTC<br>CCAATTCTTGTTGAA |
| 0105 | Mutant GD1G<br>Reverse RNGFP | DNA | Artificial<br>Sequence | AGATCTATTAATGCGGCCTGATAGGCCTTGTTTGTCTGCCGTGATGTA<br>TACATTGTG |
| 0106 | Mutant GD1G<br>altered GFP PRT<br>sequence | PRT | Artificial<br>Sequence | SHNVYITADKQGLSGRNM |
| 0107 | Mutant GD1G<br>DNA Sequence of GD1G<br>construct | DNA | Artificial<br>Sequence | TAATACGACTCACTATAGGGGAATTGTGAGCGGATAACAATTCCCCTC<br>TAGAATAATTTTGTTTAACTTTAAGAAGGAGATATACATATGAGTAAA<br>GGAGAAGAACTTTTCACTGGAGTTGTCCCAATTCTTGTTGAATTAGAT<br>GGTGATGTTAATGGGCACAAATTTTCTGTCAGTGGAGAGGGTGAAGGT<br>GATGCAACATACGGAAAACTTACCCTTAAATTTATTTGCACTACTGGA<br>AAACTACCTGTT TABLE 1-continued Illustrative Flagellin-Based Agents

| SEQ ID | Construct Name | DNA/PRT | Species | Sequence |
|---|---|---|---|---|
| | | | | GCGATTGCTAACCGCTTCACTTCTAATATCAAAGGTCTGACTCAGGCT<br>TCCCGTAACGCTAACGACGGCATTTCTATTGCGCAGACCACTGAAGGT<br>GCGCTGAATGAAATCAACAACAACCTGCAGCGTGTGCGTGAGTTGTCT<br>GTTCAGGCCACTAACGGGACTAACTCTGATTCCGATCTGAAATCTATC<br>CAGGATGAAATTCAGCAACGTCTGGAAGAAATCGATCGCGTTTCTAAT<br>CAGACTCAATTTAACGGTGTTAAAGTCCTGTCTCAGGACAACCAGATG<br>AAAATCCAGGTTGGTGCTAACGATGGTGAAACCATTACCATCGATCTG<br>CAAAAAATTGATGTGAAAAGCCTTGGCCTTGATGGGTTCAATGTTAAT<br>TCCCCGGGAAGTACCGCTAACCCACTGGCTTCAATTGATTCTGCATTG<br>TCAAAAGTGGACGCAGTTCGTTCTTCTCTGGGGGCAATTCAAAACCGC<br>TTTGATTCAGCCATTACCAACCTTGGCAATACGGTAACCAATCTGAAC<br>TCCGCGCGTAGCCGTATCGAAGATGCTGACTATGCACTGGTTCCGCCG<br>ATCTCAGGTAAGAATGGAATCAAAGCTAACTTCAAAATTCGCCACAAC<br>ATTGAAGATGGATCCGTTCAACTAGCAGACCATTATCAACAAAATACT<br>CCAATTGGCGATGGCCCTGTCCTTTTACCAGACAACCATTACCTGTCG<br>ACACAATCTGCCCTTTTGAAAGATCCCAACGAAAAGCGTGACCACATG<br>GTCCTTCTTGAGTTTGTAACTGCTGCTGGGATTACACATGGCATGGAT<br>GAACTATACAAACCGCGGGGTTCTCATCATCATCATCATCATGGTTAA<br>GTCGAC |
| 0108 | Mutant GD1G Expressed Mutant GD1G | DNA | Artificial Sequence | ATGAGTAAAGGAGAAGAACTTTTCACTGGAGTTGTCCCAATTCTTGTT<br>GAATTAGATGGTGATGTTAATGGGCACAAATTTTCTGTCAGTGGAGAG<br>GGTGAAGGTGATGCAACATACGGAAAACTTACCCTTAAATTTATTTGC<br>ACTACTGGAAAACTACCTGTTCCATGGCCAACACTTGTCACTACTCTG<br>ACGTATGGTGTTCAATGCTTTTCCCGTTATCCGGATCACATGAAACGG<br>CATGACTTTTTCAAGAGTGCCATGCCCGAAGGTTATGTACAGGAACGC<br>ACTATATCTTTCAAAGATGACGGGAACTACAAGACGCGTGCTGAAGTC<br>AAGTTTGAAGGTGATACCCTTGTTAATCGTATCGAGTTAAAAGGTATT<br>GATTTTAAAGAAGATGGAAACATTCTCGGACACAAACTCGAGTACAAC<br>TATAACTCACACAATGTATACATCACGGCAGACAAACAAGGCCTATCA<br>GGCCGCATTATGAGCGGGTTACGGATCAACAGCGCGAAAGACGATGCG<br>GCAGGCCAGGCGATTGCTAACCGCTTCACTTCTAATATCAAAGGTCTG<br>ACTCAGGCTTCCCGTAACGCTAACGACGGCATTTCTATTGCGCAGACC<br>ACTGAAGGTGCGCTGAATGAAATCAACAACAACCTGCAGCGTGTGCGT<br>GAGTTGTCTGTTCAGGCCACTAACGGGACTAACTCTGATTCCGATCTG<br>AAATCTATCCAGGATGAAATTCAGCAACGTCTGGAAGAAATCGATCGC<br>GTTTCTAATCAGACTCAATTTAACGGTGTTAAAGTCCTGTCTCAGGAC<br>AACCAGATGAAAATCCAGGTTGGTGCTAACGATGGTGAAACCATTACC<br>ATCGATCTGCAAAAAATTGATGTGAAAAGCCTTGGCCTTGATGGGTTC<br>AATGTTAATTCCCCGGGAAGTACCGCTAACCCACTGGCTTCAATTGAT<br>TCTGCATTGTCAAAAGTGGACGCAGTTCGTTCTTCTCTGGGGGCAATT<br>CAAAACCGCTTTGATTCAGCCATTACCAACCTTGGCAATACGGTAACC<br>AATCTGAACTCCGCGCGTAGCCGTATCGAAGATGCTGACTATGCACTG<br>GTTCCGCCGATCTCAGGTAAGAATGGAATCAAAGCTAACTTCAAAATT<br>CGCCACAACATTGAAGATGGATCCGTTCAACTAGCAGACCATTATCAA<br>CAAAATACTCCAATTGGCGATGGCCCTGTCCTTTTACCAGACAACCAT<br>TACCTGTCGACACAATCTGCCCTTTTGAAAGATCCCAACGAAAAGCGT<br>GACCACATGGTCCTTCTTGAGTTTGTAACTGCTGCTGGGATTACACAT<br>GGCATGGATGAACTATACAAACCGCGGGGTTCTCATCATCATCATCAT<br>CATGGTTAA |
| 0109 | Mutant GD1G Expressed Mutant GD1G | PRT | Artificial Sequence | MSKGEELFTGVVPILVELDGDVNGHKFSVSGEGEGDATYGKLTLKFIC<br>TTGKLPVPWPTLVTTLTYGVQCFSRYPDHMKRHDFFKSAMPEGYVQER<br>TISFKDDGNYKTRAEVKFEGDTLVNRIELKGIDFKEDGNILGHKLEYN<br>YNSHNVYITADKQGLSGRIMSGLRINSAKDDAAGQAIANRFTSNIKGL<br>TQASRNANDGISIAQTTEGALNEINNNLQRVRELSVQATNGTNSDSDL<br>KSIQDEIQQRLEEIDRVSNQTQFNGVKVLSQDNQMKIQVGANDGETIT<br>IDLQKIDVKSLGLDGFNVNSPGSTANPLASIDSALSKVDAVRSSLGAI<br>QNRFDSAITNLGNTVTNLNSARSRIEDADYALVPPISGKNGIKANFKI<br>RHNIEDGSVQLADHYQQNTPIGDGPVLLPDNHYLSTQSALLKDPNEKR<br>DHMVLLEFVTAAGITHGMDELYKPRGSHHHHHHG |
| 0110 | Mutant MF227C mutant 470CT template | DNA | Artificial Sequence | CTTGGCCTTGATGGGTTCAATGTTAATTCCCCGGGAATTTCCGGTGGT<br>GGTGGTGGAATTACATTAATCAATGAAGACGCTGCCGCAGCCAAGAAA<br>AGTACCGCTAACCCACTGGCTTCAATTG |
| 0111 | Mutant MF227C mutant 470CT template | PRT | Artificial Sequence | LGLDGFNVNSPGISGGGGGITLINEDAAAAKKSTANPLASI |
| 0112 | Mutant MF227C Reverse Primer R2YY | DNA | Artificial Sequence | AGATCTCCGCGGAACCAGTAAAGAGAGGACGTTTTGCGGAACCTGGTT<br>TGCATAGTCAGCATCTTCGATACG |
| 0113 | Mutant MF227C DNA sequence of Mutant MF227C | DNA | Artificial Sequence | TAATACGACTCACTATAGGGGAATTGTGAGCGGATAACAATTCCCCTC<br>TAGAATAATTTTGTTTAACTTTAAGAAGGAGATATACATATGAGCGGG<br>TTACGGATCAACAGCGCGAAAGACGATGCGGCAGGCCAGGCGATTGCT |

TABLE 1-continued

Illustrative Flagellin-Based Agents

| SEQ ID | Construct Name | DNA/PRT | Species | Sequence |
|---|---|---|---|---|
| | | | | AACCGCTTCACTTCTAATATCAAAGGTCTGACTCAGGCTTCCCGTAAC<br>GCTAACGACGGCATTTCTATTGCGCAGACCACTGAAGGTGCGCTGAAT<br>GAAATCAACAACAACCTGCAGCGTGTGCGTGAGTTGTCTGTTCAGGCC<br>ACTAACGGGACTAACTCTGATTCCGATCTGAAATCTATCCAGGATGAA<br>ATTCAGCAACGTCTGGAAGAAATCGATCGCGTTTCTAATCAGACTCAA<br>TTTAACGGTGTTAAAGTCCTGTCTCAGGACAACCAGATGAAAATCCAG<br>GTTGGTGCTAACGATGGTGAAACCATTACCATCGATCTGCAAAAAATT<br>GATGTGAAAAGCCTTGGCCTTGATGGGTTCAATGTTAATTCCCCGGGA<br>AGTACCGCTAACCCACTGGCTTCAATTGATTCTGCATTGTCAAAAGTG<br>GACGCAGTTCGTTCTTCTCTGGGGGCAATTCAAAACCGTTTTGATTCA<br>GCCATTACCAACCTTGGCAATACGGTAACCAATCTGAACTCCGCGCGT<br>AGCCGTATCGAAGATGCTGACTATGCAAACCAGGTTCCGCAAAACGTC<br>CTCTCTTTACTGGTTCCGCGGGGTTCTCATCATCATCATCATCATGGT<br>TAAGTCGAC |
| 0114 | Mutant MF227C<br>Mutant MF227C | DNA | Artificial Sequence | ATGAGCGGGTTACGGATCAACAGCGCGAAAGACGATGCGGCAGGCCAG<br>GCGATTGCTAACCGCTTCACTTCTAATATCAAAGGTCTGACTCAGGCT<br>TCCCGTAACGCTAACGACGGCATTTCTATTGCGCAGACCACTGAAGGT<br>GCGCTGAATGAAATCAACAACAACCTGCAGCGTGTGCGTGAGTTGTCT<br>GTTCAGGCCACTAACGGGACTAACTCTGATTCCGATCTGAAATCTATC<br>CAGGATGAAATTCAGCAACGTCTGGAAGAAATCGATCGCGTTTCTAAT<br>CAGACTCAATTTAACGGTGTTAAAGTCCTGTCTCAGGACAACCAGATG<br>AAAATCCAGGTTGGTGCTAACGATGGTGAAACCATTACCATCGATCTG<br>CAAAAAATTGATGTGAAAAGCCTTGGCCTTGATGGGTTCAATGTTAAT<br>TCCCCGGGAAGTACCGCTAACCCACTGGCTTCAATTGATTCTGCATTG<br>TCAAAAGTGGACGCAGTTCGTTCTTCTCTGGGGGCAATTCAAAACCGT<br>TTTGATTCAGCCATTACCAACCTTGGCAATACGGTAACCAATCTGAAC<br>TCCGCGCGTAGCCGTATCGAAGATGCTGACTATGCAAACCAGGTTCCG<br>CAAAACGTCCTCTCTTTACTGGTTCCGCGGGGTTCTCATCATCATCAT<br>CATCATGGTTAA |
| 0115 | Mutant MF227C<br>Mutant MF227C | PRT | Artificial Sequence | MSGLRINSAKDDAAGQAIANRFTSNIKGLTQASRNANDGISIAQTTEG<br>ALNEINNNLQRVRELSVQATNGTNSDSDLKSIQDEIQQRLEEIDRVSN<br>QTQFNGVKVLSQDNQMKIQVGANDGETITIDLQKIDVKSLGLDGFNVN<br>SPGSTANPLASIDSALSKVDAVRSSLGAIQNRFDSAITNLGNTVTNLN<br>SARSRIEDADYANQVPQNVLSLLVPRGSHHHHHHG |
| 0116 | Mutant MF227N<br>Reverse Primer<br>RMF227N | DNA | Artificial Sequence | AGATCTCCCGGGGAACCATCGTTAGCACCAACCTGGATTTTC |
| 0117 | Mutant MF227N<br>DNA sequence of<br>mutant MF227N | DNA | Artificial Sequence | TAATACGACTCACTATAGGGGAATTGTGAGCGGATAACAATTCCCCTC<br>TAGAATAATTTTGTTTAACTTTAAGAAGGAGATATACATATGAGCGGG<br>TTACGGATCAACAGCGCGAAAGACGATGCGGCAGGCCAGGCGATTGCT<br>AACCGCTTCACTTCTAATATCAAAGGTCTGACTCAGGCTTCCCGTAAC<br>GCTAACGACGGCATTTCTATTGCGCAGACCACTGAAGGTGCGCTGAAT<br>GAAATCAACAACAACCTGCAGCGTGTGCGTGAGTTGTCTGTTCAGGCC<br>ACTAACGGGACTAACTCTGATTCCGATCTGAAATCTATCCAGGATGAA<br>ATTCAGCAACGTCTGGAAGAAATCGATCGCGTTTCTAATCAGACTCAA<br>TTTAACGGTGTTAAAGTCCTGTCTCAGGACAACCAGATGAAAATCCAG<br>GTTGGTGCTAACGATGGTTCCCCGGGAAGTACCGCTAACCCACTGGCT<br>TCAATTGATTCTGCATTGTCAAAAGTGGACGCAGTTCGTTCTTCTCTG<br>GGGGCAATTCAAAACCGCTTTGATTCAGCCATTACCAACCTTGGCAAT<br>ACGGTAACCAATCTGAACTCCGCGCGTAGCCGTATCGAAGATGCTGAC<br>TATGCAACGGAAGTTTCTAATATGTCTAAAGCGCAGATTCTGCAGCAG<br>GCTGGTACTTCCGTTCTGGCGCAGGCTAACCAGGTTCCGCAAAACGTC<br>CTCTCTTTACTGGTTCCGCGGGGTTCTCATCATCATCATCATCATGGT<br>TAAGTCGAC |
| 0118 | Mutant MF227N<br>mutant MF227N | DNA | Artificial Sequence | ATGAGCGGGTTACGGATCAACAGCGCGAAAGACGATGCGGCAGGCCAG<br>GCGATTGCTAACCGCTTCACTTCTAATATCAAAGGTCTGACTCAGGCT<br>TCCCGTAACGCTAACGACGGCATTTCTATTGCGCAGACCACTGAAGGT<br>GCGCTGAATGAAATCAACAACAACCTGCAGCGTGTGCGTGAGTTGTCT<br>GTTCAGGCCACTAACGGGACTAACTCTGATTCCGATCTGAAATCTATC<br>CAGGATGAAATTCAGCAACGTCTGGAAGAAATCGATCGCGTTTCTAAT<br>CAGACTCAATTTAACGGTGTTAAAGTCCTGTCTCAGGACAACCAGATG<br>AAAATCCAGGTTGGTGCTAACGATGGTTCCCCGGGAAGTACCGCTAAC<br>CCACTGGCTTCAATTGATTCTGCATTGTCAAAAGTGGACGCAGTTCGT<br>TCTTCTCTGGGGGCAATTCAAAACCGCTTTGATTCAGCCATTACCAAC<br>CTTGGCAATACGGTAACCAATCTGAACTCCGCGCGTAGCCGTATCGAA<br>GATGCTGACTATGCAACGGAAGTTTCTAATATGTCTAAAGCGCAGATT<br>CTGCAGCAGGCTGGTACTTCCGTTCTGGCGCAGGCTAACCAGGTTCCG<br>CAAAACGTCCTCTCTTTACTGGTTCCGCGGGGTTCTCATCATCATCAT<br>CATCATGGTTAA |

TABLE 1-continued

Illustrative Flagellin-Based Agents

| SEQ ID | Construct Name | DNA/PRT | Species | Sequence |
|---|---|---|---|---|
| 0119 | Mutant MF227N mutant MF227N | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDRVSN QTQFNGVKVLSQDNQMKIQVGANDGSPGSTANPLASIDSALSKVDAVR SSLGAIQNRFDSAITNLGNTVTNLNSARSRIEDADYATEVSNMSKAQI LQQAGTSVLAQANQVPQNVLSLLVPRGSHHHHHG |
| 0120 | Mutant MF233 Reverse primer RMF233 | DNA | Artificial Sequence | AGATCTCCGCGGAACCAGCAGGTTATTCTGGGTCAACAGCGACAGGCT GTTTGTATTAATGACTTGTGCATAGTCAGCATCTTCGATACG |
| 0121 | Mutant MF233 DNA Sequence of construct MF233 | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCACAAGTCATTAATACAAACAGC CTGTCGCTGTTGACCCAGAATAACCTGCTGGTTCCGCGGGGTTCTCAT CATCATCATCATCATGGTTAAGTCGAC |
| 0122 | Mutant MF233 MF233 | DNA | Artificial Sequence | ATGAGCGGGTTACGGATCAACAGCGCGAAAGACGATGCGGCAGGCCAG GCGATTGCTAACCGCTTCACTTCTAATATCAAAGGTCTGACTCAGGCT TCCCGTAACGCTAACGACGGCATTTCTATTGCGCAGACCACTGAAGGT GCGCTGAATGAAATCAACAACAACCTGCAGCGTGTGCGTGAGTTGTCT GTTCAGGCCACTAACGGGACTAACTCTGATTCCGATCTGAAATCTATC CAGGATGAAATTCAGCAACGTCTGGAAGAAATCGATCGCGTTTCTAAT CAGACTCAATTTAACGGTGTTAAAGTCCTGTCTCAGGACAACCAGATG AAAATCCAGGTTGGTGCTAACGATGGTGAAACCATTACCATCGATCTG CAAAAAATTGATGTGAAAAGCCTTGGCCTTGATGGGTTCAATGTTAAT TCCCCGGGAAGTACCGCTAACCCCACTGGCTTCAATTGATTCTGCATTG TCAAAAGTGGACGCAGTTCGTTCTTCTCTGGGGGCAATTCAAAACCGC TTTGATTCAGCCATTACCAACCTTGGCAATACGGTAACCAATCTGAAC TCCGCGCGTAGCCGTATCGAAGATGCTGACTATGCACAAGTCATTAAT ACAAACAGCCTGTCGCTGTTGACCCAGAATAACCTGCTGGTTCCGCGG GGTTCTCATCATCATCATCATGGTTAA |
| 0123 | Mutant MF233 MF233 | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDRVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYAQVINTNSLSLLTQNNLLVPRGSHHHHHG |
| 0124 | Mutant MF471 Forward primer F471-77 | DNA | Artificial Sequence | GCTGACTATGCAACGGCAGTTTCTGCTATGTCTGCAGCGCAGATTCTG C |
| 0125 | Mutant MF471 Reverse Primer R471-77 | DNA | Artificial Sequence | GCAGAATCTGCGCTGCAGACATAGCAGAAACTGCCGTTGCATAGTCAG C |
| 0126 | Mutant MF471 DNA Sequence of construct MF471 | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGCAGTTTCTGCTATGTCT GCAGCGCAGATTCTGCAGCAGGCTGGTCTGGTTCCGCGGGGTTCTCAT CATCATCATCATGGTTAAGTCGAC |
| 0127 | Mutant MF471 MF471 | DNA | Artificial Sequence | ATGAGCGGGTTACGGATCAACAGCGCGAAAGACGATGCGGCAGGCCAG GCGATTGCTAACCGCTTCACTTCTAATATCAAAGGTCTGACTCAGGCT |

TABLE 1-continued

Illustrative Flagellin-Based Agents

| SEQ ID | Construct Name | DNA/PRT | Species | Sequence |
|---|---|---|---|---|
| | | | | TCCCGTAACGCTAACGACGGCATTTCTATTGCGCAGACCACTGAAGGT GCGCTGAATGAAATCAACAACAACCTGCAGCGTGTGCGTGAGTTGTCT GTTCAGGCCACTAACGGGACTAACTCTGATTCCGATCTGAAATCTATC CAGGATGAAATTCAGCAACGTCTGGAAGAAATCGATCGCGTTTCTAAT CAGACTCAATTTAACGGTGTTAAAGTCCTGTCTCAGGACAACCAGATG AAAATCCAGGTTGGTGCTAACGATGGTGAAACCATTACCATCGATCTG CAAAAAATTGATGTGAAAAGCCTTGGCCTTGATGGGTTCAATGTTAAT TCCCCGGGAAGTACCGCTAACCCACTGGCTTCAATTGATTCTGCATTG TCAAAAGTGGACGCAGTTCGTTCTTCTCTGGGGGCAATTCAAAACCGC TTTGATTCAGCCATTACCAACCTTGGCAATACGGTAACCAATCTGAAC TCCGCGCGTAGCCGTATCGAAGATGCTGACTATGCAACGGCAGTTTCT GCTATGTCTGCAGCGCAGATTCTGCAGCAGGCTGGTCTGGTTCCGCGG GGTTCTCATCATCATCATCATCATGGTTAA |
| 0128 | Mutant MF471 MF471 | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDRVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYATAVSAMSAAQILQQAGLVPRGSHHHHHG |
| 0129 | Mutant MF479 Forward primer F479-83 | DNA | Artificial Sequence | GTTTCTAATATGTCTAAAGCGGCGATTCTGGGAGCGGCTGGTCTGGTT CCGCGG |
| 0130 | Mutant MF479 Reverse Primer R479-83 | DNA | Artificial Sequence | CCGCGGAACCAGACCAGCCGCTCCCAGAATCGCCGCTTTAGACATATT AGAAAC |
| 0131 | Mutant MF479 DNA Sequence of construct MF479 | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGGCGATTCTGGGAGCGGCTGGTCTGGTTCCGCGGGGTTCTCAT CATCATCATCATCATGGTTAAGTCGAC |
| 0132 | Mutant MF479 Mutant MF479 | DNA | Artificial Sequence | ATGAGCGGGTTACGGATCAACAGCGCGAAAGACGATGCGGCAGGCCAG GCGATTGCTAACCGCTTCACTTCTAATATCAAAGGTCTGACTCAGGCT TCCCGTAACGCTAACGACGGCATTTCTATTGCGCAGACCACTGAAGGT GCGCTGAATGAAATCAACAACAACCTGCAGCGTGTGCGTGAGTTGTCT GTTCAGGCCACTAACGGGACTAACTCTGATTCCGATCTGAAATCTATC CAGGATGAAATTCAGCAACGTCTGGAAGAAATCGATCGCGTTTCTAAT CAGACTCAATTTAACGGTGTTAAAGTCCTGTCTCAGGACAACCAGATG AAAATCCAGGTTGGTGCTAACGATGGTGAAACCATTACCATCGATCTG CAAAAAATTGATGTGAAAAGCCTTGGCCTTGATGGGTTCAATGTTAAT TCCCCGGGAAGTACCGCTAACCCACTGGCTTCAATTGATTCTGCATTG TCAAAAGTGGACGCAGTTCGTTCTTCTCTGGGGGCAATTCAAAACCGC TTTGATTCAGCCATTACCAACCTTGGCAATACGGTAACCAATCTGAAC TCCGCGCGTAGCCGTATCGAAGATGCTGACTATGCAACGGAAGTTTCT AATATGTCTAAAGCGGCGATTCTGGGAGCGGCTGGTCTGGTTCCGCGG GGTTCTCATCATCATCATCATCATGGTTAA |
| 0133 | Mutant MF479 Mutant MF479 | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDRVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYATEVSNMSKAAILGAAGLVPRGSHHHHHG |
| 0134 | Mutant N45 Forward primer N45_F | DNA | Artificial Sequence | TCTAGAGGATCCGGCAGGCCAGGCG |
| 0135 | Mutant N45 Reverse R502D0 | DNA | Artificial Sequence | CGCAAGCTTGTCGACTTAACGC |
| 0136 | Mutant N45 DNA sequence of Mutant N45 | DNA | Artificial Sequence | TAATACGACTCACTATAGGGGAATTGTGAGCGGATAACAATTCCCCTC TAGAATAATTTTGTTTAACTTTAAGAAGGAGATATACATATGCGGGGT TCTCATCATCATCATCATCATGGTATGGCTAGCATGACTGGTGGACAG |

TABLE 1-continued

Illustrative Flagellin-Based Agents

| SEQ ID | Construct Name | DNA/PRT | Species | Sequence |
|---|---|---|---|---|
| | | | | CAAATGGGTCGGGATCTGTACGACCTGGTTCCGCGCGGTAGCGCGAAG GATCCGGCAGGCCAGGCGATTGCTAACCGCTTCACTTCTAATATCAAA GGTCTGACTCAGGCTTCCCGTAACGCTAACGACGGCATTTCTATTGCG CAGACCACTGAAGGTGCGCTGAATGAAATCAACAACAACCTGCAGCGT GTGCGTGAGTTGTCTGTTCAGGCCACTAACGGGACTAACTCTGATTCC GATCTGAAATCTATCCAGGATGAAATTCAGCAACGTCTGGAAGAAATC GATCGCGTTTCTAATCAGACTCAATTTAACGGTGTTAAAGTCCTGTCT CAGGACAACCAGATGAAAATCCAGGTTGGTGCTAACGATGGTGAAACC ATTACCATCGATCTGCAAAAAATTGATGTGAAAGCCTTGGCCTTGAT GGGTTCAATGTTAATTCCCCGGGAATTTCCGGTGGTGGTGGTGGAATT CTAGACTCCATGGGTACATTAATCAATGAAGACGCTGCCGCAGCCAAG AAAAGTACCGCTAACCCACTGGCTTCAATTGATTCTGCATTGTCAAAA GTGGACGCAGTTCGTTCTTCTCTGGGGGCAATTCAAAACCGTTTTGAT TCAGCCATTACCAACCTTGGCAATACGGTAACCAATCTGAACTCCGCG CGTAGCCGTATCGAAGATGCTGACTATGCAACGGAAGTTTCTAATATG TCTAAAGCGCAGATTCTGCAGCAGGCTGGTACTTCCGTTCTGGCGCAG GCTAACCAGGTTCCGCAAAACGTCCTCTCTTTACTGCGTTAAGTCGAC AAGCTTGCGG |
| 0137 | Mutant N45<br>Mutant N45 | PRT | Artificial Sequence | MRGSHHHHHHGMASMTGGQQMGRDLYDLVPRGSAKDPAGQAIANRFTS NIKGLTQASRNANDGISIAQTTEGALNEINNNLQRVRELSVQATNGTN SDSDLKSIQDEIQQRLEEIDRVSNQTQFNGVKVLSQDNQMKIQVGAND GETITIDLQKIDVKSLGLDGFNVNSPGISGGGGGILDSMGTLINEDAA AKKSTANPLASIDSALSKVDAVRSSLGAIQNRFDSAITNLGNTVTNL NSARSRIEDADYATEVSNMSKAQILQQAGTSVLAQANQVPQNVLSLLR |
| 0138 | Mutant NGD1<br>DNA Sequence of NGD1 construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGTAAA GGAGAAGAACTTTTCACTGGAGTTGTCCCAATTCTTGTTGAATTAGAT GGTGATGTTAATGGGCACAAATTTTCTGTCAGTGGAGAGGGTGAAGGT GATGCAACATACGGAAAACTTACCCTTAAATTTATTTGCACTACTGGA AAACTACCTGTTCCATGGCCAACACTTGTCACTACTCTGACGTATGGT GTTCAATGCTTTTCCCGTTATCCGGATCACATGAAACGGCATGACTTT TTCAAGAGTGCCATGCCCGAAGGTTATGTACAGGAACGCACTATATCT TTCAAAGATGACGGGAACTACAAGACGCGTGCTGAAGTCAAGTTTGAA GGTGATACCCTTGTTAATCGTATCGAGTTAAAAGGTATTGATTTTAAA GAAGATGGAAACATTCTCGGACACAAACTCGAGTACAACTATAACTCA CACAATGTATACATCACGGCAGACAAACAAGGCCTATCAGGCCGCATT ATGAGCGGGTTACGGATCAACAGCGCGAAAGACGATGCGGCAGGCCAG GCGATTGCTAACCGCTTCACTTCTAATATCAAAGGTCTGACTCAGGCT TCCCGTAACGCTAACGACGGCATTTCTATTGCGCAGACCACTGAAGGT GCGCTGAATGAAATCAACAACAACCTGCAGCGTGTGCGTGAGTTGTCT GTTCAGGCCACTAACGGGACTAACTCTGATTCCGATCTGAAATCTATC CAGGATGAAATTCAGCAACGTCTGGAAGAAATCGATCGCGTTTCTAAT CAGACTCAATTTAACGGTGTTAAAGTCCTGTCTCAGGACAACCAGATG AAAATCCAGGTTGGTGCTAACGATGGTGAAACCATTACCATCGATCTG CAAAAAATTGATGTGAAAGCCTTGGCCTTGATGGGTTCAATGTTAAT TCCCCGGGAAGTACCGCTAACCCACTGGCTTCAATTGATTCTGCATTG TCAAAAGTGGACGCAGTTCGTTCTTCTCTGGGGGCAATTCAAAACCGC TTTGATTCAGCCATTACCAACCTTGGCAATACGGTAACCAATCTGAAC TCCGCGCGTAGCCGTATCGAAGATGCTGACTATGCACTGGTTCCGCGG GGTTCTCATCATCATCATCATCATGGTTAAGTCGAC |
| 0139 | Mutant NGD1<br>Expressed Mutant SY3-GFP | DNA | Artificial Sequence | ATGAGTAAAGGAGAAGAACTTTTCACTGGAGTTGTCCCAATTCTTGTT GAATTAGATGGTGATGTTAATGGGCACAAATTTTCTGTCAGTGGAGAG GGTGAAGGTGATGCAACATACGGAAAACTTACCCTTAAATTTATTTGC ACTACTGGAAAACTACCTGTTCCATGGCCAACACTTGTCACTACTCTG ACGTATGGTGTTCAATGCTTTTCCCGTTATCCGGATCACATGAAACGG CATGACTTTTTCAAGAGTGCCATGCCCGAAGGTTATGTACAGGAACGC ACTATATCTTTCAAAGATGACGGGAACTACAAGACGCGTGCTGAAGTC AAGTTTGAAGGTGATACCCTTGTTAATCGTATCGAGTTAAAAGGTATT GATTTTAAAGAAGATGGAAACATTCTCGGACACAAACTCGAGTACAAC TATAACTCACACAATGTATACATCACGGCAGACAAACAAGGCCTATCA GGCCGCATTATGAGCGGGTTACGGATCAACAGCGCGAAAGACGATGCG GCAGGCCAGGCGATTGCTAACCGCTTCACTTCTAATATCAAAGGTCTG ACTCAGGCTTCCCGTAACGCTAACGACGGCATTTCTATTGCGCAGACC ACTGAAGGTGCGCTGAATGAAATCAACAACAACCTGCAGCGTGTGCGT GAGTTGTCTGTTCAGGCCACTAACGGGACTAACTCTGATTCCGATCTG AAATCTATCCAGGATGAAATTCAGCAACGTCTGGAAGAAATCGATCGC GTTTCTAATCAGACTCAATTTAACGGTGTTAAAGTCCTGTCTCAGGAC AACCAGATGAAAATCCAGGTTGGTGCTAACGATGGTGAAACCATTACC ATCGATCTGCAAAAAATTGATGTGAAAGCCTTGGCCTTGATGGGTTC AATGTTAATTCCCCGGGAAGTACCGCTAACCCACTGGCTTCAATTGAT TCTGCATTGTCAAAAGTGGACGCAGTTCGTTCTTCTCTGGGGGCAATT CAAAACCGCTTTGATTCAGCCATTACCAACCTTGGCAATACGGTAACC |

TABLE 1-continued

Illustrative Flagellin-Based Agents

| SEQ ID | Construct Name | DNA/PRT | Species | Sequence |
|---|---|---|---|---|
| | | | | AATCTGAACTCCGCGCGTAGCCGTATCGAAGATGCTGACTATGCACTG GTTCCGCGGGGTTCTCATCATCATCATCATCATGGTTAA |
| 0140 | Mutant NGD1 Expressed Mutant SY3-GFP/Mutant NGD1 | PRT | Artificial Sequence | MSKGEELFTGVVPILVELDGDVNGHKFSVSGEGEGDATYGKLTLKFIC TTGKLPVPWPTLVTTLTYGVQCFSRYPDHMKRHDFFKSAMPEGYVQER TISFKDDGNYKTRAEVKFEGDTLVNRIELKGIDFKEDGNILGHKLEYN YNSHNVYITADKQGLSGRIMSGLRINSAKDDAAGQAIANRFTSNIKGL TQASRNANDGISIAQTTEGALNEINNNLQRVRELSVQATNGTNSDSDL KSIQDEIQQRLEEIDRVSNQTQFNGVKVLSQDNQMKIQVGANDGETIT IDLQKIDVKSLGLDGFNVSPGSTANPLASIDSALSKVDAVRSSLGAI QNRFDSAITNLGNTVTNLNSARSRIEDADYALVPRGSHHHHHHG |
| 0141 | Mutant S33 Forward F502_S33 | DNA | Artificial Sequence | TCTAGAGGATCCGTCTGGTCTGCGTATCAACAGCGC |
| 0142 | Mutant S33 DNA sequence of Mutant S33 | DNA | Artificial Sequence | TAATACGACTCACTATAGGGGAATTGTGAGCGGATAACAATTCCCCTC TAGAATAATTTTGTTTAACTTTAAGAAGGAGATATACATATGCGGGGT TCTCATCATCATCATCATCATGGTATGGCTAGCATGACTGGTGGACAG CAAATGGGTCGGGATCTGTACGACCTGGTTCCGCGCGGTAGCGCGAAG GATCCGTCTGGTCTGCGTATCAACAGCGCGAAAGACGATGCGGCAGGC CAGGCGATTGCTAACCGCTTCACTTCTAATATCAAAGGTCTGACTCAG GCTTCCCGTAACGCTAACGACGGCATTTCTATTGCGCAGACCACTGAA GGTGCGCTGAATGAAATCAACAACAACCTGCAGCGTGTGCGTGAGTTG TCTGTTCAGGCCACTAACGGGACTAACTCTGATTCCGATCTGAAATCT ATCCAGGATGAAATTCAGCAACGTCTGGAAGAAATCGATCGCGTTTCT AATCAGACTCAATTTAACGGTGTTAAAGTCCTGTCTCAGGACAACCAG ATGAAAATCCAGGTTGGTGCTAACGATGGTGAAACCATTACCATCGAT CTGCAAAAAATTGATGTGAAAAGCCTTGGCCTTGATGGGTTCAATGTT AATTCCCCGGGAATTTCCGGTGGTGGTGGTGGAATTCTAGACTCCATG GGTACATTAATCAATGAAGACGCTGCCGCAGCCAAGAAAAGTACCGCT AACCCACTGGCTTCAATTGATTCTGCATTGTCAAAAGTGGACGCAGTT CGTTCTTCTCTGGGGGCAATTCAAAACCGTTTTGATTCAGCCATTACC AACCTTGGCAATACGGTAACCAATCTGAACTCCGCGCGTAGCCGTATC GAAGATGCTGACTATGCAACGGAAGTTTCTAATATGTCTAAAGCGCAG ATTCTGCAGCAGGCTGGTACTTCCGTTCTGGCGCAGGCTAACCAGGTT CCGCAAAACGTCCTCTCTTTACTGCGTTAAGTCGAC |
| 0143 | Mutant S33 Mutant S33 | DNA | Artificial Sequence | ATGCGGGGTTCTCATCATCATCATCATCATGGTATGGCTAGCATGACT GGTGGACAGCAAATGGGTCGGGATCTGTACGACCTGGTTCCGCGCGGT AGCGCGAAGGATCCGTCTGGTCTGCGTATCAACAGCGCGAAAGACGAT GCGGCAGGCCAGGCGATTGCTAACCGCTTCACTTCTAATATCAAAGGT CTGACTCAGGCTTCCCGTAACGCTAACGACGGCATTTCTATTGCGCAG ACCACTGAAGGTGCGCTGAATGAAATCAACAACAACCTGCAGCGTGTG CGTGAGTTGTCTGTTCAGGCCACTAACGGGACTAACTCTGATTCCGAT CTGAAATCTATCCAGGATGAAATTCAGCAACGTCTGGAAGAAATCGAT CGCGTTTCTAATCAGACTCAATTTAACGGTGTTAAAGTCCTGTCTCAG GACAACCAGATGAAAATCCAGGTTGGTGCTAACGATGGTGAAACCATT ACCATCGATCTGCAAAAAATTGATGTGAAAAGCCTTGGCCTTGATGGG TTCAATGTTAATTCCCCGGGAATTTCCGGTGGTGGTGGTGGAATTCTA GACTCCATGGGTACATTAATCAATGAAGACGCTGCCGCAGCCAAGAAA AGTACCGCTAACCCACTGGCTTCAATTGATTCTGCATTGTCAAAAGTG GACGCAGTTCGTTCTTCTCTGGGGGCAATTCAAAACCGTTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGCGTTAA |
| 0144 | Mutant S33 Mutant S33 | PRT | Artificial Sequence | MRGSHHHHHHGMASMTGGQQMGRDLYDLVPRGSAKDPSGLRINSAKDD AAGQAIANRFTSNIKGLTQASRNANDGISIAQTTEGALNEINNNLQRV RELSVQATNGTNSDSDLKSIQDEIQQRLEEIDRVSNQTQFNGVKVLSQ DNQMKIQVGANDGETITIDLQKIDVKSLGLDGFNVNSPGISGGGGGIL DSMGTLINEDAAAAKKSTANPLASIDSALSKVDAVRSSLGAIQNRFDS AITNLGNTVTNLNSARSRIEDADYATEVSNMSKAQILQQAGTSVLAQA NQVPQNVLSLLR |
| 0145 | Mutant SY3CT Reverse primer RSY3CT | DNA | Artificial Sequence | AGATCTCCGCGGAACCAGTGCATAGTCAGCATCTTCGATACGGC |
| 0146 | Mutant SY3CT DNA Sequence of SY3CT construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA |

TABLE 1-continued

Illustrative Flagellin-Based Agents

| SEQ ID | Construct Name | DNA/PRT | Species | Sequence |
|---|---|---|---|---|
| | | | | ATTCAGCAACGTCTGGAAGAAATCGATCGCGTTTCTAATCAGACTCAA<br>TTTAACGGTGTTAAAGTCCTGTCTCAGGACAACCAGATGAAAATCCAG<br>GTTGGTGCTAACGATGGTGAAACCATTACCATCGATCTGCAAAAAATT<br>GATGTGAAAAGCCTTGGCCTTGATGGGTTCAATGTTAATTCCCCGGGA<br>AGTACCGCTAACCCACTGGCTTCAATTGATTCTGCATTGTCAAAAGTG<br>GACGCAGTTCGTTCTTCTCTGGGGGCAATTCAAAACCGCTTTGATTCA<br>GCCATTACCAACCTTGGCAATACGGTAACCAATCTGAACTCCGCGCGT<br>AGCCGTATCGAAGATGCTGACTATGCACTGGTTCCGCGGGGTTCTCAT<br>CATCATCATCATCATGGTTAAGTCGAC |
| 0147 | Mutant SY3CT<br>Expressed Mutant<br>SY3CT | DNA | Artificial Sequence | ATGAGCGGGTTACGGATCAACAGCGCGAAAGACGATGCGGCAGGCCAG<br>GCGATTGCTAACCGCTTCACTTCTAATATCAAAGGTCTGACTCAGGCT<br>TCCCGTAACGCTAACGACGGCATTTCTATTGCGCAGACCACTGAAGGT<br>GCGCTGAATGAAATCAACAACAACCTGCAGCGTGTGCGTGAGTTGTCT<br>GTTCAGGCCACTAACGGACTAACTCTGATTCCGATCTGAAATCTATC<br>CAGGATGAAATTCAGCAACGTCTGGAAGAAATCGATCGCGTTTCTAAT<br>CAGACTCAATTTAACGGTGTTAAAGTCCTGTCTCAGGACAACCAGATG<br>AAAATCCAGGTTGGTGCTAACGATGGTGAAACCATTACCATCGATCTG<br>CAAAAAATTGATGTGAAAAGCCTTGGCCTTGATGGGTTCAATGTTAAT<br>TCCCCGGGAAGTACCGCTAACCCACTGGCTTCAATTGATTCTGCATTG<br>TCAAAAGTGGACGCAGTTCGTTCTTCTCTGGGGGCAATTCAAAACCGC<br>TTTGATTCAGCCATTACCAACCTTGGCAATACGGTAACCAATCTGAAC<br>TCCGCGCGTAGCCGTATCGAAGATGCTGACTATGCACTGGTTCCGCGG<br>GGTTCTCATCATCATCATCATGGTTAA |
| 0148 | Mutant SY3CT<br>Expressed Mutant<br>SY3CT | PRT | Artificial Sequence | MSGLRINSAKDDAAGQAIANRFTSNIKGLTQASRNANDGISIAQTTEG<br>ALNEINNNLQRVRELSVQATNGTNSDSDLKSIQDEIQQRLEEIDRVSN<br>QTQFNGVKVLSQDNQMKIQVGANDGETITIDLQKIDVKSLGLDGFNVN<br>SPGSTANPLASIDSALSKVDAVRSSLGAIQNRFDSAITNLGNTVTNLN<br>SARSRIEDADYALVPRGSHHHHHG |
| 0149 | Mutant 33MX<br>Mutant 33MX | DNA | Artificial Sequence | ATGAGCGGGTTACGGATCAACAGCGCGAAAGACGATGCGGCAGGCCAG<br>GCGATTGCTAACCGCTTCACTTCTAATATCAAAGGTCTGACTCAGGCT<br>TCCCGTAACGCTGCAGACGGCATTTCTATTGCGCAGACCACTGAAGGT<br>GCGCTGAATGAAATCAACAACAACCTGCAGCGTGTGCGTGAGTTGTCT<br>GTTCAGGCCACTGCCGGGGTAACGCTGATGCCGCTCTGAAAGCTATC<br>CAGGCTGAAATTCAGCAACGTCTGGAAGAAATCGATCGCGTTTCTCAG<br>CAGACTCAAGCTGCCGCTGTTAAAGTCCTGTCTCAGGACAACGCAATG<br>GCAATCCAGGTTGGTGCTAACGATGGTGCCGCTATTACCATCGATCTG<br>CAAAAAATTGATGTGAAAAGCCTTGGCCTTGATGGGTTCAATGTTAAT<br>TCCCCGGGAAGTACCGCTAACCCACTGGCTTCAATTGATTCTGCATTG<br>TCAAAAGTGGACGCAGTTCGTTCTTCTCTGGGGGCAATTCAAAACCGC<br>TTTGATTCAGCCATTACCAACCTTGGCAATACGGTAACCAATCTGAAC<br>TCCGCGCGTAGCCGTATCGAAGATGCTGACTATGCAACGGAAGTTTCT<br>CAAATGTCTAAAGCGCAGATTCTGCAGCAGGCTGGTACTTCCGTTCTG<br>GCGCAGGCTAACCAGGTTCCGCAAAACGTCCTCTCTTTACTGGTTCCG<br>CGGGGTTCTCATCATCATCATCATGGTTAA |
| 0150 | Mutant 33MX<br>Mutant 33MX | PRT | Artificial Sequence | MSGLRINSAKDDAAGQAIANRFTSNIKGLTQASRNAADGISIAQTTEG<br>ALNEINNNLQRVRELSVQATAGANADAALKAIQAEIQQRLEEIDRVSQ<br>QTQAAAVKVLSQDNAMAIQVGANDGAAITIDLQKIDVKSLGLDGFNVN<br>SPGSTANPLASIDSALSKVDAVRSSLGAIQNRFDSAITNLGNTVTNLN<br>SARSRIEDADYATEVSQMSKAQILQQAGTSVLAQANQVPQNVLSLLVP<br>RGSHHHHHG |
| 0151 | Mutant 33MX<br>DNA sequence of 33MX | DNA | Artificial Sequence | TAATACGACTCACTATAGGGGAATTGTGAGCGGATAACAATTCCCCTC<br>TAGAATAATTTTGTTTAACTTTAAGAAGGAGATATACATATGAGCGGG<br>TTACGGATCAACAGCGCGAAAGACGATGCGGCAGGCCAGGCGATTGCT<br>AACCGCTTCACTTCTAATATCAAAGGTCTGACTCAGGCTTCCCGTAAC<br>GCTGCAGACGGCATTTCTATTGCGCAGACCACTGAAGGTGCGCTGAAT<br>GAAATCAACAACAACCTGCAGCGTGTGCGTGAGTTGTCTGTTCAGGCC<br>ACTGCCGGGGCTAACGCTGATGCCGCTCTGAAAGCTATCCAGGCTGAA<br>ATTCAGCAACGTCTGGAAGAAATCGATCGCGTTTCTCAGCAGACTCAA<br>GCTGCCGCTGTTAAAGTCCTGTCTCAGGACAACGCAATGGCAATCCAG<br>GTTGGTGCTAACGATGGTGCCGCTATTACCATCGATCTGCAAAAAATT<br>GATGTGAAAAGCCTTGGCCTTGATGGGTTCAATGTTAATTCCCCGGGA<br>AGTACCGCTAACCCACTGGCTTCAATTGATTCTGCATTGTCAAAAGTG<br>GACGCAGTTCGTTCTTCTCTGGGGGCAATTCAAAACCGCTTTGATTCA<br>GCCATTACCAACCTTGGCAATACGGTAACCAATCTGAACTCCGCGCGT<br>AGCCGTATCGAAGATGCTGACTATGCAACGGAAGTTTCTCAAATGTCT<br>AAAGCGCAGATTCTGCAGCAGGCTGGTACTTCCGTTCTGGCGCAGGCT<br>AACCAGGTTCCGCAAAACGTCCTCTCTTTACTGGTTCCGCGGGGTTCT<br>CATCATCATCATCATGGTTAAGTCGAC |

TABLE 1-continued

Illustrative Flagellin-Based Agents

| SEQ ID | Construct Name | DNA/ PRT | Species | Sequence |
|---|---|---|---|---|
| 0152 | Mutant 485MX DNA Sequence of 485MX construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTGCAGACGGCATTTCTATTGCGCAGACCACTGAAGGTGCGCTGAAT GAAATCAACAACAACCTGCAGCGTGTGCGTGAGTTGTCTGTTCAGGCC ACTGCCGGGGCTAACGCTGATGCCGCTCTGAAAGCTATCCAGGCTGAA ATTCAGCAACGTCTGGAAGAAATCGATCGCGTTTCTCAGCAGACTCAA GCTGCCGCTGTTAAAGTCCTGTCTCAGGACAACGCAATGGCAATCCAG GTTGGTGCTAACGATGGTGCCGCTATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTCAAATGTCT AAAGCGCAGATTCTGCAGCAGGCTGGTCTGGTTCCGCGGGGTTCTCAT CATCATCATCATCATGGTTAAGTCGAC |
| 0153 | Mutant 485MX 485MX construct | DNA | Artificial Sequence | ATGAGCGGGTTACGGATCAACAGCGCGAAAGACGATGCGGCAGGCCAG GCGATTGCTAACCGCTTCACTTCTAATATCAAAGGTCTGACTCAGGCT TCCCGTAACGCTGCAGACGGCATTTCTATTGCGCAGACCACTGAAGGT GCGCTGAATGAAATCAACAACAACCTGCAGCGTGTGCGTGAGTTGTCT GTTCAGGCCACTGCCGGGGCTAACGCTGATGCCGCTCTGAAAGCTATC CAGGCTGAAATTCAGCAACGTCTGGAAGAAATCGATCGCGTTTCTCAG CAGACTCAAGCTGCCGCTGTTAAAGTCCTGTCTCAGGACAACGCAATG GCAATCCAGGTTGGTGCTAACGATGGTGCCGCTATTACCATCGATCTG CAAAAAATTGATGTGAAAAGCCTTGGCCTTGATGGGTTCAATGTTAAT TCCCCGGGAAGTACCGCTAACCCACTGGCTTCAATTGATTCTGCATTG TCAAAAGTGGACGCAGTTCGTTCTTCTCTGGGGGCAATTCAAAACCGC TTTGATTCAGCCATTACCAACCTTGGCAATACGGTAACCAATCTGAAC TCCGCGCGTAGCCGTATCGAAGATGCTGACTATGCAACGGAAGTTTCT CAAATGTCTAAAGCGCAGATTCTGCAGCAGGCTGGTCTGGTTCCGCGG GGTTCTCATCATCATCATCATCATGGTTAA |
| 0154 | Mutant 485MX 485MX construct | PRT | Artificial Sequence | MSGLRINSAKDDAAGQAIANRFTSNIKGLTQASRNAADGISIAQTTEG ALNEINNNLQRVRELSVQATAGANADAALKAIQAEIQQRLEEIDRVSQ QTQAAAVKVLSQDNAMAIQVGANDGAAITIDLQKIDVKSLGLDGFNVN SPGSTANPLASIDSALSKVDAVRSSLGAIQNRFDSAITNLGNTVTNLN SARSRIEDADYATEVSQMSKAQILQQAGLVPRGSHHHHHHG |
| 0155 | Mutant MIM4 CBLB502 variant | DNA | Artificial Sequence | ATGCGGGGTTCTCATCATCATCATCATCATGGTATGGCTAGCATGACT GGTGGACAGCAAATGGGTCGGGATCTGTACGACGATGACGATAAGGAT CCGATGGCACAAGTCATTAATACAAACAGCCTGTCGCTGTTGACCCAG AATAACCTGCAGAAATCTCAGTCCTCACTGAGTTCCGCTATTGAGCGT CTGTCCTCTGGTCTGCGTATCAACAGCGCGAAAGACGATGCGGCAGGC CAGGCGATTGCTAACCGCTTCACTTCTAATATCAAAGGTCTGACTCAG GCTTCCCGTAACGCTAACGACGGCATTTCTATTGCGCAGACCACTGAA GGTGCGCTGAATGAAATCAACAACAACCTGCAGCGTGTGCGTGAGTTG TCTGTTCAGGCCACTCAAGGGACTAACTCTGATTCCGATCTGAAATCT ATCCAGGATGAAATTCAGCAACGTCTGGAAGAAATCGATCGCGTTTCT CAGCAGACTCAATTTAACGGTGTTAAAGTCCTGTCTCAGGACAACCAG ATGAAAATCCAGGTTGGTGCTAACGATGGTGAAACCATTACCATCGAT CTGCAAAAAATTGATGTGAAAAGCCTTGGCCTTGATGGGTTCAATGTT AATTCCCCGGGAATTTCCGGTGGTGGTGGTGGAATTCTAGACTCCATG GGTACATTAATCAATGAAGACGCTGCCGCAGCCAAGAAAAGTACCGCT AACCCACTGGCTTCAATTGATTCTGCATTGTCAAAAGTGGACGCAGTT CGTTCTTCTCTGGGGGCAATTCAAAACCGTTTTGATTCAGCCATTACC AACCTTGGCAATACGGTAACCAATCTGAACTCCGCGCGTAGCCGTATC GAAGATGCTGACTATGCAACGGAAGTTTCTCAAATGTCTAAAGCGCAG ATTCTGCAGCAGGCTGGTACTTCCGTTCTGGCGCAGGCTAACCAGGTT CCGCAAAACGTCCTCTCTTTACTGCGTTAA |
| 0156 | Mutant MIM4 Primers design (for deletion aa Gln439; Asn440; Arg441; Phe442): | DNA | Artificial Sequence | AACCCACTGGCTTCAATTGATTCTGCATTGTCAAAAGTGGACGCAGTT CGTTCTTCTCTGGGGGCAATTCAAAACCGTTTTGATTCAGCCATTACC GCCCTTGGCGCTACGGTAACCGCTCTGGCCTCCGCGCGTAGCGCTATC GAAGATGCTGACTATGCAACGGAAGTTTCTCAAATG |
| 0157 | Mutant MIM4 Primers design (for deletion aa Gln439; Asn440; Arg441; Phe442): | PRT | Artificial Sequence | NPLASIDSALSKVDAVRSSLGAIQNRFDSAITALGATVTALASARSAI EDADYATEVSNM |

TABLE 1-continued

Illustrative Flagellin-Based Agents

| SEQ ID | Construct Name | DNA/PRT | Species | Sequence |
|---|---|---|---|---|
| 0158 | Mutant MIM4 Forward Primer MIM4 | DNA | Artificial Sequence | GCAGTTCGTTCTTCTCTGGGGGCAATTGATTCAGCCATTACCGCCCTT GG |
| 0159 | Mutant MIM4 Reverse Primer MIM4 | DNA | Artificial Sequence | CCAAGGGCGGTAATGGCTGAATCAATTGCCCCCAGAGAAGAACGAACT GC |
| 0160 | Mutant MIM4 MIM4 | DNA | Artificial Sequence | TAATACGACTCACTATAGGGGAATTGTGAGCGGATAACAATTCCCCTC TAGAAATAATTTTGTTTAACTTTAAGAAGGAGATATACATATGCGGGG TTCTCATCATCATCATCATCATGGTATGGCTAGCATGACTGGTGGACA GCAAATGGGTCGGGATCTGTACGACGATGACGATAAGGATCCGATGGC ACAAGTCATTAATACAAACAGCCTGTCGCTGTTGACCCAGAATAACCT GAACAAATCTCAGTCCTCACTGAGTTCCGCTATTGAGCGTCTGTCCTC TGGTCTGCGTATCAACAGCGCGAAAGACGATGCGGCAGGCCAGGCGAT TGCTAACCGCTTCACTTCTAATATCAAAGGTCTGACTCAGGCTTCCCG TAACGCTAACGACGGCATTTCTATTGCGCAGACCACTGAAGGTGCGCT GAATGAAATCAACAACAACCTGCAGCGTGTGCGTGAGTTGTCTGTTCA GGCCACTAACGGGACTAACTCTGATTCCGATCTGAAATCTATCCAGGA TGAAATTCAGCAACGTCTGGAAGAAATCGATCGCGTTTCTAATCAGAC TCAATTTAACGGTGTTAAAGTCCTGTCTCAGGACAACCAGATGAAAAT CCAGGTTGGTGCTAACGATGGTGAAACCATTACCATCGATCTGCAAAA AATTGATGTGAAAAGCCTTGGCCTTGATGGGTTCAATGTTAATTCCCC GGGAATTTCCGGTGGTGGTGGTGGAATTCTAGACTCCATGGGTACATT AATCAATGAAGACGCTGCCGCAGCCAAGAAAAGTACCGCTAACCCACT GGCTTCAATTGATTCTGCATTGTCAAAAGTGGACGCAGTTCGTTCTTC TCTGGGGGCAATTGATTCAGCCATTACCGCCCTTGGCGCTACGGTAAC CGCTCTGGCCTCCGCGGCTAGCCGTATCGAAGATGCTGACTATGCAAC GGAAGTTTCTAATATGTCTAAAGCGCAGATTCTGCAGCAGGCTGGTAC TTCCGTTCTGGCGCAGGCTAACCAGGTTCCGCAAAACGTCCTCTCTTT ACTGCGTTAA |
| 0161 | Mutant MIM4 MIM4 | PRT | Artificial Sequence | MRGSHHHHHHGMASMTGGQQMGRDLYDDDDKDPMAQVINTNSLSLLTQ NNLNKSQSSLSSAIERLSSGLRINSAKDDAAGQAIANRFTSNIKGLTQ ASRNANDGISIAQTTEGALNEINNNLQRVRELSVQATNGTNSDSDLKS IQDEIQRLEEIDRVSNQTQFNGVKVLSQDNQMKIQVGANDGETITID LQKIDVKSLGLDGFNVNSPGISGGGGGILDSMGTLINEDAAAAKSTA NPLASIDSALSKVDAVRSSLGAIDSAITALGATVTALASAASRIEDAD YATEVSNMSKAQILQQAGTSVLAQANQVPQNVLSLLR |
| 0162 | Mutant MIM5 Primers design (mutations Gln439Ala; Asn440Lys; Arg441Ala): | DNA | Artificial Sequence | AACCCACTGGCTTCAATTGATTCTGCATTGTCAAAAGTGGACGCAGTT CGTTCTTCTCTGGGGGCAATTGCAAAGGCTTTTGATTCAGCCATTACC GCCCTTGGCGCTACGGTAACCGCTCTGGCCTCCGCGCGTAGCGCTATC GAAGATGCTGACTATGCAACGGAAGTTTCTCAAATG |
| 0163 | Mutant MIM5 Primers design (mutations Gln439Ala; Asn440Lys; Arg441Ala): | PRT | Artificial Sequence | NPLASIDSALSKVDAVRSSLGAIAKAFDSAITALGATVTALASARSAI EDADYATEVSNM |
| 0164 | Mutant MIM5 Forward Primer MIM5 | DNA | Artificial Sequence | CGTTCTTCTCTGGGGGCAATTGCAAAGGCTTTTGATTCAGCCATTACC GC |
| 0165 | Mutant MIM5 Reverse Primer MIM5 | DNA | Artificial Sequence | GCGGTAATGGCTGAATCAAAAGCCTTTGCAATTGCCCCCAGAGAAGAA CG |
| 0166 | Mutant MIM5 MIM5 | DNA | Artificial Sequence | TAATACGACTCACTATAGGGGAATTGTGAGCGGATAACAATTCCCCTC TAGAAATAATTTTGTTTAACTTTAAGAAGGAGATATACATATGCGGGG TTCTCATCATCATCATCATCATGGTATGGCTAGCATGACTGGTGGACA GCAAATGGGTCGGGATCTGTACGACGATGACGATAAGGATCCGATGGC ACAAGTCATTAATACAAACAGCCTGTCGCTGTTGACCCAGAATAACCT GAACAAATCTCAGTCCTCACTGAGTTCCGCTATTGAGCGTCTGTCCTC TGGTCTGCGTATCAACAGCGCGAAAGACGATGCGGCAGGCCAGGCGAT TGCTAACCGCTTCACTTCTAATATCAAAGGTCTGACTCAGGCTTCCCG TAACGCTAACGACGGCATTTCTATTGCGCAGACCACTGAAGGTGCGCT GAATGAAATCAACAACAACCTGCAGCGTGTGCGTGAGTTGTCTGTTCA GGCCACTAACGGGACTAACTCTGATTCCGATCTGAAATCTATCCAGGA TGAAATTCAGCAACGTCTGGAAGAAATCGATCGCGTTTCTAATCAGAC TCAATTTAACGGTGTTAAAGTCCTGTCTCAGGACAACCAGATGAAAAT CCAGGTTGGTGCTAACGATGGTGAAACCATTACCATCGATCTGCAAAA AATTGATGTGAAAAGCCTTGGCCTTGATGGGTTCAATGTTAATTCCCC GGGAATTTCCGGTGGTGGTGGTGGAATTCTAGACTCCATGGGTACATT AATCAATGAAGACGCTGCCGCAGCCAAGAAAAGTACCGCTAACCCACT GGCTTCAATTGATTCTGCATTGTCAAAAGTGGACGCAGTTCGTTCTTC TCTGGGGGCAATTGCAAAGGCTTTTGATTCAGCCATTACCGCCCTTGG CGCTACGGTAACCGCTCTGGCCTCCGCGGCTAGCCGTATCGAAGATGC TGACTATGCAACGGAAGTTTCTAATATGTCTAAAGCGCAGATTCTGCA |

TABLE 1-continued

Illustrative Flagellin-Based Agents

| SEQ ID | Construct Name | DNA/PRT | Species | Sequence |
|---|---|---|---|---|
| | | | | GCAGGCTGGTACTTCCGTTCTGGCGCAGGCTAACCAGGTTCCGCAAAA CGTCCTCTCTTTACTGCGTTAA |
| 0167 | Mutant MIM5 MIM5 | PRT | Artificial Sequence | MRGSHHHHHHGMASMTGGQQMGRDLYDDDDKDPMAQVINTNSLSLLTQ NNLNKSQSSLSSAIERLSSGLRINSAKDDAAGQAIANRFTSNIKGLTQ ASRNANDGISIAQTTEGALNEINNNLQRVRELSVQATNGTNSDSDLKS IQDEIQQRLEEIDRVSNQTQFNGVKVLSQDNQMKIQVGANDGETITID LQKIDVKSLGLDGFNVNSPGISGGGGGILDSMGTLINEDAAAAKKSTA NPLASIDSALSKVDAVRSSLGAIAKAFDSAITALGATVTALASAASRI EDADYATEVSNMSKAQILQQAGTSVLAQANQVPQNVLSLLR |
| 0168 | Mutant MIMX Mutant 33MIMX | DNA | Artificial Sequence | ATGCGGGGTTCTCATCATCATCATCATCATGGTATGGCTAGCATGACT GGTGGACAGCAAATGGGTCGGGATCTGTACGACCTGGTTCCGCGCGGT AGCGCGAAGGATCCGTCTGGTCTGCGTATCAACAGCGCGAAAGACGAT GCGGCAGGCCAGGCGATTGCTAACCGCTTCACTTCTAATATCAAAGGT CTGACTCAGGCTTCCCGTAACGCTGCAGACGGCATTTCTATTGCGCAG ACCACTGAAGGTGCGCTGAATGAAATCAACAACAACCTGCAGCGTGTG CGTGAGTTGTCTGTTCAGGCCACTAACGGGACTAACTCTGATTCCGAT CTGAAATCTATCCAGGATGAAATTCAGCAACGTCTGGAAGAAATCGAT CGCGTTTCTAATCAGACTCAAGCTAACGGTGTTAAAGTCCTGTCTCAG GACAACGCAATGAAAATCCAGGTTGGTGCTAACGATGGTGCCGCTATT ACCATCGATCTGCAAAAAATTGATGTGAAAAGCCTTGGCCTTGATGGG TTCAATGTTAATTCCCCGGGAATTTCCGGTGGTGGTGGTGGAATTCTA GACTCCATGGGTACATTAATCAATGAAGACGCTGCCGCAGCCAAGAAA AGTACCGCTAACCCACTGGCTTCAATTGATTCTGCATTGTCAAAAGTG GACGCAGTTCGTTCTTCTCTGGGGGCAATTCAAGCTCGTTTTGCCGCG GCCATTGCTAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGCGTTAA |
| 0169 | Mutant MIMX MIMx | PRT | Artificial Sequence | MRGSHHHHHHGMASMTGGQQMGRDLYDLVPRGSAKDPSGLRINSAKDD AAGQAIANRFTSNIKGLTQASRNAADGISIAQTTEGALNEINNNLQRV RELSVQATNGTNSDSDLKSIQDEIQQRLEEIDRVSNQTQANGVKVLSQ DNAMKIQVGANDGAAITIDLQKIDVKSLGLDGFNVNSPGISGGGGGIL DSMGTLINEDAAAAKKSTANPLASIDSALSKVDAVRSSLGAIQARFAA AIANLGNTVTNLNSARSRIEDADYATEVSNMSKAQILQQAGTSVLAQA NQVPQNVLSLLR |
| 0170 | Mutant MIMX DNA sequence of 33MIMx | DNA | Artificial Sequence | TAATACGACTCACTATAGGGGAATTGTGAGCGGATAACAATTCCCCTC TAGAATAATTTTGTTTAACTTTAAGAAGGAGATATACATATGCGGGGT TCTCATCATCATCATCATCATGGTATGGCTAGCATGACTGGTGGACAG CAAATGGGTCGGGATCTGTACGACCTGGTTCCGCGCGGTAGCGCGAAG GATCCGTCTGGTCTGCGTATCAACAGCGCGAAAGACGATGCGGCAGGC CAGGCGATTGCTAACCGCTTCACTTCTAATATCAAAGGTCTGACTCAG GCTTCCCGTAACGCTGCAGACGGCATTTCTATTGCGCAGACCACTGAA GGTGCGCTGAATGAAATCAACAACAACCTGCAGCGTGTGCGTGAGTTG TCTGTTCAGGCCACTAACGGGACTAACTCTGATTCCGATCTGAAATCT ATCCAGGATGAAATTCAGCAACGTCTGGAAGAAATCGATCGCGTTTCT AATCAGACTCAAGCTAACGGTGTTAAAGTCCTGTCTCAGGACAACGCA ATGAAAATCCAGGTTGGTGCTAACGATGGTGCCGCTATTACCATCGAT CTGCAAAAAATTGATGTGAAAAGCCTTGGCCTTGATGGGTTCAATGTT AATTCCCCGGGAATTTCCGGTGGTGGTGGTGGAATTCTAGACTCCATG GGTACATTAATCAATGAAGACGCTGCCGCAGCCAAGAAAAGTACCGCT AACCCACTGGCTTCAATTGATTCTGCATTGTCAAAAGTGGACGCAGTT CGTTCTTCTCTGGGGGCAATTCAAGCTCGTTTTGCCGCGGCCATTGCT AACCTTGGCAATACGGTAACCAATCTGAACTCCGCGCGTAGCCGTATC GAAGATGCTGACTATGCAACGGAAGTTTCTAATATGTCTAAAGCGCAG ATTCTGCAGCAGGCTGGTACTTCCGTTCTGGCGCAGGCTAACCAGGTT CCGCAAAACGTCCTCTCTTTACTGCGTTAAGTCGAC |
| 0171 | Mutant MIXC Reverse primer RMIXC | DNA | Artificial Sequence | AGATCTGTCGACTTAACCATGATGATGATGATGATGAGAACCCCGCGG AACCAGTAAAGAGAGGACGTTTTGCGGAACC |
| 0172 | Mutant MIXC DNA sequence of MIXC | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA |

TABLE 1-continued

Illustrative Flagellin-Based Agents

| SEQ ID | Construct Name | DNA/PRT | Species | Sequence |
|---|---|---|---|---|
| | | | | AGTACCGCTAACCCACTGGCTTCAATTGATTCTGCATTGTCAAAAGTG GACGCAGTTCGTTCTTCTGGGGGCAATTCAAGCTCGTTTTGCCGCG GCCATTGCTAACCTTGGCAATACGGTAACCAATCTGAACTCCGCGCGT AGCCGTATCGAAGATGCTGACTATGCAACGGAAGTTTCTAATATGTCT AAAGCGCAGATT TABLE 1-continued Illustrative Flagellin-Based Agents

| SEQ ID | Construct Name | DNA/PRT | Species | Sequence |
|---|---|---|---|---|
| 0183 | Mutants MIM1; MIM2 and MIM3 Primers design (mutant MIM2_MIM1 plus R460A) | PRT | Artificial Sequence | TVTALASARSRIEDADYATE |
| 0184 | Mutants MIM1; MIM2 and MIM3 Forward Primer 460 | DNA | Artificial Sequence | GCTCTGGCCTCCGCGGCTAGCCGTATCGAAGATG |
| 0185 | Mutants MIM1; MIM2 and MIM3 Reverse Primer 460 | DNA | Artificial Sequence | CATCTTCGATACGGCTAGCCGCGGAGGCCAGAGC |
| 0186 | Mutants MIM1; MIM2 and MIM3 Primers design (mutant MIM3_MIM2 plus N448A; N451A) | DNA | Artificial Sequence | CAAAACCGTTTTGATTCAGCCATTACCAACCTTGGCAATACGGTAACCGCTCTGGCCTCC |
| 0187 | Mutants MIM1; MIM2 and MIM3 Primers design (mutant MIM3_MIM2 plus N448A; N451A) | PRT | Artificial Sequence | QNRFDSAITNLGNTVTALAS |
| 0188 | Mutants MIM1; MIM2 and MIM3 Forward Primer 448-51 | DNA | Artificial Sequence | GTTTTGATTCAGCCATTACCGCCCTTGGCGCTACGGTAACCGCTCTGG |
| 0189 | Mutants MIM1; MIM2 and MIM3 Reverse Primer 448-51 | DNA | Artificial Sequence | CCAGAGCGGTTACCGTAGCGCCAAGGGCGGTAATGGCTGAATCAAAAC |
| 0190 | Mutant ME42 Forward Primer ME42 | DNA | Artificial Sequence | CAACAGCGCGAAAGCCGATGCGGGAGGCCAGGCGATTGC |
| 0191 | Mutant ME42 Reverse Primer ME42 | DNA | Artificial Sequence | GCAATCGCCTGGCCTCCCGCATCGGCTTTCGCGCTGTTG |
| 0192 | Mutant ME42 Sequence of ME42 construct | DNA | Artificial Sequence | TAATACGACTCACTATAGGGGAATTGTGAGCGGATAACAATTCCCCTCTAGAATAATTTTGTTTAACTTTAAGAAGGAGATATACATATGAGCGGGTTACGGATCAACAGCGCGAAAGCCGATGCGGGAGGCCAGGCGATTGCTAACCGCTTCACTTCTAATATCAAAGGTCTGACTCAGGCTTCCCGTAACGCTAACGACGGCATTTCTATTGCGCAGACCACTGAAGGTGCGCTGAATGAAATCAACAACAACCTGCAGCGTGTGCGTGAGTTGTCTGTTCAGGCCACTAACGGGACTAACTCTGATTCCGATCTGAAATCTATCCAGGATGAAATTCAGCAACGTCTGGAAGAAATCGATCGCGTTTCTAATCAGACTCAATTTAACGGTGTTAAAGTCCTGTCTCAGGACAACCAGATGAAAATCCAGGTTGGTGCTAACGATGGTGAAACCATTACCATCGATCTGCAAAAAATTGATGTGAAAAGCCTTGGCCTTGATGGGTTCAATGTTAATTCCCCGGGAAGTACCGCTAACCCACTGGCTTCAATTGATTCTGCATTGTCAAAAGTGGACGCAGTTCGTTCTTCTCTGGGGGCAATTCAAAACCGCTTTGATTCAGCCATTACCAACCTTGGCAATACGGTAACCAATCTGAACTCCGCGCGTAGCCGTATCGAAGATGCTGACTATGCAACGGAAGTTTCTAATATGTCTAAAGCGCAGATTCTGCAGCAGGCTGGTACTTCCGTTCTGGCGCAGGCTAACCAGGTTCCGCAAAACGTCCTCTCTTTACTGGTTCCGCGGGGTTCTCATCATCATCATCATGGTTAAGTCGAC |
| 0193 | Mutant ME42 Mutant ME42 | PRT | Artificial Sequence | MSGLRINSAKADAGGQAIANRFTSNIKGLTQASRNANDGISIAQTTEGALNEINNNLQRVRELSVQATNGTNSDDLKSIQDEIQQRLEEIDRVSNQTQFNGVKVLSQDNQMKIQVGANDGETITIDLQKIDVKSLGLDGFNVNSPGSTANPLASIDSALSKVDAVRSSLGAIQNRFDSAITNLGNTVTNLNSARSRIEDADYATEVSNMSKAQILQQAGTSVLAQANQVPQNVLSLLVPRGSHHHHHHG |
| 0194 | Mutant ME110 Forward Primer ME100 | DNA | Artificial Sequence | GTCTGTTCAGGCCACTGCCGGGGCTAACTCTGATTCCGATCTG |
| 0195 | Mutant ME110 Reverse Primer ME100 | DNA | Artificial Sequence | CAGATCGGAATCAGAGTTAGCCCCGGCAGTGGCCTGAACAGAC |
| 0196 | Mutant ME110 Sequence of ME100 construct | DNA | Artificial Sequence | TAATACGACTCACTATAGGGGAATTGTGAGCGGATAACAATTCCCCTCTAGAATAATTTTGTTTAACTTTAAGAAGGAGATATACATATGAGCGGGTTACGGATCAACAGCGCGAAAGACGATGCGGCAGGCCAGGCGATTGCT |

TABLE 1-continued

Illustrative Flagellin-Based Agents

| SEQ ID | Construct Name | DNA/PRT | Species | Sequence |
|---|---|---|---|---|
| | | | | AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTGCCGGGGCTAACTCTGATTCCGATCTGAAATCTATCCAGGATGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATCATGGTTAAGTCGAC |
| 0197 | Mutant ME110<br>Mutant ME110 | PRT | Artificial Sequence | MSGLRINSAKDDAAGQAIANRFTSNIKGLTQASRNANDGISIAQTTEG ALNEINNNLQRVRELSVQATAGANSDSDLKSIQDEIQQRLEEIDRVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYATEVSNMSKAQILQQAGTSVLAQANQVPQNVLSLLVP RGSHHHHHHG |
| 0198 | Mutant ME100/110<br>Forward Primer ME110 | DNA | Artificial Sequence | CTGATTCCGATCTGAAAGCTATCCAGGCTGAAATTCAGCAACGTC |
| 0199 | Mutant ME100/110<br>Reverse Primer ME110 | DNA | Artificial Sequence | GACGTTGCTGAATTTCAGCCTGGATAGCTTTCAGATCGGAATCAG |
| 0200 | Mutant ME100/110<br>Sequence of ME100/110 construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTGCCGGGGCTAACTCTGATTCCGATCTGAAAGCTATCCAGGCTGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATCATGGTTAAGTCGAC |
| 0201 | Mutant ME104N<br>Intermediate Mutant ME100/110 | DNA | Artificial Sequence | ATGAGCGGGTTACGGATCAACAGCGCGAAAGACGATGCGGCAGGCCAG GCGATTGCTAACCGCTTCACTTCTAATATCAAAGGTCTGACTCAGGCT TCCCGTAACGCTAACGACGGCATTTCTATTGCGCAGACCACTGAAGGT GCGCTGAATGAAATCAACAACAACCTGCAGCGTGTGCGTGAGTTGTCT GTTCAGGCCACTGCCGGGGCTAACTCTGATTCCGATCTGAAAGCTATC CAGGCTGAAATTCAGCAACGTCTGGAAGAAATCGATCGCGTTTCTAAT CAGACTCAATTTAACGGTGTTAAAGTCCTGTCTCAGGACAACCAGATG AAAATCCAGGTTGGTGCTAACGATGGTGAAACCATTACCATCGATCTG CAAAAAATTGATGTGAAAAGCCTTGGCCTTGATGGGTTCAATGTTAAT TCCCCGGGAAGTACCGCTAACCCACTGGCTTCAATTGATTCTGCATTG TCAAAAGTGGACGCAGTTCGTTCTTCTCTGGGGGCAATTCAAAACCGC TTTGATTCAGCCATTACCAACCTTGGCAATACGGTAACCAATCTGAAC TCCGCGCGTAGCCGTATCGAAGATGCTGACTATGCAACGGAAGTTTCT AATATGTCTAAAGCGCAGATTCTGCAGCAGGCTGGTACTTCCGTTCTG GCGCAGGCTAACCAGGTTCCGCAAAACGTCCTCTCTTTACTGGTTCCG CGGGGTTCTCATCATCATCATCATCATGGTTAA |
| 0202 | Mutant ME100/110<br>Mutant ME110/110 | PRT | Artificial Sequence | MSGLRINSAKDDAAGQAIANRFTSNIKGLTQASRNANDGISIAQTTEG ALNEINNNLQRVRELSVQATAGANSDSDLKAIQAEIQQRLEEIDRVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYATEVSNMSKAQILQQAGTSVLAQANQVPQNVLSLLVP RGSHHHHHHG |
| 0203 | Mutant ME104<br>Forward Primer ME104 | DNA | Artificial Sequence | GCCACTAACGGGACTAACGCTGATGCCGCTCTGAAATCTATCCAG |

TABLE 1-continued

Illustrative Flagellin-Based Agents

| SEQ ID | Construct Name | DNA/PRT | Species | Sequence |
|---|---|---|---|---|
| 0204 | Mutant ME104 Reverse Primer ME104 | DNA | Artificial Sequence | CTGGATAGATTTCAGAGCGGCATCAGCGTTAGTCCCGTTAGTGGC |
| 0205 | Mutant ME104 Sequence of ME104 construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACGCTGATGCCGCTCTGAAATCTATCCAGGATGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATGGTTAAGTCGAC |
| 0206 | Mutant ME104 Mutant ME104 | PRT | Artificial Sequence | MSGLRINSAKDDAAGQAIANRFTSNIKGLTQASRNANDGISIAQTTEG ALNEINNNLQRVRELSVQATNGTNADAALKSIQDEIQQRLEEIDRVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYATEVSNMSKAQILQQAGTSVLAQANQVPQNVLSLLVP RGSHHHHHHG |
| 0207 | Mutant ME104N Primer FME104New | DNA | Artificial Sequence | GCCACTGCCGGGGCTAACGCTGATGCCGCTCTGAAAGCTATCCAG |
| 0208 | Mutant ME104N Primer RME104New | DNA | Artificial Sequence | CTGGATAGCTTTCAGAGCGGCATCAGCGTTAGCCCCGGCAGTGGC |
| 0209 | Mutant ME104N Sequence of construct ME104New | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTGCCGGGGCTAACGCTGATGCCGCTCTGAAAGCTATCCAGGCTGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATGGTTAAGTCGAC |
| 0210 | Mutant ME104N Mutant ME104N | PRT | Artificial Sequence | MSGLRINSAKDDAAGQAIANRFTSNIKGLTQASRNANDGISIAQTTEG ALNEINNNLQRVRELSVQATAGANADAALKAIQAEIQQRLEEIDRVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYATEVSNMSKAQILQQAGTSVLAQANQVPQNVLSLLVP RGSHHHHHHG |
| 0211 | Mutant ME110 Sequence of ME110 construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAAGCTATCCAGGCTGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT |

TABLE 1-continued

Illustrative Flagellin-Based Agents

| SEQ ID | Construct Name | DNA/PRT | Species | Sequence |
|---|---|---|---|---|
| | | | | AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATGGTTAAGTCGAC |
| 0212 | Mutant ME110 Mutant ME110 | PRT | Artificial Sequence | MSGLRINSAKDDAAGQAIANRFTSNIKGLTQASRNANDGISIAQTTEG ALNEINNNLQRVRELSVQATNGTNSDSDLKAIQAEIQQRLEEIDRVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYATEVSNMSKAQILQQAGTSVLAQANQVPQNVLSLLVP RGSHHHHHHG |
| 0213 | Mutant ME117 Forward Primer ME117 | DNA | Artificial Sequence | CTATCCAGGATGAAATTCAGGCACGTCTGGCAGAAATCGATCGCG |
| 0214 | Mutant ME117 Reverse Primer ME117 | DNA | Artificial Sequence | CGCGATCGATTTCTGCCAGACGTGCCTGAATTTCATCCTGGATAG |
| 0215 | Mutant ME117 Sequence of 33ML construct (should this say ME117?) | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGGCACGTCTGGCAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATGGTTAAGTCGAC |
| 0216 | Mutant ME117 Mutant ME117 | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQARLAEIDRVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYATEVSNMSKAQILQQAGTSVLAQANQVPQNVLSLLVP RGSHHHHHHG |
| 0217 | Mutant ME124 Forward Primer ME104 | DNA | Artificial Sequence | GGAAGAAATCGATGCCGTTTCTGCTGCGACTCAATTTAACGGTGTTAA AGTCCTGTCTC |
| 0218 | Mutant ME124 Reverse Primer ME104 | DNA | Artificial Sequence | GAGACAGGACTTTAACACCGTTAAATTGAGTCGCAGCAGAAACGGCAT CGATTTCTTCC |
| 0219 | Mutant ME124 Sequence of ME124 construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATGCCGTTTCTGCTGCGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATGGTTAAGTCGAC |
| 0220 | Mutant ME124 Mutant ME124 | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDAVSA ATQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYATEVSNMSKAQILQQAGTSVLAQANQVPQNVLSLLVP RGSHHHHHHG |

TABLE 1-continued

Illustrative Flagellin-Based Agents

| SEQ ID | Construct Name | DNA/PRT | Species | Sequence |
|---|---|---|---|---|
| 0221 | Mutant ME124P Forward Primer ME124P | DNA | Artificial Sequence | CAGCAACGTCTGGAAGAAATCGATGCCGTTTCTAATCAGACTCAATTT AACGG |
| 0222 | Mutant ME124P Reverse Primer ME124P | DNA | Artificial Sequence | CCGTTAAATTGAGTCTGATTAGAAACGGCATCGATTTCTTCCAGACGT TGCTG |
| 0223 | Mutant ME124 Expressed Mutant ME124P | DNA | Artificial Sequence | ATGAGCGGGTTACGGATCAACAGCGCGAAAGACGATGCGGCAGGCCAG GCGATTGCTAACCGCTTCACTTCTAATATCAAAGGTCTGACTCAGGCT TCCCGTAACGCTAACGACGGCATTTCTATTGCGCAGACCACTGAAGGT GCGCTGAATGAAATCAACAACAACCTGCAGCGTGTGCGTGAGTTGTCT GTTCAGGCCACTAACGGGACTAACTCTGATTCCGATCTGAAATCTATC CAGGATGAAATTCAGCAACGTCTGGAAGAAATCGATGCCGTTTCTAAT CAGACTCAATTTAACGGTGTTAAAGTCCTGTCTCAGGACAACCAGATG AAAATCCAGGTTGGTGCTAACGATGGTGAAACCATTACCATCGATCTG CAAAAAATTGATGTGAAAAGCCTTGGCCTTGATGGGTTCAATGTTAAT TCCCCGGGAAGTACCGCTAACCCACTGGCTTCAATTGATTCTGCATTG TCAAAAGTGGACGCAGTTCGTTCTTCTCTGGGGGCAATTCAAAACCGC TTTGATTCAGCCATTACCAACCTTGGCAATACGGTAACCAATCTGAAC TCCGCGCGTAGCCGTATCGAAGATGCTGACTATGCAACGGAAGTTTCT AATATGTCTAAAGCGCAGATTCTGCAGCAGGCTGGTACTTCCGTTCTG GCGCAGGCTAACCAGGTTCCGCAAAACGTCCTCTCTTTACTGGTTCCG CGGGGTTCTCATCATCATCATCATCATGGTTAA |
| 0224 | Mutant ME124P ME124P | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATGCCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATCATGGTTAAGTCGAC |
| 0225 | Mutant ME124P ME124P | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDAVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYATEVSNMSKAQILQQAGTSVLAQANQVPQNVLSLLVP RGSHHHHHHG |
| 0226 | Mutant ME132 Forward Primer ME132 | DNA | Artificial Sequence | CGTTTCTAATCAGACTCAATTTGCCGCTGTTAAAGTCCTGTCTCAGGA CAACC |
| 0227 | Mutant ME132 Reverse Primer ME132 | DNA | Artificial Sequence | GGTTGTCCTGAGACAGGACTTTAACAGCGGCAAATTGAGTCTGATTAG AAACG |
| 0228 | Mutant ME132 Sequence of ME132 construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATCGCGTTTCTAATCAGACTCAA TTTGCCGCTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATCATGGTTAAGTCGAC |

TABLE 1-continued

Illustrative Flagellin-Based Agents

| SEQ ID | Construct Name | DNA/PRT | Species | Sequence |
|---|---|---|---|---|
| 0229 | Mutant ME132 Mutant ME117 (ME132?) | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDRVSN QTQFAAVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADYATEVSNMSKAQILQQAGTSVLAQANQVPQNVLSLLVP RGSHHHHHHG |
| 0230 | Mutant ME142 Forward Primer ME142 | DNA | Artificial Sequence | GTTAAAGTCCTGTCTCAGGACAACGCGATGGCAATCCAGGTTGGTGCT AACG |
| 0231 | Mutant ME142 Reverse Primer ME142 | DNA | Artificial Sequence | CGTTAGCACCAACCTGGATTGCCATCGCGTTGTCCTGAGACAGGACTT TAAC |
| 0232 | Mutant ME142 Sequence of ME142 construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATCGCGTTTCTAATCAGACTCAA TTTAACGGTGTTAAAGTCCTGTCTCAGGACAACGCGATGGCAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATCATGGTTAAGTCGAC |
| 0233 | Mutant ME142 Mutant ME142 | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDRVSN QTQFNGVKVLSQDNAMAIQVGANDGETITIDLQKIDVKSLGLDGFNVN SPGSTANPLASIDSALSKVDAVRSSLGAIQNRFDSAITNLGNTVTNLN SARSRIEDADYATEVSNMSKAQILQQAGTSVLAQANQVPQNVLSLLVP RGSHHHHHHG |
| 0234 | Mutant ME150 Forward Primer ME150 | DNA | Artificial Sequence | GATGAAAATCCAGGTTGGTGCTAGCGCTGCTGAAACCATTACCATCGA TCTGC |
| 0235 | Mutant ME150 Reverse Primer ME150 | DNA | Artificial Sequence | GCAGATCGATGGTAATGGTTTCAGCAGCGCTAGCACCAACCTGGATTT TCATC |
| 0236 | Mutant ME150 Sequence of ME150 construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAGCGCTGCTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTTGGCAATACGGTAACCAATCTGAACTCCGCGCGT AGCCGTATCGAAGATGCTGACTATGCAACGGAAGTTTCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATCATGGTTAAGTCGAC |
| 0237 | Mutant ME150 Mutant ME150 | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDRVSN QTQFNGVKVLSQDNQMKIQVGASAAETITIDLQKIDVKSLGLDGFNVN SPGSTANPLASIDSALSKVDAVRSSLGAIQNRFDSAITNLGNTVTNLN SARSRIEDADYATEVSNMSKAQILQQAGTSVLAQANQVPQNVLSLLVP RGSHHHHHHG |
| 0238 | Mutant ME468 Forward Primer ME468 | DNA | Artificial Sequence | GCCGTATCGAAGATGCTGACGCTGGAGCGGAAGTTGCTAATATGTCTA AAGCGCAG |

TABLE 1-continued

Illustrative Flagellin-Based Agents

| SEQ ID | Construct Name | DNA/PRT | Species | Sequence |
|---|---|---|---|---|
| 0239 | Mutant ME468 Reverse Primer ME468 | DNA | Artificial Sequence | CTGCGCTTTAGACATATTAGCAACTTCCGCTCCAGCGTCAGCATCTTC GATACGGC |
| 0240 | Mutant ME468 Sequence of ME468 construct | DNA | Artificial Sequence | TAATACGACTCACTATAGGGGAATTGTGAGCGGATAACAATTCCCCTC TAGAATAATTTTGTTTAACTTTAAGAAGGAGATATACATATGAGCGGG TTACGGATCAACAGCGCGAAAGACGATGCGGCAGGCCAGGCGATTGCT AACCGCTTCACTTCTAATATCAAAGGTCTGACTCAGGCTTCCCGTAAC GCTAACGACGGCATTTCTATTGCGCAGACCACTGAAGGTGCGCTGAAT GAAATCAACAACAACCTGCAGCGTGTGCGTGAGTTGTCTGTTCAGGCC ACTAACGGGACTAACTCTGATTCCGATCTGAAATCTATCCAGGATGAA ATTCAGCAACGTCTGGAAGAAATCGATCGCGTTTCTAATCAGACTCAA TTTAACGGTGTTAAAGTCCTGTCTCAGGACAACCAGATGAAAATCCAG GTTGGTGCTAACGATGGTGAAACCATTACCATCGATCTGCAAAAAATT GATGTGAAAAGCCTTGGCCTTGATGGGTTCAATGTTAATTCCCCGGGA AGTACCGCTAACCCACTGGCTTCAATTGATTCTGCATTGTCAAAAGTG GACGCAGTTCGTTCTTCTCTGGGGGCAATTCAAAACCGCTTTGATTCA GCCATTACCAACCTGGCAATACGGTAACCAATCTGAACTCCGCGCGT AGCCGTATCGAAGATGCTGACGCTGGAGCGGAAGTTGCTAATATGTCT AAAGCGCAGATTCTGCAGCAGGCTGGTACTTCCGTTCTGGCGCAGGCT AACCAGGTTCCGCAAAACGTCCTCTCTTTACTGGTTCCGCGGGGTTCT CATCATCATCATCATCATGGTTAAGTCGAC |
| 0241 | Mutant ME468 Mutant ME468 | PRT | Artificial Sequence | MSGLRINSAKDDAAGQAIANRFTSNIKGLTQASRNANDGISIAQTTEG ALNEINNNLQRVRELSVQATNGTNSDSDLKSIQDEIQQRLEEIDRVSN QTQFNGVKVLSQDNQMKIQVGANDGETITIDLQKIDVKSLGLDGFNVN SPGSTANPLASIDSALSKVDAVRSSLGAIQNRFDSAITNLGNTVTNLN SARSRIEDADAGAEVANMSKAQILQQAGTSVLAQANQVPQNVLSLLVP RGSHHHHHHG |
| 0242 | Linker | PRT | Artificial Sequence | SPG |
| 0243 | Lru283 | PRT | Artificial Sequence | mghhhhhhsgMEEFNMRINTNVAAMNTYSRLTAANTAKSNSLAKLSSG LRINKAGDDAAGLAISEKMKSQIGGLTQAKRNAQDGISLVQTAEGALN ETHSILERMRDLAVQGSNGTLTSSDRGSINKELKALHQELTRISNTTE FNTQKLFSQTKQKSVTFTFQIGANAGQTLSVAITAMSGEALLVSTDAK FSLNAAGTNAGAMIKSIDAAIAKVSDQRADLGAVQNRLEHTINNLTAT NENLSDANSRIRDVDMAEEMMTFTKSNILSQAATSMLAQANAMPNSVL NLLQG |
| 0244 | Tpe270 | PRT | Artificial Sequence | mghhhhhhsgMRINHNISALNAWRNIDQTQYSMSKTLERLSSGLRINR AGDDAAGLAISEKMRGQIKGLNMAIKNAQDAISLIQTAEGALTEVHSI LQRMRELAVQAASDTNTNVDREQIQKEIDQLREEIDRIARTTEFNTKK LLDGKLEGFRSQVDAKVVTGGNINVQLGTVSSKAVEGTYVIEVGaAER AIMVVDDAAIHRVSTARAALGAIQNRLEHTISNLGVAAENLTAAESRIR DADMAKEMMEFTKQQILLQSSMAMLAQSNTLPQNVLQLMR |
| 0245 | Tpe159w | PRT | Artificial Sequence | mghhhhhhsGLNMAIKNAQDAISLIQTAEGALTEVHSILQRMRELAVQ AASDTNTNVDREQIQKEIDQLREEIDRIARTTEFNTKKLLDGKLEGFR SQVDAKVVTGGNINVQLGTVSSKAVEGTYVIEVGaAERAIMVVDAAIH RVSTARAALGAIQNRLEHTISNLG |
| 0246 | Chy275 | PRT | Artificial Sequence | mghhhhhhsgMSLRINNNIEALNAWRALNSTSNALQKSMEKLSSGLRI NRAGDDAAGLAISEKLRAQIRGLNQAIRNAQDGISLIQTAEGGLSEIQ NILQRMRELGVQAANGTLNNQDISAITTELNQLFNEIDRIAGATEFNT KNLLAVSTGLVVTLQVGANAGQVIAFTIDNAGTASLGLSSADLAINDN ASASAFISKVDSALQKVSTYRANLGSIQNRLEHTIANLGIASENLSAS ESRIRDVDMAAEMMNFTKNQILQQAGVAILAQANQAPQAVLQLLR |
| 0247 | Chy162w | PRT | Artificial Sequence | mghhhhhhsGLNQAIRNAQDGISLIQTAEGGLSEIQNILQRMRELGVQ AANGTLNNQDISAITTELNQLFNEIDRIAGATEFNTKNLLAVSTGLVV TLQVGANAGQVIAFTIDNAGTASLGLSSADLAINDNASASAFISKVDS ALQKVSTYRANLGSIQNRLEHTIANLG |
| 0248 | ChyU137 | PRT | Artificial Sequence | mghhhhhhsGLNQAIRNAQDGISLIQTAEGGLSEIQNILQRMRELGVQ AANGTLNNQDISAITTELNQLFNEIDRIAGATEFNTKNLLAAGTASLG LSSADLAINDNASASAFISKVDSALQKVSTYRANLGSIQNRLEHTIAN LG |
| 0249 | ChyN108 | PRT | Artificial Sequence | mghhhhhhSASAFISKVDSALQKVSTYRANLGSIQNRLEHTIANLGpd GLNQAIRNAQDGISLIQTAEGGLSEIQNILQRMRELGVQAANGTLNNQ DISAITTELNQLFNEIDRIA |

TABLE 1-continued

Illustrative Flagellin-Based Agents

| SEQ ID | Construct Name | DNA/PRT | Species | Sequence |
|---|---|---|---|---|
| 0250 | ChyZ94 | PRT | Artificial Sequence | mghhhhhhsNNQDISAITTELNQLFNEIDRIAGATgsGGLSEIQNILQ RMRELGVQAANGTLNggSASAFISKVDSALQKVSTYRANLGSIQNRLE HTIANLG |
| 0251 | Fir161B | PRT | Artificial Sequence | mghhhhhhsGLAQASRNAQDAISIAQTAEGALDETQSILQRVRELGVQ GANGTLTADDINALQAEVDQLIAEIDRIAGATEFNTQNLLDGSFTTKA FQVGANSGQNMTLTIGKMDTTTLGLSSADLAINDNAFANGAISTVDSA LQKVSAERAKLGAIQNRLEHTIANLG |
| 0252 | Fir161MNB | PRT | Artificial Sequence | mghhhhhhsGLAQASRQAQDAISIAQTAEGALDETQSILQRVRELGVQ GADGTLTADDIDALQAEVDQLIAEIDRIAGATEFATQKLLDGSFTTKA FQVGAASGQDVTLTIGKVDTTTLGLSSADLAIDSAAFADGAISTVDSA LQKVSAERAKLGAIQNRLEHTIAQLG |

In some embodiments, the aluminum gel or salt is selected from aluminum hydroxide, aluminum phosphate, and potassium aluminum sulfate, AS04 (which is composed of aluminum salt and MPL), and ALHYDROGEL. In some embodiments, the aluminum gel or salt is a formulation or mixture with any of the additional adjuvants described herein.

In some embodiments, adjuvants in addition to the described flagellin-based agent and an aluminum gel or salt find use in the present invention. In some embodiments, the additional adjuvant is selected from, oil-in-water emulsion formulations, saponin adjuvants, ovalbumin, Freunds Adjuvant, cytokines, and chitosans. Illustrative additional adjuvants include, but are not limited to: (1) ovalbumin (e.g. ENDOFIT), which is often used for biochemical studies; (2) oil-in-water emulsion formulations (with or without other specific immunostimulating agents such as muramyl peptides or bacterial cell wall components), such as for example (a) MF59 (PCT Publ. No. WO 90/14837), containing 5% Squalene, 0.5% Tween 80, and 0.5% Span 85 (optionally containing various amounts of MTP-PE) formulated into submicron particles using a microfluidizer such as, for example, Model HOy microfluidizer (Microfluidics, Newton, Mass.), (b) SAF, containing 10% Squalane, 0.4% Tween 80, 5% pluronic-blocked polymer L121, and thr-MDP either microfluidized into a submicron emulsion or vortexed to generate a larger particle size emulsion, (c) RIBI adjuvant system (RAS), (RIBI IMMUNOCHEM, Hamilton, Mo.) containing 2% Squalene, 0.2% Tween 80, and, optionally, one or more bacterial cell wall components from the group of monophosphorylipid A (MPL), trehalose dimycolate (TDM), and cell wall skeleton (CWS), including MPL+ CWS (DETOX™); and (d) ADDAVAX (Invitrogen); (3) saponin adjuvants, such as STIMULON (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (by way of non-limiting example, IL-1, IL-2, IL-4, IL-5, IL-, IL-6, IL-7, IL-12, etc.), interferons (e.g., gamma interferon), macrophage colony stimulating factor (M-CSF), tumor necrosis factor (TNF), etc; (6) chitosans and other derivatives of chitin or poly-N-acetyl-D-glucosamine in which the greater proportion of the N-acetyl groups have been removed through hydrolysis (see, e.g., European Patent Application 460 020, which is hereby incorporated by reference in its entirety, disclosing pharmaceutical formulations including chitosans as mucosal absorption enhancers; and (7) other substances that act as immunostimulating agents to enhance the effectiveness of the composition, e.g., monophosphoryl lipid A. In other embodiments, the additional adjuvant is one or more of a flagellin-based agent (e.g. CBLB502 or any of the agents of Table 1), an aluminium salt or gel, a pattern recognition receptors (PRR) agonist, CpG ODNs and imidazoquinolines. In some embodiments, the additional adjuvant is one or more of cyclic [G(3',5')pA(3',5')p] (e.g. 33'-cGAMP VACCIGRADE); cyclic [G(2,5')pA(3',5')p]2'3 (e.g. 2'3 cGAMP VACCIGRADE); cyclic [G(2',5')pA(2',5')p] (e.g. 2'2-cGAMP VACCIGRADE), cyclic diadenylate monophosphate (e.g. c-di-AMP VACCIGRADE); cyclic diguanylate monophosphate (e.g. c-di-GMP VACCIGRADE); TLR7 agonist-imidazoquinolines compound (e.g. TLR7 agonists, such as, for example, Gardiquimod VACCIGRADE, Imiquimod VACCIGRADE, R848 VACCIGRADE); lipopolysaccharides (e.g. TLR4 agonists), such as that from E. coli 0111:B4 strain (e.g. LPS-EB VACCIGRADE); monophosphoryl lipid A (e.g. MPLA-SM VACCIGRADE and MPLA Synthetic VACCIGRADE); N-glycolylated muramyldipeptide (e.g. N-Glycolyl-MDP VACCIGRADE); CpG ODN, class A and/oror CpG ODN, class B and/or CpG ODN, class C (e.g. ODN 1585 VACCIGRADE, ODN 1826 VACCIGRADE, ODN 2006 VACCIGRADE, ODN 2395 VACCIGRADE), a triacylated lipoprotein (e.g. Pam3CSK4 VACCIGRADE); Polyinosinepolycytidylic acid (e.g. Poly(I:C) (HMW) VACCIGRADE); and cord factor (i.e. mycobacterial cell wall component trehalose 6,6' dimycolate (TDM,)) or an analog thereof (e.g. TDB VACCIGRADE, TDB-HS15 VACCIGRADE). In some embodiments, the additional adjuvant is a TLR agonist (e.g. TLR1, and/or TLR2, and/or TLR3, and/or TLR4, and/or TLR5, and/or TLR6, and/or TLR7, and/or TLR8, and/or TLR9, and/or TLR10, and/or TLR11, and/or TLR12, and/or TLR13), a nucleotide-binding oligomerization domain (NOD) agonist, a stimulator of interferon genes (STING) ligand, or related agent.

In some embodiments, the additional adjuvants is one or more of a mineral adjuvant, gel-based adjuvant, tensoactive agent, bacterial product, oil emulsion, particulated adjuvant, fusion protein, and lipopeptide. Other mineral salt adjuvants, besides the aluminum adjuvants described elsewhere, include salts of calcium (e.g. calcium phosphate), iron and zirconium. Other gel-based adjuvants, besides the aluminum gel-based adjuvants described elsewhere, include Acemannan. Tensoactive agents include Quil A, saponin derived from an aqueous extract from the bark of *Quillaja saponaria*; saponins, tensoactive glycosides containing a hydrophobic nucleus of triterpenoid structure with carbohydrate chains linked to the nucleus, and QS-21. Bacterial products include cell wall peptidoglycan or lipopolysaccharide of Gram-negative bacteria (e.g. from *Mycobacterium* spp., *Corynebacterium parvum, C. granulosum, Bordetella pertussis* and *Neisseria meningitidis*), N-acetyl muramyl-L-alanyl-D-isoglutamine (MDP), different compounds derived from MDP (e.g. threonyl-MDP), lipopolysaccharides (LPS) (e.g. from the cell wall of Gram-negative bacteria), trehalose dimycolate (TDM), and DNA containing CpG motifs. Oil emulsions include FIA, Montanide, Adjuvant 65, Lipovant, the montanide family of oil-based adjuvants, and various liposomes. Among particulated and polymeric systems, poly (DL-lactide-coglycolide) microspheres have been extensively studied and find use herein.

Further, in some embodiments, cytokines are an adjuvant of the present invention (e.g. IFN-γ and granulocyte-macrophage colony stimulating factor (GM-CSF)). Also carbohydrate adjuvants (e.g. inulin-derived adjuvants, such as, gamma inulin, algammulin (a combination of γ-inulin and aluminum hydroxide), and polysaccharides based on glucose and mannose, such as glucans, dextrans, lentinans, glucomannans and galactomannans) find use in the present invention. In some embodiments, adjuvant formulations are useful in the present invention and include alum salts in combination with other adjuvants such as Lipid A, algammulin, immunostimulatory complexes (ISCOMS), which are virus like particles of 30-40 nm and dodecahedric structure, composed of Quil A, lipids, and cholesterol.

In some embodiments, the additional adjuvants are described in Jennings et al. Adjuvants and Delivery Systems for Viral Vaccines-Mechanisms and Potential. In: Brown F, Haaheim L R, (eds). *Modulation of the Immune Response to Vaccine Antigens. Dev. Bol. Stand*, Vol. 92. Basel: Karger 1998; 19-28 and/or Sayers at al. J Biomed Biotechnol. 2012; 2012: 831486, and/or Petrovsky and Aguilar, *Immunology and Cell Biology* (2004) 82, 488-496 the contents of which are hereby incorporated by reference in their entireties.

In various embodiments, the present adjuvants (e.g. flagellin-based agent and an aluminum gel or salt) may be part of live and attenuated, or killed or inactivated, or toxoid, or subunit or conjugate vaccines.

In various embodiments, the present adjuvants (e.g. flagellin-based agent and an aluminum gel or salt) may be part of one or more approved vaccines and/or the antigens of one or more approved vaccines may be the antigens of the present invention. In some embodiments, the approved vaccines include: Adenovirus; Anthrax (Biothrax); BCG (Tice); DT (Sanofi); DTaP (Daptacel); DTaP (Infanrix); DTaP-HepB-IPV (Pediarix); DTaP-IPV (Kinrix); DTaP-IPV/Hib (Pentacel); Hib (ActHIB); Hib (Hiberix); Hib (PedvaxHIB); Hib/Hep B (Comvax); Hib/Mening. CY (MenHibrix); Hep A (Havrix); Hep A (Havrix); Hp B (Engerix-B); Hep B (Recombivax); Hep A/Hep B (Twinrix); Human Papillomavirus (HPV) (Cerverix); Human Papillomavirus (HPV) (Gardasil); Influenza (Afluria); Influenza (Agriflu); Influenza (Fluarix); Influenza (Flublok); Influenza (Flucelvax); Influenza (Fluvirin); Influenza (Flulaval); Influenza (Fluzone: Standard, High-Dose, & Intradermal); Influenza (FluMist); Japanese Encephalitis (Ixiaro); Meningococcal (MCV4-Menactra); Meningococcal (MCV4-Menveo); Meningococcal (MPSV4-Menomune); MMR (MMR-II); MMRV (ProQuad); Pneumoocoal (PCV13-Prevnar 13); Pneumococcal (PPSV-23-Pneumovax); Polio (IPV-Ipol); Rabies (Imovax); Rabies (RabAvert); Rotavirus (RotaTeq); Rotavirus (Rotarix); Smallpox (Vaccinia-ACAM2000); Td (Decavac); Td (Tenivac); Td (Mass Biologics); Tdap (Adacel); Tdap (Boostrix); Typhoid (inactivated-Typhim Vi); Typhoid (oral-Ty21a); Varicella (Varivax); Yellow Fever (YF-Vax); and Zoster (Shingles-Zostavax).

In various embodiments, the present adjuvants (e.g. flagellin-based agent and an aluminum gel or salt) may be part of one or more illustrative vaccines and/or the antigens of one or more illustrative vaccines may be the antigens of the present invention. Illustrative vaccines include, by way of example, subunit vaccine and inactivated or "killed" vaccine (e.g. Infanrix-IPV/Hib (*Bordetella pertussis*), Infanrix-IPV/Hib (*Haemophilus influenzae*), Infanrix-IPV/Hib (Poliovirus), Infanrix-IPV/Hib (*Clostridium tetani*), Infanrix-IPV/Hib (*Corynebacterium diphtheriae*), Infanrix-hexa (*Bordetella perfussis*), Infanrix-hexa (*Haemophilus influenzae*), Infanrix-hexa (Poliovirus), Infanrix-hexa (Hepatitis B virus), Infanrix-hexa (*Clostridium tetani*), Infanrix-hexa (*Corynebacterium diphtheriae*), Infanrix-IPV (*Bordetella pertussis*), Infanrix-IPV (Poliovirus), Infanrix-IPV (*Clostridium tetani*), Infanrix-IPV (*Corynebacterium diphtheriae*), Infanrix/Hib (*Corynebacterium diphtheriae*), Pediarix (*Clostridium tetani*), Pediarix (Poliovirus), Pediarix (Hepatitis B virus), ViVaxim (*Salmonella* spp.), ViVaxim (Hepatitis A virus); subunit vaccines (e.g. 5CVMB (*Neisseria meningitidis*), *B. pertussis* CyaA protein vaccine (*Bordetella pertussis*), *B. pertussis* PTx protein vaccine (*Bordetella pertussis*), Cancer VEGFA protein vaccine (Cancer), *E. coli* vaccine using intimin polypeptide (*Escherichia coli*), Engerix-B (Hepatitis B virus), *H. pylori* VacA protein vaccine (*Helicobacter pylori*), HC of type C and D (*Clostridium botulinum*), Infanrix/Hib (*Bordetella pertussis*), Infanrix/Hib (*Haemophilus influenzae*), Infanrix/Hib (*Clostridium tetani*), *M. gallisepticum* TM-1 Protein Subunit Vaccine (*Mycoplasma gallisepticum*), MDA-modified human apo B-100 peptide Vaccine (Atherosclerosis), MSP3-LSP with aluminium hydroxide (*Plasmodium* spp.), Mumps HN Protein Subunit Vaccine (Mumps virus), N. miningitidis TBP2 Protein Vaccine (*Neisseria meningitidis*), *P. aeruginosa* Oprl Protein Vaccine (*Pseudomonas aeruginosa*), *P. falciparum* Subunit SE36 Protein Vaccine (*Plasmodium* spp.), *Phleum pratense* Allergy Phl p 12 Subunit Vaccine (Allergy), Recombivax HB (Hepatitis B virus), S. pneumnoniae ClpP protein Vaccine (*Streptococcus pneumoniae*); toxoid vaccine (e.g. BoNT/F(Hc) (*Clostridium botulinum*), DAPTACEL (*Corynebacterium diphtheriae*), Infanrix (*Bordetella pertussis*), Infanrix (*Clostridium tetani*), KINRIX (*Clostridium tetani*), PBT (*Clostridium botulinum*), Pediarix (*Bordetella pertussis*), inactivated or "killed" vaccines (e.g. Avaxim (Hepatitis A virus), Avaxim-Pediatric (Hepatitis A virus), FSME-IMMUN (Tick-borne Encephalitis Virus (TBEV)), Infanrix (*Corynebacterium diphtheriae*), Ixiaro (Japanese encephalitis virus), KINRIX (*Corynebacterium diphtheriae*), and Pediarix (*Corynebacterium diphtheriae*)); and conjugate vaccines (e.g., Arabinomannan-tetanus toxoid conjugate (*Mycobacterium tuberculosis*)), CCPS-P64kR (*Neisseria meningitidis*), COMVAX (*Haemophilus influenzae*), Menjugate (*Neisseria meningitidis*), Neisvac-C (*Neisseria meningitidis*), and PedvaxHIB (*Haemophilus influenzae*)).

In some embodiments, the present adjuvants (e.g. flagellin-based agent and an aluminum gel or salt) are combined in a vaccine targeting a substance abuse. For example, in one embodiment, the present adjuvants are used in vaccines against addition to fentanyl, heroin, morphine, opium, oxycodone, hydrocodone, ketamine, PCP, barbiturates, benzodiazepines, flunitrazepam, GHB, methaqualone, hashish, marijuana, LSD, mescaline, psilocybin, amphetamine, cocaine, MDMA, methamphetamine, methylphenidate, and nicotine (e.g. TA-CD (Celtic Pharma), those described in US Patent Publication No. 2013/0011432, the contents of which are hereby incorporated by reference (e.g. using 6-(2R,3S)-3-(benzoyloxy)-8-methyl-8-azabicyclo [3.2.1]octane-2-carbonyloxy-hexanoic acid (GNC) or 6-((2R,3S)-3-(benzoyloxy)-8-methyl-8-azabicyclo [3.2.1] octane-2-carboxamido) hexanoic acid) (GNE) as the antigen, and TA-NIC (Celtic Pharma)).

In some embodiments, the present adjuvants (e.g. flagellin-based agent and an aluminum gel or salt) and/or the present vaccines may comprise any one of the adjuvants or antigens annotated in the VIOLIN or Vaxjo databases (as described in He et al. *Nucleic Acids Research*. 2014. 42 (D1): D1124-D1132 and Xiang et al. *Nucleic Acids Res*. 2008 January; 36: D923-8, the contents of which are hereby incorporated by reference in their entirety).

In various embodiments, the present adjuvants (e.g. flagellin-based agent and an aluminum gel or salt) may be part of one or more cancer vaccines and/or the antigens of one or more cancer vaccines may be the antigens of the present invention. Illustrative cancer vaccines include therapeutic and preventative vaccines. For instance, cancer vaccines include ONCOPHAGE (ANTIGENICS INC., approved in Russia in 2008 for kidney cancer), APC8015/Sipuleucel-T/PROVENGE (DENDREON, for, e.g. metastatic hormone-refractory prostate cancer), CANCERVAX (CANVAXIN), GENITOPE CORP (MYVAX personalized immunotherapy), and FAVRILLE INC (FAVID), preventive vaccines which attack the cancer-causing viruses human papillomavirus (e.g. CERVARIX (GSK) and GARDASIL (MERCK)), hepatitis A virus (e.g. CERVARIX (GSK) and GARDASIL (MERCK)), and hepatitis B virus (e.g. RECOMBIVAX HB (MERCK), ENGERIX-B (GSK), ELOVAC B (HUMAN BIOLOGICALS INSTITUTE), GENEVAC B (SERUM INSTITUTE), SHANVAC B, etc.

In various embodiments, the present adjuvants (e.g. flagellin-based agent and an aluminum gel or salt) may be part of one or more allergen vaccines and/or the antigens of one or more allergen vaccines may be the antigens of the present invention. For instance, subcutaneous immunotherapy (SCIT) allergen compositions and methods are applicable to the present invention (e.g. "allergy shots"). For example, vaccinations for allergic rhinitis and conjunctivitis (e.g. pollen (including ragweed), dust mites, animal dander and airborne mold spores); allergic or extrinsic bronchial asthma (e.g. house dust mites, pollen, animal dander, mold (*Cladosporium*), latex); and insect venom hypersensitivity. Allergens include pollen (e.g. tree, grass, weed), pet dander (e.g. cat pelt), dust miles, airborne molds, occupational aeroallergens, honey bee venom, yellow jacket venom, hornet venom, wasp venom, and fire ant venom.

In various embodiments, the antigens of the present vaccines may be the antigens of live and attenuated or killed or inactivated or toxoid or a subunit or conjugate vaccines. In various embodiments, the antigen of the present vaccines is an antigen of any of the vaccines described herein. For example, in some embodiments, the present antigen is that of one or more of the following vaccines: DTP (diphtheria-tetanus-*pertussis* vaccine), DTaP (diphtheria-tetanus-acellular *pertussis* vaccine), Hib (*Haemophilus influenzae* type b) conjugate vaccines, Pneumococcal conjugate vaccine, Hepatitis A vaccines, Poliomyelitis vaccines, Yellow fever vaccines, Hepatitis B vaccines, combination DTaP, Tdap, Hib, Human Papillomavirus (HPV) vaccine, Anthrax vaccine, *Bacillus* Calmette-Guérin (Tb), and Rabies vaccine.

In various embodiments, the flagellin-based agent and antigen are adsorbed to the aluminum gel or salt. In some embodiments, the flagellin-based agent and aluminum gel or salt are mixed to form a stable complex. In some embodiments, the flagellin-based agent and aluminum gel or salt are mixed in a ratio that is substantially below a loading capacity of the aluminum salt. In some embodiments, the flagellin-based agent and aluminum gel or salt are present in a ratio that is substantially below a loading capacity of the aluminum salt. In various embodiments, the flagellin-based agent and aluminum gel or salt are mixed or present in a ratio (w/w) of about 1:500, or about 1:600, or about 1:700, or about 1:800, or about 1:900, or about 1:1000, or about 1:2000, or about 1:5000, or about 1:6000, or about 1:7000, or about 1:8000, or about 1:9000, or about 1:10000. In some embodiments, the flagellin-based agent and aluminum gel or salt are mixed in a ratio (w/w) of about 1:500 or less. In some embodiments, the flagellin-based agent and aluminum gel or salt are present in a ratio that is substantially below a loading capacity of the aluminum salt even in the presence of antigen.

The loading (or adsorption) capacity of the adjuvant (e.g. the aluminum gel or salt) can be measured using a variety of analytical methods. In general, it is done by comparing the protein content in the aqueous phase of the agent being loaded or adsorbed (e.g. flagellin-based agent and/or antigen solution) before and after adsorption onto the adjuvant. For instance, the Ramon flocculation test may be used (as is used to determine the adsorption of diphtheria and tetanus toxoid). Further, loading can be measured using immunoprecipitation techniques (e.g. quantitative immunoelectrophoresis or single radial immunodiffusion) or spectrophotometric techniques (e.g. the BCA method) ELISA methods may also be used as can immunoelectrophoresis or HPLC. The aluminum content in the final vaccine can be monitored using a number of known techniques, including spectrometric methods, such as for example atomic adsorption spectrometry.

In some embodiments, the amount of aluminum gel or salt in the vaccines and/or adjuvants described herein is about 0.05 to about 1.0 mg/dose, or about 0.125 to about 0.625 mg/dose. In some embodiments, the amount of aluminum gel or salt in the vaccines and/or adjuvants described herein is about 0.05, or about 0.10, or about 0.15, or about 0.20, or about 0.25, or about 0.30, or about 0.35, or about 0.40, or about 0.45, or about 0.50, or about 0.55, or about 0.60, or about 0.65, or about 0.70, or about 0.75, or about 0.80, or about 0.85, or about 0.90, or about 0.95, or about 1.0 mg/dose.

In some embodiments, the amount of flagellin-based agent is about 0.03 to about 5 µg/dose (e.g. about 0.03 µg/dose, about 0.1 µg/dose, about 0.3 µg/dose, about 0.5 µg/dose about 1.0 µg/dose, about 1.5 µg/dose, about 2.0 µg/dose, about 2.5 µg/dose, about 3.0 µg/dose, about 4.0 µg/dose, about 4.5 µg/dose, about 5.0 µg/dose). In various embodiments, the present compositions and methods comprise doses of flagellin-based agent that are less than about 5 µg/dose, or less than 4 µg/dose, or less than 3 µg/dose, or less than 2 µg/dose, or less than 1 µg/dose, or less than 0.5 µg/dose. In some embodiments, the present compositions and methods comprise low doses of flagellin-based agent.

In various embodiments, the present compositions and methods do not involve covalently attaching an antigen to the flagellin-based agent either as a fusion protein or via chemical conjugation. In various embodiments, the present compositions do not have either equimolar ratio of antigen to flagellin-based agent (as in a fusion) or several molecules of hapten per one molecule of flagellin-based agent (as in chemical conjugates). In various embodiments, the amount of flagellin-based agent in any of the present vaccines is less than the amount of antigen. In various embodiments, the amount of flagellin-based agent in any of the present vaccines is less than the amount of antigen. In various embodiments, the amount of flagellin-based agent in any of the present vaccines is substantially less than the amount of antigen. In various embodiments, the amount of flagellin-based agent in any of the present vaccines is about 500-fold, or about 450-fold, or about 400-fold, or about 350-fold, or about 325-fold, or about 300-fold, or about 250-fold, or about 200-fold, or about 150-fold, or about 100-fold, or about 50-fold less than the amount of antigen.

In various embodiments, the combination of flagellin-based agent and alum do not substatially effect TLR5 interaction by the flagellin-based agent.

In various embodiments, the present compositions and methods do not induce production of TNFα.

In various embodiments the present combination of flagellin-based agent and alum is subtantially stable at low temperatures for about one week (e.g. at about 4° C. for about 3 days, or about 5 days, or about 6 days, or about 7 days, or about 10 days).

In another aspect, the present invention relates to a method of vaccinating a subject against a disorder, comprising administering an effective amount of a vaccine comprising an adjuvant comprising a flagellin-based agent and an aluminum gel or salt and an antigen associated with the disorder. In another aspect, the invention relates to a use of vaccine comprising an adjuvant comprising a flagellin-based agent and an aluminum gel or salt and an antigen associated with a disorder for vaccinating a subject against the disorder. In another aspect, the invention relates to a use of an effective amount of vaccine comprising an adjuvant comprising a flagellin-based agent and an aluminum gel or salt and an antigen associated with a disorder in the manufacture of a medicament for vaccinating a subject against the disorder.

In another aspect, the present invention relates to a method of immunostimulating a subject in advance of or concurrent with vaccination, comprising administering an effective amount of an adjuvant comprising a flagellin-based agent and an aluminum gel or salt, wherein both $T_{H1}$ and $T_{H2}$-mediated immune responses are immunostimulated. In another aspect, the invention relates to a use of an effective amount of an adjuvant comprising a flagellin-based agent and an aluminum gel or salt for immunostimulating a subject in advance of or concurrent with vaccination. In another aspect, the invention relates to a use of an effective amount of an adjuvant comprising a flagellin-based agent and an aluminum gel or salt in the manufacture of a medicament for immunostimulating a subject in advance of or concurrent with vaccination.

In various embodiments, the vaccine described herein causes an improvement in adjuvant properties relative to a vaccine comprising the antigen and the aluminum gel or salt alone (or flagellin-based agent and antigen alone). In various embodiments, the vaccine and/or adjuvant described herein causes a broader, more diverse, more robust and longer lasting immunostimulatory effect than the vaccine comprising the antigen and the aluminum gel or salt alone (or flagellin-based agent and antigen alone) and/or the adjuvant comprising the aluminum gel or salt alone (or the adjuvant comprising the flagellin-based agent alone).

In some embodiments, the described vaccine and/or described adjuvant causes an increase in titer of 1 or more of, or 2 or more of, or 3 or more of, or all of IgG1, IgG2a, IgG2b, and IgG3 antibodies (e.g. relative to the adjuvant comprising the aluminum gel or salt or flagellin-based agent alone, or relative to the vaccine comprising the antigen and the aluminum gel or salt alone or flagellin-based agent alone)). In some embodiments, the described vaccine and/or described adjuvant causes a relative increase in the titer of all of IgG1, IgG2a, IgG2b, and IgG3 antibodies. In some embodiments, the described vaccine and/or described adjuvant causes a relative increase in the titer of more IgG3 antibodies than the described vaccine and/or described adjuvant in the absence of a flagellin-based agent (or the described vaccine and/or described adjuvant in the absence of an aluminum gel or salt alone).

In some embodiments, the antigen is administered simultaneously with or sequentially to the adjuvant.

In some embodiments, the disorder is selected from infectious diseases, cancer, allergy, and autoimmune diseases.

In some embodiments, the disorder is selected from diphtheria, tetanus, *pertussis*, influenza, pneumonia, hepatitis A, hepatitis B, polio, yellow fever, Human Papillomavirus (HPV) infection, anthrax, rabies, Japanese Encephalitis, meningitis, measles, mumps, rubella, gastroenteritis, smallpox, typhoid fever, varicella (chickenpox), rotavirus, and shingles.

In some embodiments, the disorder is a cancer is selected from, but not limited to, a basal cell carcinoma, biliary tract cancer, bladder cancer bone cancer brain and central nervous system cancer, breast cancer; cancer of the peritoneum; cervical cancer choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer, lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In some embodiments, the disorder is an allergy, selected from, by way of non-limiting example, allergic rhinitis and conjunctivitis, allergic or extrinsic bronchial asthma, and insect venom hypersensitivity.

In some embodiments, the disorder is a substance abuse disorder (e.g. of fentanyl, heroin, morphine, opium, oxycodone, hydrocodone, ketamine, PCP, barbiturates, benzodiazepines, flunitrazepam, GHB, methaqualone, hashish, marijuana, LSD, mescaline, psilocybin, amphetamine, cocaine, MDMA, methamphetamine, methylphenidate, and nicotine).

In some embodiments, the compositions of the present invention (e.g. the described adjuvants and vaccines) can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetals, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines, dicyclohexylamine; tributyl amine; pyridine; N-methyl, N-ethylamine; diethylamine; triethylamine; mono-, bis-, or tris-(2H-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

In some embodiments, the compositions of the present invention (e.g. the described adjuvants and vaccines) described herein are in the form of a pharmaceutically acceptable salt.

In some embodiments, the compositions of the present invention (e.g. the described adjuvants and vaccines) may comprise a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any composition described herein, if desired, can also comprise minor amounts of wetting or emulsifying agents, or pH buffering agents.

The present invention includes the compositions of the present invention (e.g. the described adjuvants and vaccines) in various formulations. Any composition of the present invention can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the compositions of the present invention can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The formulations comprising the compositions of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In one embodiment, any composition of the present invention is formulated in accordance with routine procedures as a composition adapted for a mode of administration described herein.

Routes of administration include intramuscular, e.g. by injection or infusion. In some embodiments, the described adjuvant of a flagellin-based agent (e.g. CBLB502) and aluminum gel or salt may prevent systemic delivery of the flagellin-based agent and induce localized delivery. In other embodiments, routes of administration include nasal, oral, and sublingual delivery.

Routes of administration may also be intradermal, intramuscular, intraperitoneal, intravenous, subcutaneous, intranasal, oral, sublingual, intranasal, transdermal, or by inhalation. In some embodiments, the administering is effected orally or by parenteral injection. The mode of administration can be left to the discretion of the practitioner, and depends in-part upon the site of the medical condition. In most instances, administration results in the release of any agent described herein into the bloodstream.

Any composition of the present invention (e.g. the described adjuvants and vaccines) can be administered orally. Such compositions can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

The dosage of any composition of the present invention (e.g. the described adjuvants and vaccines) as well as the dosing schedule can depend on various parameters, including, but not limited to, the disorder being treated, the subject's general health, and the administering physician's discretion.

In vitro or in vivo assays can be employed to help identify optimal dosage ranges. For example, doses may be determined with reference *Physicians' Desk Reference,* 66th Edition, PDR Network; 2012 Edition (Dec. 27, 2011), the contents of which are incorporated by reference in its entirety.

For administration of a composition of the present invention (e.g. the described adjuvants and vaccines) by parenteral injection, the dosage is normally about 0.1 mg to about 250 mg per day, about 1 mg to about 20 mg per day, or about 3 mg to about 5 mg per day. Injections may be given up to four times daily. Generally, when orally or parenterally administered, the dosage of any agent described herein is normally about 0.1 mg to about 1500 mg per day, or about 0.5 mg to about 10 mg per day, or about 0.5 mg to about 5 mg per day. A dosage of up to about 3000 mg per day can be administered.

In another embodiment, delivery can be in a vesicle, in particular a liposome (see Langer, 1990, *Science* 249:1527-1533; Treat et al., in *Liposomes in the Therapy of Infectious Disease and Cancer,* Lopez-Berestein and Fidler (eds.), Liss, New York, pp. 353-365 (1989).

Any composition of the present invention (e.g. the described adjuvants and vaccines) can be administered by controlled-release or sustained-release means or by delivery devices that are well known to those of ordinary skill in the art Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release,* Langer and Wise (eds.), CRC Pres., Boca Raton, Fla. (1974); *Controlled Drug Bioavailability, Drug Product Design and Performance,* Smolen and Ball (ads.), Wiley, New York (1984); Ranger and Peppas, 1983, *J. Macromol. Sci. Rev. Macromol. Chem.* 23:61; see also Levy at al., 1985, *Science* 228:190; During at al., 1989, *Ann. Neurol.* 25:351; Howard et al., 1989, *J. Neurosurg.* 71:105).

In another embodiment, a controlled-release system can be placed in proximity of the target area to be treated, thus requiring only a fraction of the systemic dose (see, e.g., Goodson, in *Medical Applications of Controlled Release,* supra, vol. 2, pp. 115-138 (1984)). Other controlled-release systems discussed in the review by Langer, 1990, *Science* 249:1527-1533) may be used.

Administration of a composition of the present invention (e.g. the described adjuvants and vaccines) can, independently, be once per patient or may be used in a booster strategy. Administration may be about one to about four times daily or about one to about four times per month or about one to about six times per year or once every two, three, four or five years. Administration can be for the duration of about one day or about one month, about two months, about three months, about six months, about one year, about two years, about three years, and may even be for the life of the subject. The dosage may be administered as a single dose or divided into multiple doses.

The dosage regimen utilizing any flagellin related composition (and/or additional agents) described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any flagellin related composition (and/or additional agents) described herein can be administered in a single daily dose, or the total daily dosage can be administered in divided doses of two, three or four times daily. Furthermore, any flagellin related composition (and/or additional agents) described herein can be administered continuously rather than intermittently throughout the dosage regimen.

In some embodiments, the composition of the present invention (e.g. the described adjuvants and vaccines) may be used in conjunction with one or more additional agents. In some embodiments, the invention pertains to co-administration and/or co-formulation. Any of the compositions described herein may be co-formulated and/or co-administered.

In some embodiments, any composition described herein acts synergistically when co-administered with another agent and is administered at doses that are lower than the doses commonly employed when such agents are used as monotherapy. In various embodiments, any agent referenced herein may be used in combination with any of the composition described herein.

In some embodiments, the present invention pertains to additional agents described elsewhere herein. In one embodiment, any flagellin-related agent or composition comprising the same may be used with agents that stimulate NOD receptors (e.g. NOD1 and NOD2 agonists, such as peptidoglycan, C12-iE-DAP and L18-MDP) and as described in Infect Immun. October 2013; 81(10): 3855-3864, the contents of which are hereby incorporated by reference in their entirety.

In some embodiments, the present invention pertains to chemotherapeutic agents as additional agents.

Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophyan 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Eng., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramyan, azaserine, bleomycins, cactinomycin, carabicin, caminomycin, carzinophilin, chromomycinis, dactinomycin, daunorubicin, detorubicin, 6-diazo-5-oxo-L-noreucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; def of amine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ('Ara-C'); cyclophosphamide; thiotepa; taxoids, e.g., TAXOL paclitaxel (Bristol-Myers Squibb Oncology, Princeton, N.J.), ABRAXANE Cremophor-free, alburminengineered nanoparticle formulation of paclitaxel (American Pharmaceutical Partners, Schaumberg, 111), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylomithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In some embodiments, the flagellin-based agents (and/or additional agents) described herein, include derivatives that are modified, i.e., by the covalent attachment of any type of molecule to the composition such that covalent attachment does not prevent the activity of the composition. For example, but not by way of limitation, derivatives include composition that have been modified by, inter ala, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of turicamycin, etc. Additionally, the derivative can contain one or more non-classical amino acids.

In still other embodiments, the flagellin-based agents (and/or additional agents) described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The flagellin-based agents (and/or additional agents) described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Illustrative cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the *vinca* alkaloids, vincristine and vinblastine. Other cytotoxic agents include paclitaxel (taxol), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, *vinca* alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux, Avastin, Pertuzumab, anti-CD20 antibodies, Rituxan, ocrelizumab, ofatumumab, DXL625, HERCEPTIN4, or any combination thereof. Toxic enzymes from plants and bacteria such as ricin, diphtheria toxin and *Pseudomonas* toxin may be conjugated to the therapeutic agents (e.g. antibodies) to generate cell-type-specific-killing reagents (Youle, et al., *Proc. Nat'l Acad. Sci. USA* 77:5483 (1980); Gilliland, et al., *Proc. Nat'l Acad. Sci. USA* 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the antibody, or binding fragments thereof, with or without the use of a complex-forming agent. Such radionuclides include beta-emitters such as Phosphorus-32, Scandium-47, Copper-67, Gallium-67, Yttrium-88, Yttrium-90, Iodine-125, Iodine-131, Samarium-153, Lutetium-177, Rhenium-186 or Rhenium-188, and alpha-emitters such as Astatine-211, Lead-212, Bismuth-212, Bismuth-213 and Actinium-225.

Illustrative detectable moieties further include, but are not limited to, horseradish peroxidase, acetylcholinesterase, alkaline phosphatase, beta-galactosidase and luciferase. Further illustrative fluorescent materials include, but are not limited to, rhodamine, fluorescein, fluorescein isothiocyanate, umbelliferone, dichlorotriazinylamine, phycoerythrin and dansyl chloride. Further illustrative chemiluminescent moieties include, but are not limited to, luminol. Further illustrative bioluminescent materials include, but are not limited to, luciferin and aequorin. Further illustrative radioactive materials include, but are not limited to, Iodine-125, Carbon-14, Sulfur-35, Tritium and Phosphorus-32.

In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal.

The invention provides kits that can simplify the administration of any agent described herein. An illustrative kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

The following definitions are used in connection with the invention disclosed herein. Unless defined otherwise, all technical and scientific terms used herein have the same meaning as commonly understood to one of skill in the art to which this invention belongs.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g. flagellin-based agents, flagellin-based agents (and/or additional agents) described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. For example, administration of therapeutic agents to a patient suffering from cancer provides a therapeutic benefit not only when the underlying condition is eradicated or ameliorated, but also when the patient reports a decrease in the severity or duration of the symptoms associated with the disease, e.g., a decrease in tumor burden, a decrease in circulating tumor cells, an increase in progression free survival. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

In certain embodiments, a pharmacologically effective amount that will treat cancer will modulate the symptoms typically by at least about 10%, at least about 20%, at least about 30%, at least about 40%, or at least about 50%. In illustrative embodiments, such modulations will result in, for example, statistically significant and quantifiable changes in the numbers of cancerous cells.

This invention is further illustrated by the following non-limiting examples.

EXAMPLES

Example 1: Preparation of the Model Vaccine

Alum adjuvant (IMJECT ALUM, THERMO) was used in combination with CBLB502 to challenge the mice with a model antigen, ovalbumin (OVA). Vaccine was comprised of the following components as shown in

TABLE A

| Component | Amount (per mouse) |
|---|---|
| Ovalbumin | 10 mg |
| CBLB502 | 1 ug/10 ug |
| Alum Adjuvant | 500 ug |

To achieve excellent absorption CBLB502 (either 1 ug or 10 ug) was mixed with 10 mg of OVA and 500 μg of Alum adjuvant for 30 minutes at 300 rpm at room temperature.

Example 2: Mouse Immunization Study

C57Bl/6 male mice (10 weeks of age, n=6 for each experiment) were used for injection. Mice were divided into five groups with six animals in each group (n=6). Mice were injected with 100 μl of above described vaccine in each of the hind legs (200 μl total per mouse) as shown in TABLE B.

|  | Ovalbumin | CBLB502 | Alum Adjuvant |
|---|---|---|---|
| Group 1 |  |  |  |
| Group 2 | 10 mg |  |  |
| Group 3 | 10 mg |  | 500 ug |
| Group 4 | 10 mg | 1 ug | 500 ug |
| Group 5 | 10 mg | 10 ug | 500 ug |

Figure 3:
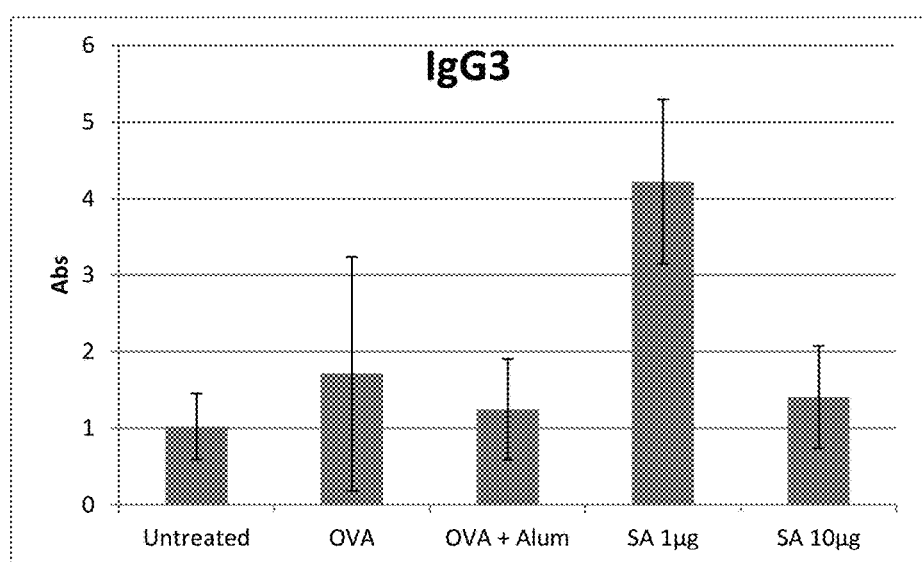
FIG. 3 shows ELISA data for the average response of five mouse treatment groups at the time point of 2 weeks post-boost. Panel A is total IgG, Panel B is IgG1, Panel C is IgG2a, Panel D is IgG2b and Panel E is IgG3. Groups 1-5 are defined in TABLE B (Example 2): Group 1 is also called "Untreated;" Group 2 is also called "OVA," Groups 3 is also called "OVA+Alum," Group 4 is also called "SA 1 µg," and Group 5 is also called "SA 10 µg."

Two weeks after the initial immunization mice were challenged with an additional booster following the same setup as the original injection. Plasma was collected one, two and four weeks after booster via mandibular vein. Using an ELISA based assay total IgG, IgG1, IgG2a, IgG2b and IgG3 were measured. Results are shown in FIGS. 2-3. In the figures, Group 1 is also called "Untreated;" Group 2 is also called "OVA," Groups 3 is also called "OVA+Alum," Group 4 is also called "SA 1 μg," and Group 5 is also called "SA 10 μg."

Figure 4:
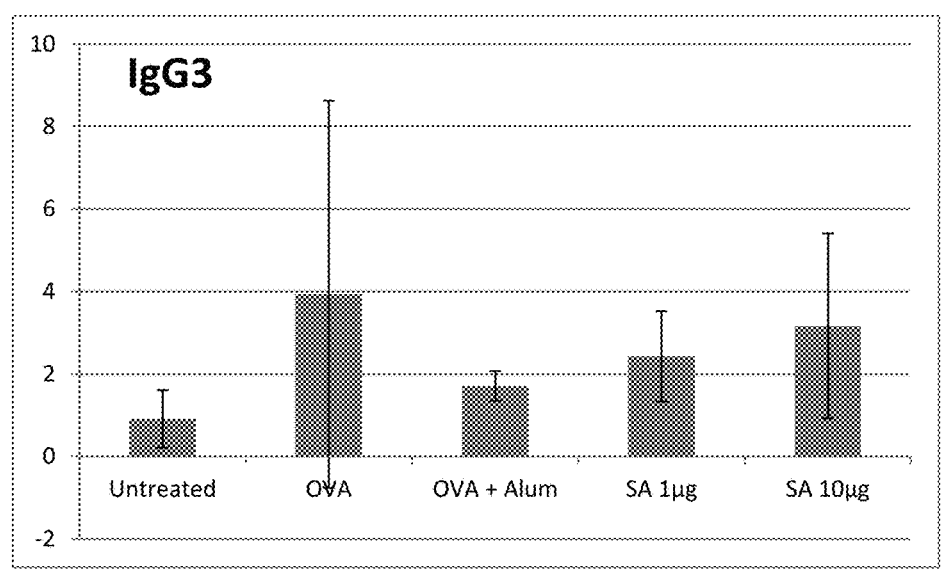
FIG. 4 shows ELISA data for the average response of five mouse treatment groups at the time point of 4 weeks post-boost Panel A is total IgG, Panel B is IgG1, Panel C is IgG2a, Panel D is IgG2b and Panel E is IgG3. Groups 1-5 are defined in TABLE B (Example 2): Group 1 is also called "Untreated;" Group 2 is also called "OVA," Groups 3 is also called "OVA+Alum," Group 4 is also called "SA 1 µg," and Group 5 is also called "SA 10 µg."

FIG. 2 shows ELISA data for the average response of the five aforementioned mouse treatment groups at the time point of 1 week post-boost. FIG. 3 shows ELISA data for the average response of the five aforementioned mouse treatment groups at the time point of 2 weeks post-boost FIG. 4 shows ELISA data for the average response of the five aforementioned mouse treatment groups at the time point of 4 weeks post-boost.

Example 3: Evaluation of CBLB502 Binding to ALHYDROGEL

The binding capacity of ALHYDROGEL for CBLB502 was evaluated. ALHYDROGEL adjuvant 2%, aluminium hydroxide wet gel (colloidal) suspension (INVIVIGEN Catalog # vac-alu-250), was mixed with CBLB502 at different volume ratios, resulting in 10 to 52% ALHYDROGEL suspension in the reaction. CBLB502 concentration was maintained at 10 μg/ml, corresponding to a 1 μg/100 μl inoculation dose (100 μl inoculation volume is the recommended maximum volume for subcutaneous injection of antigen/adjuvant mixtures per injection site for mice). After overnight incubation at 4° C., the tubes were centrifuged to sediment ALHYDROGEL and unbound CBLB502, remaining in solution was measured by ELISA. The amounts of adsorbed CBLB502 were calculated as difference between total protein added to the mixture and unbound CBLB502 (TABLE C). The maximum adsorption of CBLB502, more than 99.9% bound, was observed when the reactions were formulated with 40 to 52 μl ALHYDROGEl/100 μl; at lower ratios, the binding efficiency decreased gradually to about 83% at 10 μl/100 μl ALHYDROGEL suspension.

TABLE C

CBLB502 adsorption at different ALHYDROGEL 2% volume ratios. The binding reactions were composed of CBLB502, PBS and the indicated volumes of ALHYDROGEl adjuvant 2%.

|  | ALHYDROGEL 2% μl/100 μl | CBLB502 dose μg/100 μl | Total CBLB502 ng/ml | Unbound ng/ml | Bound ng/ml | Bound (%) |
|---|---|---|---|---|---|---|
| 1 | 52 | 1 | 10000 | 2.1 | 9997.9 | 99.98 |
| 2 | 50 | 1 | 10000 | 1.6 | 9998.4 | 99.98 |
| 3 | 40 | 1 | 10000 | 2.9 | 9997.1 | 99.97 |
| 4 | 30 | 1 | 10000 | 22.7 | 9977.3 | 99.77 |
| 5 | 20 | 1 | 10000 | 173.4 | 9826.6 | 98.27 |
| 6 | 10 | 1 | 10000 | 1692.5 | 8307.5 | 83.07 |

CBLB502 binding to ALHYDROGEL was also evaluated at different CBLB502 doses. Adsorption of CBLB502 to ALHYDROGEL (52 μl/100 μl ALHYDROGEL adjuvant 2%) was determined at CBLB502 doses, ranging from approximately 0.02 to 20 μg per 100 μl. The reactions were incubated as described above and unbound CBLB502 was measured by ELISA. The results (TABLE D) demonstrated that almost complete binding of the drug to ALHYDROGEL, 99.82 to 99.99% bound, was accomplished at all tested CBLB502 concentrations.

TABLE D

Efficiency of CBLB502 binding to ALHYDROGEl in PBS. The incubations were performed with CBLB502 at the indicated doses in PBS and 52 μl/100 μl ALHYDROGEL adjuvant 2%.

|  | CBLB502 dose μg/100 μl | Total CBLB502 ng/ml | Unbound ng/ml | Bound ng/ml | Bound (%) |
|---|---|---|---|---|---|
| 1 | 20 | 200000 | 199.3 | 199800.7 | 99.90 |
| 2 | 5 | 50000 | 90.6 | 49909.4 | 99.82 |
| 3 | 1.25 | 12500 | 0.79 | 12499.2 | 99.99 |
| 4 | 0.31 | 3125.0 | 0.029 | 3124.97 | 99.99 |

TABLE D-continued

Efficiency of CBLB502 binding to ALHYDROGEl in PBS. The incubations were performed with CBLB502 at the indicated doses in PBS and 52 μl/100 μl ALHYDROGEL adjuvant 2%.

| CBLB502 dose μg/100 μl | Total CBLB502 ng/ml | Unbound ng/ml | Bound ng/ml | Bound (%) |
|---|---|---|---|---|
| 5 | 0.078 | 781.25 | 0.023 | 781.23 | 99.99 |
| 6 | 0.02 | 195.31 | 0.011 | 195.30 | 99.99 |

CBLB502 binding to ALHYDROGEL in the presence of TT-SMA vaccine was evaluated. Binding efficiency of CBLB502 to ALHYDROGEL was tested in the presence of a vaccine candidate TT-SMA, succinyl methamphetamine (SMA) hapten conjugated to tetanus toxoid. In a separate study, shown below, this vaccine was administered to mice at a 32 μg/100 μl dose to compare efficacy with and without CBLB502. This TT-SMA dose was co-incubated with CBLB502 (0.02 to 20 μg/100 μl) and ALHYDROGEL (52 μl/100 μl) under standard conditions and unbound CBLB502 was measured by ELISA. The binding efficiency was 99.7 to 99.9% at all tested CBLB502 concentrations, indicating that CBLB502 adsorption to ALHYDROGEL was unaffected with addition of TT-SMA to the reaction mixture

TABLE E

CBLB502 binding to ALHYDROGEL in the presence of TT-SMA. The incubations were performed with CBLB502 at the indicated doses in PBS, 52 μl/100 μl ALHYDROGEL adjuvant 2% and 32 μg/100 μl TT-SMA conjugate.

| CBLB502 dose μg/100 μl | Total CBLB502 ng/ml | Unbound ng/ml | Bound ng/ml | Bound (%) |
|---|---|---|---|---|
| 1 | 20 | 200000 | 668.88 | 199331.1 | 99.67 |
| 2 | 5 | 50000 | 50.21 | 49949.8 | 99.90 |
| 3 | 1.25 | 12500 | 11.44 | 12488.6 | 99.91 |
| 4 | 0.31 | 3125.0 | 1.65 | 3123.4 | 99.95 |
| 5 | 0.078 | 781.25 | 0.13 | 781.1 | 99.98 |
| 6 | 0.02 | 195.31 | 0.06 | 195.2 | 99.96 |

Example 4: Analysis of In Vitro CBLB502 Activity after Adsorption to ALHYDROGEL

An activity assay of CBLB502/ALHYDROGEL using 293-hTLR5-LacZ reporter cells was undertaken. Biological activity of CBLB502 after adsorption to ALHYDROGEL was tested using an in vitro assay which measures activation of a NF-κB-controlled reporter enzyme, β-galactosidase, in HEK293-hTLR5::NF-κB-lacZ (293-hTLR5-LacZ) cells. Since 293-hTLR5-LacZ cells express only one cell membrane-bound toll-like receptor, human TLR5, CBLB502 activity could be determined without interference from other toll-like receptor ligands such as LPS (endotoxin).

Figure 5:
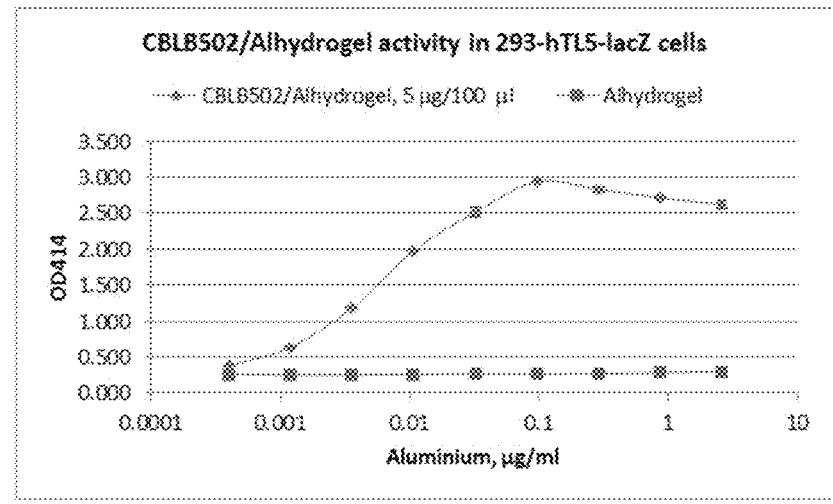
FIG. 5 shows a determination of CBLB502/ALHYDROGEL activity using a cell-based NF-κB activation assay. CBLB502/ALHYDROGEL formulation (5 µg/100 µl) and ALHYDROGEL control were serially diluted in assay media 2000- to 13122000-fold (2.6-0.0004 µg/ml aluminium) and incubated with 293-hTLR5-LacZ cells for 20 hr. Activity of β-galactosidase was measured after addition of cell lysis buffer and ONPG substrate and expressed as optical density at 414 nm (OD414).

Specific induction of the β-galactosidase reporter by CBLB502/ALHYDROGEL was demonstrated after incubating the cells with a serially diluted CBLB502/ALHYDROGEL formulation (5 μg/100 μl), starting with a 2000-fold dilution in cell growth media and resulting in the concentration range of ALHYDROGEL-adsorbed CBLB502 from 25 to 0.004 ng/ml (FIG. 5). The maximum β-galactosidase activity was observed at 0.93 ng/ml ALHYDROGEL-adsorbed CBLB502; this value was consistent with typical results of the assay using soluble CBLB502 where the reporter enzyme activity would normally peak around 1 ng/ml. ALHYDROGEL alone tested at same dilutions did not induce the reporter. Therefore, it could be concluded, inter alia, that CBLB502 retains its biological activity after adsorption to ALHYDROGEL and becomes readily available for interaction with its target receptor (TLR5) under regular cell culture conditions.

Figure 6:
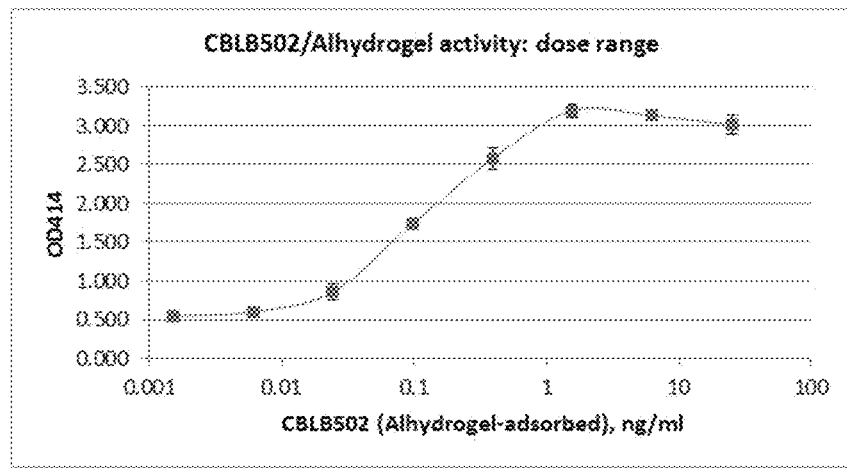
FIG. 6 shows NF-κB-inducing activity of CBLB502/ALHYDROGEL formulated with different CBLB502 doses. 293-hTLR5-LacZ cells were incubated with CBLB502/ALHYDROGEL suspensions prepared at CBLB502 doses ranging from 2.5 to 0.00015 µg/100 µl and diluted 200-fold with media. Activity of β-galactosidase reporter enzyme was measured after 20 hr incubation.

Next, CBLB502/ALHYDROGEL suspensions were prepared at CBLB502 inoculation doses ranging from 2.5 to 0.00015 μg/100 μl and were added to 293-hTLR5-LacZ cells at 200-fold dilution (FIG. 6). NF-κB-inducing activity followed a typical dose-response pattern and was measured at sub-nanogram doses of CBLB502/ALHYDROGEL (less than 0.001 μg/100 μl), indicating that at such low doses, CBLB502 was not irreversibly bound to the alum adjuvant and remained active.

An activity titration of CBLB502/ALHYDROGEL at different CBLB502 doses was undertaken. CBLB502/ALHYDROGEL suspensions were titrated in cell culture media and incubated with 293-hTLR5-LacZ cells. CBLB502 standards were included in the assay to compare the recovered activity. The resulting reporter enzyme activity was plotted against theoretical concentrations of ALHYDROGEL-bound CBLB502, assuming that the protein was completely available (FIG. 7).

The results of titration assay demonstrated that at a formulation dose of 20 μg/100 μl, the activity of CBLB502 followed the expected concentrations, essentially matching the activity of soluble standards. However, reduction of the dose 64- and 256-fold to respectively, about 0.31 and 0.078 μg/100 μl, resulted in lower relative recovery of NF-κB-inducing activity to approximately 15-30%. This apparent loss of CBLB502 activity could be due to stronger binding of the particular amounts of the protein relative to the amounts of alum in the formulation. These fixed amounts could represent a small fraction of total CBLB502 at the higher doses such as 20 μg/100 μl and would not affect significantly the measured activity. However, at lower doses, this tightly adsorbed fraction may become substantial compared to the total protein, leading to a lower measurable activity of CBLB502

Example 5: Assessment of CBLB502/ALHYDROGEL Short-Term Storage Stability at 4° C.

Figure 8:
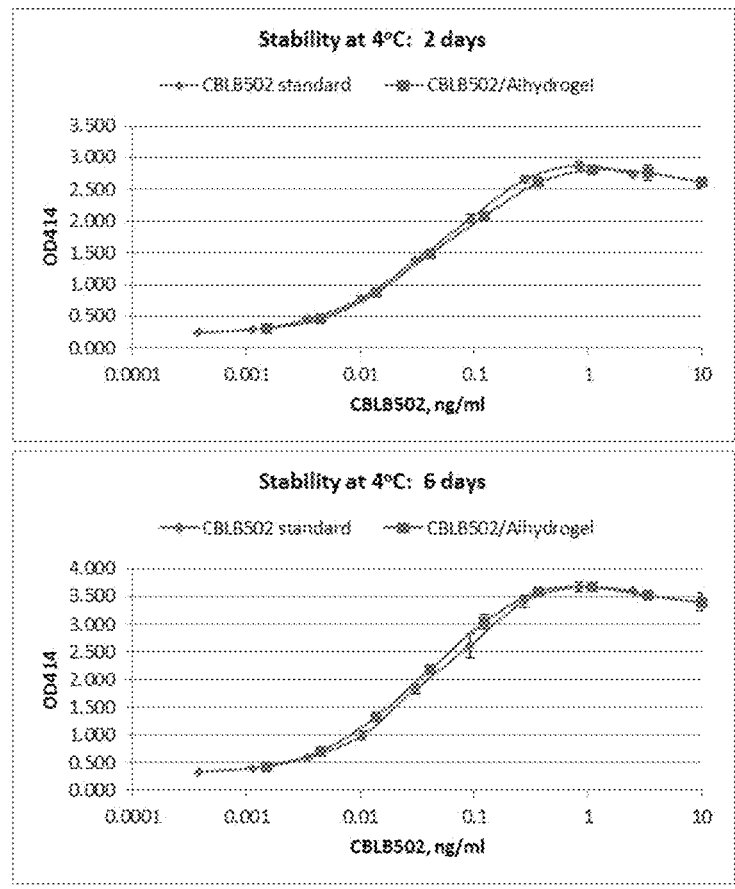
FIG. 8 shows the activity of CBLB502/ALHYDROGEL (1 µg/100 µl dose) stored at 4° C. for 2 and 6 days. NF-κB-inducing activity was measured using 293-hTLR5-LacZ reporter cell assay.

A formulation of 1 μg/100 μl CBLB502 (52 μl/100 μl ALHYDROGEL 2%) was prepared and tested for activity after 2 and 6 days storage at 4° C. The results of CBLB502 activity assay using 293-hTLR5-LacZ reporter cells are shown in FIG. 8. Based on comparison with the soluble CBLB502 standard, in can be concluded that NF-κB-inducing activity of ALHYDROGEL-adsorbed CBLB502 remained unchanged after 6 days under the storage conditions.

Example 6: Evaluation of CBLB502 Dissociation from ALHYDROGEL in PBS and Cell Media Aliquots of CBLB502/ALHYDROGEL (1 μg/100 μl dose; 52 μl/100 μl ALHYDROGEL 2%) were re-suspended in PBS or cell media (DMEM supplemented with 10% FBS) and incubated for 3 hr at 22° C. and 37° C. After centrifugation to remove ALHYDROGEL, dissociated CBLB502 was measured in supernatants by ELISA. The calculation of CBLB502 amounts that were recovered during incubation demonstrated that the protein remained stably associated with ALHYDROGEL in PBS; however, in cell media, 28 and 53% CBLB502 was released from the complex at 22° C. and 37° C., respectively (TABLE F). Such rapid dissociation from ALHYDROGEL in media may be facilitated by serum proteins which could displace CBLB502 from the complex with alum, explaining how the protein becomes readily available in the cell-based activity assay.

TABLE F

CBLB502 recovery from ALHYDROGEL after incubation in PBS and cell media

| Incubation conditions | CBLB502 dose µg/100 µl | Total CBLB502 ng/ml | 22° C. Recovered ng/ml | 22° C. Desorption (%) | 37° C. Recovered ng/ml | 37° C. Desorption (%) |
|---|---|---|---|---|---|---|
| PBS | 1 | 10000 | 2.3 | 0.02 | 33.2 | 0.33 |
| Media | 1 | 10000 | 2807.6 | 28.1 | 5300.9 | 53.0 |

Example 7: Quantitation of CBLB502 and Cytokine Levels in Mouse Serum after Subcutaneous Administration of CBLB502/ALHYDROGEL An animal study was conducted to evaluate feasibility of methods to determine the levels of CBLB502 and cytokines in serum after administration of a CBLB502/ALHYDROGEL formulation. The study design is presented in TABLE G. In this study, mice were injected subcutaneously with a 1 µg dose CBLB502 adsorbed to 52 µl/100 µl ALHYDROGEL 2% and serum samples were collected between 0.5 and 24 hr post inoculation.

TABLE G

Study design.

| Group No. | Group Size | Age Strain Sex | Treatment | Injection volume, µl | Time Point, blood collection | Evaluation |
|---|---|---|---|---|---|---|
| 1 | 3 | 8 wk old | ALHYDROGEL/PBS, sc | 100 | 1 hr | Serum prepared from |
| 2 | 3 | C57BL/6 | ALHYDROGEL/PBS/CBLB502, | 100 | 30 min | collected blood and |
| 3 | 3 | Female | (1 µg/100 µl CBLB502; 52 µl/ | 100 | 1 h | analyzed for |
| 4 | 3 | | 100 µl ALHYDROGEL 2%) | 100 | 2 h | entolimod |
| 5 | 3 | | sc | 100 | 4 h | concentration and |
| 6 | 3 | | | 100 | 8 h | cytokine levels by |
| 7 | 3 | | | 100 | 24 h | ELISA |

Figure 9:
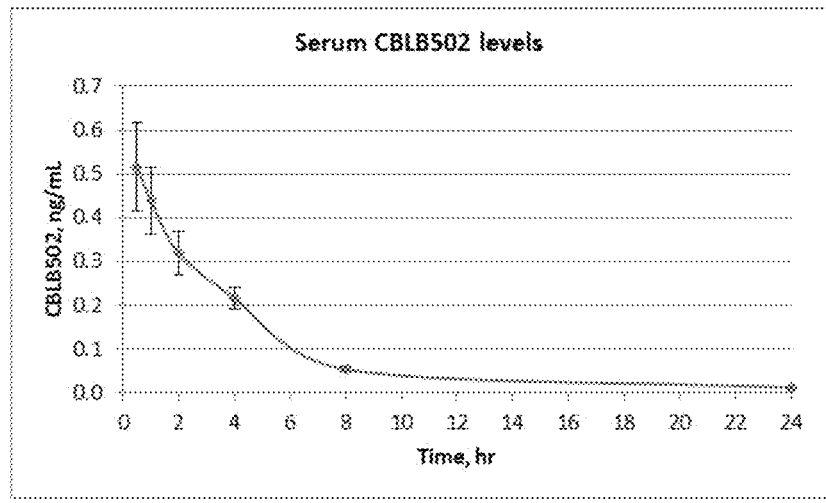
FIG. 9 shows pharmacokinetics of CBLB502 in mouse serum after subcutaneous injection of a 1 µg dose of CBLB502 adsorbed to ALHYDROGEL 2%. The graph shows per-group mean serum CBLB502 concentrations and SEM (standard error of the mean) for each time point.

Serum concentrations of CBLB502 were determined by ELISA and were found at measurable levels in all groups of animals inoculated with CBLB502/ALHYDROGEL. The pharmacokinetic profile representing per-group mean serum CBLB502 concentrations is shown in FIG. 9. The maximum mean CBLB502 concentration, 0.516 ng/ml, was observed at the first blood collection time point, 0.5 hr post administration; the minimum concentration was 0.012 ng/ml at 24 hr. Half-time elimination of CBLB502 was calculated at 2.4 hr. As discussed above, CBLB502 dissociated rapidly from the complex with ALHYDROGEL after incubation in cell media, containing 10% fetal bovine serum. Therefore, it should be expected to see the protein released from alum into animal bloodstream shortly after inoculation.

Figure 10:
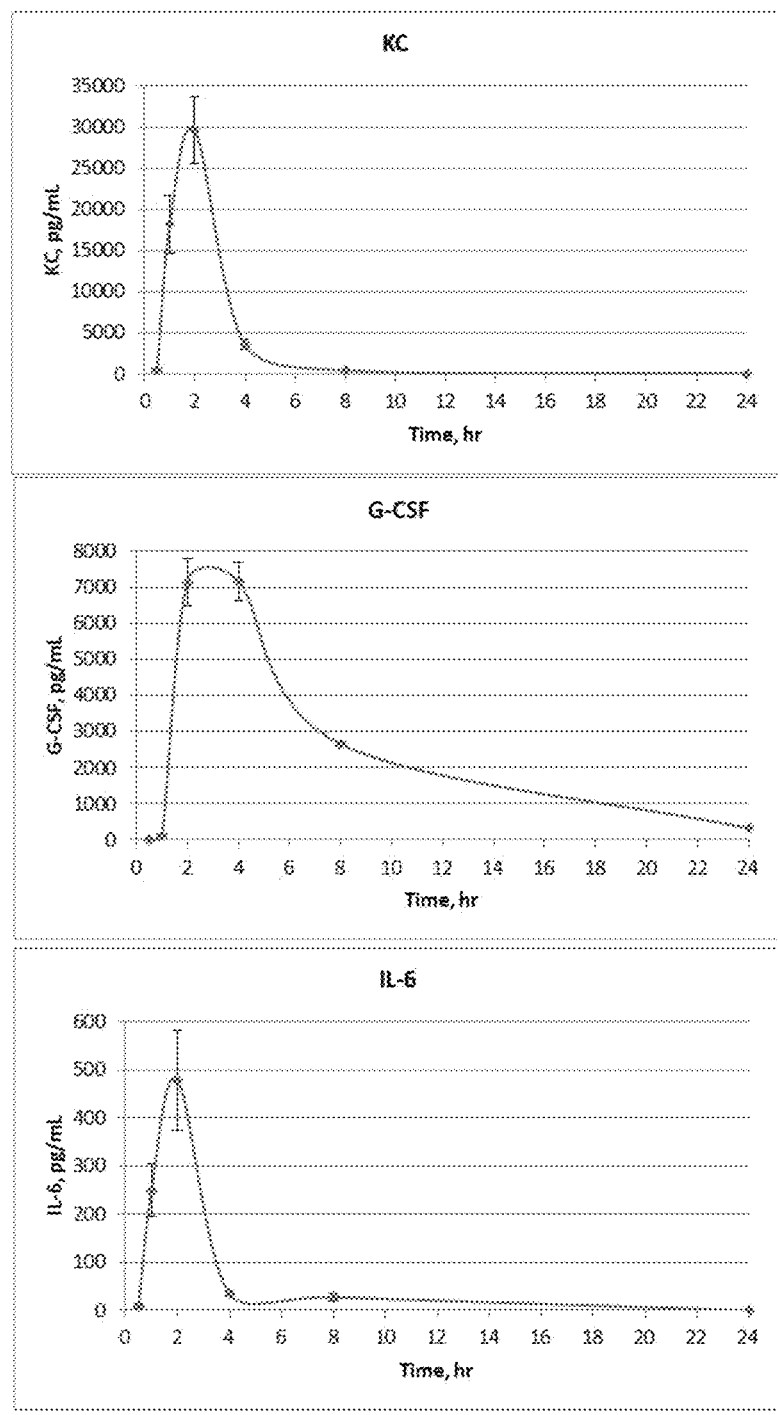
FIG. 10 shows induction of KC, G-CSF and IL-6 following s.c. administration of a 1 µg dose of CBLB502 adsorbed to ALHYDROGEL 2%. Serum concentrations of the cytokines were determined using R&D Systems DuoSet kits DY453 (KC, top panel), DY414 (G-CSF, middle panel) and DY406 (IL-6, bottom panel). The graphs show per-group mean serum cytokine concentrations and SEM (standard error of the mean) for each time point.

The concentrations of three cytokines, KC, G-CSF and IL-6, were measured in the collected mouse serum samples by ELISA (FIG. 10). Rapid induction of KC and IL-6 was detected 1 hr after CBLB502/ALHYDROGEL administration; the maximum per-group mean concentrations, 29624 and 479 pg/ml, respectively, were determined at 2 hr time point. After reaching maximum, the blood levels of these cytokines decreased to baseline at 4 to 8 hr post injection. The serum G-CSF concentration increased about an hour later compared to KC and IL-6 and was maximal between 2 and 4 hr after CBLB502/ALHYDROGEL administration (7141 and 7169 pg/ml per-group mean concentrations at 2 and 4 hr, respectively). However, CBLB502-induced G-CSF level was decreasing at a slower rate, remaining above baseline at 24 hr time point. In general, the kinetics of cytokine induction after CBLB502/ALHYDROGEL administration was similar to the kinetics observed after injection of the soluble CBLB502 preparations, suggesting consistent effects of this drug formulation.

Example 8: CBLB502 Adjuvant with Methamphetamine Vaccine

This study evaluated CBLB502 adjuvant at a 32 µg dose of human methamphetamine vaccine (SMA-TT) to achieve high and long lasting levels of anti-MA antibody in mice. A low to high dose of CBLB502 ranging from 0.03 to 20 µg with TT-SMA and alum was studied. Ten groups (n=5) of Balb/c female mice were employed to test 0, 0.03, 0.1, 0.3, 1, 3, 10, 20 µg of 502 in combination with 32 µg of TT-SMA and 1.5 mg alum compared to unvaccinated controls and TT-SMA with 502 alone. All vaccinated groups were administered two boosters, at 3 and 6 weeks after the initial vaccination. Levels of anti-MA IgG were assessed by ELISA in pooled sera samples collected at 2, 4, and 6 weeks after initial vaccination. The antibody levels were higher at 0.03 to 0.3 µg 502 in comparison to the higher doses (1 to 20 µg) of 502. In this experiment, antibody levels were 2 fold higher in the groups with 0.1 µg of 502 in combination with TT-SMA and alum (group 4) than in the comparison group with TT-SMA and alum alone (group 1) and approx. 4 fold higher when compared to a group with TT-SMA and 502 alone (group 2), as demonstrated in FIG. 11 (panel A). Anti-502 antibodies in the same sera sample were also evaluated. As shown in FIG. 11 (panel B), the level of anti-502 antibodies was minimal at the low dose range of 502 and increases at higher doses of 502.

Example 9: Generation of Vaccines with Various Antigens

In this Example, the composition of an adjuvant component for adjuvant-enhanced vaccine is established by testing a range of doses of CBLB502 and CBLB502 optionally combined with an antigen, such as, by way of non-limitation, NOD1 agonist C12-iE-DAP. Additionally, characterization of the effects of these agents on humoral immune response to a model antigen (ovalbumin) is undertaken.

As shown above, aluminum hydroxide and CBLB502 form a complex which, without wishing to be bound by theory, is stabilized by electrostatic forces as substances with opposite charges in aqueous medium. To test relative efficacy of different compositions of the adjuvant component of the vaccine, a standard dose of aluminum is used (1.5 μg per injection) loaded with a range of doses of CBLB502 (up to 30 μg and including 10 μg, 3 μg, 1 μg, 0.3 μg and 0.1 μg). CBLB502 in aqueous solution is added to the alum suspension in PBS and stirred for 10 min at room temperature. Aluminum hydroxide is then spun down by centrifugation and traces of CBLB502 in supernatants are determined using two quantitative analytical assays: (i) ELISA-based and (ii) reporter cell based (TLR5-positive 293 cells carrying NF-kB responsive reporter and calibrated for detection of CBLB 502 in the medium). In light of, inter alia, the above Examples, it is expected that a substantial fraction of CBLB 502 will be stably bound to alum under these conditions and within the chosen range of doses of TLR5 agonists.

To determine whether this adjuvant remains localized at the vaccine injection site, adult BALB/c female mice (n=10) carrying in their germ line firefly luciferase cDNA under the control of NF-kB-responsive promoter will be used. These "NF-kB reporter mice" are a sensitive tool for the detection of release of CBLB502 from the injection site by monitoring the luciferase activity in TLR5-positive tissues such as liver or small intestine. Only one dose of CBLB502-containing adjuvant formulation will be used that corresponds to the highest dose that demonstrated stability as a composition with Alum in vitro (presumably 30 μg). Two doses of free CBLB502 (1 and 3 μg in aqueous solution, s.c. injection) will be used for comparison as positive controls of systemically distributed TLR5 agonist. Luciferase detection will be done using a luminescent imager in vivo following luciferin injection at 2, 4, 6 and 18 hours post injection of the adjuvant. For a more accurate and sensitive detection, 3 animals from each group are sacrificed 6 hours post injection of the adjuvant formulation and tissues will be collected from the injection site, lymph nodes nearest to injection site and the liver. The level of luciferase activity indicative of the presence of CBLB 502 is quantitated in these tissue samples following tissue lysis. In addition to functional detection of CBLB 502 based on its expected NF-kB-inducing activity, an alternative analytical method of an established sensitive ELISA assay for direct detection of CBLB502 in tissue extracts is used.

Adjuvant formulations containing the above-described range of doses of CBLB502 are mixed with 10 mg of ovalbumin and vaccination is performed, as described herein, followed by the ELISA determination of titers of different classes of anti-albumin IgG (IgG1, IgG2a, IgG2b and IgG3) antibodies. The results are compared with "Alum only" control. Determination of the effects on different IgG types provides definition of the degrees of engagement of different immunization paths (e.g. $T_{H1}$-versus $T_{H2}$-mediated routes) by the adjuvant.

After determination of the composition of the adjuvant (in terms of anti-ovalbumin antibody inducing efficacy), additional enhancement of immunization is tested by adding into the formulation a NOD1 agonist, C12-iE-DAP.

Also, determination of vaccine efficacy at different CBLB 502 doses to generate antibodies to antigen is undertaken in mice. Female mice are chosen because they have stronger immune responses than male mice and BALB/c mice are a commonly used strain in immunological studies due to their robust immune responses. At the beginning of the study, mice weigh about 25 g and are group-housed (5 per cage) in standard acrylic cages (7"×11"×5 with corncob bedding polycarbonate and tops. Mice will have ad libitum access to food (Harlan) and water. The vivarium will be maintained at 22±1° C. and on a 12:12 light/dark cycle (lights on at 6 AM). All experimental procedures are approved by the Institutional Animal Care and Use Committee (IACUC) and are within the guidelines delineated in the Guide for the Care and Use of Laboratory Animals.

Mice are intramuscularly injected with the vaccine in the gluteal muscle. Each group is optionally immunized with a booster dose with the same vaccine formulation at 3 and 6 weeks post initial immunization. If persistent antibody levels are not maintained for at least 4 weeks, an additional immunization will be given at week 10.

Blood is drawn at 14, 28, 42, 56 and 84 days post initial immunization and allowed to clot at room temperature for 2 hours. Serum is collected after centrifugation at 4000 rpm for 15 min. Samples are stored at −80 degrees until ready to run the enzyme linked immunosorbent assays (ELISA). In the context of a vaccine with antigen X, anti-antigen X specific antibodies are assessed by ELISAs. To measure the antibodies, ELISA plates (Immulon 2HB, Daigger, Vernon Hills, Ill.) are coated overnight in carbonate buffer (0.05 M; pH 9.6) using fish gelatin, which is a heterologous carrier protein, as the conjugate partner for SMA. Pooled or individual serum samples are added to plates in 2 fold serial dilutions starting at 1K in phosphate buffered saline (PBS)-Tween (0.1%) and incubated for 2 hours. Plates are washed with PBS-Tween prior to adding goat anti-mouse IgG conjugated to horse-radish peroxidase (HRP) (Southern Biotech, Birmingham, Ala.). Plates are incubated for another 30 min and washed before adding substrate (Tetramethylbenzidine, Sigma, St Louis, Mo.). Plates are incubated for 45 min in the dark prior to stopping the reaction with 1M HCl. The optical density (OD) of the resulting dark spots on the plates from the antibody with antigen X linking are used to measure titer levels on a microplate reader (iMark Microplate Absorbance Reader) using Microplate Manager v 6.1 software.

ELISA data is analyzed using SigmaPlot (Systat Software Inc.) and background antibody binding to the carrier alone will be subtracted from each sample. Comparisons are made in each plate with a standard curve of purified mouse IgG (Sigma) bound directly in the wells in serial dilution.

Example 10: Comparison of CBLB502-Based Adjuvants/Vaccines with Flagellin-Based Adjuvants/Vaccines The CBLB502/alum adjuvant of the above Examples is tested head to head against a flagellin/alum adjuvant using the methods and study design of, for instance, Example 9 (optionally with an antigen). Further, the alum binding and dissociation studies, as well as the mouse evaluation studies, al described in the above Examples, are repeated with a flagellin/alum adjuvant for comparison to the CBLB502/ alum adjuvant. The efficacy of the CBLB502 variant, i.e., CBLB502-S33MX is also tested.

In one comparison experiment, a group of mice (n=6) is immunized with TT-SMA, which is a methamphetamine vaccine and is used illustratively, co-adsorbed onto Alhydrogel with either flagellin, CBLB502, or CBLB502-S33MX. Immunization is carried out on days 0, 14, and 28 of the study. Each immunization dose includes 32 μg of TT-SMA and adjuvants as follows: Group 1: 0.03 μg flagellin, Group 2: 0.1 μg flagellin, Group 3: 0.3 μg flagellin, Group 4: 1 μg flagellin, Group 5: 0.03 μg CBLB502, Group 6: 0.1 μg CBLB502, Group 7: 0.3 μg CBLB502, Group 8: 1 μg CBLB502, Group 9: 0.03 μg CBLB502-S33MX, Group 10: 0.1 μg CBLB502-S33MX, Group 11:0.3 μg CBLB502-S33MX, and Group 12: 1 μg CBLB502-S33MX.

Serum samples are collected and analyzed on days −1 (pre-immune serum), 14 (post-prime), 28 (post first boost), and 35 (post second boost). For example, the serum samples are analyzed for the levels of anti-methamphetamine and anti-entolimod antibodies. Analysis indicates that CBLB502/alum and CBLB502-S33MX/alum cause a broader, more diverse, more robust and longer immunostimulatory effect than flagellin/alum. In addition, CBLB502/alum and CBLB502-S33MX/alum activate both $T_{H1}$ and $T_{H2}$-mediated immune response and a greater $T_{H1}$-mediated immune response than flagellin/alum.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

1. Yoon S I, Kumasov O, Natarajan V, Hong M, Gudkov A V, Osterman A L, Wilson I A., 2012. Structural Basis of TLR5-Flagellin Recognition and Signaling. Science 335: 859-864 (PMID: 22344444)
2. Smith K D, Andersen-Nissen E, Hayashi F, Strobe K, Bergman M A, Barrett S L, Cookson B T, Aderem A. 2003. Toll-like receptor 5 recognizes a conserved site on flagellin required for protofilament formation and bacterial motility. Nat Immunol. 4:1247-53 (PMID: 14625549)
3. Mizel, S. B., A. P. West, R. R. Hantgan. 2003. Identification of a sequence in human Toll-like receptor 5 required for the binding of Gram-negative flagellin. J. Biol. Chem. 278:23624-23629 (PMID: 12711596)
4. Murthy, K. G., Deb, A., Goonesekera, S., Szabo, C. & Salzman, A. L (2004) J. Biol. Chem. 279:5667-5675 (PMID: 14634022)
5. Andersen-Nissen E., Smith K. D., Strobe K. L., Barrett S. L., Cookson B. T., Logan S. M., Aderem A. (2005) Evasion of Toll-like receptor 5 by flagellated bacteria. Proc. Natl. Acad. Sci. U.S.A. 102: 9247-9252 (PMID: 15956202)
6. Andersen-Nissen E, Smith K D, Bonneau R, Strong R K, Aderem A. 2007. A conserved surface on Toll-like receptor 5 recognizes bacterial flagellin. J Exp Med. 204:393-403 (PMID: 17283206)
7. Burdelya L G, Krivokrysenko V I, Tallant T C, Strom E, Gleiberman A S, Gupta D, Kumasov O V, Fort F L, Osterman A L, Didonato J A, Feinstein E, Gudkov A V., 2008. An agonist of Toll-like receptor 5 has radioprotective activity in mouse and primate models. Science 320: 226-230 (PMID: 18403709).
8. Huleatt J W, Nakaar V, Desai P, Huang Y, Hewitt D, Jacobs A, Tang J, McDonald W, Song L, Evans R K et al. 2008. Potent immunogenicity and efficacy of a universal influenza vaccine candidate comprising a recombinant fusion protein linking influenza M2e to the TRL5 ligand flagellin. Vaccine. 26:201-214.

What is claimed is:

1. A method of vaccinating a subject against a disorder, comprising administering an effective amount of a vaccine comprising:
   (a) an adjuvant comprising:
      a flagellin-based agent comprising an amino acid sequence having at least 95% identity with SEQ ID NO: 2, and
      an aluminum gel or salt,
         wherein the ratio (w/w) of flagellin-based agent to aluminum gel or salt is about 1:500 or less and
   (b) an antigen which stimulates protective immunity against the disorder,
      wherein the antigen is a constituent of an infectious agent selected from a live and attenuated, killed, inactivated, and toxoid infectious agent;
      and wherein the disorder is selected from infectious diseases, cancers, and allergies.

2. The method of claim 1, wherein the disorder is selected from diphtheria, tetanus, *pertussis*, influenza, pneumonia, hepatitis A, hepatitis B, polio, yellow fever, Human Papillomavirus (HPV) infection, anthrax, rabies, Japanese Encephalitis, meningitis, measles, mumps, rubella, gastroenteritis, smallpox, typhoid fever, varicella (chickenpox), rotavirus, and shingles.

3. The method of claim 1, wherein the flagellin-based agent comprises the amino sequence of SEQ ID NO: 2.

4. The method of claim 1, wherein the flagellin-based agent inhibits and abrogates the ability of neutralizing anti-flagellin antibodies to neutralize the adjuvant.

5. The method of claim 1, wherein the aluminum gel or salt is selected from aluminum hydroxide, aluminum phosphate, and aluminum sulfate.

6. The method of claim 1, wherein one or more of the flagellin-based agent and/or the antigen is adsorbed to the aluminum gel or salt.

7. The method of claim 1, wherein the flagellin-based agent and aluminum gel or salt are mixed to form a stable complex.

8. The method of claim 1, wherein the flagellin-based agent and aluminum gel or salt are mixed in a ratio that is substantially below a loading capacity of the aluminum salt.

9. The method of claim 7, wherein the flagellin-based agent and aluminum gel or salt are mixed in a ratio (w/w) of about 1:500, or about 1:600, or about 1:700, or about 1:800, or about 1:900, or about 1:1000, or about 1:2000, or about 1:5000, or about 1:10000.

10. The method of claim 1, wherein the antigen is that of one or more of the following vaccines: DTP (diphtheia-tetanus-*pertussis* vaccine), DTaP (diphtheria-tetanus-acellular *pertussis* vaccine), Hib (*Haemophilus influenzae* type b) conjugate vaccines, Pneumococcal conjugate vaccine, Hepatitis A vaccines, Poliomyelitis vaccines, Yellow fever vaccines, Hepatitis B vaccines, combination DTaP, Tdap, Hib, Human Papillomavirus (HPV) vaccine, Anthrax vaccine, and Rabies vaccine.

11. The method of claim 1, wherein the vaccine further comprises an additional adjuvant selected from oil-in-water emulsion formulations, saponin adjuvants, ovalbumin, Freund's Adjuvant, cytokines, and chitosans.

12. The method of claim 1, wherein the vaccine and/or adjuvant causes immunostimulation of one or more of a $T_{H1}$ and $T_{H2}$-mediated immune response.

13. The method of claim 1, wherein the administering is orally or by parenteral injection.

14. The method of claim 1, wherein the administering takes place by controlled-release or sustained-release.

15. The method of claim 1, wherein the vaccine is administered once per subject or is used in a booster strategy.

* * * * *